US005667992A

United States Patent [19]
Casey et al.

[11] Patent Number: 5,667,992
[45] Date of Patent: Sep. 16, 1997

[54] MAMMALIAN EXPRESSION SYSTEMS FOR HCV PROTEINS

[75] Inventors: James M. Casey; Suzanne L. Bode, both of Zion; Billy J. Zeck, Gurnee; Julie Yamaguchi, Chicago; Donald E. Frail; Suresh M. Desai, both of Libertyville; Sushil G. Devare, Northbrook, all of Ill.

[73] Assignee: Abbott Laboratories, Abbott Park, Ill.

[21] Appl. No.: 453,552

[22] Filed: May 30, 1995

Related U.S. Application Data

[62] Division of Ser. No. 417,478, Apr. 5, 1995, abandoned, which is a continuation of Ser. No. 144,099, Oct. 28, 1993, abandoned, which is a continuation of Ser. No. 830,024, Jan. 31, 1992, abandoned.

[51] Int. Cl.$^6$ .............................. C12P 21/00; C12Q 1/70
[52] U.S. Cl. .............................. 435/69.3; 435/5; 530/409
[58] Field of Search .................. 435/5, 69.3; 530/409

[56] References Cited

U.S. PATENT DOCUMENTS 5,106,726  4/1992  Wang .
5,308,750  5/1994  Mehta ........................................ 435/5

FOREIGN PATENT DOCUMENTS 0318216  5/1989  European Pat. Off. .
0388232  9/1990  European Pat. Off. .
2212511  7/1989  United Kingdom .

OTHER PUBLICATIONS

Hijikata, M. et al., *Proc. Natl. Acad. Sci. USA* 88, 5547–5551 (1991). see entire article.

Malon Kit, et al., "Bovine herpesvirus–1 . . .," *Vaccine,* 9:564–572 Aug. 1991.

Shelley B. Blam, et al., "Addition of growth hormone secretion . . .", *Oncogene,* 3:129–136.

N. Kato, et al., "Molecular cloning of the human . . .", *Natl Acad. of Science USA,* 87:9524–9528, (1990).

H. Okamoto, et al., "Nucleotide sequence of the . . .", *Journal of General Virology,* 72:2697–2704.

A. Weidemann, et al., "Identification, Biogenesis . . .", *Cell,* 57:115–126 (1989).

D. E. Lowery, et al., "Alzheimer's Amyloid . . . ", *The Journal of Biological Chemistry,* 266:19842–19850 (1991).

J. Li, et al., "Two French Genotypes . . . ", *Gene,* 105:167–172 (1991).

Q. –L. Choo et al., "Genetic organization and diversity . . .", *Pro. Natl. Acad. of Science USA,* 88:2451–2455 (1991).

D. Kremsdorf, et al., "Partial nucleotide . . . ", *Journal of General Virology,* 72:2557–2561 (1991).

A. Takamizawa, et al., "Structure and Organization of the Hepatitis C Virus . . . ", *Journal of Virology,* 65:1105–1113 (1991).

Uhlen et al., "Gene Fusions for Purpose of Expression: An Introduction", *Methods In Enzymology,* 185:129–143 (1991).

*Primary Examiner*—Paula K. Hutzell
*Assistant Examiner*—Benet Prickril
*Attorney, Agent, or Firm*—Cheryl L. Becker; Priscilla E. Porembski

[57] ABSTRACT

Mammalian expression systems for the production of HCV proteins. Such expression systems provide high yields of HCV proteins, and enable the development of diagnostic and therapeutic reagents which contain glycosylated structural antigens and also allow for the isolation of the HCV etiological agent.

2 Claims, 15 Drawing Sheets

HCV AA# 192-384
HGH SECRETION SIGNAL
CMV PROMOTER
HEK CELLS

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 3011 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

```
Met Ser Thr Asn Pro Lys Pro Gln Arg Lys Thr Lys Arg Asn Thr Asn
  1               5                  10                  15

Arg Arg Pro Gln Asp Val Lys Phe Pro Gly Gly Gly Gln Ile Val Gly
                 20                  25                  30

Gly Val Tyr Leu Leu Pro Arg Arg Gly Pro Arg Leu Gly Val Arg Ala
             35                  40                  45

Thr Arg Lys Thr Ser Glu Arg Ser Gln Pro Arg Gly Arg Arg Gln Pro
         50                  55                  60

Ile Pro Lys Ala Arg Arg Pro Glu Gly Arg Thr Trp Ala Gln Pro Gly
 65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Pro Thr Asp Pro
                100                 105                 110
```

-continued

| | | | | | | | | | | | | | | |
|---|---|---|---|---|---|---|---|---|---|---|---|---|---|---|
| Arg | Arg | Arg 115 | Ser | Arg | Asn | Leu | Gly 120 | Lys | Val | Ile | Asp | Thr 125 | Leu | Thr | Cys |
| Gly 130 | Phe | Ala | Asp | Leu | Met | Gly 135 | Tyr | Ile | Pro | Leu | Val 140 | Gly | Ala | Pro | Leu |
| Gly 145 | Gly | Ala | Ala | Arg | Ala 150 | Leu | Ala | His | Gly | Val 155 | Arg | Val | Leu | Glu | Asp 160 |
| Gly | Val | Asn | Tyr | Ala 165 | Thr | Gly | Asn | Leu | Pro 170 | Gly | Cys | Ser | Phe 175 | Ser | Ile |
| Phe | Leu | Leu | Ala 180 | Leu | Leu | Ser | Cys | Leu 185 | Thr | Val | Pro | Ala 190 | Ser | Ala | Tyr |
| Gln | Val | Arg 195 | Asn | Ser | Ser | Gly | Leu 200 | Tyr | His | Val | Thr | Asn 205 | Asp | Cys | Pro |
| Asn 210 | Ser | Ser | Ile | Val | Tyr 215 | Glu | Ala | Ala | Asp | Ala 220 | Ile | Leu | His | Thr | Pro |
| Gly 225 | Cys | Val | Pro | Cys | Val 230 | Arg | Glu | Gly | Asn | Ala 235 | Ser | Arg | Cys | Trp 240 | Val |
| Ala | Val | Thr | Pro | Thr 245 | Val | Ala | Thr | Arg | Asp 250 | Gly | Lys | Leu | Pro 255 | Thr | Thr |
| Gln | Leu | Arg | Arg 260 | His | Ile | Asp | Leu | Leu 265 | Val | Gly | Ser | Ala | Thr 270 | Leu | Cys |
| Ser | Ala | Leu 275 | Tyr | Val | Gly | Asp | Leu 280 | Cys | Gly | Ser | Val | Phe 285 | Leu | Val | Gly |
| Gln | Leu 290 | Phe | Thr | Phe | Ser | Pro 295 | Arg | Arg | His | Trp | Thr 300 | Thr | Gln | Asp | Cys |
| Asn 305 | Cys | Ser | Ile | Tyr | Pro 310 | Gly | His | Ile | Thr | Gly 315 | His | Arg | Met | Ala | Trp 320 |
| Asp | Met | Met | Met | Asn 325 | Trp | Ser | Pro | Thr | Ala 330 | Ala | Leu | Val | Val | Ala 335 | Gln |
| Leu | Leu | Arg | Ile 340 | Pro | Gln | Ala | Ile | Leu 345 | Asp | Met | Ile | Ala | Gly 350 | Ala | His |
| Trp | Gly | Val 355 | Leu | Ala | Gly | Ile | Ala 360 | Tyr | Phe | Ser | Met | Val 365 | Gly | Asn | Trp |
| Ala | Lys 370 | Val | Leu | Val | Val | Leu 375 | Leu | Leu | Phe | Ala | Gly 380 | Val | Asp | Ala | Glu |
| Thr 385 | His | Val | Thr | Gly | Gly 390 | Ser | Ala | Gly | His | Thr 395 | Thr | Ala | Gly | Leu | Val 400 |
| Arg | Leu | Leu | Ser | Pro 405 | Gly | Ala | Lys | Gln | Asn 410 | Ile | Gln | Leu | Ile | Asn 415 | Thr |
| Asn | Gly | Ser | Trp 420 | His | Ile | Asn | Ser | Thr 425 | Ala | Leu | Asn | Cys | Asn 430 | Glu | Ser |
| Leu | Asn | Thr 435 | Gly | Trp | Leu | Ala | Gly 440 | Leu | Phe | Tyr | His | His 445 | Lys | Phe | Asn |
| Ser | Ser 450 | Gly | Cys | Pro | Glu | Arg 455 | Leu | Ala | Ser | Cys | Arg 460 | Arg | Leu | Thr | Asp |
| Phe 465 | Ala | Gln | Gly | Gly | Gly 470 | Pro | Ile | Ser | Tyr | Ala 475 | Asn | Gly | Ser | Gly | Leu 480 |
| Asp | Glu | Arg | Pro | Tyr 485 | Cys | Trp | His | Tyr | Pro 490 | Pro | Arg | Pro | Cys | Gly 495 | Ile |
| Val | Pro | Ala | Lys 500 | Ser | Val | Cys | Gly | Pro 505 | Val | Tyr | Cys | Phe | Thr 510 | Pro | Ser |
| Pro | Val | Val 515 | Val | Gly | Thr | Thr | Asp 520 | Arg | Ser | Gly | Ala | Pro 525 | Thr | Tyr | Ser |
| Trp | Gly 530 | Ala | Asn | Asp | Thr | Asp 535 | Val | Phe | Val | Leu | Asn 540 | Asn | Thr | Arg | Pro |

```
Pro Leu Gly Asn Trp Phe Gly Cys Thr Trp Met Asn Ser Thr Gly Phe
545                 550                 555                 560
Thr Lys Val Cys Gly Ala Pro Pro Cys Val Ile Gly Gly Val Gly Asn
                565             570                 575
Asn Thr Leu Leu Cys Pro Thr Asp Cys Phe Arg Lys His Pro Glu Ala
            580             585                 590
Thr Tyr Ser Arg Cys Gly Ser Gly Pro Trp Ile Thr Pro Arg Cys Met
        595             600                 605
Val Asp Tyr Pro Tyr Arg Leu Trp His Tyr Pro Cys Thr Ile Asn Tyr
    610             615             620
Thr Ile Phe Lys Val Arg Met Tyr Val Gly Gly Val Glu His Arg Leu
625             630             635                 640
Glu Ala Ala Cys Asn Trp Thr Arg Gly Glu Arg Cys Asp Leu Glu Asp
                645             650                 655
Arg Asp Arg Ser Glu Leu Ser Pro Leu Leu Leu Ser Thr Thr Gln Trp
                660             665             670
Gln Val Leu Pro Cys Ser Phe Thr Thr Leu Pro Ala Leu Ser Thr Gly
            675             680             685
Leu Ile His Leu His Gln Asn Ile Val Asp Val Gln Tyr Leu Tyr Gly
        690             695             700
Val Gly Ser Ser Ile Ala Ser Trp Ala Ile Lys Trp Glu Tyr Val Val
705             710             715                 720
Leu Leu Phe Leu Leu Leu Ala Asp Ala Arg Val Cys Ser Cys Leu Trp
            725             730             735
Met Met Leu Leu Ile Ser Gln Ala Glu Ala Ala Leu Glu Asn Leu Val
        740             745             750
Ile Leu Asn Ala Ala Ser Leu Ala Gly Thr His Gly Phe Val Ser Phe
        755             760             765
Leu Val Phe Phe Cys Phe Ala Trp Tyr Leu Lys Gly Arg Trp Val Pro
    770             775             780
Gly Ala Ala Tyr Ala Leu Tyr Gly Ile Trp Pro Leu Leu Leu Leu Leu
785             790             795                 800
Leu Ala Leu Pro Gln Arg Ala Tyr Ala Leu Asp Thr Glu Val Ala Ala
            805             810             815
Ser Cys Gly Gly Val Val Leu Val Gly Leu Met Ala Leu Thr Leu Ser
            820             825             830
Pro Tyr Tyr Lys Arg Tyr Ile Ser Trp Cys Met Trp Trp Leu Gln Tyr
        835             840             845
Phe Leu Thr Arg Val Glu Ala Gln Leu His Val Trp Val Pro Pro Leu
    850             855             860
Asn Val Arg Gly Gly Arg Asp Ala Val Ile Leu Leu Met Cys Ala Val
865             870             875                 880
His Pro Thr Leu Val Phe Asp Ile Thr Lys Leu Leu Leu Ala Ile Phe
            885             890                 895
Gly Pro Leu Trp Ile Leu Gln Ala Ser Leu Leu Lys Val Pro Tyr Phe
            900             905             910
Val Arg Val Gln Gly Leu Leu Arg Ile Cys Ala Leu Ala Arg Lys Ile
    915             920             925
Ala Gly Gly His Tyr Val Gln Met Ile Phe Ile Lys Leu Gly Ala Leu
    930             935             940
Thr Gly Thr Tyr Val Tyr Asn His Leu Thr Pro Leu Arg Asp Trp Ala
945             950             955                 960
His Asn Gly Leu Arg Asp Leu Ala Val Ala Val Glu Pro Val Val Phe
```

|   |   |   |   |   | 965 |   |   |   |   | 970 |   |   |   |   | 975 |   |
|---|---|---|---|---|---|---|---|---|---|---|---|---|---|---|---|---|

Ser Arg Met Glu Thr Lys Leu Ile Thr Trp Gly Ala Asp Thr Ala Ala
                980                 985                 990

Cys Gly Asp Ile Ile Asn Gly Leu Pro Val Ser Ala Arg Arg Gly Gln
        995                 1000                1005

Glu Ile Leu Leu Gly Pro Ala Asp Gly Met Val Ser Lys Gly Trp Arg
1010                1015                1020

Leu Leu Ala Pro Ile Thr Ala Tyr Ala Gln Gln Thr Arg Gly Leu Leu
1025                1030                1035                1040

Gly Cys Ile Ile Thr Ser Leu Thr Gly Arg Asp Lys Asn Gln Val Glu
            1045                1050                1055

Gly Glu Val Gln Ile Val Ser Thr Ala Thr Gln Thr Phe Leu Ala Thr
            1060                1065                1070

Cys Ile Asn Gly Val Cys Trp Thr Val Tyr His Gly Ala Gly Thr Arg
            1075                1080                1085

Thr Ile Ala Ser Pro Lys Gly Pro Val Ile Gln Met Tyr Thr Asn Val
        1090                1095                1100

Asp Gln Asp Leu Val Gly Trp Pro Ala Pro Gln Gly Ser Arg Ser Leu
1105                1110                1115                1120

Thr Pro Cys Thr Cys Gly Ser Ser Asp Leu Tyr Leu Val Thr Arg His
                1125                1130                1135

Ala Asp Val Ile Pro Val Arg Arg Gln Gly Asp Ser Arg Gly Ser Leu
            1140                1145                1150

Leu Ser Pro Arg Pro Ile Ser Tyr Leu Lys Gly Ser Ser Gly Gly Pro
            1155                1160                1165

Leu Leu Cys Pro Ala Gly His Ala Val Gly Leu Phe Arg Ala Ala Val
            1170                1175                1180

Cys Thr Arg Gly Val Ala Lys Ala Val Asp Phe Ile Pro Val Glu Asn
1185                1190                1195                1200

Leu Glu Thr Thr Met Arg Ser Pro Val Phe Thr Asp Asn Ser Ser Pro
                1205                1210                1215

Pro Ala Val Pro Gln Ser Phe Gln Val Ala His Leu His Ala Pro Thr
            1220                1225                1230

Gly Ser Gly Lys Ser Thr Lys Val Pro Ala Ala Tyr Ala Ala Gln Gly
            1235                1240                1245

Tyr Lys Val Leu Val Leu Asn Pro Ser Val Ala Ala Thr Leu Gly Phe
1250                1255                1260

Gly Ala Tyr Met Ser Lys Ala His Gly Val Asp Pro Asn Ile Arg Thr
1265                1270                1275                1280

Gly Val Arg Thr Ile Thr Thr Gly Ser Pro Ile Thr Tyr Ser Thr Tyr
            1285                1290                1295

Gly Lys Phe Leu Ala Asp Gly Gly Cys Ser Gly Gly Ala Tyr Asp Ile
            1300                1305                1310

Ile Ile Cys Asp Glu Cys His Ser Thr Asp Ala Thr Ser Ile Leu Gly
        1315                1320                1325

Ile Gly Thr Val Leu Asp Gln Ala Glu Thr Ala Gly Ala Arg Leu Val
        1330                1335                1340

Val Leu Ala Thr Ala Thr Pro Pro Gly Ser Val Thr Val Pro His Pro
1345                1350                1355                1360

Asn Ile Glu Glu Val Ala Leu Ser Thr Thr Gly Glu Ile Pro Phe Tyr
                1365                1370                1375

Gly Lys Ala Ile Pro Leu Glu Val Ile Lys Gly Gly Arg His Leu Ile
            1380                1385                1390

Phe Cys His Ser Lys Lys Lys Cys Asp Glu Leu Ala Ala Lys Leu Val
1395                     1400                1405

Ala Leu Gly Ile Asn Ala Val Ala Tyr Tyr Arg Gly Leu Asp Val Ser
1410                1415                1420

Val Ile Pro Ala Ser Gly Asp Val Val Val Ser Thr Asp Ala Leu
1425                1430                1435                1440

Met Thr Gly Phe Thr Gly Asp Phe Asp Pro Val Ile Asp Cys Asn Thr
                1445                1450                1455

Cys Val Thr Gln Thr Val Asp Phe Ser Leu Asp Pro Thr Phe Thr Ile
                1460                1465                1470

Glu Thr Thr Thr Leu Pro Gln Asp Ala Val Ser Arg Thr Gln Arg Arg
                1475                1480                1485

Gly Arg Thr Gly Arg Gly Lys Pro Gly Ile Tyr Arg Phe Val Ala Pro
                1490                1495                1500

Gly Glu Arg Pro Ser Gly Met Phe Asp Ser Ser Val Leu Cys Glu Cys
1505                1510                1515                1520

Tyr Asp Ala Gly Cys Ala Trp Tyr Glu Leu Thr Pro Ala Glu Thr Thr
                1525                1530                1535

Val Arg Leu Arg Ala Tyr Met Asn Thr Pro Gly Leu Pro Val Cys Gln
                1540                1545                1550

Asp His Leu Glu Phe Trp Glu Gly Val Phe Thr Gly Leu Thr His Ile
                1555                1560                1565

Asp Ala His Phe Leu Ser Gln Thr Lys Gln Ser Gly Glu Asn Phe Pro
1570                1575                1580

Tyr Leu Val Ala Tyr Gln Ala Thr Val Cys Ala Arg Ala Gln Ala Pro
1585                1590                1595                1600

Pro Pro Ser Trp Asp Gln Met Trp Lys Cys Leu Ile Arg Leu Lys Pro
                1605                1610                1615

Thr Leu His Gly Pro Thr Pro Leu Leu Tyr Arg Leu Gly Ala Val Gln
                1620                1625                1630

Asn Glu Ile Thr Leu Thr His Pro Val Thr Lys Tyr Ile Met Thr Cys
                1635                1640                1645

Met Ser Ala Asn Pro Glu Val Val Thr Ser Thr Trp Val Leu Val Gly
                1650                1655                1660

Gly Val Leu Ala Ala Leu Ala Ala Tyr Cys Leu Ser Thr Gly Cys Val
1665                1670                1675                1680

Val Ile Val Gly Arg Ile Val Leu Ser Gly Lys Pro Ala Ile Ile Pro
                1685                1690                1695

Asp Arg Glu Val Leu Tyr Gln Glu Phe Asp Glu Met Glu Glu Cys Ser
                1700                1705                1710

Gln His Leu Pro Tyr Ile Glu Gln Gly Met Met Leu Ala Glu Gln Phe
                1715                1720                1725

Lys Gln Glu Ala Leu Gly Leu Leu Gln Thr Ala Ser Arg Gln Ala Glu
                1730                1735                1740

Val Ile Thr Pro Ala Val Gln Thr Asn Trp Gln Lys Leu Glu Ala Phe
                1745                1750                1755                1760

Trp Ala Lys His Met Trp Asn Phe Ile Ser Gly Thr Gln Tyr Leu Ala
                        1765                1770                1775

Gly Leu Ser Thr Leu Pro Gly Asn Pro Ala Ile Ala Ser Leu Met Ala
                1780                1785                1790

Phe Thr Ala Ala Val Thr Ser Pro Leu Thr Thr Ser Gln Thr Leu Leu
                1795                1800                1805

Phe Asn Ile Leu Gly Gly Trp Val Ala Ala Gln Leu Ala Ala Pro Gly
                1810                1815                1820

```
Ala Ala Thr Ala Phe Val Gly Ala Gly Leu Ala Gly Ala Ala Ile Gly
1825                1830                1835                1840

Ser Val Gly Leu Gly Lys Val Leu Val Asp Ile Leu Ala Gly Tyr Gly
                1845                1850                1855

Ala Gly Val Ala Gly Ala Leu Val Ala Phe Lys Ile Met Ser Gly Glu
            1860                1865                1870

Val Pro Ser Thr Glu Asp Leu Val Asn Leu Leu Pro Ala Ile Leu Ser
        1875                1880                1885

Pro Gly Ala Leu Val Val Gly Val Val Cys Ala Ala Ile Leu Arg Arg
        1890                1895                1900

His Val Gly Pro Gly Glu Gly Ala Val Gln Trp Met Asn Arg Leu Ile
1905                1910                1915                1920

Ala Phe Ala Ser Arg Gly Asn His Val Ser Pro Thr His Tyr Val Pro
                1925                1930                1935

Glu Ser Asp Ala Ala Ala Arg Val Thr Ala Ile Leu Ser Asn Leu Thr
            1940                1945                1950

Val Thr Gln Leu Leu Arg Arg Leu His Gln Trp Ile Gly Ser Glu Cys
        1955                1960                1965

Thr Thr Pro Cys Ser Gly Ser Trp Leu Arg Asp Ile Trp Asp Trp Ile
        1970                1975                1980

Cys Glu Val Leu Ser Asp Phe Lys Thr Trp Leu Lys Ala Lys Leu Met
1985                1990                1995                2000

Pro Gln Leu Pro Gly Ile Pro Phe Val Ser Cys Gln Arg Gly Tyr Arg
                2005                2010                2015

Gly Val Trp Arg Gly Asp Gly Ile Met His Thr Arg Cys His Cys Gly
            2020                2025                2030

Ala Glu Ile Thr Gly His Val Lys Asn Gly Thr Met Arg Ile Val Gly
        2035                2040                2045

Pro Arg Thr Cys Arg Asn Met Trp Ser Gly Thr Phe Pro Ile Asn Ala
        2050                2055                2060

Tyr Thr Thr Gly Pro Cys Thr Pro Leu Pro Ala Pro Asn Tyr Lys Phe
2065                2070                2075                2080

Ala Leu Trp Arg Val Ser Ala Glu Glu Tyr Val Glu Ile Arg Arg Val
                2085                2090                2095

Gly Asp Phe His Tyr Val Ser Gly Met Thr Thr Asp Asn Leu Lys Cys
            2100                2105                2110

Pro Cys Gln Ile Pro Ser Pro Glu Phe Phe Thr Glu Leu Asp Gly Val
        2115                2120                2125

Arg Leu His Arg Phe Ala Pro Pro Cys Lys Pro Leu Leu Arg Glu Glu
        2130                2135                2140

Val Ser Phe Arg Val Gly Leu His Glu Tyr Pro Val Gly Ser Gln Leu
2145                2150                2155                2160

Pro Cys Glu Pro Glu Pro Asp Val Ala Val Leu Thr Ser Met Leu Thr
                2165                2170                2175

Asp Pro Ser His Ile Thr Ala Glu Ala Ala Gly Arg Arg Leu Ala Arg
            2180                2185                2190

Gly Ser Pro Pro Ser Met Ala Ser Ser Ser Ala Ser Gln Leu Ser Ala
        2195                2200                2205

Pro Ser Leu Lys Ala Thr Cys Thr Thr Asn His Asp Ser Pro Asp Ala
        2210                2215                2220

Glu Leu Ile Glu Ala Asn Leu Leu Trp Arg Gln Glu Met Gly Gly Asn
2225                2230                2235                2240

Ile Thr Arg Val Glu Ser Glu Asn Lys Val Val Ile Leu Asp Ser Phe
```

-continued

```
                     2245                    2250                    2255
 Asp  Pro  Leu  Val  Ala  Glu  Glu  Asp  Glu  Arg  Glu  Val  Ser  Val  Pro  Ala
                2260                    2265                    2270
 Glu  Ile  Leu  Arg  Lys  Ser  Gln  Arg  Phe  Ala  Arg  Ala  Leu  Pro  Val  Trp
                2275                    2280                    2285
 Ala  Arg  Pro  Asp  Tyr  Asn  Pro  Pro  Leu  Ile  Glu  Thr  Trp  Lys  Glu  Pro
                2290                    2295                    2300
 Asp  Tyr  Glu  Pro  Pro  Val  His  Gly  Cys  Pro  Leu  Pro  Pro  Pro  Arg
 2305                2310                    2315                    2320
 Ser  Pro  Pro  Val  Pro  Pro  Pro  Arg  Lys  Lys  Arg  Thr  Val  Val  Leu  Thr
                2325                    2330                    2335
 Glu  Ser  Thr  Leu  Ser  Thr  Ala  Leu  Ala  Glu  Leu  Ala  Thr  Lys  Ser  Phe
                2340                    2345                    2350
 Gly  Ser  Ser  Ser  Thr  Ser  Gly  Ile  Thr  Gly  Asp  Asn  Thr  Thr  Thr  Ser
                2355                    2360                    2365
 Ser  Glu  Pro  Ala  Pro  Ser  Gly  Cys  Pro  Pro  Asp  Ser  Asp  Val  Glu  Ser
                2370                    2375                    2380
 Tyr  Ser  Ser  Met  Pro  Pro  Leu  Glu  Gly  Glu  Pro  Gly  Asp  Pro  Asp  Phe
 2385                2390                    2395                    2400
 Ser  Asp  Gly  Ser  Trp  Ser  Thr  Val  Ser  Ser  Gly  Ala  Asp  Thr  Glu  Asp
                2405                    2410                    2415
 Val  Val  Cys  Cys  Ser  Met  Ser  Tyr  Ser  Trp  Thr  Gly  Ala  Leu  Val  Thr
                2420                    2425                    2430
 Pro  Cys  Ala  Ala  Glu  Glu  Gln  Lys  Leu  Pro  Ile  Asn  Ala  Leu  Ser  Asn
                2435                    2440                    2445
 Ser  Leu  Leu  Arg  His  His  Asn  Leu  Val  Tyr  Ser  Thr  Thr  Ser  Arg  Ser
                2450                    2455                    2460
 Ala  Cys  Gln  Arg  Gln  Lys  Lys  Val  Thr  Phe  Asp  Arg  Leu  Gln  Val  Leu
 2465                2470                    2475                    2480
 Asp  Ser  His  Tyr  Gln  Asp  Val  Leu  Lys  Glu  Val  Lys  Ala  Ala  Ala  Ser
                2485                    2490                    2495
 Arg  Val  Lys  Ala  Asn  Leu  Leu  Ser  Val  Glu  Glu  Ala  Cys  Ser  Leu  Thr
                2500                    2505                    2510
 Pro  Pro  His  Ser  Ala  Lys  Ser  Lys  Phe  Gly  Tyr  Gly  Ala  Lys  Asp  Val
                2515                    2520                    2525
 Arg  Cys  His  Ala  Arg  Lys  Ala  Val  Ala  His  Ile  Asn  Ser  Val  Trp  Lys
                2530                    2535                    2540
 Asp  Leu  Leu  Glu  Asp  Ser  Val  Thr  Pro  Ile  Asp  Thr  Thr  Ile  Met  Ala
 2545                2550                    2555                    2560
 Lys  Asn  Glu  Val  Phe  Cys  Val  Gln  Pro  Glu  Lys  Gly  Gly  Arg  Lys  Pro
                2565                    2570                    2575
 Ala  Arg  Leu  Ile  Val  Phe  Pro  Asp  Leu  Gly  Val  Arg  Val  Cys  Glu  Lys
                2580                    2585                    2590
 Met  Ala  Leu  Tyr  Asp  Val  Val  Ser  Lys  Leu  Pro  Leu  Ala  Val  Met  Gly
                2595                    2600                    2605
 Ser  Ser  Tyr  Gly  Phe  Gln  Tyr  Ser  Pro  Gly  Gln  Arg  Val  Glu  Phe  Leu
                2610                    2615                    2620
 Val  Gln  Ala  Trp  Lys  Ser  Lys  Lys  Thr  Pro  Met  Gly  Phe  Ser  Tyr  Asp
 2625                2630                    2635                    2640
 Thr  Arg  Cys  Phe  Asp  Ser  Thr  Val  Thr  Glu  Ser  Asp  Ile  Arg  Thr  Glu
                2645                    2650                    2655
 Glu  Ala  Ile  Tyr  Gln  Cys  Cys  Asp  Leu  Asp  Pro  Gln  Ala  Arg  Val  Ala
                2660                    2665                    2670
```

-continued

```
Ile Lys Ser Leu Thr Glu Arg Leu Tyr Val Gly Gly Pro Leu Thr Asn
                2675                2680                2685

Ser Arg Gly Glu Asn Cys Gly Tyr Arg Arg Cys Arg Ala Ser Gly Val
        2690                2695                2700

Leu Thr Thr Ser Cys Gly Asn Thr Leu Thr Cys Tyr Ile Lys Ala Arg
2705                2710                2715                2720

Ala Ala Cys Arg Ala Ala Gly Leu Gln Asp Arg Thr Met Leu Val Cys
                2725                2730                2735

Gly Asp Asp Leu Val Val Ile Cys Glu Ser Ala Gly Val Gln Glu Asp
                2740                2745                2750

Ala Ala Ser Leu Arg Ala Phe Thr Glu Ala Met Thr Arg Tyr Ser Ala
                2755                2760                2765

Pro Pro Gly Asp Pro Pro Gln Pro Glu Tyr Asp Leu Glu Leu Ile Thr
                2770                2775                2780

Ser Cys Ser Ser Asn Val Ser Val Ala His Asp Gly Ala Gly Lys Arg
2785                2790                2795                2800

Val Tyr Tyr Leu Thr Arg Asp Pro Thr Thr Pro Leu Ala Arg Ala Ala
                2805                2810                2815

Trp Glu Thr Ala Arg His Thr Pro Val Asn Ser Trp Leu Gly Asn Ile
                2820                2825                2830

Ile Met Phe Ala Pro Thr Leu Trp Ala Arg Met Ile Leu Met Thr His
                2835                2840                2845

Phe Phe Ser Val Leu Ile Ala Arg Asp Gln Phe Glu Gln Ala Leu Asn
                2850                2855                2860

Cys Glu Ile Tyr Gly Ala Cys Tyr Ser Ile Glu Pro Leu Asp Leu Pro
2865                2870                2875                2880

Pro Ile Ile Gln Arg Leu His Gly Leu Ser Ala Phe Ser Leu His Ser
                2885                2890                2895

Tyr Ser Pro Gly Glu Ile Asn Arg Val Ala Ala Cys Leu Arg Lys Leu
                2900                2905                2910

Gly Val Pro Pro Leu Arg Ala Trp Lys His Arg Ala Arg Ser Val Arg
                2915                2920                2925

Ala Arg Leu Leu Ser Arg Gly Gly Arg Ala Ala Ile Cys Gly Lys Tyr
                2930                2935                2940

Leu Phe Asn Trp Ala Val Arg Thr Lys Pro Lys Leu Thr Pro Ile Ala
2945                2950                2955                2960

Ala Ala Gly Arg Leu Asp Leu Ser Gly Trp Phe Thr Ala Gly Tyr Ser
                2965                2970                2975

Gly Gly Asp Ile Tyr His Ser Val Ser His Ala Arg Pro Arg Trp Ser
                2980                2985                2990

Trp Phe Cys Leu Leu Leu Leu Ala Ala Gly Val Gly Ile Tyr Leu Leu
                2995                3000                3005

Pro Asn Arg
        3010
```

( 2 ) INFORMATION FOR SEQ ID NO:2:

( i ) SEQUENCE CHARACTERISTICS:
        ( A ) LENGTH: 3011 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Met Ser Thr Asn Pro Lys Pro Gln Arg Lys Thr Lys Arg Asn Thr Asn
```

| 1 | | | | 5 | | | | | 10 | | | | | 15 | |
|---|---|---|---|---|---|---|---|---|---|---|---|---|---|---|---|
| Arg | Arg | Pro | Gln | Asp | Val | Lys | Phe | Pro | Gly | Gly | Gly | Gln | Ile | Val | Gly |
| | | | 20 | | | | 25 | | | | | 30 | | | |
| Gly | Val | Tyr | Leu | Leu | Pro | Arg | Arg | Gly | Pro | Arg | Leu | Gly | Val | Arg | Ala |
| | | 35 | | | | 40 | | | | 45 | | | | | |
| Thr | Arg | Lys | Thr | Ser | Glu | Arg | Ser | Gln | Pro | Arg | Gly | Arg | Arg | Gln | Pro |
| | 50 | | | | 55 | | | | | 60 | | | | | |
| Ile | Pro | Lys | Ala | Arg | Arg | Pro | Glu | Gly | Arg | Thr | Trp | Ala | Gln | Pro | Gly |
| 65 | | | | | 70 | | | | 75 | | | | | | 80 |
| Tyr | Pro | Trp | Pro | Leu | Tyr | Gly | Asn | Glu | Gly | Cys | Gly | Trp | Ala | Gly | Trp |
| | | | 85 | | | | 90 | | | | | 95 | | | |
| Leu | Leu | Ser | Pro | Arg | Gly | Ser | Arg | Pro | Ser | Trp | Gly | Pro | Thr | Asp | Pro |
| | | | 100 | | | | 105 | | | | | 110 | | | |
| Arg | Arg | Arg | Ser | Arg | Asn | Leu | Gly | Lys | Val | Ile | Asp | Thr | Leu | Thr | Cys |
| | | | 115 | | | | 120 | | | | | 125 | | | |
| Gly | Phe | Ala | Asp | Leu | Met | Gly | Tyr | Ile | Pro | Leu | Val | Gly | Ala | Pro | Leu |
| | | 130 | | | | 135 | | | | 140 | | | | | |
| Gly | Gly | Ala | Ala | Arg | Ala | Leu | Ala | His | Gly | Val | Arg | Val | Leu | Glu | Asp |
| 145 | | | | | 150 | | | | 155 | | | | | | 160 |
| Gly | Val | Asn | Tyr | Ala | Thr | Gly | Asn | Leu | Pro | Gly | Cys | Ser | Phe | Ser | Ile |
| | | | | 165 | | | | 170 | | | | | 175 | | |
| Phe | Leu | Leu | Ala | Leu | Leu | Ser | Cys | Leu | Thr | Val | Pro | Ala | Ser | Ala | Tyr |
| | | | 180 | | | | 185 | | | | | 190 | | | |
| Gln | Val | Arg | Asn | Ser | Ser | Gly | Leu | Tyr | His | Val | Thr | Asn | Asp | Cys | Pro |
| | | 195 | | | | 200 | | | | | 205 | | | | |
| Asn | Ser | Ser | Ile | Val | Tyr | Glu | Thr | Ala | Asp | Thr | Ile | Leu | His | Ser | Pro |
| | 210 | | | | 215 | | | | | 220 | | | | | |
| Gly | Cys | Val | Pro | Cys | Val | Arg | Glu | Gly | Asn | Thr | Ser | Lys | Cys | Trp | Val |
| 225 | | | | 230 | | | | 235 | | | | | | | 240 |
| Ala | Val | Ala | Pro | Thr | Val | Thr | Thr | Arg | Asp | Gly | Lys | Leu | Pro | Ser | Thr |
| | | | | 245 | | | | 250 | | | | | 255 | | |
| Gln | Leu | Arg | Arg | His | Ile | Asp | Leu | Leu | Val | Gly | Ser | Ala | Thr | Leu | Cys |
| | | | 260 | | | | 265 | | | | | 270 | | | |
| Ser | Ala | Leu | Tyr | Val | Gly | Asp | Leu | Cys | Gly | Ser | Val | Phe | Leu | Val | Ser |
| | | 275 | | | | 280 | | | | | 285 | | | | |
| Gln | Leu | Phe | Thr | Phe | Ser | Pro | Arg | Arg | His | Trp | Thr | Thr | Gln | Asp | Cys |
| | | 290 | | | | 295 | | | | | 300 | | | | |
| Asn | Cys | Ser | Ile | Tyr | Pro | Gly | His | Ile | Thr | Gly | His | Arg | Met | Ala | Trp |
| 305 | | | | | 310 | | | | | 315 | | | | | 320 |
| Asp | Met | Met | Met | Asn | Trp | Ser | Pro | Thr | Thr | Ala | Leu | Val | Val | Ala | Gln |
| | | | | 325 | | | | 330 | | | | | 335 | | |
| Leu | Leu | Arg | Ile | Pro | Gln | Ala | Ile | Leu | Asp | Met | Ile | Ala | Gly | Ala | His |
| | | | 340 | | | | 345 | | | | | 350 | | | |
| Trp | Gly | Val | Leu | Ala | Gly | Ile | Ala | Tyr | Phe | Ser | Met | Val | Gly | Asn | Trp |
| | | 355 | | | | 360 | | | | | 365 | | | | |
| Ala | Lys | Val | Leu | Val | Val | Leu | Leu | Leu | Phe | Ser | Gly | Val | Asp | Ala | Ala |
| | 370 | | | | 375 | | | | | 380 | | | | | |
| Thr | Tyr | Thr | Thr | Gly | Gly | Ser | Val | Ala | Arg | Thr | Thr | His | Gly | Leu | Ser |
| 385 | | | | 390 | | | | 395 | | | | | | | 400 |
| Ser | Leu | Phe | Ser | Gln | Gly | Ala | Lys | Gln | Asn | Ile | Gln | Leu | Ile | Asn | Thr |
| | | | 405 | | | | 410 | | | | | 415 | | | |
| Asn | Gly | Ser | Trp | His | Ile | Asn | Arg | Thr | Ala | Leu | Asn | Cys | Asn | Ala | Ser |
| | | | 420 | | | | 425 | | | | | 430 | | | |

-continued

| | | | | | | | | | | | | | | |
|---|---|---|---|---|---|---|---|---|---|---|---|---|---|---|
| Leu | Asp | Thr 435 | Gly | Trp | Val | Ala | Gly 440 | Leu | Phe | Tyr | Tyr | His 445 | Lys | Phe | Asn |
| Ser | Ser 450 | Gly | Cys | Pro | Glu | Arg 455 | Met | Ala | Ser | Cys | Arg 460 | Pro | Leu | Ala | Asp |
| Phe 465 | Asp | Gln | Gly | Trp | Gly 470 | Pro | Ile | Ser | Tyr | Thr 475 | Asn | Gly | Ser | Gly | Pro 480 |
| Glu | His | Arg | Pro | Tyr 485 | Cys | Trp | His | Tyr | Pro 490 | Pro | Lys | Pro | Cys | Gly 495 | Ile |
| Val | Pro | Ala | Gln 500 | Ser | Val | Cys | Gly | Pro 505 | Val | Tyr | Cys | Phe | Thr 510 | Pro | Ser |
| Pro | Val | Val 515 | Val | Gly | Thr | Thr | Asp 520 | Lys | Ser | Gly | Ala | Pro 525 | Thr | Tyr | Thr |
| Trp | Gly 530 | Ser | Asn | Asp | Thr | Asp 535 | Val | Phe | Val | Leu | Asn 540 | Asn | Thr | Arg | Pro |
| Pro 545 | Pro | Gly | Asn | Trp | Phe 550 | Gly | Cys | Thr | Trp | Met 555 | Asn | Ser | Ser | Gly | Phe 560 |
| Thr | Lys | Val | Cys | Gly 565 | Ala | Pro | Pro | Cys | Val 570 | Ile | Gly | Gly | Ala | Gly 575 | Asn |
| Asn | Thr | Leu | His 580 | Cys | Pro | Thr | Asp | Cys 585 | Phe | Arg | Lys | His | Pro 590 | Glu | Ala |
| Thr | Tyr | Ser 595 | Arg | Cys | Gly | Ser | Gly 600 | Pro | Trp | Ile | Thr | Pro 605 | Arg | Cys | Leu |
| Val | His 610 | Tyr | Pro | Tyr | Arg | Leu 615 | Trp | His | Tyr | Pro | Cys 620 | Thr | Ile | Asn | Tyr |
| Thr 625 | Leu | Phe | Lys | Val | Arg 630 | Met | Tyr | Val | Gly | Gly 635 | Val | Glu | His | Arg | Leu 640 |
| Glu | Val | Ala | Cys | Asn 645 | Trp | Thr | Arg | Gly | Glu 650 | Arg | Cys | Asp | Leu | Asp 655 | Asp |
| Arg | Asp | Arg | Ser 660 | Glu | Leu | Ser | Pro | Leu 665 | Leu | Leu | Ser | Thr | Thr 670 | Gln | Trp |
| Gln | Val | Leu 675 | Pro | Cys | Ser | Phe | Thr 680 | Thr | Leu | Pro | Ala | Leu 685 | Thr | Thr | Gly |
| Leu | Ile 690 | His | Leu | His | Gln | Asn 695 | Ile | Val | Asp | Val | Gln 700 | Tyr | Leu | Tyr | Gly |
| Val 705 | Gly | Ser | Ser | Ile | Val 710 | Ser | Trp | Ala | Ile | Lys 715 | Trp | Glu | Tyr | Val | Ile 720 |
| Leu | Leu | Phe | Leu | Leu 725 | Leu | Ala | Asp | Ala | Arg 730 | Ile | Cys | Ser | Cys | Leu 735 | Trp |
| Met | Met | Leu | Leu 740 | Ile | Ser | Gln | Ala | Glu 745 | Ala | Ala | Leu | Glu | Asn 750 | Leu | Val |
| Leu | Leu | Asn 755 | Ala | Ala | Ser | Leu | Ala 760 | Gly | Thr | His | Gly | Leu 765 | Val | Ser | Phe |
| Leu | Val 770 | Phe | Phe | Cys | Phe | Ala 775 | Trp | Tyr | Leu | Lys | Gly 780 | Lys | Trp | Val | Pro |
| Gly 785 | Val | Ala | Tyr | Ala | Phe 790 | Tyr | Gly | Met | Trp | Pro 795 | Phe | Leu | Leu | Leu | Leu 800 |
| Leu | Ala | Leu | Pro | Gln 805 | Arg | Ala | Tyr | Ala | Leu 810 | Asp | Thr | Glu | Met | Ala 815 | Ala |
| Ser | Cys | Gly | Gly 820 | Val | Val | Leu | Val | Gly 825 | Leu | Met | Ala | Leu | Thr 830 | Leu | Ser |
| Pro | His | Tyr 835 | Lys | Arg | Tyr | Ile | Cys 840 | Trp | Cys | Val | Trp | Trp 845 | Leu | Gln | Tyr |
| Phe | Leu 850 | Thr | Arg | Ala | Glu | Ala 855 | Leu | Leu | His | Gly | Trp 860 | Val | Pro | Pro | Leu |

```
Asn Val Arg Gly Gly Arg Asp Ala Val Ile Leu Leu Met Cys Val Val
865                 870                 875                 880

His Pro Ala Leu Val Phe Asp Ile Thr Lys Leu Leu Leu Ala Val Leu
                885                 890                 895

Gly Pro Leu Trp Ile Leu Gln Thr Ser Leu Leu Lys Val Pro Tyr Phe
                900                 905                 910

Val Arg Val Gln Gly Leu Leu Arg Ile Cys Ala Leu Ala Arg Lys Met
            915                 920                 925

Ala Gly Gly His Tyr Val Gln Met Val Thr Ile Lys Met Gly Ala Leu
            930                 935                 940

Ala Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
                965                 970                 975

Ser Gln Met Glu Thr Lys Leu Ile Thr Trp Gly Ala Asp Thr Ala Ala
            980                 985                 990

Cys Gly Asp Ile Ile Asn Gly Leu Pro Val Ser Ala Arg Arg Gly Arg
            995                 1000                1005

Glu Ile Leu Leu Gly Pro Ala Asp Gly Met Val Ser Lys Gly Trp Arg
    1010                1015                1020

Leu Leu Ala Pro Ile Thr Ala Tyr Ala Gln Gln Thr Arg Gly Leu Leu
1025                1030                1035                1040

Gly Cys Ile Ile Thr Ser Leu Thr Gly Arg Asp Lys Asn Gln Val Glu
            1045                1050                1055

Gly Glu Val Gln Ile Val Ser Thr Ala Ala Gln Thr Phe Leu Ala Thr
            1060                1065                1070

Cys Ile Asn Gly Val Cys Trp Thr Val Tyr His Gly Ala Gly Thr Arg
            1075                1080                1085

Thr Ile Ala Ser Pro Lys Gly Pro Val Ile Gln Met Tyr Thr Asn Val
            1090                1095                1100

Asp Arg Asp Leu Val Gly Trp Pro Ala Pro Gln Gly Ala Arg Ser Leu
1105                1110                1115                1120

Thr Pro Cys Thr Cys Gly Ser Ser Asp Leu Tyr Leu Val Thr Arg His
            1125                1130                1135

Ala Asp Val Ile Pro Val Arg Arg Arg Gly Asp Ser Arg Gly Ser Leu
            1140                1145                1150

Leu Ser Pro Arg Pro Ile Ser Tyr Leu Lys Gly Ser Ser Gly Gly Pro
            1155                1160                1165

Leu Leu Cys Pro Ala Gly His Ala Val Gly Ile Phe Arg Ala Ala Val
            1170                1175                1180

Cys Thr Arg Gly Val Ala Lys Ala Val Asp Phe Ile Pro Val Glu Ser
1185                1190                1195                1200

Leu Glu Thr Thr Met Arg Ser Pro Val Phe Thr Asp Asn Ser Ser Pro
                1205                1210                1215

Pro Ala Val Pro Gln Ser Phe Gln Val Ala His Leu His Ala Pro Thr
            1220                1225                1230

Gly Ser Gly Lys Ser Thr Lys Val Pro Ala Ala Tyr Ala Ala Gln Gly
            1235                1240                1245

Tyr Lys Val Leu Val Leu Asn Pro Ser Val Ala Ala Thr Leu Gly Phe
    1250                1255                1260

Gly Ala Tyr Met Ser Lys Ala His Gly Ile Asp Pro Asn Ile Arg Thr
1265                1270                1275                1280

Gly Val Arg Thr Ile Thr Thr Gly Ser Pro Ile Thr Tyr Ser Thr Tyr
```

-continued

```
                          1285                      1290                      1295
        Gly  Lys  Phe  Leu  Ala  Asp  Gly  Gly  Cys  Ser  Gly  Gly  Ala  Tyr  Asp  Ile
                         1300                     1305                     1310
        Ile  Ile  Cys  Asp  Glu  Cys  His  Ser  Thr  Asp  Ala  Thr  Ser  Ile  Leu  Gly
                         1315                     1320                     1325
        Ile  Gly  Thr  Val  Leu  Asp  Gln  Ala  Glu  Thr  Ala  Gly  Ala  Arg  Leu  Val
                         1330                     1335                     1340
Val  Leu  Ala  Thr  Ala  Thr  Pro  Pro  Gly  Ser  Val  Thr  Val  Pro  His  Pro
1345                     1350                     1355                     1360
Asn  Ile  Glu  Glu  Val  Ala  Leu  Ser  Thr  Thr  Gly  Glu  Ile  Pro  Phe  Tyr
                    1365                     1370                     1375
    Gly  Lys  Ala  Ile  Pro  Leu  Glu  Ala  Ile  Lys  Gly  Gly  Arg  His  Leu  Ile
                         1380                     1385                     1390
Phe  Cys  His  Ser  Lys  Lys  Lys  Cys  Asp  Glu  Leu  Ala  Ala  Lys  Leu  Val
                    1395                     1400                     1405
Thr  Leu  Gly  Ile  Asn  Ala  Val  Ala  Tyr  Tyr  Arg  Gly  Leu  Asp  Val  Ser
                    1410                     1415                     1420
Val  Ile  Pro  Thr  Ser  Gly  Asp  Val  Val  Val  Ala  Thr  Asp  Ala  Leu
1425                     1430                     1435                     1440
Met  Thr  Gly  Phe  Thr  Gly  Asp  Phe  Asp  Ser  Val  Ile  Asp  Cys  Asn  Thr
                         1445                     1450                     1455
Cys  Val  Thr  Gln  Ala  Val  Asp  Phe  Ser  Leu  Asp  Pro  Thr  Phe  Thr  Ile
                    1460                     1465                     1470
Glu  Thr  Thr  Thr  Leu  Pro  Gln  Asp  Ala  Val  Ser  Arg  Thr  Gln  Arg  Arg
                    1475                     1480                     1485
    Gly  Arg  Thr  Gly  Arg  Gly  Lys  Pro  Gly  Ile  Tyr  Arg  Phe  Val  Ala  Pro
                         1490                     1495                     1500
Gly  Glu  Arg  Pro  Ser  Gly  Met  Phe  Asp  Ser  Ser  Val  Leu  Cys  Glu  Cys
1505                     1510                     1515                     1520
Tyr  Asp  Ala  Gly  Cys  Ala  Trp  Tyr  Glu  Leu  Thr  Pro  Ala  Glu  Thr  Thr
                         1525                     1530                     1535
Val  Arg  Leu  Arg  Ala  Tyr  Met  Asn  Thr  Pro  Gly  Leu  Pro  Val  Cys  Gln
                         1540                     1545                     1550
Asp  His  Leu  Glu  Phe  Trp  Glu  Gly  Val  Phe  Thr  Gly  Leu  Thr  His  Ile
                    1555                     1560                     1565
Asp  Ala  His  Phe  Leu  Ser  Gln  Thr  Lys  Gln  Ser  Gly  Glu  Asn  Leu  Pro
1570                     1575                     1580
Tyr  Leu  Val  Ala  Tyr  Gln  Ala  Thr  Val  Cys  Ala  Arg  Ala  Gln  Ala  Pro
1585                     1590                     1595                     1600
Pro  Pro  Ser  Trp  Asp  Gln  Met  Trp  Lys  Cys  Leu  Ile  Arg  Leu  Lys  Pro
                    1605                     1610                     1615
Thr  Leu  His  Gly  Pro  Thr  Pro  Leu  Leu  Tyr  Arg  Leu  Gly  Ala  Val  Gln
                    1620                     1625                     1630
Asn  Glu  Val  Thr  Leu  Thr  His  Pro  Ile  Thr  Lys  Tyr  Ile  Met  Thr  Cys
                    1635                     1640                     1645
Met  Ser  Ala  Asp  Leu  Glu  Val  Val  Thr  Ser  Thr  Trp  Val  Leu  Val  Gly
                    1650                     1655                     1660
Gly  Val  Leu  Ala  Ala  Leu  Ala  Ala  Tyr  Cys  Leu  Ser  Thr  Gly  Cys  Val
1665                     1670                     1675                     1680
Val  Ile  Val  Gly  Arg  Ile  Val  Leu  Ser  Gly  Lys  Pro  Ala  Ile  Ile  Pro
                         1685                     1690                     1695
Asp  Arg  Glu  Val  Leu  Tyr  Arg  Glu  Phe  Asp  Glu  Met  Glu  Glu  Cys  Ser
                    1700                     1705                     1710
```

-continued

```
Gln His Leu Pro Tyr Ile Glu Gln Gly Met Met Leu Ala Glu Gln Phe
    1715                1720                1725
Lys Gln Lys Ala Leu Gly Leu Leu Gln Thr Ala Ser His Gln Ala Glu
    1730                1735                1740
Val Ile Ala Pro Ala Val Gln Thr Asn Trp Gln Arg Leu Glu Thr Phe
1745                1750                1755                1760
Trp Ala Lys His Met Trp Asn Phe Ile Ser Gly Ile Gln Tyr Leu Ala
                1765                1770                1775
Gly Leu Ser Thr Leu Pro Gly Asn Pro Ala Ile Ala Ser Leu Met Ala
            1780                1785                1790
Phe Thr Ala Ala Val Thr Ser Pro Leu Thr Thr Ser Gln Thr Leu Leu
            1795                1800                1805
Phe Asn Ile Leu Gly Gly Trp Val Ala Ala Gln Leu Ala Ala Pro Ser
            1810                1815                1820
Ala Ala Thr Ala Phe Val Gly Ala Gly Leu Ala Gly Ala Ala Ile Gly
1825                1830                1835                1840
Ser Val Gly Leu Gly Lys Val Leu Val Asp Ile Leu Ala Gly Tyr Gly
                1845                1850                1855
Ala Gly Val Ala Gly Ala Leu Val Ala Phe Lys Ile Met Ser Gly Glu
            1860                1865                1870
Val Pro Ser Thr Glu Asp Leu Val Asn Leu Leu Pro Ala Ile Leu Ser
            1875                1880                1885
Pro Gly Ala Leu Val Val Gly Val Val Cys Ala Ala Ile Leu Arg Arg
            1890                1895                1900
His Val Gly Pro Gly Glu Gly Ala Val Gln Trp Met Asn Arg Leu Ile
1905                1910                1915                1920
Ala Phe Ala Ser Arg Gly Asn His Val Ser Pro Thr His Tyr Val Pro
                1925                1930                1935
Gly Ser Asp Ala Ala Ala Arg Val Thr Ala Ile Leu Ser Ser Leu Thr
            1940                1945                1950
Val Thr Gln Leu Leu Arg Arg Leu His Gln Trp Val Ser Ser Glu Cys
            1955                1960                1965
Thr Thr Pro Cys Ser Gly Ser Trp Leu Arg Asp Ile Trp Asp Trp Ile
    1970                1975                1980
Cys Glu Val Leu Ser Asp Phe Lys Thr Trp Leu Lys Ala Lys Leu Met
1985                1990                1995                2000
Pro Gln Leu Pro Gly Ile Pro Phe Val Ser Cys Gln Arg Gly Tyr Lys
                2005                2010                2015
Gly Val Trp Arg Gly Asp Gly Ile Met His Thr Arg Cys His Cys Gly
            2020                2025                2030
Ala Glu Ile Ala Gly His Val Lys Asn Gly Thr Met Arg Ile Val Gly
    2035                2040                2045
Pro Lys Thr Cys Arg Asn Met Trp Ser Gly Thr Phe Pro Ile Asn Ala
    2050                2055                2060
Tyr Thr Thr Gly Pro Cys Thr Pro Leu Pro Ala Pro Asn Tyr Lys Phe
2065                2070                2075                2080
Ala Leu Trp Arg Val Ser Ala Glu Glu Tyr Val Glu Ile Arg Gln Val
            2085                2090                2095
Gly Asp Phe His Tyr Val Thr Gly Met Thr Ala Asp Asn Leu Lys Cys
                2100                2105                2110
Pro Cys Gln Val Pro Ser Pro Glu Phe Phe Thr Glu Leu Asp Gly Val
            2115                2120                2125
Arg Leu His Arg Phe Ala Pro Pro Cys Lys Pro Leu Leu Arg Asp Glu
            2130                2135                2140
```

Val Ser Phe Arg Val Gly Leu His Asp Tyr Pro Val Gly Ser Gln Leu
2145                2150                2155                2160

Pro Cys Glu Pro Glu Pro Asp Val Ala Val Leu Thr Ser Met Leu Thr
            2165            2170            2175

Asp Pro Ser His Ile Thr Ala Glu Thr Ala Gly Arg Arg Leu Ala Arg
            2180            2185            2190

Gly Ser Pro Pro Ser Met Ala Ser Ser Ala Ser Gln Leu Ser Ala
            2195            2200            2205

Pro Ser Leu Lys Ala Thr Cys Thr Thr Asn His Asp Ser Pro Asp Ala
            2210            2215            2220

Glu Leu Leu Glu Ala Asn Leu Leu Trp Arg Gln Glu Met Gly Gly Asn
2225                2230            2235                2240

Ile Thr Arg Val Glu Ser Glu Asn Lys Val Val Val Leu Asp Ser Phe
            2245            2250            2255

Asp Pro Leu Val Ala Glu Glu Asp Glu Arg Glu Val Ser Val Pro Ala
            2260            2265            2270

Glu Ile Leu Arg Lys Ser Arg Arg Phe Ala Gln Ala Leu Pro Ser Trp
            2275            2280            2285

Ala Arg Pro Asp Tyr Asn Pro Pro Leu Leu Glu Thr Trp Lys Lys Pro
            2290            2295            2300

Asp Tyr Glu Pro Pro Val Val His Gly Cys Pro Leu Pro Pro Pro Gln
2305                2310            2315                2320

Ser Pro Pro Val Pro Pro Pro Arg Lys Lys Arg Thr Val Val Leu Thr
            2325            2330            2335

Glu Ser Thr Val Ser Ser Ala Leu Ala Glu Leu Ala Thr Lys Ser Phe
            2340            2345            2350

Gly Ser Ser Ser Thr Ser Gly Ile Thr Gly Asp Asn Thr Thr Thr Ser
            2355            2360            2365

Ser Glu Pro Ala Pro Ser Val Cys Pro Pro Asp Ser Asp Ala Glu Ser
            2370            2375            2380

Tyr Ser Ser Met Pro Pro Leu Glu Gly Glu Pro Gly Asp Pro Asp Leu
2385                2390            2395                2400

Ser Asp Gly Ser Trp Ser Thr Val Ser Ser Gly Ala Asp Thr Glu Asp
            2405            2410            2415

Val Val Cys Cys Ser Met Ser Tyr Ser Trp Thr Gly Ala Leu Ile Thr
            2420            2425            2430

Pro Cys Ala Ala Glu Glu Gln Lys Leu Pro Ile Asn Ala Leu Ser Asn
            2435            2440            2445

Ser Leu Leu Arg His His Asn Leu Val Tyr Ser Thr Thr Ser Arg Asn
            2450            2455            2460

Ala Cys Leu Arg Gln Lys Lys Val Thr Phe Asp Arg Leu Gln Val Leu
2465                2470            2475                2480

Asp Asn His Tyr Gln Asp Val Leu Lys Glu Val Lys Ala Ala Ala Ser
            2485            2490            2495

Lys Val Lys Ala Asn Leu Leu Ser Val Glu Glu Ala Cys Ser Leu Thr
            2500            2505            2510

Pro Pro His Ser Ala Arg Ser Lys Phe Gly Tyr Gly Ala Lys Asp Val
            2515            2520            2525

Arg Cys His Ala Arg Lys Ala Val Ser His Ile Asn Ser Val Trp Lys
            2530            2535            2540

Asp Leu Leu Glu Asp Ser Val Thr Pro Ile Asp Thr Thr Ile Met Ala
2545                2550            2555                2560

Lys Asn Glu Val Phe Cys Val Gln Pro Glu Lys Gly Gly Arg Lys Pro

|  |  |  | 2565 |  |  |  |  | 2570 |  |  |  |  | 2575 |  |
|---|---|---|---|---|---|---|---|---|---|---|---|---|---|---|
| Ala | Arg | Leu | Ile | Val | Phe | Pro | Asp | Leu | Gly | Val | Arg | Val | Cys | Glu | Lys |
|  |  |  | 2580 |  |  |  |  | 2585 |  |  |  |  | 2590 |  |  |
| Met | Ala | Leu | Tyr | Asp | Val | Val | Ser | Lys | Leu | Pro | Leu | Ala | Val | Met | Gly |
|  |  |  | 2595 |  |  |  |  | 2600 |  |  |  |  | 2605 |  |  |
| Ser | Ser | Tyr | Gly | Phe | Gln | Tyr | Ser | Pro | Gly | Gln | Arg | Val | Glu | Phe | Leu |
|  |  |  | 2610 |  |  |  |  | 2615 |  |  |  |  | 2620 |  |  |
| Val | Gln | Ala | Trp | Lys | Ser | Lys | Lys | Thr | Pro | Met | Gly | Phe | Ser | Tyr | Asp |
| 2625 |  |  |  |  | 2630 |  |  |  |  | 2635 |  |  |  |  | 2640 |
| Thr | Arg | Cys | Phe | Asp | Ser | Thr | Val | Thr | Glu | Ser | Asp | Ile | Arg | Thr | Glu |
|  |  |  |  | 2645 |  |  |  |  | 2650 |  |  |  |  | 2655 |  |
| Glu | Ala | Ile | Tyr | Gln | Cys | Cys | Asp | Leu | Asp | Pro | Gln | Ala | Arg | Val | Ala |
|  |  |  |  | 2660 |  |  |  |  | 2665 |  |  |  |  | 2670 |  |
| Ile | Lys | Ser | Leu | Thr | Glu | Arg | Leu | Tyr | Val | Gly | Gly | Pro | Leu | Thr | Asn |
|  |  |  |  | 2675 |  |  |  |  | 2680 |  |  |  |  | 2685 |  |
| Ser | Arg | Gly | Glu | Asn | Cys | Gly | Tyr | Arg | Arg | Cys | Arg | Ala | Ser | Gly | Val |
|  |  |  |  | 2690 |  |  |  |  | 2695 |  |  |  |  | 2700 |  |
| Leu | Thr | Thr | Ser | Cys | Gly | Asn | Thr | Leu | Thr | Cys | Tyr | Ile | Lys | Ala | Arg |
| 2705 |  |  |  |  | 2710 |  |  |  |  | 2715 |  |  |  |  | 2720 |
| Ala | Ala | Cys | Arg | Ala | Ala | Gly | Leu | Gln | Asp | Cys | Thr | Met | Leu | Val | Cys |
|  |  |  |  | 2725 |  |  |  |  | 2730 |  |  |  |  | 2735 |  |
| Gly | Asp | Asp | Leu | Val | Val | Ile | Cys | Glu | Ser | Gln | Gly | Val | Gln | Glu | Asp |
|  |  |  |  | 2740 |  |  |  |  | 2745 |  |  |  |  | 2750 |  |
| Ala | Ala | Ser | Leu | Arg | Ala | Phe | Thr | Glu | Ala | Met | Thr | Arg | Tyr | Ser | Ala |
|  |  |  |  | 2755 |  |  |  |  | 2760 |  |  |  |  | 2765 |  |
| Pro | Pro | Gly | Asp | Pro | Pro | Gln | Pro | Glu | Tyr | Asp | Leu | Glu | Leu | Ile | Thr |
|  |  |  |  | 2770 |  |  |  |  | 2775 |  |  |  |  | 2780 |  |
| Pro | Cys | Ser | Ser | Asn | Val | Ser | Val | Ala | His | Asp | Gly | Ala | Gly | Lys | Arg |
| 2785 |  |  |  |  | 2790 |  |  |  |  | 2795 |  |  |  |  | 2800 |
| Val | Tyr | Tyr | Leu | Thr | Arg | Asp | Pro | Thr | Thr | Pro | Leu | Ala | Arg | Ala | Ala |
|  |  |  |  | 2805 |  |  |  |  | 2810 |  |  |  |  | 2815 |  |
| Trp | Glu | Thr | Ala | Arg | His | Thr | Pro | Val | Asn | Ser | Trp | Leu | Gly | Asn | Ile |
|  |  |  |  | 2820 |  |  |  |  | 2825 |  |  |  |  | 2830 |  |
| Ile | Met | Phe | Ala | Pro | Thr | Leu | Trp | Ala | Arg | Met | Ile | Leu | Met | Thr | His |
|  |  |  |  | 2835 |  |  |  |  | 2840 |  |  |  |  | 2845 |  |
| Phe | Phe | Ser | Val | Leu | Ile | Ala | Arg | Asp | Gln | Leu | Glu | Gln | Ala | Leu | Asp |
|  |  |  |  | 2850 |  |  |  |  | 2855 |  |  |  |  | 2860 |  |
| Cys | Glu | Ile | Tyr | Gly | Ala | Cys | Tyr | Ser | Ile | Glu | Pro | Leu | Asp | Leu | Pro |
| 2865 |  |  |  |  | 2870 |  |  |  |  | 2875 |  |  |  |  | 2880 |
| Pro | Ile | Ile | Gln | Arg | Leu | His | Gly | Leu | Ser | Ala | Phe | Ser | Leu | His | Ser |
|  |  |  |  | 2885 |  |  |  |  | 2890 |  |  |  |  | 2895 |  |
| Tyr | Ser | Pro | Gly | Glu | Ile | Asn | Arg | Val | Ala | Ala | Cys | Leu | Arg | Lys | Leu |
|  |  |  |  | 2900 |  |  |  |  | 2905 |  |  |  |  | 2910 |  |
| Gly | Val | Pro | Pro | Leu | Arg | Ala | Trp | Arg | His | Arg | Ala | Arg | Ser | Val | Arg |
|  |  |  |  | 2915 |  |  |  |  | 2920 |  |  |  |  | 2925 |  |
| Ala | Arg | Leu | Leu | Ser | Arg | Gly | Gly | Arg | Ala | Ala | Ile | Cys | Gly | Lys | Tyr |
|  |  |  |  | 2930 |  |  |  |  | 2935 |  |  |  |  | 2940 |  |
| Leu | Phe | Asn | Trp | Ala | Val | Arg | Thr | Lys | Leu | Lys | Leu | Thr | Pro | Ile | Ala |
| 2945 |  |  |  |  | 2950 |  |  |  |  | 2955 |  |  |  |  | 2960 |
| Ala | Ala | Gly | Gln | Leu | Asp | Leu | Ser | Gly | Trp | Phe | Thr | Ala | Gly | Tyr | Gly |
|  |  |  |  | 2965 |  |  |  |  | 2970 |  |  |  |  | 2975 |  |
| Gly | Gly | Asp | Ile | Tyr | His | Ser | Val | Ser | Arg | Ala | Arg | Pro | Arg | Trp | Phe |
|  |  |  |  | 2980 |  |  |  |  | 2985 |  |  |  |  | 2990 |  |

```
                    Trp Phe Cys Leu Leu Leu Leu Ala Ala Gly Val Gly Ile Tyr Leu Leu
                        2995                3000                3005

Pro Asn Arg
                        3010
```

(2) INFORMATION FOR SEQ ID NO:3:

(i) SEQUENCE CHARACTERISTICS:
        (A) LENGTH: 7298 base pairs
        (B) TYPE: nucleic acid
        (C) STRANDEDNESS: single
        (D) TOPOLOGY: circular (ii) MOLECULE TYPE: DNA (genomic)

(ix) FEATURE:
        (A) NAME/KEY: CDS
        (B) LOCATION: 922..2532

(xi) SEQUENCE DESCRIPTION: SEQ ID NO:3:

```
GACGGATCGG  GAGATCTCCC  GATCCCCTAT  GGTCGACTCT  CAGTACAATC  TGCTCTGATG     60

CCGCATAGTT  AAGCCAGTAT  CTGCTCCCTG  CTTGTGTGTT  GGAGGTCGCT  GAGTAGTGCG    120

CGAGCAAAAT  TTAAGCTACA  ACAAGGCAAG  GCTTGACCGA  CAATTGCATG  AAGAATCTGC    180

TTAGGGTTAG  GCGTTTTGCG  CTGCTTCGCG  ATGTACGGGC  AGATATACG   CGTTGACATT    240

GATTATTGAC  TAGTTATTAA  TAGTAATCAA  TTACGGGGTC  ATTAGTTCAT  AGCCCATATA    300

TGGAGTTCCG  CGTTACATAA  CTTACGGTAA  ATGGCCCGCC  TGGCTGACCG  CCCAACGACC    360

CCCGCCCATT  GACGTCAATA  ATGACGTATG  TTCCCATAGT  AACGCCAATA  GGGACTTTCC    420

ATTGACGTCA  ATGGGTGGAC  TATTTACGGT  AAACTGCCCA  CTTGGCAGTA  CATCAAGTGT    480

ATCATATGCC  AAGTACGCCC  CCTATTGACG  TCAATGACGG  TAAATGGCCC  GCCTGGCATT    540

ATGCCCAGTA  CATGACCTTA  TGGGACTTTC  CTACTTGGCA  GTACATCTAC  GTATTAGTCA    600

TCGCTATTAC  CATGGTGATG  CGGTTTTGGC  AGTACATCAA  TGGGCGTGGA  TAGCGGTTTG    660

ACTCACGGGG  ATTTCCAAGT  CTCCACCCCA  TTGACGTCAA  TGGGAGTTTG  TTTTGGCACC    720

AAAATCAACG  GGACTTTCCA  AAATGTCGTA  ACAACTCCGC  CCCATTGACG  CAAATGGGCG    780

GTAGGCGTGT  ACGGTGGGAG  GTCTATATAA  GCAGAGCTCT  CTGGCTAACT  AGAGAACCCA    840

CTGCTTAACT  GGCTTATCGA  AATTAATACG  ACTCACTATA  GGGAGACCGG  AAGCTTTGCT    900

CTAGACTGGA  ATTCGGGCGC  G ATG CTG CCC GGT TTG GCA CTG CTC CTG CTG         951
            Met Leu Pro Gly Leu Ala Leu Leu Leu Leu
              1               5                  10

GCC GCC TGG ACG GCT CGG GCG CTG GAG GTA CCC ACT GAT GGT AAT GCT           999
Ala Ala Trp Thr Ala Arg Ala Leu Glu Val Pro Thr Asp Gly Asn Ala
             15                  20                  25

GGC CTG CTG GCT GAA CCC CAG ATT GCC ATG TTC TGT GGC AGA CTG AAC          1047
Gly Leu Leu Ala Glu Pro Gln Ile Ala Met Phe Cys Gly Arg Leu Asn
         30                  35                  40

ATG CAC ATG AAT GTC CAG AAT GGG AAG TGG GAT TCA GAT CCA TCA GGG          1095
Met His Met Asn Val Gln Asn Gly Lys Trp Asp Ser Asp Pro Ser Gly
         45                  50                  55

ACC AAA ACC TGC ATT GAT ACC AAG GAA ACC CAC GTC ACC GGG GGA AGT          1143
Thr Lys Thr Cys Ile Asp Thr Lys Glu Thr His Val Thr Gly Gly Ser
     60                  65                  70

GCC GGC CAC ACC ACG GCT GGG CTT GTT CGT CTC CTT TCA CCA GGC GCC          1191
Ala Gly His Thr Thr Ala Gly Leu Val Arg Leu Leu Ser Pro Gly Ala
 75                  80                  85                  90

AAG CAG AAC ATC CAA CTG ATC AAC ACC AAC GGC AGT TGG CAC ATC AAT          1239
Lys Gln Asn Ile Gln Leu Ile Asn Thr Asn Gly Ser Trp His Ile Asn
             95                 100                 105
```

| | | | | | | | | | | | | | | | | |
|---|---|---|---|---|---|---|---|---|---|---|---|---|---|---|---|---|
| AGC | ACG | GCC | TTG | AAC | TGC | AAT | GAA | AGC | CTT | AAC | ACC | GGC | TGG | TTA | GCA | 1287 |
| Ser | Thr | Ala | Leu | Asn | Cys | Asn | Glu | Ser | Leu | Asn | Thr | Gly | Trp | Leu | Ala | |
| | | | | 110 | | | | 115 | | | | 120 | | | | |
| GGG | CTC | TTC | TAT | CAC | CAC | AAA | TTC | AAC | TCT | TCA | GGT | TGT | CCT | GAG | AGG | 1335 |
| Gly | Leu | Phe | Tyr | His | His | Lys | Phe | Asn | Ser | Ser | Gly | Cys | Pro | Glu | Arg | |
| | | | 125 | | | | 130 | | | | | 135 | | | | |
| TTG | GCC | AGC | TGC | CGA | CGC | CTT | ACC | GAT | TTT | GCC | CAG | GGC | GGG | GGT | CCT | 1383 |
| Leu | Ala | Ser | Cys | Arg | Arg | Leu | Thr | Asp | Phe | Ala | Gln | Gly | Gly | Gly | Pro | |
| | 140 | | | | | 145 | | | | | 150 | | | | | |
| ATC | AGT | TAC | GCC | AAC | GGA | AGC | GGC | CTC | GAT | GAA | CGC | CCC | TAC | TGC | TGG | 1431 |
| Ile | Ser | Tyr | Ala | Asn | Gly | Ser | Gly | Leu | Asp | Glu | Arg | Pro | Tyr | Cys | Trp | |
| 155 | | | | | 160 | | | | | 165 | | | | | 170 | |
| CAC | TAC | CCT | CCA | AGA | CCT | TGT | GGC | ATT | GTG | CCC | GCA | AAG | AGC | GTG | TGT | 1479 |
| His | Tyr | Pro | Pro | Arg | Pro | Cys | Gly | Ile | Val | Pro | Ala | Lys | Ser | Val | Cys | |
| | | | | 175 | | | | | 180 | | | | | 185 | | |
| GGC | CCG | GTA | TAT | TGC | TTC | ACT | CCC | AGC | CCC | GTG | GTG | GTG | GGA | ACG | ACC | 1527 |
| Gly | Pro | Val | Tyr | Cys | Phe | Thr | Pro | Ser | Pro | Val | Val | Val | Gly | Thr | Thr | |
| | | | 190 | | | | | 195 | | | | | | 200 | | |
| GAC | AGG | TCG | GGC | GCG | CCT | ACC | TAC | AGC | TGG | GGT | GCA | AAT | GAT | ACG | GAT | 1575 |
| Asp | Arg | Ser | Gly | Ala | Pro | Thr | Tyr | Ser | Trp | Gly | Ala | Asn | Asp | Thr | Asp | |
| | | 205 | | | | | 210 | | | | | 215 | | | | |
| GTC | TTT | GTC | CTT | AAC | AAC | ACC | AGG | CCA | CCG | CTG | GGC | AAT | TGG | TTC | GGT | 1623 |
| Val | Phe | Val | Leu | Asn | Asn | Thr | Arg | Pro | Pro | Leu | Gly | Asn | Trp | Phe | Gly | |
| | | 220 | | | | | 225 | | | | | 230 | | | | |
| TGC | ACC | TGG | ATG | AAC | TCA | ACT | GGA | TTC | ACC | AAA | GTG | TGC | GGA | GCG | CCC | 1671 |
| Cys | Thr | Trp | Met | Asn | Ser | Thr | Gly | Phe | Thr | Lys | Val | Cys | Gly | Ala | Pro | |
| 235 | | | | | 240 | | | | | 245 | | | | | 250 | |
| CCT | TGT | GTC | ATC | GGA | GGG | GTG | GGC | AAC | AAC | ACC | TTG | CTC | TGC | CCC | ACT | 1719 |
| Pro | Cys | Val | Ile | Gly | Gly | Val | Gly | Asn | Asn | Thr | Leu | Leu | Cys | Pro | Thr | |
| | | | | 255 | | | | | 260 | | | | | 265 | | |
| GAT | TGC | TTC | CGC | AAG | CAT | CCG | GAA | GCC | ACA | TAC | TCT | CGG | TGC | GGC | TCC | 1767 |
| Asp | Cys | Phe | Arg | Lys | His | Pro | Glu | Ala | Thr | Tyr | Ser | Arg | Cys | Gly | Ser | |
| | | | 270 | | | | | 275 | | | | | 280 | | | |
| GGT | CCC | TGG | ATT | ACA | CCC | AGG | TGC | ATG | GTC | GAC | TAC | CCG | TAT | AGG | CTT | 1815 |
| Gly | Pro | Trp | Ile | Thr | Pro | Arg | Cys | Met | Val | Asp | Tyr | Pro | Tyr | Arg | Leu | |
| | | 285 | | | | | 290 | | | | | 295 | | | | |
| TGG | CAC | TAT | CCT | TGT | ACC | ATC | AAT | TAC | ACC | ATA | TTC | AAA | GTC | AGG | ATG | 1863 |
| Trp | His | Tyr | Pro | Cys | Thr | Ile | Asn | Tyr | Thr | Ile | Phe | Lys | Val | Arg | Met | |
| | 300 | | | | | 305 | | | | | 310 | | | | | |
| TAC | GTG | GGA | GGG | GTC | GAG | CAC | AGG | CTG | GAA | GCG | GCC | TGC | AAC | TGG | ACG | 1911 |
| Tyr | Val | Gly | Gly | Val | Glu | His | Arg | Leu | Glu | Ala | Ala | Cys | Asn | Trp | Thr | |
| 315 | | | | | 320 | | | | | 325 | | | | | 330 | |
| CGG | GGC | GAA | CGC | TGT | GAT | CTG | GAA | GAC | AGG | GAC | AGG | TCC | GAG | CTC | AGC | 1959 |
| Arg | Gly | Glu | Arg | Cys | Asp | Leu | Glu | Asp | Arg | Asp | Arg | Ser | Glu | Leu | Ser | |
| | | | | 335 | | | | | 340 | | | | | 345 | | |
| CCG | TTA | CTG | CTG | TCC | ACC | ACG | CAG | TGG | CAG | GTC | CTT | CCG | TGT | TCT | TTC | 2007 |
| Pro | Leu | Leu | Leu | Ser | Thr | Thr | Gln | Trp | Gln | Val | Leu | Pro | Cys | Ser | Phe | |
| | | | 350 | | | | | 355 | | | | | 360 | | | |
| ACG | ACC | CTG | CCA | GCC | TTG | TCC | ACC | GGC | CTC | ATC | CAC | CTC | CAC | CAG | AAC | 2055 |
| Thr | Thr | Leu | Pro | Ala | Leu | Ser | Thr | Gly | Leu | Ile | His | Leu | His | Gln | Asn | |
| | | 365 | | | | | 370 | | | | | 375 | | | | |
| ATT | GTG | GAC | GTG | CAG | TAC | TTG | TAC | GGG | GTA | GGG | TCA | AGC | ATC | GCG | TCC | 2103 |
| Ile | Val | Asp | Val | Gln | Tyr | Leu | Tyr | Gly | Val | Gly | Ser | Ser | Ile | Ala | Ser | |
| | 380 | | | | | 385 | | | | | 390 | | | | | |
| TGG | GCT | ATT | AAG | TGG | GAG | TAC | GAC | GTT | CTC | CTG | TTC | CTT | CTG | CTT | GCA | 2151 |
| Trp | Ala | Ile | Lys | Trp | Glu | Tyr | Asp | Val | Leu | Leu | Phe | Leu | Leu | Leu | Ala | |
| 395 | | | | | 400 | | | | | 405 | | | | | 410 | |
| GAC | GCG | CGC | GTT | TGC | TCC | TGC | TTG | TGG | ATG | ATG | TTA | CTC | ATA | TCC | CAA | 2199 |
| Asp | Ala | Arg | Val | Cys | Ser | Cys | Leu | Trp | Met | Met | Leu | Leu | Ile | Ser | Gln | |
| | | | | 415 | | | | | 420 | | | | | 425 | | |

```
GCG GAG GCG GCT TTG GAG ATC TCT GAA GTG AAG ATG GAT GCA GAA TTC          2247
Ala Glu Ala Ala Leu Glu Ile Ser Glu Val Lys Met Asp Ala Glu Phe
            430                 435                 440

CGA CAT GAC TCA GGA TAT GAA GTT CAT CAT CAA AAA TTG GTG TTC TTT          2295
Arg His Asp Ser Gly Tyr Glu Val His His Gln Lys Leu Val Phe Phe
            445                 450                 455

GCA GAA GAT GTG GGT TCA AAC AAA GGT GCA ATC ATT GGA CTC ATG GTG          2343
Ala Glu Asp Val Gly Ser Asn Lys Gly Ala Ile Ile Gly Leu Met Val
    460                 465                 470

GGC GGT GTT GTC ATA GCG ACA GTG ATC GTC ATC ACC TTG GTG ATG CTG          2391
Gly Gly Val Val Ile Ala Thr Val Ile Val Ile Thr Leu Val Met Leu
475                 480                 485                 490

AAG AAG AAA CAG TAC ACA TCC ATT CAT CAT GGT GTG GTG GAG GTT GAC          2439
Lys Lys Lys Gln Tyr Thr Ser Ile His His Gly Val Val Glu Val Asp
                495                 500                 505

GCC GCT GTC ACC CCA GAG GAG CGC CAC CTG TCC AAG ATG CAG CAG AAC          2487
Ala Ala Val Thr Pro Glu Glu Arg His Leu Ser Lys Met Gln Gln Asn
            510                 515                 520

GGC TAC GAA AAT CCA ACC TAC AAG TTC TTT GAG CAG ATG CAG AAC              2532
Gly Tyr Glu Asn Pro Thr Tyr Lys Phe Phe Glu Gln Met Gln Asn
            525                 530                 535

TAGACCCCCG CCACAGCAGC CTCTGAAGTT GGACAGCAAA ACCATTGCTT CACTACCCAT        2592

CGGTGTCCAT TTATAGAATA ATGTGGGAAG AAACAAACCC GTTTTATGAT TTACTCATTA        2652

TCGCCTTTTG ACAGCTGTGC TGTAACACAA GTAGATGCCT GAACTTGAAT TAATCCACAC        2712

ATCAGTATTG TATTCTATCT CTCTTTACAT TTTGGTCTCT ATACTACATT ATTAATGGGT        2772

TTTGTGTACT GTAAAGAATT TAGCTGTATC AAACTAGTGC ATGAATAGGC CGCTCGAGCA        2832

TGCATCTAGA GGGCCCTATT CTATAGTGTC ACCTAAATGC TCGCTGATCA GCCTCGACTG        2892

TGCCTTCTAG TTGCCAGCCA TCTGTTGTTT GCCCCTCCCC CGTGCCTTCC TTGACCCTGG        2952

AAGGTGCCAC TCCCACTGTC CTTTCCTAAT AAAATGAGGA AATTGCATCG CATTGTCTGA        3012

GTAGGTGTCA TTCTATTCTG GGGGGTGGGG TGGGCAGGA CAGCAAGGGG GAGGATTGGG         3072

AAGACAATAG CAGGCATGCT GGGGATGCGG TGGGCTCTAT GGAACCAGCT GGGGCTCGAG        3132

GGGGGATCCC CACGCGCCCT GTAGCGGCGC ATTAAGCGCG GCGGGTGTGG TGGTTACGCG        3192

CAGCGTGACC GCTACACTTG CCAGCGCCCT AGCGCCCGCT CCTTTCGCTT TCTTCCCTTC        3252

CTTTCTCGCC ACGTTCGCCG GCTTTCCCCG TCAAGCTCTA AATCGGGGCA TCCCTTTAGG        3312

GTTCCGATTT AGTGCTTTAC GGCACCTCGA CCCCAAAAAA CTTGATTAGG GTGATGGTTC        3372

ACGTAGTGGG CCATCGCCCT GATAGACGGT TTTTCGCCTT TACTGAGCAC TCTTTAATAG        3432

TGGACTCTTG TTCCAAACTG GAACAACACT CAACCCTATC TCGGTCTATT CTTTTGATTT       3492

ATAAGATTTC CATCGCCATG TAAAAGTGTT ACAATTAGCA TTAAATTACT TCTTTATATG       3552

CTACTATTCT TTTGGCTTCG TTCACGGGGT GGGTACCGAG CTCGAATTCT GTGGAATGTG       3612

TGTCAGTTAG GGTGTGGAAA GTCCCCAGGC TCCCCAGGCA GGCAGAAGTA TGCAAAGCAT       3672

GCATCTCAAT TAGTCAGCAA CCAGGTGTGG AAAGTCCCCA GGCTCCCCAG CAGGCAGAAG       3732

TATGCAAAGC ATGCATCTCA ATTAGTCAGC AACCATAGTC CCGCCCCTAA CTCCGCCCAT       3792

CCCGCCCCTA ACTCCGCCCA GTTCCGCCCA TTCTCCGCCC CATGGCTGAC TAATTTTTTT       3852

TATTTATGCA GAGGCCGAGG CCGCCTCGGC CTCTGAGCTA TTCCAGAAGT AGTGAGGAGG       3912

CTTTTTTGGA GGCCTAGGCT TTTGCAAAAA GCTCCCGGGA GCTTGGATAT CCATTTTCGG       3972

ATCTGATCAA GAGACAGGAT GAGGATCGTT TCGCATGATT GAACAAGATG GATTGCACGC       4032

AGGTTCTCCG GCCGCTTGGG TGGAGAGGCT ATTCGGCTAT GACTGGGCAC AACAGACAAT       4092
```

```
CGGCTGCTCT GATGCCGCCG TGTTCCGGCT GTCAGCGCAG GGGCGCCCGG TTCTTTTTGT      4152
CAAGACCGAC CTGTCCGGTG CCCTGAATGA ACTGCAGGAC GAGGCAGCGC GGCTATCGTG      4212
GCTGGCCACG ACGGGCGTTC CTTGCGCAGC TGTGCTCGAC GTTGTCACTG AAGCGGGAAG      4272
GGACTGGCTG CTATTGGGCG AAGTGCCGGG GCAGGATCTC CTGTCATCTC ACCTTGCTCC      4332
TGCCGAGAAA GTATCCATCA TGGCTGATGC AATGCGGCGG CTGCATACGC TTGATCCGGC      4392
TACCTGCCCA TTCGACCACC AAGCGAAACA TCGCATCGAG CGAGCACGTA CTCGGATGGA      4452
AGCCGGTCTT GTCGATCAGG ATGATCTGGA CGAAGAGCAT CAGGGGCTCG CGCCAGCCGA      4512
ACTGTTCGCC AGGCTCAAGG CGCGCATGCC CGACGGCGAG GATCTCGTCG TGACCCATGG      4572
CGATGCCTGC TTGCCGAATA TCATGGTGGA AAATGGCCGC TTTTCTGGAT TCATCGACTG      4632
TGGCCGGCTG GGTGTGGCGG ACCGCTATCA GGACATAGCG TTGGCTACCC GTGATATTGC      4692
TGAAGAGCTT GGCGGCGAAT GGGCTGACCG CTTCCTCGTG CTTTACGGTA TCGCCGCTCC      4752
CGATTCGCAG CGCATCGCCT TCTATCGCCT TCTTGACGAG TTCTTCTGAG CGGGACTCTG      4812
GGGTTCGAAA TGACCGACCA AGCGACGCCC AACCTGCCAT CACGAGATTT CGATTCCACC      4872
GCCGCCTTCT ATGAAAGGTT GGGCTTCGGA ATCGTTTTCC GGGACGCCGG CTGGATGATC      4932
CTCCAGCGCG GGGATCTCAT GCTGGAGTTC TTCGCCCACC CCAACTTGTT TATTGCAGCT      4992
TATAATGGTT ACAAATAAAG CAATAGCATC ACAAATTTCA CAAATAAAGC ATTTTTTTCA      5052
CTGCATTCTA GTTGTGGTTT GTCCAAACTC ATCAATGTAT CTTATCATGT CTGGATCCCG      5112
TCGACCTCGA GAGCTTGGCG TAATCATGGT CATAGCTGTT TCCTGTGTGA AATTGTTATC      5172
CGCTCACAAT TCCACACAAC ATACGAGCCG GAAGCATAAA GTGTAAAGCC TGGGGTGCCT      5232
AATGAGTGAG CTAACTCACA TTAATTGCGT TGCGCTCACT GCCCGCTTTC CAGTCGGGAA      5292
ACCTGTCGTG CCAGCTGCAT TAATGAATCG GCCAACGCGC GGGGAGAGGC GGTTTGCGTA      5352
TTGGGCGCTC TTCCGCTTCC TCGCTCACTG ACTCGCTGCG CTCGGTCGTT CGGCTGCGGC      5412
GAGCGGTATC AGCTCACTCA AAGGCGGTAA TACGGTTATC CACAGAATCA GGGGATAACG      5472
CAGGAAAGAA CATGTGAGCA AAAGGCCAGC AAAAGGCCAG GAACCGTAAA AAGGCCGCGT      5532
TGCTGGCGTT TTTCCATAGG CTCCGCCCCC CTGACGAGCA TCACAAAAAT CGACGCTCAA      5592
GTCAGAGGTG GCGAAACCCG ACAGGACTAT AAAGATACCA GGCGTTTCCC CCTGGAAGCT      5652
CCCTCGTGCG CTCTCCTGTT CCGACCCTGC CGCTTACCGG ATACCTGTCC GCCTTTCTCC      5712
CTTCGGGAAG CGTGGCGCTT TCTCAATGCT CACGCTGTAG GTATCTCAGT TCGGTGTAGG      5772
TCGTTCGCTC CAAGCTGGGC TGTGTGCACG AACCCCCCGT TCAGCCCGAC CGCTGCGCCT      5832
TATCCGGTAA CTATCGTCTT GAGTCCAACC CGGTAAGACA CGACTTATCG CCACTGGCAG      5892
CAGCCACTGG TAACAGGATT AGCAGAGCGA GGTATGTAGG CGGTGCTACA GAGTTCTTGA      5952
AGTGGTGGCC TAACTACGGC TACACTAGAA GGACAGTATT TGGTATCTGC GCTCTGCTGA      6012
AGCCAGTTAC CTTCGGAAAA AGAGTTGGTA GCTCTTGATC CGGCAAACAA ACCACCGCTG      6072
GTAGCGGTGG TTTTTTTGTT TGCAAGCAGC AGATTACGCG CAGAAAAAAA GGATCTCAAG      6132
AAGATCCTTT GATCTTTTCT ACGGGGTCTG ACGCTCAGTG GAACGAAAAC TCACGTTAAG      6192
GGATTTTGGT CATGAGATTA TCAAAAGGA TCTTCACCTA GATCCTTTTA AATTAAAAAT      6252
GAAGTTTTAA ATCAATCTAA AGTATATATG AGTAAACTTG GTCTGACAGT TACCAATGCT      6312
TAATCAGTGA GGCACCTATC TCAGCGATCT GTCTATTTCG TTCATCCATA GTTGCCTGAC      6372
TCCCCGTCGT GTAGATAACT ACGATACGGG AGGGCTTACC ATCTGGCCCC AGTGCTGCAA      6432
TGATACCGCG AGACCCACGC TCACCGGCTC CAGATTTATC AGCAATAAAC CAGCCAGCCG      6492
```

-continued

```
GAAGGGCCGA GCGCAGAAGT GGTCCTGCAA CTTTATCCGC CTCCATCCAG TCTATTAATT    6552

GTTGCCGGGA AGCTAGAGTA AGTAGTTCGC CAGTTAATAG TTTGCGCAAC GTTGTTGCCA    6612

TTGCTACAGG CATCGTGGTG TCACGCTCGT CGTTTGGTAT GGCTTCATTC AGCTCCGGTT    6672

CCCAACGATC AAGGCGAGTT ACATGATCCC CCATGTTGTG CAAAAAAGCG GTTAGCTCCT    6732

TCGGTCCTCC GATCGTTGTC AGAAGTAAGT TGGCCGCAGT GTTATCACTC ATGGTTATGG    6792

CAGCACTGCA TAATTCTCTT ACTGTCATGC CATCCGTAAG ATGCTTTCT GTGACTGGTG    6852

AGTACTCAAC CAAGTCATTC TGAGAATAGT GTATGCGGCG ACCGAGTTGC TCTTGCCCGG    6912

CGTCAATACG GGATAATACC GCGCCACATA GCAGAACTTT AAAAGTGCTC ATCATTGGAA    6972

AACGTTCTTC GGGGCGAAAA CTCTCAAGGA TCTTACCGCT GTTGAGATCC AGTTCGATGT    7032

AACCCACTCG TGCACCCAAC TGATCTTCAG CATCTTTTAC TTTCACCAGC GTTTCTGGGT    7092

GAGCAAAAAC AGGAAGGCAA AATGCCGCAA AAAGGGAAT AAGGGCGACA CGGAAATGTT    7152

GAATACTCAT ACTCTTCCTT TTTCAATATT ATTGAAGCAT TTATCAGGGT TATTGTCTCA    7212

TGAGCGGATA CATATTTGAA TGTATTTAGA AAAATAAACA AATAGGGGTT CCGCGCACAT    7272

TTCCCCGAAA AGTGCCACCT GACGTC                                         7298
```

( 2 ) INFORMATION FOR SEQ ID NO:4:

( i ) SEQUENCE CHARACTERISTICS:
  ( A ) LENGTH: 537 amino acids
  ( B ) TYPE: amino acid
  ( D ) TOPOLOGY: linear ( i i ) MOLECULE TYPE: protein ( x i ) SEQUENCE DESCRIPTION: SEQ ID NO:4:

```
Met Leu Pro Gly Leu Ala Leu Leu Leu Ala Ala Trp Thr Ala Arg
  1               5                  10                  15

Ala Leu Glu Val Pro Thr Asp Gly Asn Ala Gly Leu Leu Ala Glu Pro
             20                  25                  30

Gln Ile Ala Met Phe Cys Gly Arg Leu Asn Met His Met Asn Val Gln
             35                  40                  45

Asn Gly Lys Trp Asp Ser Asp Pro Ser Gly Thr Lys Thr Cys Ile Asp
         50                  55                  60

Thr Lys Glu Thr His Val Thr Gly Gly Ser Ala Gly His Thr Thr Ala
 65                  70                  75                  80

Gly Leu Val Arg Leu Leu Ser Pro Gly Ala Lys Gln Asn Ile Gln Leu
                 85                  90                  95

Ile Asn Thr Asn Gly Ser Trp His Ile Asn Ser Thr Ala Leu Asn Cys
                100                 105                 110

Asn Glu Ser Leu Asn Thr Gly Trp Leu Ala Gly Leu Phe Tyr His His
                115                 120                 125

Lys Phe Asn Ser Ser Gly Cys Pro Glu Arg Leu Ala Ser Cys Arg Arg
        130                 135                 140

Leu Thr Asp Phe Ala Gln Gly Gly Gly Pro Ile Ser Tyr Ala Asn Gly
145                 150                 155                 160

Ser Gly Leu Asp Glu Arg Pro Tyr Cys Trp His Tyr Pro Pro Arg Pro
                165                 170                 175

Cys Gly Ile Val Pro Ala Lys Ser Val Cys Gly Pro Val Tyr Cys Phe
                180                 185                 190

Thr Pro Ser Pro Val Val Val Gly Thr Thr Asp Arg Ser Gly Ala Pro
            195                 200                 205
```

| | | | | | | | | | | | | | | | |
|---|---|---|---|---|---|---|---|---|---|---|---|---|---|---|---|
| Thr | Tyr | Ser | Trp | Gly | Ala | Asn | Asp | Thr | Asp | Val | Phe | Val | Leu | Asn | Asn |
| 210 | | | | | 215 | | | | | 220 | | | | | |
| Thr | Arg | Pro | Pro | Leu | Gly | Asn | Trp | Phe | Gly | Cys | Thr | Trp | Met | Asn | Ser |
| 225 | | | | | 230 | | | | | 235 | | | | | 240 |
| Thr | Gly | Phe | Thr | Lys | Val | Cys | Gly | Ala | Pro | Pro | Cys | Val | Ile | Gly | Gly |
| | | | | 245 | | | | | 250 | | | | | 255 | |
| Val | Gly | Asn | Asn | Thr | Leu | Leu | Cys | Pro | Thr | Asp | Cys | Phe | Arg | Lys | His |
| | | | 260 | | | | | 265 | | | | | 270 | | |
| Pro | Glu | Ala | Thr | Tyr | Ser | Arg | Cys | Gly | Ser | Gly | Pro | Trp | Ile | Thr | Pro |
| | | 275 | | | | | 280 | | | | | 285 | | | |
| Arg | Cys | Met | Val | Asp | Tyr | Pro | Tyr | Arg | Leu | Trp | His | Tyr | Pro | Cys | Thr |
| | 290 | | | | | 295 | | | | | 300 | | | | |
| Ile | Asn | Tyr | Thr | Ile | Phe | Lys | Val | Arg | Met | Tyr | Val | Gly | Gly | Val | Glu |
| 305 | | | | | 310 | | | | | 315 | | | | | 320 |
| His | Arg | Leu | Glu | Ala | Ala | Cys | Asn | Trp | Thr | Arg | Gly | Glu | Arg | Cys | Asp |
| | | | | 325 | | | | | 330 | | | | | 335 | |
| Leu | Glu | Asp | Arg | Asp | Arg | Ser | Glu | Leu | Ser | Pro | Leu | Leu | Leu | Ser | Thr |
| | | | 340 | | | | | 345 | | | | | 350 | | |
| Thr | Gln | Trp | Gln | Val | Leu | Pro | Cys | Ser | Phe | Thr | Thr | Leu | Pro | Ala | Leu |
| | | 355 | | | | | 360 | | | | | 365 | | | |
| Ser | Thr | Gly | Leu | Ile | His | Leu | His | Gln | Asn | Ile | Val | Asp | Val | Gln | Tyr |
| | 370 | | | | | 375 | | | | | 380 | | | | |
| Leu | Tyr | Gly | Val | Gly | Ser | Ser | Ile | Ala | Ser | Trp | Ala | Ile | Lys | Trp | Glu |
| 385 | | | | | 390 | | | | | 395 | | | | | 400 |
| Tyr | Asp | Val | Leu | Leu | Phe | Leu | Leu | Leu | Ala | Asp | Ala | Arg | Val | Cys | Ser |
| | | | | 405 | | | | | 410 | | | | | 415 | |
| Cys | Leu | Trp | Met | Met | Leu | Leu | Ile | Ser | Gln | Ala | Glu | Ala | Ala | Leu | Glu |
| | | | 420 | | | | | 425 | | | | | 430 | | |
| Ile | Ser | Glu | Val | Lys | Met | Asp | Ala | Glu | Phe | Arg | His | Asp | Ser | Gly | Tyr |
| | | 435 | | | | | 440 | | | | | 445 | | | |
| Glu | Val | His | His | Gln | Lys | Leu | Val | Phe | Phe | Ala | Glu | Asp | Val | Gly | Ser |
| | 450 | | | | | 455 | | | | | 460 | | | | |
| Asn | Lys | Gly | Ala | Ile | Ile | Gly | Leu | Met | Val | Gly | Gly | Val | Val | Ile | Ala |
| 465 | | | | | 470 | | | | | 475 | | | | | 480 |
| Thr | Val | Ile | Val | Ile | Thr | Leu | Val | Met | Leu | Lys | Lys | Lys | Gln | Tyr | Thr |
| | | | | 485 | | | | | 490 | | | | | 495 | |
| Ser | Ile | His | His | Gly | Val | Val | Glu | Val | Asp | Ala | Ala | Val | Thr | Pro | Glu |
| | | | 500 | | | | | 505 | | | | | 510 | | |
| Glu | Arg | His | Leu | Ser | Lys | Met | Gln | Gln | Asn | Gly | Tyr | Glu | Asn | Pro | Thr |
| | | 515 | | | | | 520 | | | | | 525 | | | |
| Tyr | Lys | Phe | Phe | Glu | Gln | Met | Gln | Asn | | | | | | | |
| | 530 | | | | | 535 | | | | | | | | | |

( 2 ) INFORMATION FOR SEQ ID NO:5:

( i ) SEQUENCE CHARACTERISTICS:
        ( A ) LENGTH: 7106 base pairs
        ( B ) TYPE: nucleic acid
        ( C ) STRANDEDNESS: single
        ( D ) TOPOLOGY: circular ( i i ) MOLECULE TYPE: DNA (genomic)

( i x ) FEATURE:
        ( A ) NAME/KEY: CDS
        ( B ) LOCATION: 922..2022

( x i ) SEQUENCE DESCRIPTION: SEQ ID NO:5:

```
GACGGATCGG GAGATCTCCC GATCCCCTAT GGTCGACTCT CAGTACAATC TGCTCTGATG    60

CCGCATAGTT AAGCCAGTAT CTGCTCCCTG CTTGTGTGTT GGAGGTCGCT GAGTAGTGCG   120

CGAGCAAAAT TTAAGCTACA ACAAGGCAAG GCTTGACCGA CAATTGCATG AAGAATCTGC   180

TTAGGGTTAG GCGTTTTGCG CTGCTTCGCG ATGTACGGGC CAGATATACG CGTTGACATT   240

GATTATTGAC TAGTTATTAA TAGTAATCAA TTACGGGGTC ATTAGTTCAT AGCCCATATA   300

TGGAGTTCCG CGTTACATAA CTTACGGTAA ATGGCCCGCC TGGCTGACCG CCCAACGACC   360

CCCGCCCATT GACGTCAATA ATGACGTATG TTCCCATAGT AACGCCAATA GGGACTTTCC   420

ATTGACGTCA ATGGGTGGAC TATTTACGGT AAACTGCCCA CTTGGCAGTA CATCAAGTGT   480

ATCATATGCC AAGTACGCCC CCTATTGACG TCAATGACGG TAAATGGCCC GCCTGGCATT   540

ATGCCCAGTA CATGACCTTA TGGGACTTTC CTACTTGGCA GTACATCTAC GTATTAGTCA   600

TCGCTATTAC CATGGTGATG CGGTTTTGGC AGTACATCAA TGGGCGTGGA TAGCGGTTTG   660

ACTCACGGGG ATTTCCAAGT CTCCACCCCA TTGACGTCAA TGGGAGTTTG TTTTGGCACC   720

AAAATCAACG GGACTTTCCA AAATGTCGTA ACAACTCCGC CCCATTGACG CAAATGGGCG   780

GTAGGCGTGT ACGGTGGGAG GTCTATATAA GCAGAGCTCT CTGGCTAACT AGAGAACCCA   840

CTGCTTAACT GGCTTATCGA AATTAATACG ACTCACTATA GGGAGACCGG AAGCTTGCT    900

CTAGACTGGA ATTCGGGCGC G ATG CTG CCC GGT TTG GCA CTG CTC CTG CTG    951
                       Met Leu Pro Gly Leu Ala Leu Leu Leu Leu
                        1               5                   10

GCC GCC TGG ACG GCT CGG GCG CTG GAG GTA CCC ACT GAT GGT AAT GCT    999
Ala Ala Trp Thr Ala Arg Ala Leu Glu Val Pro Thr Asp Gly Asn Ala
                15                  20                  25

GGC CTG CTG GCT GAA CCC CAG ATT GCC ATG TTC TGT GGC AGA CTG AAC   1047
Gly Leu Leu Ala Glu Pro Gln Ile Ala Met Phe Cys Gly Arg Leu Asn
            30                  35                  40

ATG CAC ATG AAT GTC CAG AAT GGG AAG TGG GAT TCA GAT CCA TCA GGG   1095
Met His Met Asn Val Gln Asn Gly Lys Trp Asp Ser Asp Pro Ser Gly
                45                  50                  55

ACC AAA ACC TGC ATT GAT ACC AAG GAA ACC CAC GTC ACC GGG GGA AGT   1143
Thr Lys Thr Cys Ile Asp Thr Lys Glu Thr His Val Thr Gly Gly Ser
    60                  65                  70

GCC GGC CAC ACC ACG GCT GGG CTT GTT CGT CTC CTT TCA CCA GGC GCC   1191
Ala Gly His Thr Thr Ala Gly Leu Val Arg Leu Leu Ser Pro Gly Ala
75                  80                  85                  90

AAG CAG AAC ATC CAA CTG ATC AAC ACC AAC GGC AGT TGG CAC ATC AAT   1239
Lys Gln Asn Ile Gln Leu Ile Asn Thr Asn Gly Ser Trp His Ile Asn
                95                  100                 105

AGC ACG GCC TTG AAC TGC AAT GAA AGC CTT AAC ACC GGC TGG TTA GCA   1287
Ser Thr Ala Leu Asn Cys Asn Glu Ser Leu Asn Thr Gly Trp Leu Ala
        110                 115                 120

GGG CTC TTC TAT CAC CAC AAA TTC AAC TCT TCA GGT TGT CCT GAG AGG   1335
Gly Leu Phe Tyr His His Lys Phe Asn Ser Ser Gly Cys Pro Glu Arg
            125                 130                 135

TTG GCC AGC TGC CGA CGC CTT ACC GAT TTT GCC CAG GGC GGG GGT CCT   1383
Leu Ala Ser Cys Arg Arg Leu Thr Asp Phe Ala Gln Gly Gly Gly Pro
            140                 145                 150

ATC AGT TAC GCC AAC GGA AGC GGC CTC GAT GAA CGC CCC TAC TGC TGG   1431
Ile Ser Tyr Ala Asn Gly Ser Gly Leu Asp Glu Arg Pro Tyr Cys Trp
155                 160                 165                 170

CAC TAC CCT CCA AGA CCT TGT GGC ATT GTG CCC GCA AAG AGC GTG TGT   1479
His Tyr Pro Pro Arg Pro Cys Gly Ile Val Pro Ala Lys Ser Val Cys
                175                 180                 185

GGC CCG GTA TAT TGC TTC ACT CCC AGC CCC GTG GTG GTG GGA ACG ACC   1527
Gly Pro Val Tyr Cys Phe Thr Pro Ser Pro Val Val Val Gly Thr Thr
```

```
                190                          195                          200
GAC AGG TCG GGC GCG CCT ACC TAC AGC TGG GGT GCA AAT GAT ACG GAT              1575
Asp Arg Ser Gly Ala Pro Thr Tyr Ser Trp Gly Ala Asn Asp Thr Asp
        205                         210                         215

GTC TTT GTC CTT AAC AAC ACC AGG CCA CCG CTG GGC AAT TGG TTC GGT              1623
Val Phe Val Leu Asn Asn Thr Arg Pro Pro Leu Gly Asn Trp Phe Gly
220                         225                         230

TGC ACC TGG ATG AAC TCA ACT GGA TTC ACC AAA GTG TGC GGA GCG CCC              1671
Cys Thr Trp Met Asn Ser Thr Gly Phe Thr Lys Val Cys Gly Ala Pro
235                         240                         245                         250

CCT TGT GTC ATC GGA GGG GTG GGC AAC AAC ACC TTG CTC TGC CCC ACT              1719
Pro Cys Val Ile Gly Gly Val Gly Asn Asn Thr Leu Leu Cys Pro Thr
                        255                         260                         265

GAT TGC TTC CGC AAG CAT CCG GAA GCC ACA TAC TCT CGG TGC GGC TCC              1767
Asp Cys Phe Arg Lys His Pro Glu Ala Thr Tyr Ser Arg Cys Gly Ser
                270                         275                         280

GGT CCC TGG ATT ACA CCC AGG TGC ATG GTC GAC TAC CCG TAT AGG CTT              1815
Gly Pro Trp Ile Thr Pro Arg Cys Met Val Asp Tyr Pro Tyr Arg Leu
        285                         290                         295

TGG CAC TAT CCT TGT ACC ATC AAT TAC ACC ATA TTC AAA GTC AGG ATG              1863
Trp His Tyr Pro Cys Thr Ile Asn Tyr Thr Ile Phe Lys Val Arg Met
300                         305                         310

TAC GTG GGA GGG GTC GAG CAC AGG CTG GAA GCG GCC TGC AAC TGG ACG              1911
Tyr Val Gly Gly Val Glu His Arg Leu Glu Ala Ala Cys Asn Trp Thr
315                         320                         325                         330

CGG GGC GAA CGC TGT GAT CTG GAA GAC AGG GAC AGG TCC GAG CTC AGC              1959
Arg Gly Glu Arg Cys Asp Leu Glu Asp Arg Asp Arg Ser Glu Leu Ser
                        335                         340                         345

CCG TTA CTG CTG TCC ACC ACG CAG TGG CAG GTC CTT CCG TGT TCT TTC              2007
Pro Leu Leu Leu Ser Thr Thr Gln Trp Gln Val Leu Pro Cys Ser Phe
                    350                         355                         360

ACG ACC CTG CCA GCC TAGATCTCTG AAGTGAAGAT GGATGCAGAA TTCCGACATG              2062
Thr Thr Leu Pro Ala
                365

ACTCAGGATA TGAAGTTCAT CATCAAAAAT TGGTGTTCTT TGCAGAAGAT GTGGGTTCAA           2122
ACAAAGGTGC AATCATTGGA CTCATGGTGG GCGGTGTTGT CATAGCGACA GTGATCGTCA           2182
TCACCTTGGT GATGCTGAAG AAGAAACAGT ACACATCCAT TCATCATGGT GTGGTGGAGG           2242
TTGACGCCGC TGTCACCCCA GAGGAGCGCC ACCTGTCCAA GATGCAGCAG AACGGCTACG           2302
AAAATCCAAC CTACAAGTTC TTTGAGCAGA TGCAGAACTA GACCCCCGCC ACAGCAGCCT           2362
CTGAAGTTGG ACAGCAAAAC CATTGCTTCA CTACCCATCG GTGTCCATTT ATAGAATAAT           2422
GTGGGAAGAA ACAAACCCGT TTTATGATTT ACTCATTATC GCCTTTTGAC AGCTGTGCTG           2482
TAACACAAGT AGATGCCTGA ACTTGAATTA ATCCACACAT CAGTAATGTA TTCTATCTCT           2542
CTTTACATTT TGGTCTCTAT ACTACATTAT TAATGGGTTT TGTGTACTGT AAAGAATTTA           2602
GCTGTATCAA ACTAGTGCAT GAATAGGCCG CTCGAGCATG CATCTAGAGG GCCCTATTCT           2662
ATAGTGTCAC CTAAATGCTC GCTGATCAGC CTCGACTGTG CCTTCTAGTT GCCAGCCATC           2722
TGTTGTTTGC CCCTCCCCCG TGCCTTCCTT GACCCTGGAA GGTGCCACTC CCACTGTCCT           2782
TTCCTAATAA AATGAGGAAA TTGCATCGCA TTGTCTGAGT AGGTGTCATT CTATTCTGGG           2842
GGGTGGGGTG GGCAGGACA GCAAGGGGA GGATTGGGAA GACAATAGCA GGCATGCTGG             2902
GGATGCGGTG GGCTCTATGG AACCAGCTGG GGCTCGAGGG GGGATCCCCA CGCGCCCTGT           2962
AGCGGCGCAT TAAGCGCGGC GGGTGTGGTG GTTACGCGCA GCGTGACCGC TACACTTGCC           3022
AGCGCCCTAG CGCCCGCTCC TTTCGCTTTC TTCCCTTCCT TTCTCGCCAC GTTCGCCGGC           3082
```

```
TTTCCCCGTC AAGCTCTAAA TCGGGGCATC CCTTTAGGGT TCCGATTTAG TGCTTTACGG    3142
CACCTCGACC CCAAAAAACT TGATTAGGGT GATGGTTCAC GTAGTGGGCC ATCGCCCTGA    3202
TAGACGGTTT TTCGCCTTTA CTGAGCACTC TTTAATAGTG GACTCTTGTT CCAAACTGGA    3262
ACAACACTCA ACCCTATCTC GGTCTATTCT TTTGATTTAT AAGATTTCCA TCGCCATGTA    3322
AAAGTGTTAC AATTAGCATT AAATTACTTC TTTATATGCT ACTATTCTTT TGGCTTCGTT    3382
CACGGGGTGG GTACCGAGCT CGAATTCTGT GGAATGTGTG TCAGTTAGGG TGTGGAAAGT    3442
CCCCAGGCTC CCCAGGCAGG CAGAAGTATG CAAAGCATGC ATCTCAATTA GTCAGCAACC    3502
AGGTGTGGAA AGTCCCCAGG CTCCCCAGCA GGCAGAAGTA TGCAAAGCAT GCATCTCAAT    3562
TAGTCAGCAA CCATAGTCCC GCCCCTAACT CCGCCCATCC CGCCCCTAAC TCCGCCCAGT    3622
TCCGCCCATT CTCCGCCCCA TGGCTGACTA ATTTTTTTA TTTATGCAGA GGCCGAGGCC    3682
GCCTCGGCCT CTGAGCTATT CCAGAAGTAG TGAGGAGGCT TTTTGGAGG CCTAGGCTTT    3742
TGCAAAAAGC TCCCGGGAGC TTGGATATCC ATTTTCGGAT CTGATCAAGA GACAGGATGA    3802
GGATCGTTTC GCATGATTGA ACAAGATGGA TTGCACGCAG GTTCTCCGGC CGCTTGGGTG    3862
GAGAGGCTAT TCGGCTATGA CTGGGCACAA CAGACAATCG GCTGCTCTGA TGCCGCCGTG    3922
TTCCGGCTGT CAGCGCAGGG GCGCCCGGTT CTTTTTGTCA AGACCGACCT GTCCGGTGCC    3982
CTGAATGAAC TGCAGGACGA GGCAGCGCGG CTATCGTGGC TGGCCACGAC GGGCGTTCCT    4042
TGCGCAGCTG TGCTCGACGT TGTCACTGAA GCGGGAAGGG ACTGGCTGCT ATTGGGCGAA    4102
GTGCCGGGGC AGGATCTCCT GTCATCTCAC CTTGCTCCTG CCGAGAAAGT ATCCATCATG    4162
GCTGATGCAA TGCGGCGGCT GCATACGCTT GATCCGGCTA CCTGCCCATT CGACCACCAA    4222
GCGAAACATC GCATCGAGCG AGCACGTACT CGGATGGAAG CCGGTCTTGT CGATCAGGAT    4282
GATCTGGACG AAGAGCATCA GGGGCTCGCG CCAGCCGAAC TGTTCGCCAG GCTCAAGGCG    4342
CGCATGCCCG ACGGCGAGGA TCTCGTCGTG ACCCATGGCG ATGCCTGCTT GCCGAATATC    4402
ATGGTGGAAA ATGGCCGCTT TTCTGGATTC ATCGACTGTG GCCGGCTGGG TGTGGCGGAC    4462
CGCTATCAGG ACATAGCGTT GGCTACCCGT GATATTGCTG AAGAGCTTGG CGGCGAATGG    4522
GCTGACCGCT TCCTCGTGCT TTACGGTATC GCCGCTCCCG ATTCGCAGCG CATCGCCTTC    4582
TATCGCCTTC TTGACGAGTT CTTCTGAGCG GGACTCTGGG GTTCGAAATG ACCGACCAAG    4642
CGACGCCCAA CCTGCCATCA CGAGATTTCG ATTCCACCGC CGCCTTCTAT GAAAGGTTGG    4702
GCTTCGGAAT CGTTTTCCGG GACGCCGGCT GGATGATCCT CCAGCGCGGG GATCTCATGC    4762
TGGAGTTCTT CGCCCACCCC AACTTGTTTA TTGCAGCTTA TAATGGTTAC AAATAAAGCA    4822
ATAGCATCAC AAATTTCACA AATAAAGCAT TTTTTTCACT GCATTCTAGT TGTGGTTTGT    4882
CCAAACTCAT CAATGTATCT TATCATGTCT GGATCCCGTC GACCTCGAGA GCTTGGCGTA    4942
ATCATGGTCA TAGCTGTTTC CTGTGTGAAA TTGTTATCCG CTCACAATTC CACACAACAT    5002
ACGAGCCGGA AGCATAAAGT GTAAAGCCTG GGGTGCCTAA TGAGTGAGCT AACTCACATT    5062
AATTGCGTTG CGCTCACTGC CCGCTTTCCA GTCGGGAAAC CTGTCGTGCC AGCTGCATTA    5122
ATGAATCGGC CAACGCGCGG GGAGAGGCGG TTTGCGTATT GGGCGCTCTT CCGCTTCCTC    5182
GCTCACTGAC TCGCTGCGCT CGGTCGTTCG GCTGCGGCGA GCGGTATCAG CTCACTCAAA    5242
GGCGGTAATA CGGTTATCCA CAGAATCAGG GGATAACGCA GGAAAGAACA TGTGAGCAAA    5302
AGGCCAGCAA AAGGCCAGGA ACCGTAAAAA GGCCGCGTTG CTGGCGTTTT TCCATAGGCT    5362
CCGCCCCCCT GACGAGCATC ACAAAAATCG ACGCTCAAGT CAGAGGTGGC GAAACCCGAC    5422
AGGACTATAA AGATACCAGG CGTTTCCCCC TGGAAGCTCC CTCGTGCGCT CTCCTGTTCC    5482
```

-continued

```
GACCCTGCCG CTTACCGGAT ACCTGTCCGC CTTTCTCCCT TCGGGAAGCG TGGCGCTTTC    5542
TCAATGCTCA CGCTGTAGGT ATCTCAGTTC GGTGTAGGTC GTTCGCTCCA AGCTGGGCTG    5602
TGTGCACGAA CCCCCCGTTC AGCCCGACCG CTGCGCCTTA TCCGGTAACT ATCGTCTTGA    5662
GTCCAACCCG GTAAGACACG ACTTATCGCC ACTGGCAGCA GCCACTGGTA ACAGGATTAG    5722
CAGAGCGAGG TATGTAGGCG GTGCTACAGA GTTCTTGAAG TGGTGGCCTA ACTACGGCTA    5782
CACTAGAAGG ACAGTATTTG GTATCTGCGC TCTGCTGAAG CCAGTTACCT TCGGAAAAAG    5842
AGTTGGTAGC TCTTGATCCG GCAAACAAAC CACCGCTGGT AGCGGTGGTT TTTTGTTTG    5902
CAAGCAGCAG ATTACGCGCA GAAAAAAGG ATCTCAAGAA GATCCTTTGA TCTTTTCTAC    5962
GGGGTCTGAC GCTCAGTGGA ACGAAAACTC ACGTTAAGGG ATTTTGGTCA TGAGATTATC    6022
AAAAAGGATC TTCACCTAGA TCCTTTTAAA TTAAAAATGA AGTTTTAAAT CAATCTAAAG    6082
TATATATGAG TAAACTTGGT CTGACAGTTA CCAATGCTTA ATCAGTGAGG CACCTATCTC    6142
AGCGATCTGT CTATTTCGTT CATCCATAGT TGCCTGACTC CCCGTCGTGT AGATAACTAC    6202
GATACGGGAG GGCTTACCAT CTGGCCCCAG TGCTGCAATG ATACCGCGAG ACCCACGCTC    6262
ACCGGCTCCA GATTTATCAG CAATAAACCA GCCAGCCGGA AGGGCCGAGC GCAGAAGTGG    6322
TCCTGCAACT TTATCCGCCT CCATCCAGTC TATTAATTGT TGCCGGGAAG CTAGAGTAAG    6382
TAGTTCGCCA GTTAATAGTT TGCGCAACGT TGTTGCCATT GCTACAGGCA TCGTGGTGTC    6442
ACGCTCGTCG TTTGGTATGG CTTCATTCAG CTCCGGTTCC CAACGATCAA GGCGAGTTAC    6502
ATGATCCCCC ATGTTGTGCA AAAAAGCGGT TAGCTCCTTC GGTCCTCCGA TCGTTGTCAG    6562
AAGTAAGTTG GCCGCAGTGT TATCACTCAT GGTTATGGCA GCACTGCATA ATTCTCTTAC    6622
TGTCATGCCA TCCGTAAGAT GCTTTTCTGT GACTGGTGAG TACTCAACCA AGTCATTCTG    6682
AGAATAGTGT ATGCGGCGAC CGAGTTGCTC TTGCCCGGCG TCAATACGGG ATAATACCGC    6742
GCCACATAGC AGAACTTTAA AAGTGCTCAT CATTGGAAAA CGTTCTTCGG GGCGAAAACT    6802
CTCAAGGATC TTACCGCTGT TGAGATCCAG TTCGATGTAA CCCACTCGTG CACCCAACTG    6862
ATCTTCAGCA TCTTTTACTT TCACCAGCGT TTCTGGGTGA GCAAAAACAG GAAGGCAAAA    6922
TGCCGCAAAA AAGGGAATAA GGGCGACACG GAAATGTTGA ATACTCATAC TCTTCCTTTT    6982
TCAATATTAT TGAAGCATTT ATCAGGGTTA TTGTCTCATG AGCGGATACA TATTTGAATG    7042
TATTTAGAAA AATAAACAAA TAGGGGTTCC GCGCACATTT CCCCGAAAAG TGCCACCTGA    7102
CGTC                                                                7106
```

( 2 ) INFORMATION FOR SEQ ID NO:6:

( i ) SEQUENCE CHARACTERISTICS:
       ( A ) LENGTH: 367 amino acids
       ( B ) TYPE: amino acid
       ( D ) TOPOLOGY: linear ( i i ) MOLECULE TYPE: protein ( x i ) SEQUENCE DESCRIPTION: SEQ ID NO:6:

```
Met Leu Pro Gly Leu Ala Leu Leu Leu Ala Ala Trp Thr Ala Arg
 1               5                  10                  15

Ala Leu Glu Val Pro Thr Asp Gly Asn Ala Gly Leu Leu Ala Glu Pro
             20                  25                  30

Gln Ile Ala Met Phe Cys Gly Arg Leu Asn Met His Met Asn Val Gln
         35                  40                  45

Asn Gly Lys Trp Asp Ser Asp Pro Ser Gly Thr Lys Thr Cys Ile Asp
     50                  55                  60
```

| | | | | | | | | | | | | | | |
|---|---|---|---|---|---|---|---|---|---|---|---|---|---|---|
| Thr | Lys | Glu | Thr | His | Val | Thr | Gly | Gly | Ser | Ala | Gly | His | Thr | Thr | Ala |
| 65 | | | | 70 | | | | | 75 | | | | | 80 |
| Gly | Leu | Val | Arg | Leu | Leu | Ser | Pro | Gly | Ala | Lys | Gln | Asn | Ile | Gln | Leu |
| | | | | 85 | | | | | 90 | | | | | 95 | |
| Ile | Asn | Thr | Asn | Gly | Ser | Trp | His | Ile | Asn | Ser | Thr | Ala | Leu | Asn | Cys |
| | | | 100 | | | | | 105 | | | | | 110 | | |
| Asn | Glu | Ser | Leu | Asn | Thr | Gly | Trp | Leu | Ala | Gly | Leu | Phe | Tyr | His | His |
| | | 115 | | | | | 120 | | | | | 125 | | | |
| Lys | Phe | Asn | Ser | Ser | Gly | Cys | Pro | Glu | Arg | Leu | Ala | Ser | Cys | Arg | Arg |
| | 130 | | | | | 135 | | | | | 140 | | | | |
| Leu | Thr | Asp | Phe | Ala | Gln | Gly | Gly | Gly | Pro | Ile | Ser | Tyr | Ala | Asn | Gly |
| 145 | | | | | 150 | | | | | 155 | | | | | 160 |
| Ser | Gly | Leu | Asp | Glu | Arg | Pro | Tyr | Cys | Trp | His | Tyr | Pro | Pro | Arg | Pro |
| | | | | 165 | | | | | 170 | | | | | 175 | |
| Cys | Gly | Ile | Val | Pro | Ala | Lys | Ser | Val | Cys | Gly | Pro | Val | Tyr | Cys | Phe |
| | | | 180 | | | | | 185 | | | | | 190 | | |
| Thr | Pro | Ser | Pro | Val | Val | Val | Gly | Thr | Thr | Asp | Arg | Ser | Gly | Ala | Pro |
| | | 195 | | | | | 200 | | | | | 205 | | | |
| Thr | Tyr | Ser | Trp | Gly | Ala | Asn | Asp | Thr | Asp | Val | Phe | Val | Leu | Asn | Asn |
| | 210 | | | | | 215 | | | | | 220 | | | | |
| Thr | Arg | Pro | Pro | Leu | Gly | Asn | Trp | Phe | Gly | Cys | Thr | Trp | Met | Asn | Ser |
| 225 | | | | | 230 | | | | | 235 | | | | | 240 |
| Thr | Gly | Phe | Thr | Lys | Val | Cys | Gly | Ala | Pro | Pro | Cys | Val | Ile | Gly | Gly |
| | | | | 245 | | | | | 250 | | | | | 255 | |
| Val | Gly | Asn | Asn | Thr | Leu | Leu | Cys | Pro | Thr | Asp | Cys | Phe | Arg | Lys | His |
| | | | 260 | | | | | 265 | | | | | 270 | | |
| Pro | Glu | Ala | Thr | Tyr | Ser | Arg | Cys | Gly | Ser | Gly | Pro | Trp | Ile | Thr | Pro |
| | | 275 | | | | | 280 | | | | | 285 | | | |
| Arg | Cys | Met | Val | Asp | Tyr | Pro | Tyr | Arg | Leu | Trp | His | Tyr | Pro | Cys | Thr |
| | 290 | | | | | 295 | | | | | 300 | | | | |
| Ile | Asn | Tyr | Thr | Ile | Phe | Lys | Val | Arg | Met | Tyr | Val | Gly | Gly | Val | Glu |
| 305 | | | | | 310 | | | | | 315 | | | | | 320 |
| His | Arg | Leu | Glu | Ala | Ala | Cys | Asn | Trp | Thr | Arg | Gly | Glu | Arg | Cys | Asp |
| | | | | 325 | | | | | 330 | | | | | 335 | |
| Leu | Glu | Asp | Arg | Asp | Arg | Ser | Glu | Leu | Ser | Pro | Leu | Leu | Leu | Ser | Thr |
| | | | 340 | | | | | 345 | | | | | 350 | | |
| Thr | Gln | Trp | Gln | Val | Leu | Pro | Cys | Ser | Phe | Thr | Thr | Leu | Pro | Ala | |
| | | 355 | | | | | 360 | | | | | 365 | | | |

( 2 ) INFORMATION FOR SEQ ID NO:7:

( i ) SEQUENCE CHARACTERISTICS:
        ( A ) LENGTH: 4810 base pairs
        ( B ) TYPE: nucleic acid
        ( C ) STRANDEDNESS: single
        ( D ) TOPOLOGY: circular ( i i ) MOLECULE TYPE: DNA (genomic)

( i x ) FEATURE:
        ( A ) NAME/KEY: CDS
        ( B ) LOCATION: 2227..2910

( x i ) SEQUENCE DESCRIPTION: SEQ ID NO:7:

```
GCGTAATCTG CTGCTTGCAA ACAAAAAAAC CACCGCTACC AGCGGTGGTT TGTTTGCCGG      60

ATCAAGAGCT ACCAACTCTT TTTCCGAAGG TAACTGGCTT CAGCAGAGCG CAGATACCAA     120

ATACTGTCCT TCTAGTGTAG CCGTAGTTAG GCCACCACTT CAAGAACTCT GTAGCACCGC     180
```

-continued

| | | | | |
|---|---|---|---|---|
| CTACATACCT | CGCTCTGCTA | ATCCTGTTAC | CAGTGGCTGC | TGCCAGTGGC GATAAGTCGT | 240 |
| GTCTTACCGG | GTTGGACTCA | AGACGATAGT | TACCGGATAA | GGCGCAGCGG TCGGGCTGAA | 300 |
| CGGGGGGTTC | GTGCACACAG | CCCAGCTTGG | AGCGAACGAC | CTACACCGAA CTGAGATACC | 360 |
| TACAGCGTGA | GCATTGAGAA | AGCGCCACGC | TTCCCGAAGG | GAGAAAGGCG GACAGGTATC | 420 |
| CGGTAAGCGG | CAGGGTCGGA | ACAGGAGAGC | GCACGAGGGA | GCTTCCAGGG GGAAACGCCT | 480 |
| GGTATCTTTA | TAGTCCTGTC | GGGTTTCGCC | ACCTCTGACT | TGAGCGTCGA TTTTTGTGAT | 540 |
| GCTCGTCAGG | GGGGCGGAGC | CTATGGAAAA | ACGCCAGCAA | CGCAAGCTAG CTTCTAGCTA | 600 |
| GAAATTGTAA | ACGTTAATAT | TTTGTTAAAA | TTCGCGTTAA | ATTTTGTTA AATCAGCTCA | 660 |
| TTTTTTAACC | AATAGGCCGA | AATCGGCAAA | ATCCCTTATA | AATCAAAAGA ATAGCCCGAG | 720 |
| ATAGGGTTGA | GTGTTGTTCC | AGTTTGGAAC | AAGAGTCCAC | TATTAAAGAA CGTGGACTCC | 780 |
| AACGTCAAAG | GGCGAAAAAC | CGTCTATCAG | GGCGATGGCC | GCCCACTACG TGAACCATCA | 840 |
| CCCAAATCAA | GTTTTTTGGG | GTCGAGGTGC | CGTAAAGCAC | TAAATCGGAA CCCTAAAGGG | 900 |
| AGCCCCCGAT | TTAGAGCTTG | ACGGGGAAAG | CCGGCGAACG | TGGCGAGAAA GGAAGGGAAG | 960 |
| AAAGCGAAAG | GAGCGGGCGC | TAGGGCGCTG | GCAAGTGTAG | CGGTCACGCT GCGCGTAACC | 1020 |
| ACCACACCCG | CCGCGCTTAA | TGCGCCGCTA | CAGGGCGCGT | ACTATGGTTG CTTTGACGAG | 1080 |
| ACCGTATAAC | GTGCTTTCCT | CGTTGGAATC | AGAGCGGGAG | CTAAACAGGA GGCCGATTAA | 1140 |
| AGGGATTTTA | GACAGGAACG | GTACGCCAGC | TGGATCACCG | CGGTCTTTCT CAACGTAACA | 1200 |
| CTTTACAGCG | GCGCGTCATT | TGATATGATG | CGCCCCGCTT | CCCGATAAGG GAGCAGGCCA | 1260 |
| GTAAAAGCAT | TACCCGTGGT | GGGGTTCCCG | AGCGGCCAAA | GGGAGCAGAC TCTAAATCTG | 1320 |
| CCGTCATCGA | CTTCGAAGGT | TCGAATCCTT | CCCCCACCAC | CATCACTTTC AAAAGTCCGA | 1380 |
| AAGAATCTGC | TCCCTGCTTG | TGTGTTGGAG | GTCGCTGAGT | AGTGCGCGAG TAAAATTTAA | 1440 |
| GCTACAACAA | GGCAAGGCTT | GACCGACAAT | TGCATGAAGA | ATCTGCTTAG GGTTAGGCGT | 1500 |
| TTTGCGCTGC | TTCGCGATGT | ACGGGCCAGA | TATACGCGTT | GACATTGATT ATTGACTAGT | 1560 |
| TATTAATAGT | AATCAATTAC | GGGGTCATTA | GTTCATAGCC | CATATATGGA GTTCCGCGTT | 1620 |
| ACATAACTTA | CGGTAAATGG | CCCGCCTGGC | TGACCGCCCA | ACGACCCCG CCCATTGACG | 1680 |
| TCAATAATGA | CGTATGTTCC | CATAGTAACG | CCAATAGGGA | CTTTCCATTG ACGTCAATGG | 1740 |
| GTGGACTATT | TACGGTAAAC | TGCCCACTTG | GCAGTACATC | AAGTGTATCA TATGCCAAGT | 1800 |
| ACGCCCCCTA | TTGACGTCAA | TGACGGTAAA | TGGCCCGCCT | GGCATTATGC CCAGTACATG | 1860 |
| ACCTTATGGG | ACTTTCCTAC | TTGGCAGTAC | ATCTACGTAT | TAGTCATCGC TATTACCATG | 1920 |
| GTGATGCGGT | TTTGGCAGTA | CATCAATGGG | CGTGGATAGC | GGTTGACTC ACGGGGATTT | 1980 |
| CCAAGTCTCC | ACCCCATTGA | CGTCAATGGG | AGTTTGTTTT | GGCACCAAAA TCAACGGGAC | 2040 |
| TTTCCAAAAT | GTCGTAACAA | CTCCGCCCCA | TTGACGCAAA | TGGGCGGTAG GCGTGTACGG | 2100 |
| TGGGAGGTCT | ATATAAGCAG | AGCTCTCTGG | CTAACTAGAG | AACCCACTGC TTAACTGGCT | 2160 |
| TATCGAAATT | AATACGACTC | ACTATAGGGA | GACCGGAAGC | TTGGTACCGA GCTCGGATCT | 2220 |

| GCCACC | ATG | GCA | ACA | GGA | TCA | AGA | ACA | TCA | CTG | CTG | CTG | GCA | TTT | GGA | 2268 |
| | Met | Ala | Thr | Gly | Ser | Arg | Thr | Ser | Leu | Leu | Leu | Ala | Phe | Gly | |
| | 1 | | | 5 | | | | | 10 | | | | | | |

| CTG | CTG | TGT | CTG | CCA | TGG | CTG | CAA | GAA | GGA | TCA | GCA | GCA | GCA | GCA | GCG | 2316 |
| Leu | Leu | Cys | Leu | Pro | Trp | Leu | Gln | Glu | Gly | Ser | Ala | Ala | Ala | Ala | Ala |
| 15 | | | | 20 | | | | | 25 | | | | | 30 | |

| AAT | TCG | GAT | CCC | TAC | CAA | GTG | CGC | AAT | TCC | TCG | GGG | CTT | TAC | CAT | GTC | 2364 |
| Asn | Ser | Asp | Pro | Tyr | Gln | Val | Arg | Asn | Ser | Ser | Gly | Leu | Tyr | His | Val |
| | | | | 35 | | | | | 40 | | | | | 45 | |

```
ACC AAT GAT TGC CCT AAT TCG AGT ATT GTG TAC GAG GCG GCC GAT GCC      2412
Thr Asn Asp Cys Pro Asn Ser Ser Ile Val Tyr Glu Ala Ala Asp Ala
             50              55                      60

ATC CTA CAC ACT CCG GGG TGT GTC CCT TGC GTT CGC GAG GGT AAC GCC      2460
Ile Leu His Thr Pro Gly Cys Val Pro Cys Val Arg Glu Gly Asn Ala
         65              70              75

TCG AGG TGT TGG GTG GCG GTG ACC CCC ACG GTG GCC ACC AGG GAC GGC      2508
Ser Arg Cys Trp Val Ala Val Thr Pro Thr Val Ala Thr Arg Asp Gly
     80              85              90

AAA CTC CCC ACA ACG CAG CTT CGA CGT CAT ATC GAT CTG CTC GTC GGG      2556
Lys Leu Pro Thr Thr Gln Leu Arg Arg His Ile Asp Leu Leu Val Gly
 95              100             105                 110

AGC GCC ACC CTC TGC TCG GCC CTC TAC GTG GGG GAC CTG TGC GGG TCT      2604
Ser Ala Thr Leu Cys Ser Ala Leu Tyr Val Gly Asp Leu Cys Gly Ser
                 115             120                 125

GTC TTT CTT GTT GGT CAA CTG TTT ACC TTC TCT CCC AGG CGC CAC TGG      2652
Val Phe Leu Val Gly Gln Leu Phe Thr Phe Ser Pro Arg Arg His Trp
             130             135             140

ACG ACG CAA GAC TGC AAT TGT TCT ATC TAT CCC GGC CAT ATA ACG GGT      2700
Thr Thr Gln Asp Cys Asn Cys Ser Ile Tyr Pro Gly His Ile Thr Gly
         145             150             155

CAT CGT ATG GCA TGG GAT ATG ATG ATG AAC TGG TCC CCT ACG GCA GCG      2748
His Arg Met Ala Trp Asp Met Met Met Asn Trp Ser Pro Thr Ala Ala
     160             165             170

TTG GTG GTA GCT CAG CTG CTC CGG ATC CCA CAA GCC ATC TTG GAC ATG      2796
Leu Val Val Ala Gln Leu Leu Arg Ile Pro Gln Ala Ile Leu Asp Met
175             180             185                     190

ATC GCT GGT GCC CAC TGG GGA GTC CTG GCG GGC ATA GCG TAT TTC TCC      2844
Ile Ala Gly Ala His Trp Gly Val Leu Ala Gly Ile Ala Tyr Phe Ser
                 195             200             205

ATG GTG GGG AAC TGG GCG AAG GTC CTG GTA GTG CTG CTG CTA TTT GCC      2892
Met Val Gly Asn Trp Ala Lys Val Leu Val Val Leu Leu Leu Phe Ala
             210             215                 220

GGC GTT GAC GCG GAG ATC TAATCTAGAG GGCCCTATTC TATAGTGTCA             2940
Gly Val Asp Ala Glu Ile
             225

CCTAAATGCT AGAGGATCTT TGTGAAGGAA CCTTACTTCT GTGGTGTGAC ATAATTGGAC    3000
AAACTACCTA CAGAGATTTA AAGCTCTAAG GTAAATATAA AATTTTTAAG TGTATAATGT    3060
GTTAAACTAC TGATTCTAAT TGTTTGTGTA TTTTAGATTC CAACCTATGG AACTGATGAA    3120
TGGGAGCAGT GGTGGAATGC CTTTAATGAG GAAAACCTGT TTGCTCAGA  AGAAATGCCA    3180
TCTAGTGATG ATGAGGCTAC TGCTGACTCT CAACATTCTA CTCCTCCAAA AAAGAAGAGA    3240
AAGGTAGAAG ACCCCAAGGA CTTTCCTTCA GAATTGCTAA GTTTTTGAG  TCATGCTGTG    3300
TTTAGTAATA GAACTCTTGC TTGCTTTGCT ATTTACACCA CAAAGGAAAA AGCTGCACTG    3360
CTATACAAGA AAATTATGGA AAAATATTCT GTAACCTTTA TAAGTAGGCA TAACAGTTAT    3420
AATCATAACA TACTGTTTTT TCTTACTCCA CACAGGCATA GAGTGTCTGC TATTAATAAC    3480
TATGCTCAAA AATTGTGTAC CTTTAGCTTT TTAATTTGTA AAGGGGTTAA TAAGGAATAT    3540
TTGATGTATA GTGCCTTGAC TAGAGATCAT AATCAGCCAT ACCACATTTG TAGAGGTTTT    3600
ACTTGCTTTA AAAAACCTCC CACACCTCCC CCTGAACCTG AAACATAAAA TGAATGCAAT    3660
TGTTGTTGTT AACTTGTTTA TTGCAGCTTA TAATGGTTAC AAATAAAGCA ATAGCATCAC    3720
AAATTTCACA AATAAAGCAT TTTTTCACT GCATTCTAGT TGTGGTTTGT CCAAACTCAT     3780
CAATGTATCT TATCATGTCT GGATCGATCC CGCCATGGTA TCAACGCCAT ATTTCTATTT    3840
ACAGTAGGGA CCTCTTCGTT GTGTAGGTAC CGCTGTATTC CTAGGGAAAT AGTAGAGGCA    3900
```

-continued

| | | | | | |
|---|---|---|---|---|---|
| CCTTGAACTG | TCTGCATCAG | CCATATAGCC | CCCGCTGTTC | GACTTACAAA | CACAGGCACA | 3960 |
| GTACTGACAA | ACCCATACAC | CTCCTCTGAA | ATACCCATAG | TTGCTAGGGC | TGTCTCCGAA | 4020 |
| CTCATTACAC | CCTCCAAAGT | CAGAGCTGTA | ATTTCGCCAT | CAAGGGCAGC | GAGGGCTTCT | 4080 |
| CCAGATAAAA | TAGCTTCTGC | CGAGAGTCCC | GTAAGGGTAG | ACACTTCAGC | TAATCCCTCG | 4140 |
| ATGAGGTCTA | CTAGAATAGT | CAGTGCGGCT | CCCATTTTGA | AAATTCACTT | ACTTGATCAG | 4200 |
| CTTCAGAAGA | TGGCGGAGGG | CCTCCAACAC | AGTAATTTTC | CTCCCGACTC | TTAAAATAGA | 4260 |
| AAATGTCAAG | TCAGTTAAGC | AGGAAGTGGA | CTAACTGACG | CAGCTGGCCG | TGCGACATCC | 4320 |
| TCTTTTAATT | AGTTGCTAGG | CAACGCCCTC | CAGAGGGCGT | GTGGTTTTGC | AAGAGGAAGC | 4380 |
| AAAAGCCTCT | CCACCCAGGC | CTAGAATGTT | TCCACCCAAT | CATTACTATG | ACAACAGCTG | 4440 |
| TTTTTTTTAG | TATTAAGCAG | AGGCCGGGGA | CCCCTGGCCC | GCTTACTCTG | GAGAAAAAGA | 4500 |
| AGAGAGGCAT | TGTAGAGGCT | TCCAGAGGCA | ACTTGTCAAA | ACAGGACTGC | TTCTATTTCT | 4560 |
| GTCACACTGT | CTGGCCCTGT | CACAAGGTCC | AGCACCTCCA | TACCCCCTTT | AATAAGCAGT | 4620 |
| TTGGGAACGG | GTGCGGGTCT | TACTCCGCCC | ATCCCGCCCC | TAACTCCGCC | CAGTTCCGCC | 4680 |
| CATTCTCCGC | CCCATGGCTG | ACTAATTTTT | TTTATTTATG | CAGAGGCCGA | GGCCGCCTCG | 4740 |
| GCCTCTGAGC | TATTCCAGAA | GTAGTGAGGA | GGCTTTTTTG | GAGGCCTAGG | CTTTTGCAAA | 4800 |
| AAGCTAATTC | | | | | | 4810 |

( 2 ) INFORMATION FOR SEQ ID NO:8:

( i ) SEQUENCE CHARACTERISTICS:
( A ) LENGTH: 228 amino acids
( B ) TYPE: amino acid
( D ) TOPOLOGY: linear ( i i ) MOLECULE TYPE: protein ( x i ) SEQUENCE DESCRIPTION: SEQ ID NO:8:

```
Met Ala Thr Gly Ser Arg Thr Ser Leu Leu Leu Ala Phe Gly Leu Leu
  1               5                  10                  15

Cys Leu Pro Trp Leu Gln Glu Gly Ser Ala Ala Ala Ala Asn Ser
             20                  25                  30

Asp Pro Tyr Gln Val Arg Asn Ser Ser Gly Leu Tyr His Val Thr Asn
             35                  40                  45

Asp Cys Pro Asn Ser Ser Ile Val Tyr Glu Ala Ala Asp Ala Ile Leu
         50              55                  60

His Thr Pro Gly Cys Val Pro Cys Val Arg Glu Gly Asn Ala Ser Arg
 65                  70                  75                  80

Cys Trp Val Ala Val Thr Pro Thr Val Ala Thr Arg Asp Gly Lys Leu
                 85                  90                  95

Pro Thr Thr Gln Leu Arg Arg His Ile Asp Leu Leu Val Gly Ser Ala
                100                 105                 110

Thr Leu Cys Ser Ala Leu Tyr Val Gly Asp Leu Cys Gly Ser Val Phe
            115                 120                 125

Leu Val Gly Gln Leu Phe Thr Phe Ser Pro Arg Arg His Trp Thr Thr
        130                 135                 140

Gln Asp Cys Asn Cys Ser Ile Tyr Pro Gly His Ile Thr Gly His Arg
145                 150                 155                 160

Met Ala Trp Asp Met Met Asn Trp Ser Pro Thr Ala Ala Leu Val
                165                 170                 175

Val Ala Gln Leu Leu Arg Ile Pro Gln Ala Ile Leu Asp Met Ile Ala
            180                 185                 190
```

```
Gly Ala His Trp Gly Val Leu Ala Gly Ile Ala Tyr Phe Ser Met Val
        195                 200                 205

Gly Asn Trp Ala Lys Val Leu Val Val Leu Leu Phe Ala Gly Val
        210                 215                 220

Asp Ala Glu Ile
225
```

( 2 ) INFORMATION FOR SEQ ID NO:9:

( i ) SEQUENCE CHARACTERISTICS:
      ( A ) LENGTH: 5323 base pairs
      ( B ) TYPE: nucleic acid
      ( C ) STRANDEDNESS: single
      ( D ) TOPOLOGY: circular ( i i ) MOLECULE TYPE: DNA (genomic)

( i x ) FEATURE:
      ( A ) NAME/KEY: CDS
      ( B ) LOCATION: 2227..3423

( x i ) SEQUENCE DESCRIPTION: SEQ ID NO:9:

```
GCGTAATCTG CTGCTTGCAA ACAAAAAAAC CACCGCTACC AGCGGTGGTT TGTTTGCCGG      60
ATCAAGAGCT ACCAACTCTT TTTCCGAAGG TAACTGGCTT CAGCAGAGCG CAGATACCAA     120
ATACTGTCCT TCTAGTGTAG CCGTAGTTAG GCCACCACTT CAAGAACTCT GTAGCACCGC     180
CTACATACCT CGCTCTGCTA ATCCTGTTAC CAGTGGCTGC TGCCAGTGGC GATAAGTCGT     240
GTCTTACCGG GTTGGACTCA AGACGATAGT TACCGGATAA GGCGCAGCGG TCGGGCTGAA     300
CGGGGGGTTC GTGCACACAG CCCAGCTTGG AGCGAACGAC CTACACCGAA CTGAGATACC     360
TACAGCGTGA GCATTGAGAA AGCGCCACGC TTCCCGAAGG GAGAAAGGCG ACAGGTATC      420
CGGTAAGCGG CAGGGTCGGA ACAGGAGAGC GCACGAGGGA GCTTCCAGGG GGAAACGCCT     480
GGTATCTTTA TAGTCCTGTC GGGTTTCGCC ACCTCTGACT TGAGCGTCGA TTTTTGTGAT     540
GCTCGTCAGG GGGCGGAGC  CTATGGAAAA ACGCCAGCAA CGCAAGCTAG CTTCTAGCTA     600
GAAATTGTAA ACGTTAATAT TTTGTTAAAA TTCGCGTTAA ATTTTTGTTA AATCAGCTCA     660
TTTTTTAACC AATAGGCCGA AATCGGCAAA ATCCCTTATA AATCAAAAGA ATAGCCCGAG     720
ATAGGGTTGA GTGTTGTTCC AGTTTGGAAC AAGAGTCCAC TATTAAAGAA CGTGGACTCC     780
AACGTCAAAG GGCGAAAAAC CGTCTATCAG GGCGATGGCC GCCCACTACG TGAACCATCA     840
CCCAAATCAA GTTTTTTGGG GTCGAGGTGC CGTAAAGCAC TAAATCGGAA CCCTAAAGGG     900
AGCCCCCGAT TTAGAGCTTG ACGGGGAAAG CCGGCGAACG TGGCGAGAAA GGAAGGGAAG     960
AAAGCGAAAG GAGCGGGCGC TAGGGCGCTG GCAAGTGTAG CGGTCACGCT GCGCGTAACC    1020
ACCACACCCG CCGCGCTTAA TGCGCCGCTA CAGGGCGCGT ACTATGGTTG CTTTGACGAG    1080
ACCGTATAAC GTGCTTTCCT CGTTGGAATC AGAGCGGGAG CTAAACAGGA GGCCGATTAA    1140
AGGGATTTTA GACAGGAACG GTACGCCAGC TGGATCACCG CGGTCTTTCT CAACGTAACA    1200
CTTTACAGCG GCGCGTCATT TGATATGATG CGCCCCGCTT CCCGATAAGG GAGCAGGCCA    1260
GTAAAAGCAT TACCCGTGGT GGGGTTCCCG AGCGGCCAAA GGGAGCAGAC TCTAAATCTG    1320
CCGTCATCGA CTTCGAAGGT TCGAATCCTT CCCCCACCAC CATCACTTTC AAAAGTCCGA    1380
AAGAATCTGC TCCCTGCTTG TGTGTTGGAG GTCGCTGAGT AGTGCGCGAG TAAAATTTAA    1440
GCTACAACAA GGCAAGGCTT GACCGACAAT TGCATGAAGA ATCTGCTTAG GGTTAGGCGT    1500
TTTGCGCTGC TTCGCGATGT ACGGGCCAGA TATACGCGTT GACATTGATT ATTGACTAGT    1560
TATTAATAGT AATCAATTAC GGGGTCATTA GTTCATAGCC CATATATGGA GTTCCGCGTT    1620
```

```
ACATAACTTA CGGTAAATGG CCCGCCTGGC TGACCGCCCA ACGACCCCCG CCCATTGACG    1680

TCAATAATGA CGTATGTTCC CATAGTAACG CCAATAGGGA CTTTCCATTG ACGTCAATGG    1740

GTGGACTATT TACGGTAAAC TGCCCACTTG GCAGTACATC AAGTGTATCA TATGCCAAGT    1800

ACGCCCCCTA TTGACGTCAA TGACGGTAAA TGGCCCGCCT GGCATTATGC CCAGTACATG    1860

ACCTTATGGG ACTTTCCTAC TTGGCAGTAC ATCTACGTAT TAGTCATCGC TATTACCATG    1920

GTGATGCGGT TTTGGCAGTA CATCAATGGG CGTGGATAGC GGTTTGACTC ACGGGGATTT    1980

CCAAGTCTCC ACCCCATTGA CGTCAATGGG AGTTTGTTTT GGCACCAAAA TCAACGGGAC    2040

TTTCCAAAAT GTCGTAACAA CTCCGCCCCA TTGACGCAAA TGGGCGGTAG GCGTGTACGG    2100

TGGGAGGTCT ATATAAGCAG AGCTCTCTGG CTAACTAGAG AACCCACTGC TTAACTGGCT    2160

TATCGAAATT AATACGACTC ACTATAGGGA GACCGGAAGC TTGGTACCGA GCTCGGATCT    2220

GCCACC ATG GCA ACA GGA TCA AGA ACA TCA CTG CTG CTG GCA TTT GGA       2268
       Met Ala Thr Gly Ser Arg Thr Ser Leu Leu Leu Ala Phe Gly
         1               5                  10

CTG CTG TGT CTG CCA TGG CTG CAA GAA GGA TCA GCA GCA GCA GCA GCG     2316
Leu Leu Cys Leu Pro Trp Leu Gln Glu Gly Ser Ala Ala Ala Ala Ala
 15              20                  25                      30

AAT TCA GAA ACC CAC GTC ACC GGG GGA AGT GCC GGC CAC ACC ACG GCT     2364
Asn Ser Glu Thr His Val Thr Gly Gly Ser Ala Gly His Thr Thr Ala
             35                  40                  45

GGG CTT GTT CGT CTC CTT TCA CCA GGC GCC AAG CAG AAC ATC CAA CTG     2412
Gly Leu Val Arg Leu Leu Ser Pro Gly Ala Lys Gln Asn Ile Gln Leu
              50                  55                  60

ATC AAC ACC AAC GGC AGT TGG CAC ATC AAT AGC ACG GCC TTG AAC TGC     2460
Ile Asn Thr Asn Gly Ser Trp His Ile Asn Ser Thr Ala Leu Asn Cys
             65                  70                  75

AAT GAA AGC CTT AAC ACC GGC TGG TTA GCA GGG CTC TTC TAT CAC CAC     2508
Asn Glu Ser Leu Asn Thr Gly Trp Leu Ala Gly Leu Phe Tyr His His
         80                  85                  90

AAA TTC AAC TCT TCA GGT TGT CCT GAG AGG TTG GCC AGC TGC CGA CGC     2556
Lys Phe Asn Ser Ser Gly Cys Pro Glu Arg Leu Ala Ser Cys Arg Arg
 95              100                 105                     110

CTT ACC GAT TTT GCC CAG GGC GGG GGT CCT ATC AGT TAC GCC AAC GGA     2604
Leu Thr Asp Phe Ala Gln Gly Gly Gly Pro Ile Ser Tyr Ala Asn Gly
              115                 120                 125

AGC GGC CTC GAT GAA CGC CCC TAC TGC TGG CAC TAC CCT CCA AGA CCT     2652
Ser Gly Leu Asp Glu Arg Pro Tyr Cys Trp His Tyr Pro Pro Arg Pro
              130                 135                 140

TGT GGC ATT GTG CCC GCA AAG AGC GTG TGT GGC CCG GTA TAT TGC TTC     2700
Cys Gly Ile Val Pro Ala Lys Ser Val Cys Gly Pro Val Tyr Cys Phe
              145                 150                 155

ACT CCC AGC CCC GTG GTG GTG GGA ACG ACC GAC AGG TCG GGC GCG CCT     2748
Thr Pro Ser Pro Val Val Val Gly Thr Thr Asp Arg Ser Gly Ala Pro
 160                 165                 170

ACC TAC AGC TGG GGT GCA AAT GAT ACG GAT GTC TTT GTC CTT AAC AAC     2796
Thr Tyr Ser Trp Gly Ala Asn Asp Thr Asp Val Phe Val Leu Asn Asn
175                 180                 185                 190

ACC AGG CCA CCG CTG GGC AAT TGG TTC GGT TGC ACC TGG ATG AAC TCA     2844
Thr Arg Pro Pro Leu Gly Asn Trp Phe Gly Cys Thr Trp Met Asn Ser
             195                 200                 205

ACT GGA TTC ACC AAA GTG TGC GGA GCG CCC CCT TGT GTC ATC GGA GGG     2892
Thr Gly Phe Thr Lys Val Cys Gly Ala Pro Pro Cys Val Ile Gly Gly
             210                 215                 220

GTG GGC AAC AAC ACC TTG CTC TGC CCC ACT GAT TGC TTC CGC AAG CAT     2940
Val Gly Asn Asn Thr Leu Leu Cys Pro Thr Asp Cys Phe Arg Lys His
             225                 230                 235
```

```
CCG GAA GCC ACA TAC TCT CGG TGC GGC TCC GGT CCC TGG ATT ACA CCC      2988
Pro Glu Ala Thr Tyr Ser Arg Cys Gly Ser Gly Pro Trp Ile Thr Pro
    240                 245                 250

AGG TGC ATG GTC GAC TAC CCG TAT AGG CTT TGG CAC TAT CCT TGT ACC      3036
Arg Cys Met Val Asp Tyr Pro Tyr Arg Leu Trp His Tyr Pro Cys Thr
255                 260                 265                 270

ATC AAT TAC ACC ATA TTC AAA GTC AGG ATG TAC GTG GGA GGG GTC GAG      3084
Ile Asn Tyr Thr Ile Phe Lys Val Arg Met Tyr Val Gly Gly Val Glu
                275                 280                 285

CAC AGG CTG GAA GCG GCC TGC AAC TGG ACG CGG GGC GAA CGC TGT GAT      3132
His Arg Leu Glu Ala Ala Cys Asn Trp Thr Arg Gly Glu Arg Cys Asp
            290                 295                 300

CTG GAA GAC AGG GAC AGG TCC GAG CTC AGC CCG TTA CTG CTG TCC ACC      3180
Leu Glu Asp Arg Asp Arg Ser Glu Leu Ser Pro Leu Leu Leu Ser Thr
        305                 310                 315

ACG CAG TGG CAG GTC CTT CCG TGT TCT TTC ACG ACC CTG CCA GCC TTG      3228
Thr Gln Trp Gln Val Leu Pro Cys Ser Phe Thr Thr Leu Pro Ala Leu
320                 325                 330

TCC ACC GGC CTC ATC CAC CTC CAC CAG AAC ATT GTG GAC GTG CAG TAC      3276
Ser Thr Gly Leu Ile His Leu His Gln Asn Ile Val Asp Val Gln Tyr
335                 340                 345                 350

TTG TAC GGG GTA GGG TCA AGC ATC GCG TCC TGG GCT ATT AAG TGG GAG      3324
Leu Tyr Gly Val Gly Ser Ser Ile Ala Ser Trp Ala Ile Lys Trp Glu
                355                 360                 365

TAC GAC GTT CTC CTG TTC CTT CTG CTT GCA GAC GCG CGC GTT TGC TCC      3372
Tyr Asp Val Leu Leu Phe Leu Leu Leu Ala Asp Ala Arg Val Cys Ser
            370                 375                 380

TGC TTG TGG ATG ATG TTA CTC ATA TCC CAA GCG GAG GCG GCT TTG GAG      3420
Cys Leu Trp Met Met Leu Leu Ile Ser Gln Ala Glu Ala Ala Leu Glu
        385                 390                 395

AAC TAATCTAGAG GGCCCTATTC TATAGTGTCA CCTAAATGCT AGAGGATCTT           3473
Asn

TGTGAAGGAA CCTTACTTCT GTGGTGTGAC ATAATTGGAC AAACTACCTA CAGAGATTTA    3533
AAGCTCTAAG GTAAATATAA AATTTTTAAG TGTATAATGT GTTAAACTAC TGATTCTAAT    3593
TGTTTGTGTA TTTTAGATTC CAACCTATGG AACTGATGAA TGGGAGCAGT GGTGGAATGC    3653
CTTTAATGAG GAAAACCTGT TTTGCTCAGA AGAAATGCCA TCTAGTGATG ATGAGGCTAC    3713
TGCTGACTCT CAACATTCTA CTCCTCCAAA AAAGAAGAGA AAGGTAGAAG ACCCCAAGGA    3773
CTTTCCTTCA GAATTGCTAA GTTTTTGAG TCATGCTGTG TTTAGTAATA GAACTCTTGC     3833
TTGCTTTGCT ATTTACACCA CAAAGGAAAA AGCTGCACTG CTATACAAGA AAATTATGGA    3893
AAAATATTCT GTAACCTTTA TAAGTAGGCA TAACAGTTAT AATCATAACA TACTGTTTTT    3953
TCTTACTCCA CACAGGCATA GAGTGTCTGC TATTAATAAC TATGCTCAAA AATTGTGTAC    4013
CTTTAGCTTT TTAATTTGTA AAGGGGTTAA TAAGGAATAT TTGATGTATA GTGCCTTGAC    4073
TAGAGATCAT AATCAGCCAT ACCACATTTG TAGAGGTTTT ACTTGCTTTA AAAAACCTCC    4133
CACACCTCCC CCTGAACCTG AAACATAAAA TGAATGCAAT TGTTGTTGTT AACTTGTTTA    4193
TTGCAGCTTA TAATGGTTAC AAATAAAGCA ATAGCATCAC AAATTTCACA ATAAAGCAT     4253
TTTTTTCACT GCATTCTAGT TGTGGTTTGT CCAAACTCAT CAATGTATCT TATCATGTCT    4313
GGATCGATCC CGCCATGGTA TCAACGCCAT ATTTCTATTT ACAGTAGGGA CCTCTTCGTT    4373
GTGTAGGTAC CGCTGTATTC CTAGGGAAAT AGTAGAGGCA CCTTGAACTG TCTGCATCAG    4433
CCATATAGCC CCCGCTGTTC GACTTACAAA CACAGGCACA GTACTGACAA ACCCATACAC    4493
CTCCTCTGAA ATACCCATAG TTGCTAGGGC TGTCTCCGAA CTCATTACAC CCTCCAAAGT    4553
CAGAGCTGTA ATTTCGCCAT CAAGGGCAGC GAGGGCTTCT CCAGATAAAA TAGCTTCTGC    4613
```

```
CGAGAGTCCC GTAAGGGTAG ACACTTCAGC TAATCCCTCG ATGAGGTCTA CTAGAATAGT    4673

CAGTGCGGCT CCCATTTTGA AAATTCACTT ACTTGATCAG CTTCAGAAGA TGGCGGAGGG    4733

CCTCCAACAC AGTAATTTTC CTCCCGACTC TTAAAATAGA AAATGTCAAG TCAGTTAAGC    4793

AGGAAGTGGA CTAACTGACG CAGCTGGCCG TGCGACATCC TCTTTTAATT AGTTGCTAGG    4853

CAACGCCCTC CAGAGGGCGT GTGGTTTTGC AAGAGGAAGC AAAAGCCTCT CCACCCAGGC    4913

CTAGAATGTT TCCACCCAAT CATTACTATG ACAACAGCTG TTTTTTTTAG TATTAAGCAG    4973

AGGCCGGGGA CCCCTGGCCC GCTTACTCTG GAGAAAAAGA AGAGAGGCAT TGTAGAGGCT    5033

TCCAGAGGCA ACTTGTCAAA ACAGGACTGC TTCTATTTCT GTCACACTGT CTGGCCCTGT    5093

CACAAGGTCC AGCACCTCCA TACCCCCTTT AATAAGCAGT TTGGGAACGG GTGCGGGTCT    5153

TACTCCGCCC ATCCCGCCCC TAACTCCGCC CAGTTCCGCC CATTCTCCGC CCCATGGCTG    5213

ACTAATTTTT TTTATTTATG CAGAGGCCGA GGCCGCCTCG GCCTCTGAGC TATTCCAGAA    5273

GTAGTGAGGA GGCTTTTTTG GAGGCCTAGG CTTTTGCAAA AAGCTAATTC              5323
```

( 2 ) INFORMATION FOR SEQ ID NO:10:

( i ) SEQUENCE CHARACTERISTICS:
       ( A ) LENGTH: 399 amino acids
       ( B ) TYPE: amino acid
       ( D ) TOPOLOGY: linear ( i i ) MOLECULE TYPE: protein ( x i ) SEQUENCE DESCRIPTION: SEQ ID NO:10:

```
Met Ala Thr Gly Ser Arg Thr Ser Leu Leu Leu Ala Phe Gly Leu Leu
 1               5                  10                  15

Cys Leu Pro Trp Leu Gln Glu Gly Ser Ala Ala Ala Ala Ala Asn Ser
            20                  25                  30

Glu Thr His Val Thr Gly Gly Ser Ala Gly His Thr Thr Ala Gly Leu
        35                  40                  45

Val Arg Leu Leu Ser Pro Gly Ala Lys Gln Asn Ile Gln Leu Ile Asn
    50                  55                  60

Thr Asn Gly Ser Trp His Ile Asn Ser Thr Ala Leu Asn Cys Asn Glu
65                  70                  75                  80

Ser Leu Asn Thr Gly Trp Leu Ala Gly Leu Phe Tyr His His Lys Phe
                85                  90                  95

Asn Ser Ser Gly Cys Pro Glu Arg Leu Ala Ser Cys Arg Arg Leu Thr
            100                 105                 110

Asp Phe Ala Gln Gly Gly Gly Pro Ile Ser Tyr Ala Asn Gly Ser Gly
        115                 120                 125

Leu Asp Glu Arg Pro Tyr Cys Trp His Tyr Pro Pro Arg Pro Cys Gly
    130                 135                 140

Ile Val Pro Ala Lys Ser Val Cys Gly Pro Val Tyr Cys Phe Thr Pro
145                 150                 155                 160

Ser Pro Val Val Val Gly Thr Thr Asp Arg Ser Gly Ala Pro Thr Tyr
                165                 170                 175

Ser Trp Gly Ala Asn Asp Thr Asp Val Phe Val Leu Asn Asn Thr Arg
            180                 185                 190

Pro Pro Leu Gly Asn Trp Phe Gly Cys Thr Trp Met Asn Ser Thr Gly
        195                 200                 205

Phe Thr Lys Val Cys Gly Ala Pro Pro Cys Val Ile Gly Gly Val Gly
    210                 215                 220

Asn Asn Thr Leu Leu Cys Pro Thr Asp Cys Phe Arg Lys His Pro Glu
```

|     |     |     |     | 225 |     |     |     |     | 230 |     |     |     |     | 235 |     |     |     |     | 240 |
| --- | --- | --- | --- | --- | --- | --- | --- | --- | --- | --- | --- | --- | --- | --- | --- | --- | --- | --- | --- |
| Ala | Thr | Tyr | Ser | Arg | Cys | Gly | Ser | Gly | Pro | Trp | Ile | Thr | Pro | Arg | Cys |
|     |     |     |     | 245 |     |     |     |     | 250 |     |     |     |     | 255 |     |
| Met | Val | Asp | Tyr | Pro | Tyr | Arg | Leu | Trp | His | Tyr | Pro | Cys | Thr | Ile | Asn |
|     |     |     |     | 260 |     |     |     |     | 265 |     |     |     |     | 270 |     |
| Tyr | Thr | Ile | Phe | Lys | Val | Arg | Met | Tyr | Val | Gly | Gly | Val | Glu | His | Arg |
|     |     |     |     | 275 |     |     |     |     | 280 |     |     |     |     | 285 |     |
| Leu | Glu | Ala | Ala | Cys | Asn | Trp | Thr | Arg | Gly | Glu | Arg | Cys | Asp | Leu | Glu |
|     |     |     |     | 290 |     |     |     |     | 295 |     |     |     |     | 300 |     |
| Asp | Arg | Asp | Arg | Ser | Glu | Leu | Ser | Pro | Leu | Leu | Leu | Ser | Thr | Thr | Gln |
| 305 |     |     |     |     |     |     |     |     | 310 |     |     |     |     | 315 |     |     |     |     | 320 |
| Trp | Gln | Val | Leu | Pro | Cys | Ser | Phe | Thr | Thr | Leu | Pro | Ala | Leu | Ser | Thr |
|     |     |     |     | 325 |     |     |     |     | 330 |     |     |     |     | 335 |     |
| Gly | Leu | Ile | His | Leu | His | Gln | Asn | Ile | Val | Asp | Val | Gln | Tyr | Leu | Tyr |
|     |     |     |     | 340 |     |     |     |     | 345 |     |     |     |     | 350 |     |
| Gly | Val | Gly | Ser | Ser | Ile | Ala | Ser | Trp | Ala | Ile | Lys | Trp | Glu | Tyr | Asp |
|     |     |     |     | 355 |     |     |     |     | 360 |     |     |     |     | 365 |     |
| Val | Leu | Leu | Phe | Leu | Leu | Leu | Ala | Asp | Ala | Arg | Val | Cys | Ser | Cys | Leu |
|     |     |     |     | 370 |     |     |     |     | 375 |     |     |     |     | 380 |     |
| Trp | Met | Met | Leu | Leu | Ile | Ser | Gln | Ala | Glu | Ala | Leu | Glu | Asn |
| 385 |     |     |     |     | 390 |     |     |     |     | 395 |     |     |     |

( 2 ) INFORMATION FOR SEQ ID NO:11:

( i ) SEQUENCE CHARACTERISTICS:
        ( A ) LENGTH: 5125 base pairs
        ( B ) TYPE: nucleic acid
        ( C ) STRANDEDNESS: single
        ( D ) TOPOLOGY: circular ( i i ) MOLECULE TYPE: DNA (genomic)

( i x ) FEATURE:
        ( A ) NAME/KEY: CDS
        ( B ) LOCATION: 2227..3225

( x i ) SEQUENCE DESCRIPTION: SEQ ID NO:11:

```
GCGTAATCTG CTGCTTGCAA ACAAAAAAAC CACCGCTACC AGCGGTGGTT TGTTTGCCGG      60
ATCAAGAGCT ACCAACTCTT TTTCCGAAGG TAACTGGCTT CAGCAGAGCG CAGATACCAA     120
ATACTGTCCT TCTAGTGTAG CCGTAGTTAG GCCACCACTT CAAGAACTCT GTAGCACCGC     180
CTACATACCT CGCTCTGCTA ATCCTGTTAC CAGTGGCTGC TGCCAGTGGC GATAAGTCGT     240
GTCTTACCGG GTTGGACTCA AGACGATAGT TACCGGATAA GGCGCAGCGG TCGGGCTGAA     300
CGGGGGGTTC GTGCACACAG CCCAGCTTGG AGCGAACGAC CTACACCGAA CTGAGATACC     360
TACAGCGTGA GCATTGAGAA AGCGCCACGC TTCCCGAAGG GAGAAAGGCG GACAGGTATC     420
CGGTAAGCGG CAGGGTCGGA ACAGGAGAGC GCACGAGGGA GCTTCCAGGG GGAAACGCCT     480
GGTATCTTTA TAGTCCTGTC GGGTTTCGCC ACCTCTGACT TGAGCGTCGA TTTTTGTGAT     540
GCTCGTCAGG GGGCGGAGC CTATGGAAAA ACGCCAGCAA CGCAAGCTAG CTTCTAGCTA     600
GAAATTGTAA ACGTTAATAT TTTGTTAAAA TTCGCGTTAA ATTTTTGTTA AATCAGCTCA     660
TTTTTTAACC AATAGGCCGA AATCGGCAAA ATCCCTTATA AATCAAAAGA ATAGCCCGAG     720
ATAGGGTTGA GTGTTGTTCC AGTTTGGAAC AAGAGTCCAC TATTAAAGAA CGTGGACTCC     780
AACGTCAAAG GGCGAAAAAC CGTCTATCAG GGCGATGGCC GCCCACTACG TGAACCATCA     840
CCCAAATCAA GTTTTTTGGG GTCGAGGTGC CGTAAAGCAC TAAATCGGAA CCCTAAAGGG     900
AGCCCCCGAT TTAGAGCTTG ACGGGGAAAG CCGGCGAACG TGGCGAGAAA GGAAGGGAAG     960
```

```
AAAGCGAAAG  GAGCGGGCGC  TAGGGCGCTG  GCAAGTGTAG  CGGTCACGCT  GCGCGTAACC     1020
ACCACACCCG  CCGCGCTTAA  TGCGCCGCTA  CAGGGCGCGT  ACTATGGTTG  CTTTGACGAG     1080
ACCGTATAAC  GTGCTTTCCT  CGTTGGAATC  AGAGCGGGAG  CTAAACAGGA  GGCCGATTAA     1140
AGGGATTTTA  GACAGGAACG  GTACGCCAGC  TGGATCACCG  CGGTCTTTCT  CAACGTAACA     1200
CTTTACAGCG  GCGCGTCATT  TGATATGATG  CGCCCCGCTT  CCCGATAAGG  GAGCAGGCCA     1260
GTAAAAGCAT  TACCCGTGGT  GGGGTTCCCG  AGCGGCCAAA  GGGAGCAGAC  TCTAAATCTG     1320
CCGTCATCGA  CTTCGAAGGT  TCGAATCCTT  CCCCCACCAC  CATCACTTTC  AAAAGTCCGA     1380
AGAATCTGC   TCCCTGCTTG  TGTGTTGGAG  GTCGCTGAGT  AGTGCGCGAG  TAAAATTTAA     1440
GCTACAACAA  GGCAAGGCTT  GACCGACAAT  GCATGAAGA   ATCTGCTTAG  GGTTAGGCGT     1500
TTTGCGCTGC  TTCGCGATGT  ACGGGCCAGA  TATACGCGTT  GACATTGATT  ATTGACTAGT     1560
TATTAATAGT  AATCAATTAC  GGGGTCATTA  GTTCATAGCC  CATATATGGA  GTTCCGCGTT     1620
ACATAACTTA  CGGTAAATGG  CCCGCCTGGC  TGACCGCCCA  ACGACCCCG   CCCATTGACG     1680
TCAATAATGA  CGTATGTTCC  CATAGTAACG  CCAATAGGGA  CTTTCCATTG  ACGTCAATGG     1740
GTGGACTATT  TACGGTAAAC  TGCCCACTTG  GCAGTACATC  AAGTGTATCA  TATGCCAAGT     1800
ACGCCCCCTA  TTGACGTCAA  TGACGGTAAA  TGGCCCGCCT  GGCATTATGC  CCAGTACATG     1860
ACCTTATGGG  ACTTTCCTAC  TTGGCAGTAC  ATCTACGTAT  TAGTCATCGC  TATTACCATG     1920
GTGATGCGGT  TTTGGCAGTA  CATCAATGGG  CGTGGATAGC  GGTTTGACTC  ACGGGGATTT     1980
CCAAGTCTCC  ACCCCATTGA  CGTCAATGGG  AGTTTGTTTT  GGCACCAAAA  TCAACGGGAC     2040
TTTCCAAAAT  GTCGTAACAA  CTCCGCCCCA  TTGACGCAAA  TGGGCGGTAG  GCGTGTACGG     2100
TGGGAGGTCT  ATATAAGCAG  AGCTCTCTGG  CTAACTAGAG  AACCCACTGC  TTAACTGGCT     2160
TATCGAAATT  AATACGACTC  ACTATAGGGA  GACCGGAAGC  TTGGTACCGA  GCTCGGATCT     2220
```

```
GCCACC ATG GCA ACA GGA TCA AGA ACA TCA CTG CTG CTG GCA TTT GGA            2268
       Met Ala Thr Gly Ser Arg Thr Ser Leu Leu Leu Ala Phe Gly
         1           5                      10

CTG CTG TGT CTG CCA TGG CTG CAA GAA GGA TCA GCA GCA GCA GCA GCG           2316
Leu Leu Cys Leu Pro Trp Leu Gln Glu Gly Ser Ala Ala Ala Ala Ala
 15              20                  25                      30

AAT TCA GAA ACC CAC GTC ACC GGG GGA AGT GCC GGC CAC ACC ACG GCT           2364
Asn Ser Glu Thr His Val Thr Gly Gly Ser Ala Gly His Thr Thr Ala
                 35                  40                  45

GGG CTT GTT CGT CTC CTT TCA CCA GGC GCC AAG CAG AAC ATC CAA CTG           2412
Gly Leu Val Arg Leu Leu Ser Pro Gly Ala Lys Gln Asn Ile Gln Leu
             50                  55                  60

ATC AAC ACC AAC GGC AGT TGG CAC ATC AAT AGC ACG GCC TTG AAC TGC           2460
Ile Asn Thr Asn Gly Ser Trp His Ile Asn Ser Thr Ala Leu Asn Cys
         65                  70                  75

AAT GAA AGC CTT AAC ACC GGC TGG TTA GCA GGG CTC TTC TAT CAC CAC           2508
Asn Glu Ser Leu Asn Thr Gly Trp Leu Ala Gly Leu Phe Tyr His His
     80                  85                  90

AAA TTC AAC TCT TCA GGT TGT CCT GAG AGG TTG GCC AGC TGC CGA CGC           2556
Lys Phe Asn Ser Ser Gly Cys Pro Glu Arg Leu Ala Ser Cys Arg Arg
 95                 100                 105                 110

CTT ACC GAT TTT GCC CAG GGC GGG GGT CCT ATC AGT TAC GCC AAC GGA           2604
Leu Thr Asp Phe Ala Gln Gly Gly Gly Pro Ile Ser Tyr Ala Asn Gly
                115                 120                 125

AGC GGC CTC GAT GAA CGC CCC TAC TGC TGG CAC TAC CCT CCA AGA CCT           2652
Ser Gly Leu Asp Glu Arg Pro Tyr Cys Trp His Tyr Pro Pro Arg Pro
            130                 135                 140

TGT GGC ATT GTG CCC GCA AAG AGC GTG TGT GGC CCG GTA TAT TGC TTC           2700
```

```
                Cys Gly Ile Val Pro Ala Lys Ser Val Cys Gly Pro Val Tyr Cys Phe
                        145                 150                 155

ACT CCC AGC CCC GTG GTG GTG GGA ACG ACC GAC AGG TCG GGC GCG CCT              2748
Thr Pro Ser Pro Val Val Val Gly Thr Thr Asp Arg Ser Gly Ala Pro
    160                 165                 170

ACC TAC AGC TGG GGT GCA AAT GAT ACG GAT GTC TTT GTC CTT AAC AAC              2796
Thr Tyr Ser Trp Gly Ala Asn Asp Thr Asp Val Phe Val Leu Asn Asn
175                 180                 185                 190

ACC AGG CCA CCG CTG GGC AAT TGG TTC GGT TGC ACC TGG ATG AAC TCA              2844
Thr Arg Pro Pro Leu Gly Asn Trp Phe Gly Cys Thr Trp Met Asn Ser
                195                 200                 205

ACT GGA TTC ACC AAA GTG TGC GGA GCG CCC CCT TGT GTC ATC GGA GGG              2892
Thr Gly Phe Thr Lys Val Cys Gly Ala Pro Pro Cys Val Ile Gly Gly
        210                 215                 220

GTG GGC AAC AAC ACC TTG CTC TGC CCC ACT GAT TGC TTC CGC AAG CAT              2940
Val Gly Asn Asn Thr Leu Leu Cys Pro Thr Asp Cys Phe Arg Lys His
            225                 230                 235

CCG GAA GCC ACA TAC TCT CGG TGC GGC TCC GGT CCC TGG ATT ACA CCC              2988
Pro Glu Ala Thr Tyr Ser Arg Cys Gly Ser Gly Pro Trp Ile Thr Pro
    240                 245                 250

AGG TGC ATG GTC GAC TAC CCG TAT AGG CTT TGG CAC TAT CCT TGT ACC              3036
Arg Cys Met Val Asp Tyr Pro Tyr Arg Leu Trp His Tyr Pro Cys Thr
255                 260                 265                 270

ATC AAT TAC ACC ATA TTC AAA GTC AGG ATG TAC GTG GGA GGG GTC GAG              3084
Ile Asn Tyr Thr Ile Phe Lys Val Arg Met Tyr Val Gly Gly Val Glu
                275                 280                 285

CAC AGG CTG GAA GCG GCC TGC AAC TGG ACG CGG GGC GAA CGC TGT GAT              3132
His Arg Leu Glu Ala Ala Cys Asn Trp Thr Arg Gly Glu Arg Cys Asp
                290                 295                 300

CTG GAA GAC AGG GAC AGG TCC GAG CTC AGC CCG TTA CTG CTG TCC ACC              3180
Leu Glu Asp Arg Asp Arg Ser Glu Leu Ser Pro Leu Leu Leu Ser Thr
        305                 310                 315

ACG CAG TGG CAG GTC CTT CCG TGT TCT TTC ACG ACC CTG CCA GCC                  3225
Thr Gln Trp Gln Val Leu Pro Cys Ser Phe Thr Thr Leu Pro Ala
320                 325                 330

TAATCTAGAG GGCCCTATTC TATAGTGTCA CCTAAATGCT AGAGGATCTT TGTGAAGGAA            3285
CCTTACTTCT GTGGTGTGAC ATAATTGGAC AAACTACCTA CAGAGATTTA AAGCTCTAAG            3345
GTAAATATAA AATTTTTAAG TGTATAATGT GTTAAACTAC TGATTCTAAT TGTTTGTGTA            3405
TTTTAGATTC CAACCTATGG AACTGATGAA TGGGAGCAGT GGTGGAATGC CTTTAATGAG            3465
GAAAACCTGT TTTGCTCAGA AGAAATGCCA TCTAGTGATG ATGAGGCTAC TGCTGACTCT            3525
CAACATTCTA CTCCTCCAAA AAAGAAGAGA AAGGTAGAAG ACCCCAAGGA CTTTCCTTCA            3585
GAATTGCTAA GTTTTTGAG TCATGCTGTG TTTAGTAATA GAACTCTTGC TTGCTTTGCT            3645
ATTTACACCA CAAAGGAAAA AGCTGCACTG CTATACAAGA AAATTATGGA AAAATATTCT            3705
GTAACCTTTA TAAGTAGGCA TAACAGTTAT AATCATAACA TACTGTTTTT TCTTACTCCA            3765
CACAGGCATA GAGTGTCTGC TATTAATAAC TATGCTCAAA AATTGTGTAC CTTTAGCTTT            3825
TTAATTTGTA AAGGGGTTAA TAAGGAATAT TTGATGTATA GTGCCTTGAC TAGAGATCAT            3885
AATCAGCCAT ACCACATTTG TAGAGGTTTT ACTTGCTTTA AAAAACCTCC CACACCTCCC            3945
CCTGAACCTG AAACATAAAA TGAATGCAAT TGTTGTTGTT AACTTGTTTA TTGCAGCTTA            4005
TAATGGTTAC AAATAAAGCA ATAGCATCAC AAATTTCACA AATAAAGCAT TTTTTCACT            4065
GCATTCTAGT TGTGGTTTGT CCAAACTCAT CAATGTATCT TATCATGTCT GGATCGATCC            4125
CGCCATGGTA TCAACGCCAT ATTTCTATTT ACAGTAGGGA CCTCTTCGTT GTGTAGGTAC            4185
CGCTGTATTC CTAGGGAAAT AGTAGAGGCA CCTTGAACTG TCTGCATCAG CCATATAGCC            4245
```

-continued

```
CCCGCTGTTC GACTTACAAA CACAGGCACA GTACTGACAA ACCCATACAC CTCCTCTGAA    4305
ATACCCATAG TTGCTAGGGC TGTCTCCGAA CTCATTACAC CCTCCAAAGT CAGAGCTGTA    4365
ATTTCGCCAT CAAGGGCAGC GAGGGCTTCT CCAGATAAAA TAGCTTCTGC CGAGAGTCCC    4425
GTAAGGGTAG ACACTTCAGC TAATCCCTCG ATGAGGTCTA CTAGAATAGT CAGTGCGGCT    4485
CCCATTTTGA AAATTCACTT ACTTGATCAG CTTCAGAAGA TGGCGGAGGG CCTCCAACAC    4545
AGTAATTTTC CTCCCGACTC TTAAAATAGA AAATGTCAAG TCAGTTAAGC AGGAAGTGGA    4605
CTAACTGACG CAGCTGGCCG TGCGACATCC TCTTTTAATT AGTTGCTAGG CAACGCCCTC    4665
CAGAGGGCGT GTGGTTTTGC AAGAGGAAGC AAAAGCCTCT CCACCCAGGC CTAGAATGTT    4725
TCCACCCAAT CATTACTATG ACAACAGCTG TTTTTTTTAG TATTAAGCAG AGGCCGGGGA    4785
CCCCTGGCCC GCTTACTCTG GAGAAAAAGA AGAGAGGCAT TGTAGAGGCT TCCAGAGGCA    4845
ACTTGTCAAA ACAGGACTGC TTCTATTTCT GTCACACTGT CTGGCCCTGT CACAAGGTCC    4905
AGCACCTCCA TACCCCCTTT AATAAGCAGT TTGGGAACGG GTGCGGGTCT TACTCCGCCC    4965
ATCCCGCCCC TAACTCCGCC CAGTTCCGCC CATTCTCCGC CCCATGGCTG ACTAATTTTT    5025
TTTATTTATG CAGAGGCCGA GGCCGCCTCG GCCTCTGAGC TATTCCAGAA GTAGTGAGGA    5085
GGCTTTTTTG GAGGCCTAGG CTTTTGCAAA AAGCTAATTC                          5125
```

( 2 ) INFORMATION FOR SEQ ID NO:12:

( i ) SEQUENCE CHARACTERISTICS:
      ( A ) LENGTH: 333 amino acids
      ( B ) TYPE: amino acid
      ( D ) TOPOLOGY: linear ( i i ) MOLECULE TYPE: protein ( x i ) SEQUENCE DESCRIPTION: SEQ ID NO:12:

```
Met Ala Thr Gly Ser Arg Thr Ser Leu Leu Leu Ala Phe Gly Leu Leu
 1               5                  10                  15

Cys Leu Pro Trp Leu Gln Glu Gly Ser Ala Ala Ala Ala Ala Asn Ser
                20                  25                  30

Glu Thr His Val Thr Gly Gly Ser Ala Gly His Thr Thr Ala Gly Leu
            35                  40                  45

Val Arg Leu Leu Ser Pro Gly Ala Lys Gln Asn Ile Gln Leu Ile Asn
        50                  55                  60

Thr Asn Gly Ser Trp His Ile Asn Ser Thr Ala Leu Asn Cys Asn Glu
 65                  70                  75                  80

Ser Leu Asn Thr Gly Trp Leu Ala Gly Leu Phe Tyr His His Lys Phe
                85                  90                  95

Asn Ser Ser Gly Cys Pro Glu Arg Leu Ala Ser Cys Arg Arg Leu Thr
               100                 105                 110

Asp Phe Ala Gln Gly Gly Gly Pro Ile Ser Tyr Ala Asn Gly Ser Gly
           115                 120                 125

Leu Asp Glu Arg Pro Tyr Cys Trp His Tyr Pro Pro Arg Pro Cys Gly
       130                 135                 140

Ile Val Pro Ala Lys Ser Val Cys Gly Pro Val Tyr Cys Phe Thr Pro
145                 150                 155                 160

Ser Pro Val Val Val Gly Thr Thr Asp Arg Ser Gly Ala Pro Thr Tyr
                165                 170                 175

Ser Trp Gly Ala Asn Asp Thr Asp Val Phe Val Leu Asn Asn Thr Arg
           180                 185                 190

Pro Pro Leu Gly Asn Trp Phe Gly Cys Thr Trp Met Asn Ser Thr Gly
```

|     |     | 195 |     |     |     |     | 200 |     |     |     |     | 205 |     |     |     |
| --- | --- | --- | --- | --- | --- | --- | --- | --- | --- | --- | --- | --- | --- | --- | --- |
| Phe | Thr | Lys | Val | Cys | Gly | Ala | Pro | Pro | Cys | Val | Ile | Gly | Gly | Val | Gly |
|     | 210 |     |     |     |     | 215 |     |     |     |     | 220 |     |     |     |     |
| Asn | Asn | Thr | Leu | Leu | Cys | Pro | Thr | Asp | Cys | Phe | Arg | Lys | His | Pro | Glu |
| 225 |     |     |     |     | 230 |     |     |     |     | 235 |     |     |     |     | 240 |
| Ala | Thr | Tyr | Ser | Arg | Cys | Gly | Ser | Gly | Pro | Trp | Ile | Thr | Pro | Arg | Cys |
|     |     |     |     | 245 |     |     |     |     | 250 |     |     |     |     | 255 |     |
| Met | Val | Asp | Tyr | Pro | Tyr | Arg | Leu | Trp | His | Tyr | Pro | Cys | Thr | Ile | Asn |
|     |     |     | 260 |     |     |     |     |     | 265 |     |     |     | 270 |     |     |
| Tyr | Thr | Ile | Phe | Lys | Val | Arg | Met | Tyr | Val | Gly | Gly | Val | Glu | His | Arg |
|     |     | 275 |     |     |     |     | 280 |     |     |     |     | 285 |     |     |     |
| Leu | Glu | Ala | Ala | Cys | Asn | Trp | Thr | Arg | Gly | Glu | Arg | Cys | Asp | Leu | Glu |
|     | 290 |     |     |     |     | 295 |     |     |     |     | 300 |     |     |     |     |
| Asp | Arg | Asp | Arg | Ser | Glu | Leu | Ser | Pro | Leu | Leu | Leu | Ser | Thr | Thr | Gln |
| 305 |     |     |     |     | 310 |     |     |     |     | 315 |     |     |     |     | 320 |
| Trp | Gln | Val | Leu | Pro | Cys | Ser | Phe | Thr | Thr | Leu | Pro | Ala |     |     |     |
|     |     |     |     | 325 |     |     |     |     | 330 |     |     |     |     |     |     |

MAMMALIAN EXPRESSION SYSTEMS FOR HCV PROTEINS

This is a division of U.S. patent application Ser. No. 08/417,478 filed Apr. 5, 1995 now abandoned, which is a continuation of 08/144,099 filed Oct. 28, 1993 now abandoned, which is a continuation of 07/830,024 filed Jan. 31, 1992, now abandoned.

BACKGROUND OF THE INVENTION

This invention relates generally to Hepatitis C Virus (HCV), and more particularly, relates to mammalian expression systems capable of generating HCV proteins and uses of these proteins.

Descriptions of Hepatitis diseases causing jaundice and icterus have been known to man since antiquity. Viral hepatitis is now known to include a group of viral agents with distinctive viral organization protein structure and mode of replication, causing hepatitis with different degrees of severity of hepatic damage through different routes of transmission. Acute viral hepatitis is clinically diagnosed by well-defined patient symptoms including jaundice, hepatic tenderness and an elevated level of liver transaminases such as Aspartate Transaminase and Alanine Transaminase.

Serological assays currently are employed to further distinguish between Hepatitis-A and Hepatitis-B. Non-A Non-B Hepatitis (NANBH) is a term first used in 1975 that described cases of post-transfusion hepatitis not caused by either Hepatitis A Virus or Hepatitis B Virus. Feinstone et al., *New Engl. J. Med.* 292:454–457 (1975). The diagnosis of NANBH has been made primarily by means of exclusion on the basis of serological analysis for the presence of Hepatitis A and Hepatitis B. NANBH is responsible for about 90% of the cases of post-transfusion hepatitis. Hollinger et al. in N. R. Rose et al., eds., *Manual of Clinical Immunology*, American Society for Microbiology, Washington, D.C., 558–572 (1986).

Attempts to identify the NANBH virus by virtue of genomic similarity to one of the known hepatitis viruses have failed thus far, suggesting that NANBH has a distinctive genomic organization and structure. Fowler et al., *J. Med. Virol.* 12:205–213 (1983), and Weiner et al., *J. Med. Virol.* 21:239–247 (1987). Progress in developing assays to detect antibodies specific for NANBH has been hampered by difficulties encountered in identifying antigens associated with the virus. Wands et al., U.S. Pat. No. 4,870,076; Wands et al., *Proc. Natl. Acad. Sci.* 83:6608–6612 (1986); Ohori et al., *J. Med. Virol.* 12:161–178 (1983); Bradley et al., *Proc. Natl. Acad. Sci.* 84:6277–6281 (1987); Akatsuka et al., *J. Med. Virol.* 20:43–56 (1986).

In May of 1988, a collaborative effort of Chiron Corporation with the Centers for Disease Control resulted in the identification of a putative NANB agent, Hepatitis C Virus (HCV). M. Houghton et al. cloned and expressed in *E. coli* a NANB agent obtained from the infectious plasma of a chimp. Kuo et al., *Science* 244:359–361 (1989); Choo et al., *Science* 244:362–364 (1989). CDNA sequences from HCV were identified which encode antigens that react immunologically with antibodies present in a majority of the patients clinically diagnosed with NANBH. Based on the information available and on the molecular structure of HCV, the genetic makeup of the virus consists of single stranded linear RNA (positive strand) of molecular weight approximately 9.5 kb, and possessing one continuous translational open reading frame. J. A. Cuthbert, *Amer. J. Med. Sci.* 299:346–355 (1990). It is a small enveloped virus resembling the Flaviviruses. Investigators have made attempts to identify the NANB agent by ultrastructural changes in hepatocytes in infected individuals. H. Gupta, *Liver* 8:111–115 (1988); D. W. Bradley *J. Virol. Methods* 10:307–319 (1985). Similar ultrastructural changes in hepatocytes as well as PCR amplified HCV RNA sequences have been detected in NANBH patients as well as in chimps experimentally infected with infectious HCV plasma. T. Shimizu et al., *Proc. Natl. Acad. Sci.* 87:6441–6444 (1990).

Considerable serological evidence has been found to implicate HCV as the etiological agent for post-transfusion NANBH. H. Alter et al., *N. Eng. J. Med.* 321:1494–1500 (1989); Estaben et al., *The Lancet:* August 5:294–296 (1989); C. Van Der Poel et al., *The Lancet* August 5:297–298 (1989); G. Sbolli, *J. Med. Virol.* 30:230–232 (1990); M. Makris et al., *The Lancet* 335:1117–1119 (1990). Although the detection of HCV antibodies eliminates 70 to 80% of NANBH infected blood from the blood supply system, the antibodies apparently are readily detected during the chronic state of the disease, while only 60% of the samples from the acute NANBH stage are HCV antibody positive. H. Alter et al., *New Eng. J. Med.* 321:1994–1500 (1989). The prolonged interval between exposure to HCV and antibody detection, and the lack of adequate information regarding the profile of immune response to various structural and non-structural proteins raises questions regarding the infectious state of the patient in the latent and antibody negative phase during NANBH infection.

Since discovery of the putative HCV etiological agent as discussed supra, investigators have attempted to express the putative HCV proteins in human expression systems and also to isolate the virus. To date, no report has been published in which HCV has been expressed efficiently in mammalian expression systems, and the virus has not been propagated in tissue culture systems.

Therefore, there is a need for the development of assay reagents and assay systems to identify acute infection and viremia which may be present, and not currently detected by commercially-available assays. These tools are needed to help distinguish between acute and persistent, on-going and/or chronic infection from those likely to be resolved, and to define the prognostic course of NANBH infection, in order to develop preventive and/or therapeutic strategies. Also, the expression systems that allow for secretion of these glycosylated antigens would be helpful to purify and manufacture diagnostic and therapeutic reagents.

SUMMARY OF THE INVENTION

This invention provides novel mammalian expression systems that are capable of generating high levels of expressed proteins of HCV. In particular, full-length structural fragments of HCV are expressed as a fusion with the Amyloid Precursor Protein (APP) or Human Growth Hormone (HGH) secretion signal. These unique expression systems allow for the production of high levels of HCV proteins, contributing to the proper processing, gycolsylation and folding of the viral protein(s) in the system. In particular, the present invention provides the plasmids pHCV-162, pHCV-167, pHCV-168, pHCV-169 and pHCV-170. The APP-HCV-E2 fusion proteins expressed by mammalian expression vectors pHCV-162 and pHCV-167 also are included. Further, HGH-HCV-E2 fusion proteins expressed by a mammalian expression vectors pHCV-168, pHCV-169 and pHCV-170 are provided.

The present invention also provides a method for detecting HCV antigen or antibody in a test sample suspected of containing HCV antigen or antibody, wherein the improvement comprises contacting the test sample with a glycosylated HCV antigen produced in a mammalian expression system. Also provided is a method for detecting HCV antigen or antibody in a test sample suspected of containing HCV antigen or antibody, wherein the improvement comprises contacting the test sample with an antibody produced by using a glycosylated HCV antigen produced in a mammalian expression system. The antibody can be monoclonal or polyclonal.

The present invention further provides a test kit for detecting the presence of HCV antigen or HCV antigen in a test sample suspected of containing said HCV antigen or antibody, comprising a container containing a glycosylated HCV antigen produced in a mammalian expression system. The test kit also can include an antibody produced by using a glycosylated HCV antigen produced in a mammalian expression system. Another test kit provided by the present invention comprises a container containing an antibody produced by using a glycosylated HCV antigen produced in a mammalian expression system. The antibody provided by the test kits can be monoclonal or polyclonal.

DETAILED DESCRIPTION OF THE INVENTION

Figure 1:
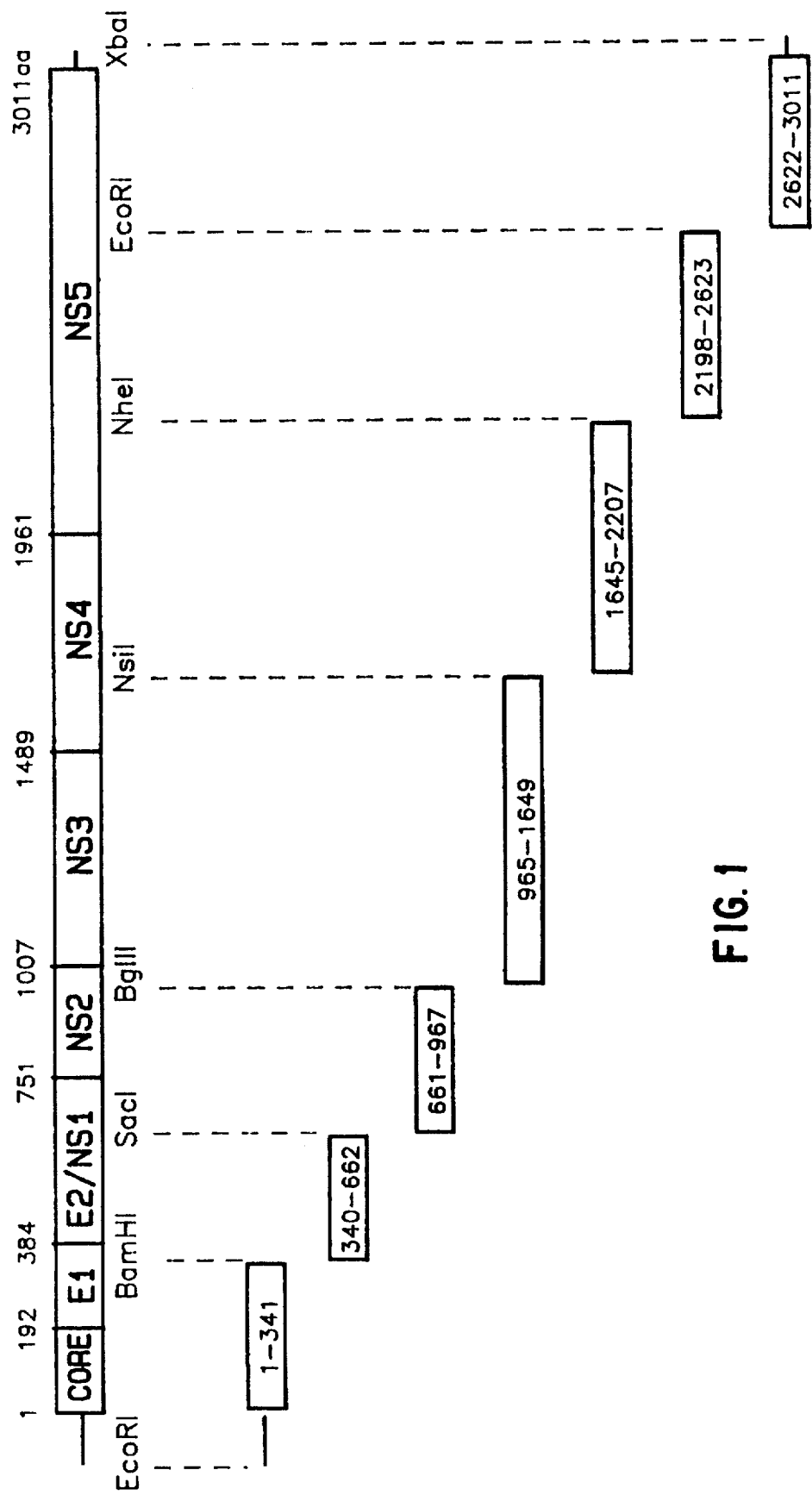
FIG. 1 presents a schematic representation of the strategy employed to generate and assemble HCV genomic clones.
Figure 2:
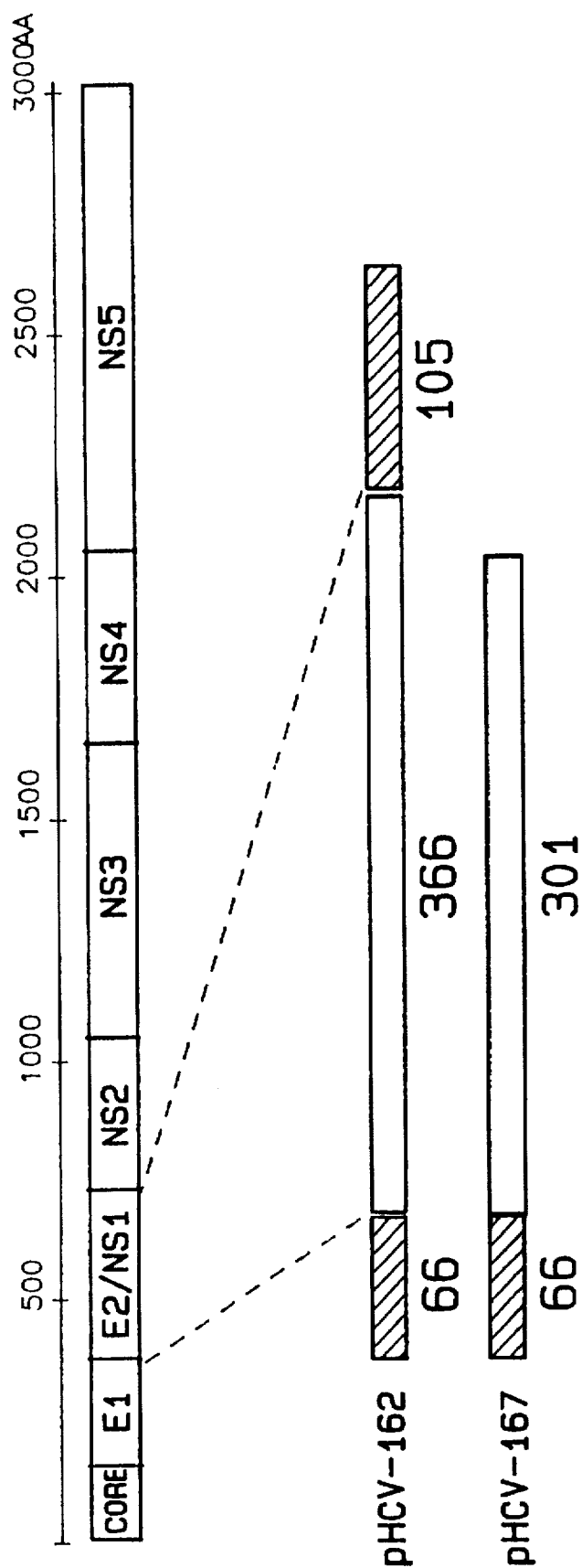
FIG. 2 presents a schematic representation of the location and amino acid composition of the APP-HCV-E2 fusion proteins expressed by the mammalian expression vectors pHCV-162 and pHCV-167.
Figure 3:
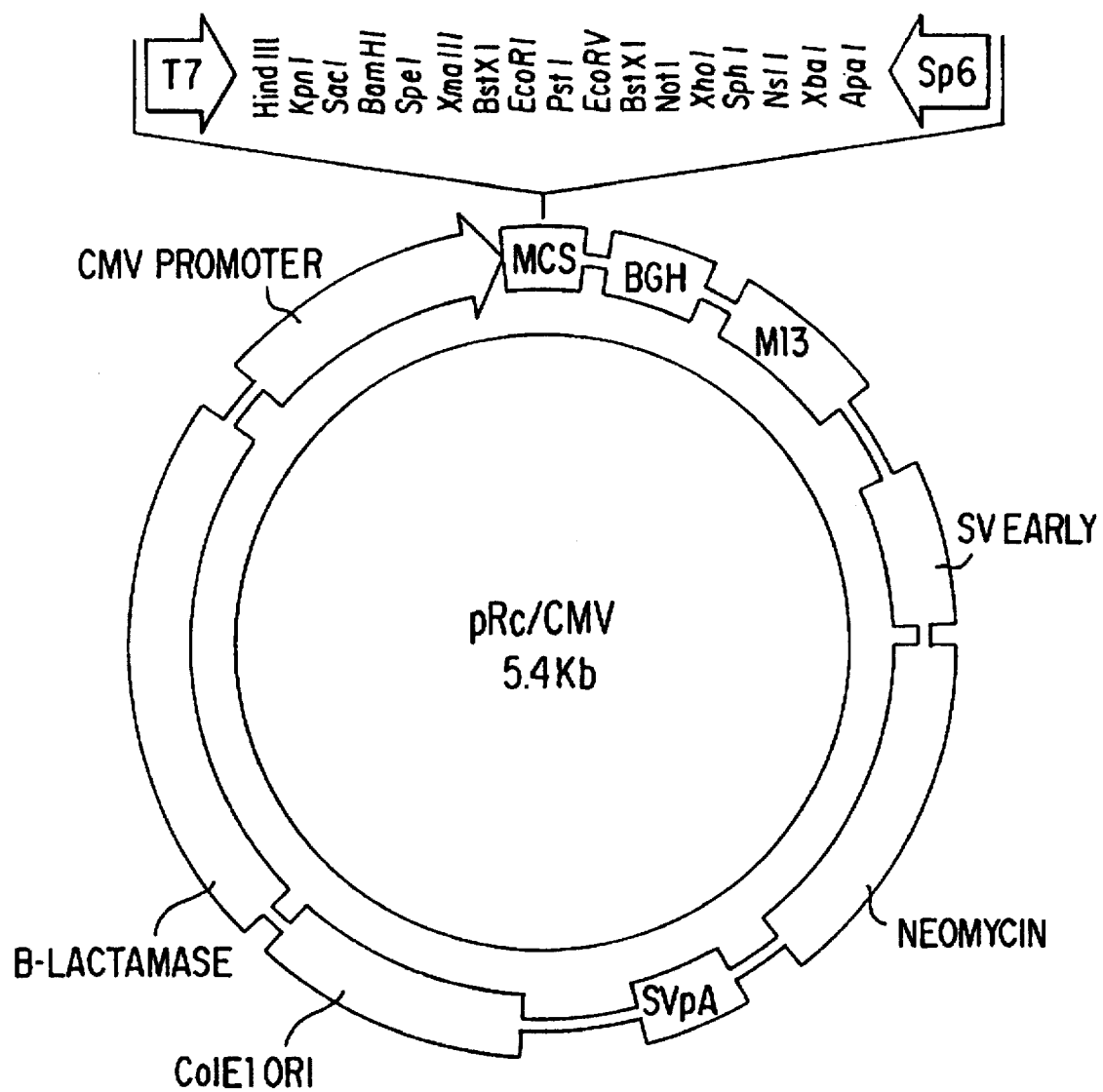
FIG. 3 presents a schematic representation of the mammalian expression vector pRC/CMV.

The present invention provides full-length genomic clones useful in a variety of aspects. Such full-length genomic clones can allow culture of the HCV virus which in turn is useful for a variety of purposes. Successful culture of the HCV virus can allow for the development of viral replication inhibitors, viral proteins for diagnostic applications, viral proteins for therapeutics, and specifically structural viral antigens, including, for example, HCV putative envelope, HCV putative E1 and HCV putative E2 fragments.

Cell lines which can be used for viral replication are numerous, and include (but are not limited to), for example, primary hepatocytes, permanent or semi-permanent hepatocytes, cultures transfected with transforming viruses or transforming genes. Especially useful cell lines could include, for example, permanent hepatocyte cultures that continuously express any of several heterologous RNA polymerase genes to amplify HCV RNA sequences under the control of these specific RNA polymerase sequences.

Sources of HCV viral sequences encoding structural antigens include putative core, putative E1 and putative E2 fragments. Expression can be performed in both prokaryotic and eukaryotic systems. The expression of HCV proteins in mammalian expression systems allows for glycosylated proteins such as the E1 and E2 proteins, to be produced. These glycosylated proteins have diagnostic utility in a variety of aspects, including, for example, assay systems for screening and prognostic applications. The mammalian expression of HCV viral proteins allows for inhibitor studies including elucidation of specific viral attachment sites or sequences and/or viral receptors on susceptible cell types, for example, liver cells and the like.

The procurement of specific expression clones developed as described herein in mammalian expression systems provides antigens for diagnostic assays which can determine the stage of HCV infection, such as, for example, acute versus on-going or persistent infections, and/or recent infection versus past exposure. These specific expression clones also provide prognostic markers for resolution of disease such as to distinguish resolution of disease from chronic hepatitis caused by HCV. It is contemplated that earlier seroconversion to glycosylated structural antigens possibly may be detected by using proteins produced in these mammalian expression systems. Antibodies, both monoclonal and polyclonal, also may be produced from the proteins derived from these mammalian expression systems which then in turn may be used for diagnostic, prognostic and therapeutic applications. Also, reagents produced from these novel expression systems described herein may be useful in the characterization and or isolation of other infectious agents.

Proteins produced from these mammalian expression systems, as well as reagents produced from these proteins, can be placed into appropriate container and packaged as test kits for convenience in performing assays. Other aspects of the present invention include a polypeptide comprising an HCV epitope attached to a solid phase and an antibody to an HCV epitope attached to a solid phase. Also included are methods for producing a polypeptide containing an HCV epitope comprising incubating host cells transformed with a mammalian expression vector containing a sequence encoding a polypeptide containing an HCV epitope under conditions which allow expression of the polypeptide, and a polypeptide containing an HCV epitope produced by this method.

The present invention provides assays which utilize the recombinant or synthetic polypeptides provided by the invention, as well as the antibodies described herein in various formats, any of which may employ a signal generating compound in the assay. Assays which do not utilize signal generating compounds to provide a means of detection also are provided. All of the assays described generally detect either antigen or antibody, or both, and include contacting a test sample with at least one reagent provided herein to form at least one antigen/antibody complex and detecting the presence of the complex. These assays are described in detail herein.

Vaccines for treatment of HCV infection comprising an immunogenic peptide obtained from a mammalian expression system containing an HCV epitope, or an inactivated preparation of HCV, or an attenuated preparation of HCV also are included in the present invention. Also included in the present invention is a method for producing antibodies to HCV comprising administering to an individual an isolated immunogenic polypeptide containing an HCV epitope in an amount sufficient to produce an immune response in the inoculated individual.

Also provided by the present invention is a tissue culture grown cell infected with HCV.

The term "antibody containing body component" (or test sample) refers to a component of an individual's body which is the source of the antibodies of interest. These components are well known in the art. These samples include biological samples which can be tested by the methods of the present invention described herein and include human and animal body fluids such as whole blood, serum, plasma, cerebrospinal fluid, urine, lymph fluids, and various external sections of the respiratory, intestinal and genitourinary tracts, tears, saliva, milk, white blood cells, myelomas and the like, biological fluids such as cell culture supernatants, fixed tissue specimens and fixed cell specimens.

After preparing recombinant proteins, as described by the present invention, the recombinant proteins can be used to develop unique assays as described herein to detect either the presence of antigen or antibody to HCV. These compositions also can be used to develop monoclonal and/or polyclonal antibodies with a specific recombinant protein which specifically binds to the immunological epitope of HCV which is desired by the routineer. Also, it is contemplated that at least one recombinant protein of the invention can be used to develop vaccines by following methods known in the art.

It is contemplated that the reagent employed for the assay can be provided in the form of a kit with one or more containers such as vials or bottles, with each container containing a separate reagent such as a monoclonal antibody, or a cocktail of monoclonal antibodies, or a polypeptide (either recombinant or synthetic) employed in the assay.

"Solid phases" ("solid supports") are known to those in the art and include the walls of wells of a reaction tray, test tubes, polystyrene beads, magnetic beads, nitrocellulose strips, membranes, microparticles such as latex particles, and others. The "solid phase" is not critical and can be selected by one skilled in the art. Thus, latex particles, microparticles, magnetic or non-magnetic beads, membranes, plastic tubes, walls of microtiter wells, glass or silicon chips and sheep red blood cells are all suitable examples. Suitable methods for immobilizing peptides on solid phases include ionic, hydrophobic, covalent interactions and the like. A "solid phase", as used herein, refers to any material which is insoluble, or can be made insoluble by a subsequent reaction. The solid phase can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid phase and which has the ability to immobilize the capture reagent through a specific binding reaction. The receptor molecule enables the indirect binding of the capture reagent to a solid phase material before the performance of the assay or during the performance of the assay. The solid phase thus can be a plastic, derivatized plastic, magnetic or non-magnetic metal, glass or silicon surface of a test tube, microliter well, sheet, bead, microparticle, chip, and other configurations known to those of ordinary skill in the art.

It is contemplated and within the scope of the invention that the solid phase also can comprise any suitable porous material with sufficient porosity to allow access by detection antibodies and a suitable surface affinity to bind antigens. Microporous structures are generally preferred, but materials with gel structure in the hydrated state may be used as well. Such useful solid supports include:

natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer. All of these materials may be used in suitable shapes, such as films, sheets, or plates, or they may be coated onto or bonded or laminated to appropriate inert carriers, such as paper, glass, plastic films, or fabrics.

The porous structure of nitrocellulose has excellent absorption and adsorption qualities for a wide variety of reagents including monoclonal antibodies. Nylon also possesses similar characteristics and also is suitable. It is contemplated that such porous solid supports described hereinabove are preferably in the form of sheets of thickness from about 0.01 to 0.5 mm, preferably about 0.1 mm. The pore size may vary within wide limits, and is preferably from about 0.025 to 15 microns, especially from about 0.15 to 15 microns. The surfaces of such supports may be activated by chemical processes which cause covalent linkage of the antigen or antibody to the support. The irreversible binding of the antigen or antibody is obtained, however, in general, by adsorption on the porous material by poorly understood hydrophobic forces. Suitable solid supports also are described in U.S. patent application Ser. No. 227,272.

The "indicator reagent" comprises a "signal generating compound" (label) which is capable of generating a measurable signal detectable by external means conjugated (attached) to a specific binding member for HCV. "Specific binding member" as used herein means a member of a specific binding pair. That is, two different molecules where one of the molecules through chemical or physical means specifically binds to the second molecule. In addition to being an antibody member of a specific binding pair for HCV, the indicator reagent also can be a member of any specific binding pair, including either hapten-anti-hapten systems such as biotin or anti-biotin, avidin or biotin, a carbohydrate or a lectin, a complementary nucleotide sequence, an effector or a receptor molecule, an enzyme cofactor and an enzyme, an enzyme inhibitor or an enzyme, and the like. An immunoreactive specific binding member can be an antibody, an antigen, or an antibody/antigen complex that is capable of binding either to HCV as in a sandwich assay, to the capture reagent as in a competitive assay, or to the ancillary specific binding member as in an indirect assay.

The various "signal generating compounds" (labels) contemplated include chromogens, catalysts such as enzymes, luminescent compounds such as fluorescein and rhodamine, chemiluminescent compounds, radioactive elements, and direct visual labels. Examples of enzymes include alkaline phosphatase, horseradish peroxidase, beta-galactosidase, and the like. The selection of a particular label is not critical, but it will be capable of producing a signal either by itself or in conjunction with one or more additional substances.

The various "signal generating compounds" (labels) contemplated include chromogens, catalysts such as enzymes, luminescent compounds such as fluorescein and rhodamine, chemiluminescent compounds such as acridinium, phenanthridinium and dioxetane compounds, radioactive elements, and direct visual labels. Examples of enzymes include alkaline phosphatase, horseradish peroxidase, beta-galactosidase, and the like. The selection of a particular label is not critical, but it will be capable of producing a signal either by itself or in conjunction with one or more additional substances.

Other embodiments which utilize various other solid phases also are contemplated and are within the scope of this invention. For example, ion capture procedures for immobilizing an immobilizable reaction complex with a negatively charged polymer, described in co-pending U.S. patent application Ser. No. 150,278 corresponding to EP publication 0326100, and U.S. patent application Ser. No. 375,029 (EP publication no. 0406473) both of which enjoy common ownership and are incorporated herein by reference, can be employed according to the present invention to effect a fast solution-phase immunochemical reaction. An immobilizable immune complex is separated from the rest of the reaction mixture by ionic interactions between the negatively charged poly-anion/immune complex and the previously treated, positively charged porous matrix and detected by using various signal generating systems previously described, including those described in chemiluminescent signal measurements as described in co-pending U.S. patent application Ser. No. 921,979 corresponding to EPO Publication No. 0 273,115, which enjoys common ownership and which is incorporated herein by reference.

Also, the methods of the present invention can be adapted for use in systems which utilize microparticle technology including in automated and semi-automated systems wherein the solid phase comprises a microparticle. Such systems include those described in pending U.S. patent application Ser. Nos. 425,651 and 425,643, which correspond to published EPO applications Nos. EP 0 425 633 and EP 0 424 634, respectively, which are incorporated herein by reference.

The use of scanning probe microscopy (SPM) for immunoassays also is a technology to which the monoclonal antibodies of the present invention are easily adaptable. In scanning probe microscopy, in particular in atomic force microscopy, the capture phase, for example, at least one of the monoclonal antibodies of the invention, is adhered to a solid phase and a scanning probe microscope is utilized to detect antigen/antibody complexes which may be present on the surface of the solid phase. The use of scanning tunnelling microscopy eliminates the need for labels which normally must be utilized in many immunoassay systems to detect antigen/antibody complexes. Such a system is described in pending U.S. patent application Ser. No. 662,147, which enjoys common ownership and is incorporated herein by reference.

The use of SPM to monitor specific binding reactions can occur in many ways. In one embodiment, one member of a specific binding partner (analyte specific substance which is the monoclonal antibody of the invention) is attached to a surface suitable for scanning. The attachment of the analyte specific substance may be by adsorption to a test piece which comprises a solid phase of a plastic or metal surface, following methods known to those of ordinary skill in the art. Or, covalent attachment of a specific binding partner (analyte specific substance) to a test piece which test piece comprises a solid phase of derivatized plastic, metal, silicon, or glass may be utilized. Covalent attachment methods are known to those skilled in the art and include a variety of means to irreversibly link specific binding partners to the test piece. If the test piece is silicon or glass, the surface must be activated prior to attaching the specific binding partner. Activated silane compounds such as triethoxy amino propyl silane (available from Sigma Chemical Co., St. Louis, Mo.), triethoxy vinyl silane (Aldrich Chemical Co., Milwaukee, Wis.), and (3-mercapto-propyl)-trimethoxy silane (Sigma Chemical Co., St. Louis, Mo.) can be used to introduce reactive groups such as amino-, vinyl, and thiol, respectively. Such activated surfaces can be used to link the binding partner directly (in the cases of amino or thiol) or the activated surface can be further reacted with linkers such as glutaraldehyde, bis(succinimidyl)suberate, SPPD 9 succinimidyl 3-[2-pyridyldithio]propionate), SMCC (succinimidyl-4-[N-maleimidomethyl]cyclohexane-1-carboxylate), SIAB (succinimidyl[4-iodoacetyl] aminobenzoate), and SMPB (succinimidyl 4-[1- maleimidophenyl]butyrate) to separate the binding partner from the surface. The vinyl group can be oxidized to provide a means for covalent attachment. It also can be used as an anchor for the polymerization of various polymers such as poly acrylic acid, which can provide multiple attachment points for specific binding partners. The amino surface can be reacted with oxidized dextrans of various molecular weights to provide hydrophilic linkers of different size and capacity. Examples of oxidizable dextrans include Dextran T-40 (molecular weight 40,000 daltons), Dextran T-110 (molecular weight 110,000 daltons), Dextran T-500 (molecular weight 500,000 daltons), Dextran T-2M (molecular weight 2,000,000 daltons) (all of which are available from Pharmacia, LOCATION), or Ficoll (molecular weight 70,000 daltons (available from Sigma Chemical Co., St. Louis, Mo.). Also, polyelectrolyte interactions may be used to immobilize a specific binding partner on a surface of a test piece by using techniques and chemistries described by pending U.S. patent application Ser. No. 150,278, filed Jan. 29, 1988, and Ser. No. 375,029, filed Jul. 7, 1989, each of which enjoys common ownership and each of which is incorporated herein by reference. The preferred method of attachment is by covalent means. Following attachment of a specific binding member, the surface may be further treated with materials such as serum, proteins, or other blocking agents to minimize non-specific binding. The surface also may be scanned either at the site of manufacture or point of use to verify its suitability for assay purposes. The scanning process is not anticipated to alter the specific binding properties of the test piece.

Various other assay formats may be used, including "sandwich" immunoassays and competitive probe assays. For example, the monoclonal antibodies produced from the proteins of the present invention can be employed in various assay systems to determine the presence, if any, of HCV proteins in a test sample. Fragments of these monoclonal antibodies provided also may be used. For example, in a first assay format, a polyclonal or monoclonal anti-HCV antibody or fragment thereof, or a combination of these antibodies, which has been coated on a solid phase, is contacted with a test sample which may contain HCV proteins, to form a mixture. This mixture is incubated for a time and under conditions sufficient to form antigen/antibody complexes. Then, an indicator reagent comprising a monoclonal or a polyclonal antibody or a fragment thereof, which specifically binds to the HCV fragment, or a combination of these antibodies, to which a signal generating compound has been attached, is contacted with the antigen/antibody complexes to form a second mixture. This second mixture then is incubated for a time and under conditions sufficient to form antibody/antigen/antibody complexes. The presence of HCV antigen present in the test sample and captured on the solid phase, if any, is determined by detecting the measurable signal generated by the signal generating compound. The amount of HCV antigen present in the test sample is proportional to the signal generated.

Alternatively, a polyclonal or monoclonal anti-HCV antibody or fragment thereof, or a combination of these antibodies which is bound to a solid support, the test sample and an indicator reagent comprising a monoclonal or polyclonal antibody or fragments thereof, which specifically binds to HCV antigen, or a combination of these antibodies to which a signal generating compound is attached, are contacted to form a mixture. This mixture is incubated for a time and under conditions sufficient to form antibody/antigen/antibody complexes. The presence, if any, of HCV proteins present in the test sample and captured on the solid phase is determined by detecting the measurable signal generated by the signal generating compound. The amount of HCV proteins present in the test sample is proportional to the signal generated.

In another alternate assay format, one or a combination of one or more monoclonal antibodies of the invention can be employed as a competitive probe for the detection of antibodies to HCV protein. For example, HCV proteins, either alone or in combination, can be coated on a solid phase. A test sample suspected of containing antibody to HCV antigen then is incubated with an indicator reagent comprising a signal generating compound and at least one monoclonal antibody of the invention for a time and under conditions sufficient to form antigen/antibody complexes of either the test sample and indicator reagent to the solid phase or the indicator reagent to the solid phase. The reduction in binding of the monoclonal antibody to the solid phase can be quantitatively measured. A measurable reduction in the signal compared to the signal generated from a confirmed negative NANB hepatitis test sample indicates the presence of anti-HCV antibody in the test sample.

In yet another detection method, each of the monoclonal antibodies of the present invention can be employed in the detection of HCV antigens in fixed tissue sections, as well as fixed cells by immunohistochemical analysis.

In addition, these monoclonal antibodies can be bound to matrices similar to CNBr-activated Sepharose and used for the affinity purification of specific HCV proteins from cell cultures, or biological tissues such as blood and liver.

The monoclonal antibodies of the invention can also be used for the generation of chimeric antibodies for therapeutic use, or other similar applications.

The monoclonal antibodies or fragments thereof can be provided individually to detect HCV antigens. Combinations of the monoclonal antibodies (and fragments thereof) provided herein also may be used together as components in a mixture or "cocktail" of at least one anti-HCV antibody of the invention with antibodies to other HCV regions, each having different binding specificities. Thus, this cocktail can include the monoclonal antibodies of the invention which are directed to HCV proteins and other monoclonal antibodies to other antigenic determinants of the HCV genome.

The polyclonal antibody or fragment thereof which can be used in the assay formats should specifically bind to a specific HCV region or other HCV proteins used in the assay. The polyclonal antibody used preferably is of mammalian origin; human, goat, rabbit or sheep anti-HCV polyclonal antibody can be used. Most preferably, the polyclonal antibody is rabbit polyclonal anti-HCV antibody. The polyclonal antibodies used in the assays can be used either alone or as a cocktail of polyclonal antibodies. Since the cocktails used in the assay formats are comprised of either monoclonal antibodies or polyclonal antibodies having different HCV specificity, they would be useful for diagnosis, evaluation and prognosis of HCV infection, as well as for studying HCV protein differentiation and specificity.

In another assay format, the presence of antibody and/or antigen to HCV can be detected in a simultaneous assay, as follows. A test sample is simultaneously contacted with a capture reagent of a first analyte, wherein said capture reagent comprises a first binding member specific for a first analyte attached to a solid phase and a capture reagent for a second analyte, wherein said capture reagent comprises a first binding member for a second analyte attached to a second solid phase, to thereby form a mixture. This mixture is incubated for a time and under conditions sufficient to form capture reagent/first analyte and capture reagent/ second analyte complexes. These so-formed complexes then are contacted with an indicator reagent comprising a member of a binding pair specific for the first analyte labelled with a signal generating compound and an indicator reagent comprising a member of a binding pair specific for the second analyte labelled with a signal generating compound to form a second mixture. This second mixture is incubated for a time and under conditions sufficient to form capture reagent/first analyte/indicator reagent complexes and capture reagent/second analyte/indicator reagent complexes. The presence of one or more analytes is determined by detecting a signal generated in connection with the complexes formed on either or both solid phases as an indication of the presence of one or more analytes in the test sample. In this assay format, proteins derived from human expression systems may be utilized as well as monoclonal antibodies produced from the proteins derived from the mammalian expression systems as disclosed herein. Such assay systems are described in greater detail in pending U.S. patent application Ser. No. 07/574,821 entitled Simultaneous Assay for Detecting One Or More Analytes, filed Aug. 29, 1990, which enjoys common ownership and is incorporated herein by reference.

In yet other assay formats, recombinant proteins may be utilized to detect the presence of anti-HCV in test samples. For example, a test sample is incubated with a solid phase to which at least one recombinant protein has been attached. These are reacted for a time and under conditions sufficient to form antigen/antibody complexes. Following incubation, the antigen/antibody complex is detected. Indicator reagents may be used to facilitate detection, depending upon the assay system chosen. In another assay format, a test sample is contacted with a solid phase to which a recombinant protein produced as described herein is attached and also is contacted with a monoclonal or polyclonal antibody specific for the protein, which preferably has been labelled with an indicator reagent. After incubation for a time and under conditions sufficient for antibody/antigen complexes to form, the solid phase is separated from the free phase, and the label is detected in either the solid or free phase as an indication of the presence of HCV antibody. Other assay formats utilizing the proteins of the present invention are contemplated. These include contacting a test sample with a solid phase to which at least one recombinant protein produced in the mammalian expression system has been attached, incubating the solid phase and test sample for a time and under conditions sufficient to form antigen/antibody complexes, and then contacting the solid phase with a labelled recombinant antigen. Assays such as this and others are described in pending U.S. patent application Ser. No. 07/787,710, which enjoys common ownership and is incorporated herein by reference.

While the present invention discloses the preference for the use of solid phases, it is contemplated that the proteins of the present invention can be utilized in non-solid phase assay systems. These assay systems are known to those skilled in the art, and are considered to be within the scope of the present invention.

The present invention will now be described by way of examples, which are meant to illustrate, but not to limit, the spirit and scope of the invention.

EXAMPLES

Example 1

Generation of HCV Genomic Clones

RNA isolated from the serum or plasma of a chimpanzee (designated as "CO") experimentally infected with HCV, or an HCV seropositive human patient (designated as "LG") was transcribed to cDNA using reverse transcriptase employing either random hexamer primers or specific antisense primers derived from the prototype HCV-1 sequence. The sequence has been reported by Choo et al. (Choo et al., *Proc. Nat'l. Acad. Sci. USA* 88:2451–2455 [1991], and is available through GenBank data base, Accession No. M62321). This cDNA then was amplified using PCR and AmpliTaq® DNA polymerase. (available in the Gene Amp Kit® from Perkin Elmer Cetus, Norwalk, Conn. 06859) employing either a second sense primer located approximately 1000–2000 nucleotides upstream of the specific antisense primer or a pair of sense and antisense primers flanking a 1000–2000 nucleotide fragment of HCV. After 25 to 35 cycles of amplification following standard procedures known in the art, an aliquot of this reaction mixture was subjected to nested PCR (or "PCR-2"), wherein a pair of sense and antisense primers located internal to the original pair of PCR primers was employed to further amplify HCV gene segments in quantities sufficient for analysis and subcloning, utilizing endonuclease recognition sequences present in the second set of PCR primers. In this manner, seven adjacent HCV DNA fragments were generated which then could be assembled using the generic cloning strategy presented and described in FIG. 1. The location of the specific primers used in this manner are presented in Table 1 and are numbered according to the HCV-1 sequence reported by Choo et al (GenBank data base, Accession No. M62321). Prior to assembly, the DNA sequence of each of the individual fragments was determined and translated into the genomic amino acid sequences presented in SEQUENCE ID. NO. 1 and 2, respectively, for CO and LG, respectively. Comparison of the genomic polypeptide of CO with that of HCV-1 demonstrated 98 amino acid differences. Comparison of the genomic polypeptide of CO with that of LG. demonstrated 150 amino acid differences. Comparison of the genomic polypeptide of LG with that of HCV-1 demonstrated 134 amino acid differences.

Example 2

Expression of the HCV E2 Protein As A Fusion With The Amyloid Precursor Protein (APP)

The HCV E2 protein from CO developed as described in Example 1 was expressed as a fusion with the Amyloid Precursor Protein (APP). APP has been described by Kang et al., *Nature* 325:733–736 (1987). Briefly, HCV amino acids 384–749 of the CO isolate were used to replace the majority of the APP coding sequence as demonstrated in FIG. 2. A HindIII-StyI DNA fragment representing the amino-terminal 66 amino acids and a BglII-XbaI fragment representing the carboxyl-terminal 105 amino acids of APP were ligated to a PCR derived HCV fragment from CO representing HCV amino acids 384–749 containing StyI and BglII restriction sites on its 5' and 3' ends, respectively. This APP-HCV-E2 fusion gene cassette then was cloned into the commercially available mammalian expression vector pRC/CMV shown in FIG. 3, (available from Invitrogen, San Diego, Calif.) at the unique HindIII and XbaI sites. After transformation into *E. coli* DH5α, a clone designated pHCV-162 was isolated, which placed the expression of the APP-HCV-E2 fusion gene cassette under control of the strong CMV promotor. The complete nucleotide sequence of the mammalian expression vector pHCV-162 is presented in SEQUENCE ID. NO. 3. Translation of nucleotides 922 through 2535 results in the complete amino acid sequence of the APP-HCV-E2 fusion protein expressed by pHCV-162 as presented in SEQUENCE ID. NO. 4.

A primary Human Embryonic Kidney (HEK) cell line transformed with human adenovirus type 5, designated as HEK-293, was used for all transfections and expression analyses. HEK-293 cells were maintained in Minimum Essential Medium (MEM) which was supplemented with 10% fetal calf serum (FCS), penicillin and streptomycin.

Figure 4:
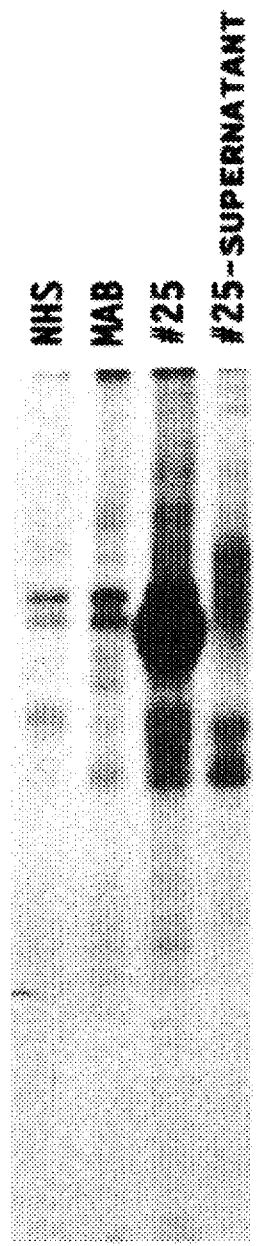
FIG. 4 presents the RIPA results obtained for the APP-HCV-E2 fusion protein expressed by pHCV-162 in HEK-293 cells using HCV antibody positive human sera.
Figure 5:
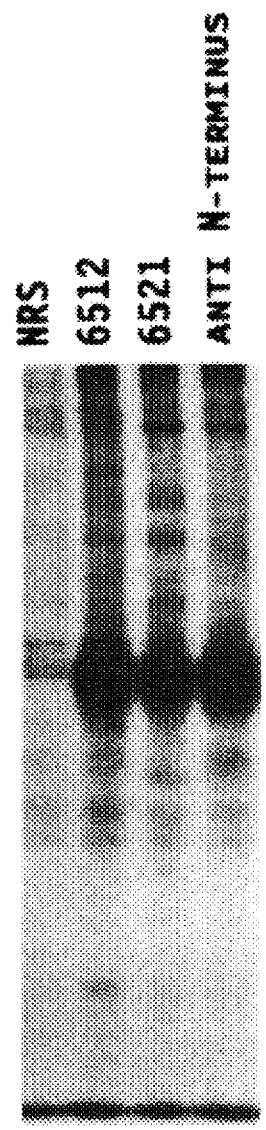
FIG. 5 presents the RIPA results obtained for the APP-HCV-E2 fusion protein expressed by pHCV-162 in HEK-293 cells using rabbit polyclonal sera directed against synthetic peptides.
Figure 6:
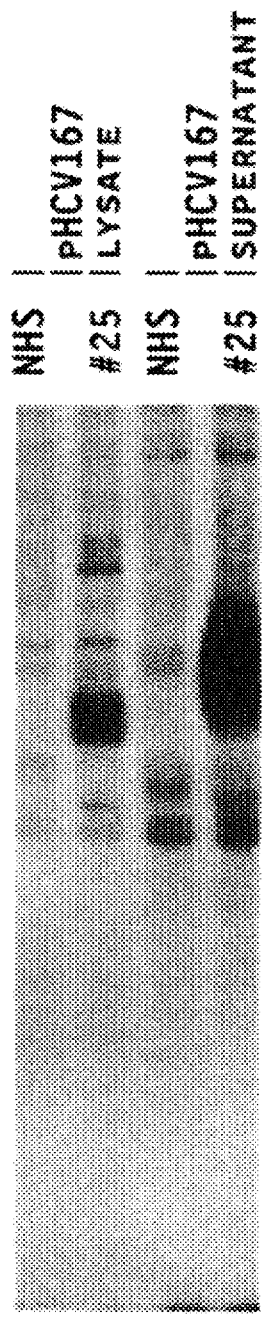
FIG. 6 presents the RIPA results obtained for the APP-HCV-E2 fusion protein expressed by pHCV-167 in HEK-293 cells using HCV antibody positive human sera.
Figure 7:
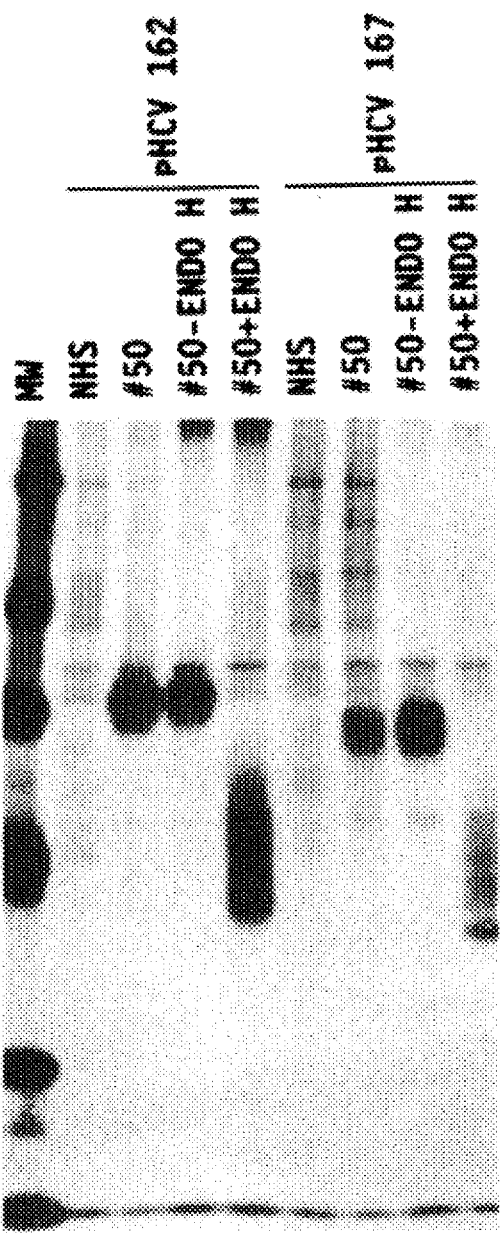
FIG. 7 presents the Endoglycosidase-H digestion of the immunoprecipitated APP-HCV-E2 fusion proteins expressed by pHCV-162 and pHCV-167 in HEK-293 cells.

Approximately 20 µg of purified DNA from pHCV-162 was transfected into HEK-293 cells using the modified calcium phosphate protocol as reported by Chen et al., *Molecular and Cellular Biology* 7(8):2745–2752. (1987). The calcium-phosphate-DNA solution was incubated on the HEK-293 cells for about 15 to 24 hours. The solution was removed, the cells were washed twice with MEM media, and then the cells were incubated in MEM media for an additional 24 to 48 hours. In order to analyze protein expression, the transfected cells were metabolically labelled with 100 µCi/ml S-35 methionine and cysteine for 12 to 18 hours. The culture media was removed and stored, and the cells were washed in MEM media and then lysed in phosphate buffered saline (PBS) containing 1% Triton X-100® (available from Sigma Chemical Co., St. Louis, Mo.), 0.1% sodium dodecyl sulfate (SDS), and 0.5% deoxychloate, designated as PBS-TDS. This cell lysate then was frozen at −70° C. for 2 to 24 hours, thawed on ice and then clarified by centrifugation at 50,000×g force for one hour at 4° C. Standard radio-immunoprecipitation assays (RIPAs) then were conducted on those labelled cell lysates and/or culture medias. Briefly, labelled cell lysates and/or culture medias were incubated with 2 to 5 µl of specific sera at 4° C. for one hour. Protein-A Sepharose then was added and the samples were further incubated for one hour at 4° C. with agitation. The samples were then centrifuged and the pellets washed several times with PBS-TDS buffer. Proteins recovered by immunoprecipitation were eluted by heating in an electrophoresis sample buffer (50 mM Tris-HCl, pH 6.8, 100 mM dithiothreitol [DTT], 2% SDS, 0.1% bromophenol blue, and 10% glycerol) for five minutes at 95° C. The eluted proteins then were separated by SDS polyacrylamide gels which were subsequently treated with a fluorographic reagent such as Enlightening® (available from NEN [DuPont], Boston, Mass.), dried under vacuum and exposed to x-ray film at −70° C. with intensifying screens. FIG. 4 presents a RIPA analysis of pHCV-162 transfected HEK cell lysate precipitated with normal human sera (NHS), a monoclonal antibody directed against APP sequences which were replaced in this construct (MAB), and an HCV antibody positive human sera (#25). Also presented in FIG. 4 is the culture media (supernatant) precipitated with the same HCV antibody positive human sera (#25). From FIG. 4, it can be discerned that while only low levels of an HCV specific protein of approximately 75K daltons is detected in the culture media of HEK-293 cells transfected with pHCV-162, high levels of intracellular protein expression of the APP-HCV-E2 fusion protein of approximately 70K daltons is evident.

In order to further characterize this APP-HCV-E2 fusion protein, rabbit polyclonal antibody raised against synthetic peptides were used in a similar RIPA, the results of which are illustrated in FIG. 5. As can be discerned from this Figure, normal rabbit serum (NRS) does not precipitate the 70K dalton protein while rabbit sera raised against HCV amino acids 509–551 (6512), HCV amino acids 380–436 (6521), and APP amino acids 45–62 (anti-N-terminus) are highly specific for the 70K dalton APP-HCV-E2 fusion protein.

In order to enhance secretion of this APP-HCV-E2 fusion protein, another clone was generated which fused only the amino-terminal 66 amino acids of APP, which contain the putative secretion signal sequences to the HCV-E2 sequences. In addition, a strongly hydrophobic sequence at the carboxyl-terminal end of the HCV-E2 sequence which was identified as a potential transmembrane spanning region was deleted. The resulting clone was designated as pHCV-167 and is schematically illustrated in FIG. 2. The complete nucleotide sequence of the mammalian expression vector pHCV-167 is presented in SEQUENCE ID. NO. 5 Translation of nucleotides 922 through 2025 results in the complete amino acid sequence of the APP-HCV-E2 fusion protein expressed by pHCV-167 as presented in SEQUENCE ID. NO. 6. Purified DNA of pHCV-167 was transfected into HEK-293 cells and analyzed by RIPA and polyacrylamide SDS gels as described previously herein. FIG. 6 presents the results in which a normal human serum sample (NHS) failed to recognize the APP-HCV-E2 fusion protein present in either the cell lysate or the cell supernatant of HEK-293 cells transfected with pHCV-167. The positive control HCV serum sample (#25), however, precipitated an approximately 65K dalton APP-HCV-E2 fusion protein present in the cell lysate of HEK-293 cells transfected with pHCV-167. In addition, substantial quantities of secreted APP-HCV-E2 protein of approximately 70K daltons was precipitated from the culture media by serum #25.

Digestion with Endoglycosidase-H (Endo-H) was conducted to ascertain the extent and composition of N-linked glycosylation in the APP-HCV E2 fusion proteins expressed by pHCV-167 and pHCV-162 in HEK-293 cells. Briefly, multiple aliquots of labelled cell lysates from pHCV-162 and pHCV-167 transfected HEK-293 cells were precipitated with human serum #50 which contained antibody to HCV E2 as previously described. The Protein-A sepharose pellet containing the immunoprecipitated protein-antibody complex was then resuspended in buffer (75 mM sodium acetate, 0.05% SDS) containing or not containing 0.05 units per ml of Endo-H (Sigma). Digestions were performed at 37° C. for 12 to 18 hours and all samples were analyzed by polyacrylamide SDS gels as previously described. FIG. 7 presents the results of Endo-H digestion. Carbon-14 labelled molecular weight standards (MW) (obtained from Amersham, Arlington Heights, Ill.) are common on all gels and represent 200K, 92.5K, 69K, 46K, 30K and 14.3K daltons, respectively. Normal human serum (NHS) does not immunoprecipitate the APP-HCV-E2 fusion protein expressed by either pHCV-162 or pHCV-167, while human serum positive for HCV E2 antibody (#50) readily detects the 72K dalton APP-HCV-E2 fusion protein in pHCV-162 and the 65K dalton APP-HCV E2 fusion protein in pHCV-167. Incubation of these immunoprecipitated proteins in the absence of Endo-H (#50 −Endo-H) does not significantly affect the quantity or mobility of either pHCV-162 or pHCV-167 expressed proteins. Incubation in the presence of Endo-H (#50 +Endo-H), however, drastically reduces the mobility of the proteins expressed by pHCV-162 and pHCV-167, producing a heterogenous size distribution. The predicted molecular weight of the non-glycosylated polypeptide backbone of pHCV-162 is approximately 59K daltons. Endo-H treatment of pHCV-162 lowers the mobility to a minimum of approximately 44K daltons, indicating that the APP-HCV-E2 fusion protein produced by pHCV-162 is proteolytically cleaved at the carboxyl-terminal end. A size of approximately 44K daltons is consistent with cleavage at or near HCV amino acid 720. Similarly, Endo-H treatment of pHCV-167 lowers the mobility to a minimum of approximately 41K daltons, which compares favorably with the predicted molecular weight of approximately 40K daltons for the intact APP-HCV-E2 fusion protein expressed by pHCV-167.

Example 3

Detection of HCV E2 Antibodies

Radio-immunoprecipitation assay (RIPA) and polyacrylamide SDS gel analysis previously described was used to screen numerous serum samples for the presence of antibody directed against HCV E2 epitopes. HEK-293 cells transfected with pHCV-162 were metabolically labelled and cell lysates prepared as previously described. In addition to RIPA analysis, all serum samples were screened for the presence of antibodies directed against specific HCV recombinant antigens representing distinct areas of the HCV genome using the Abbott Matrix® System. (available from Abbott Laboratories, Abbott Park, Ill. 60064, U.S. Pat. No. 5,075,077). In the Matrix data presented in Tables 2 through 7, C100 yeast represents the NS4 region containing HCV amino acids 1569–1930, C100 E. coli represents HCV amino acids 1676–1930, NS3 represents HCV amino acids 1192–1457, and CORE represents HCV amino acids 1–150.

Figure 8:
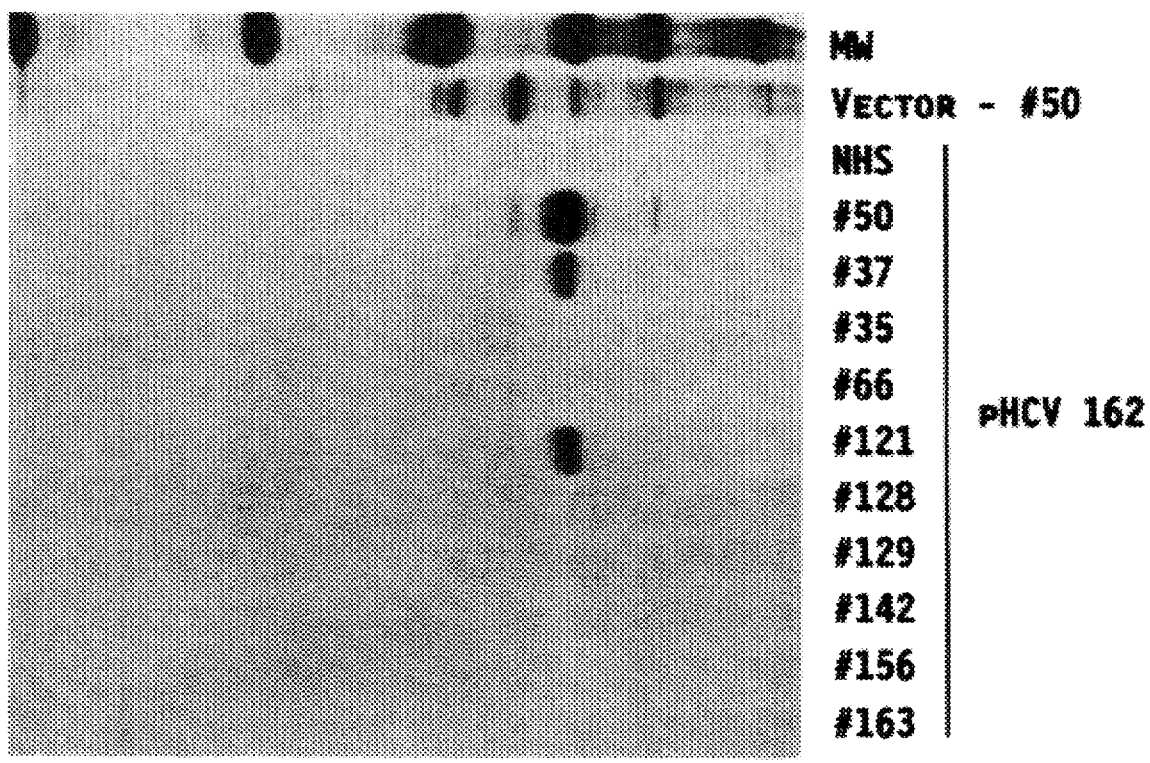
FIG. 8 presents the RIPA results obtained when American HCV antibody positive sera were screened against the APP-HCV-E2 fusion protein expressed by pHCV-162 in HEK-293 cells.
Figure 9:
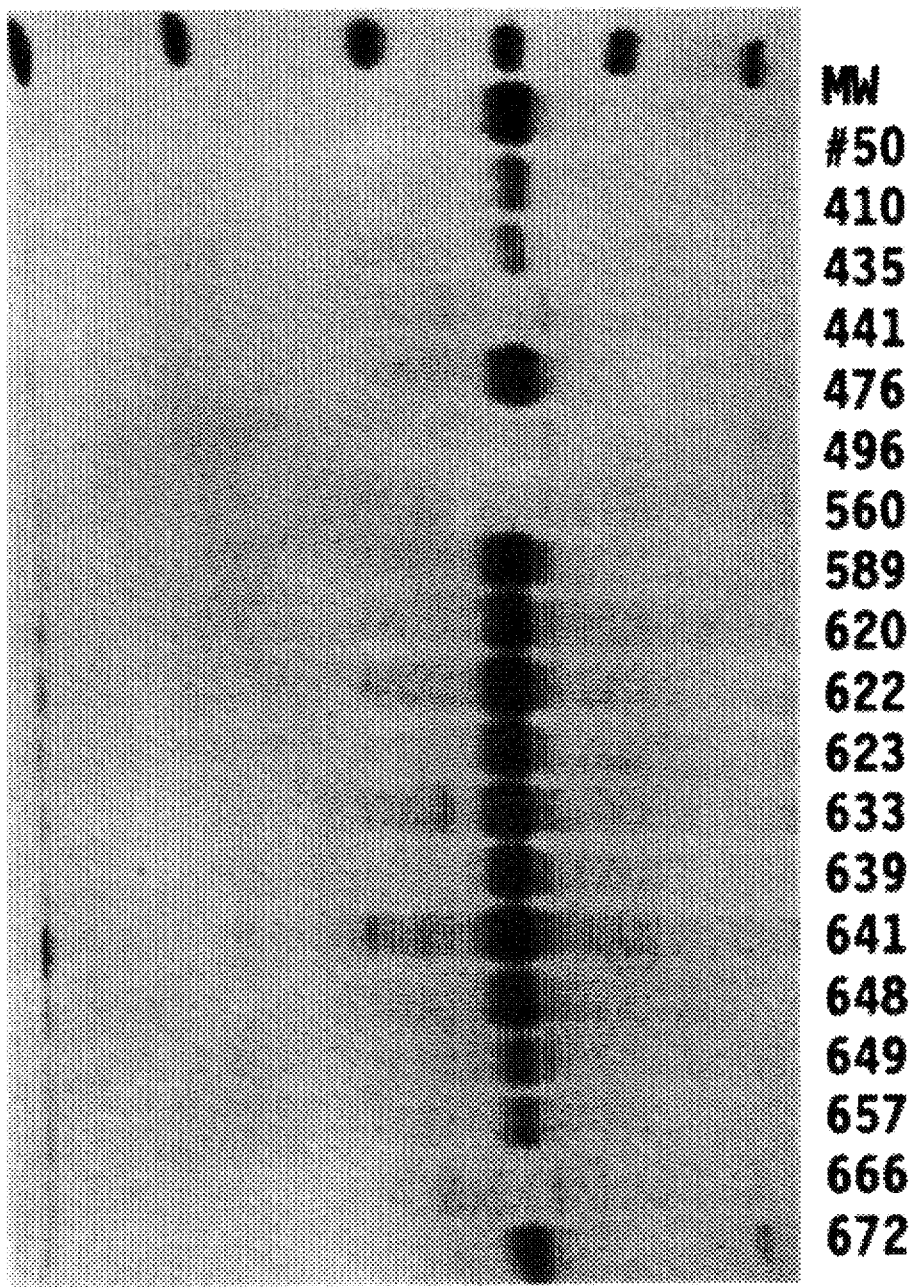
FIG. 9 presents the RIPA results obtained when the sera from Japanese volunteer blood donors were screened against the APP-HCV-E2 fusion protein expressed by pHCV-162 in HEK-293 cells.
Figure 10:
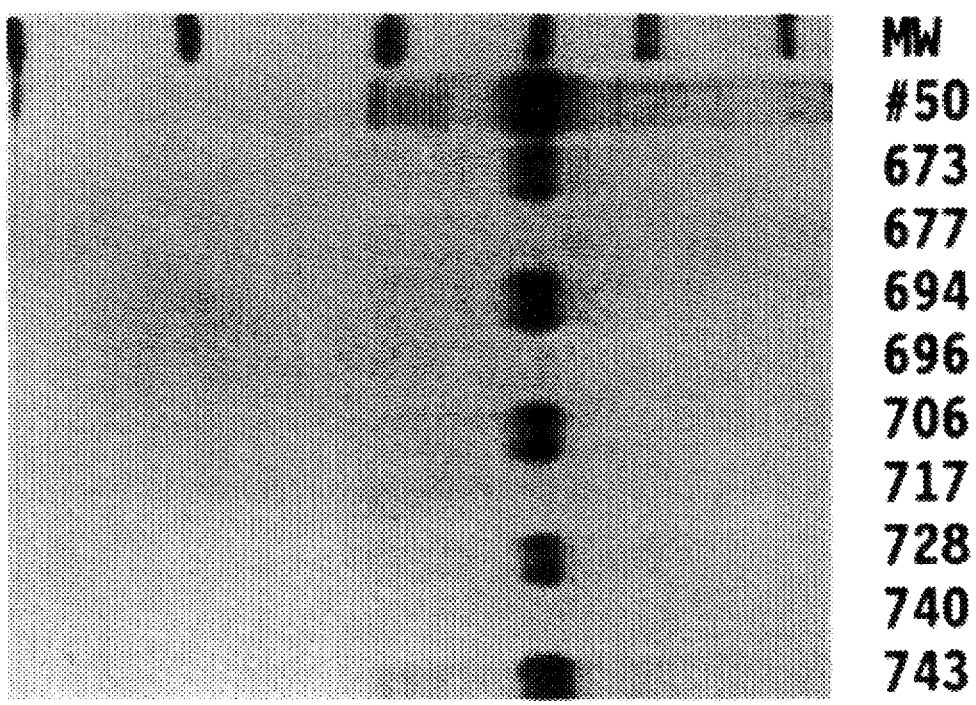
FIG. 10 presents the RIPA results obtained when the sera from Japanese volunteer blood donors were screened against the APP-HCV-E2 fusion protein expressed by pHCV-162 in HEK-293 cells.

FIG. 8 presents a representative RIPA result obtained using pHCV-162 cell lysate to screen HCV antibody positive American blood donors and transfusion recipients. Table 2 summarizes the antibody profile of these various American blood samples, with seven of seventeen (41%) samples demonstrating HCV E2 antibody. Genomic variability in the E2 region has been demonstrated between different HCV isolates, particularly in geographically distinct isolates which may lead to differences in antibody responses. We therefore screened twenty-six Japanese volunteer blood donors and twenty Spanish hemodialysis patients previously shown to contain HCV antibody for the presence of specific antibody to the APP-HCV E2 fusion protein expressed by pHCV-162. FIGS. 9 and 10 present the RIPA analysis on twenty-six Japanese volunteer blood donors. Positive control human sera (#50) and molecular weight standards (MW) appear in both figures in which the specific immunoprecipitation of the approximately 72K dalton APP-HCV-E2 fusion protein is demonstrated for several of the serum samples tested. Table 3 presents both the APP-HCV-E2 RIPA and Abbott Matrix® results summarizing the antibody profiles of each of the twenty-six Japanese samples tested. Table 4 presents similar data for the twenty Spanish hemodialysis patients tested. Table 5 summarizes the RIPA results obtained using pHCV-162 to detect HCV E2 specific antibody in these various samples. Eighteen of twenty-six (69%) Japanese volunteers blood donors, fourteen of twenty (70%) Spanish hemodialysis patients, and seven of seventeen (41%) American blood donors or transfusion recipients demonstrated a specific antibody response against the HCV E2 fusion protein. The broad immunoreactivity demonstrated by the APP-HCV-E2 fusion protein expressed by pHCV-162 suggests the recognition of conserved epitopes within HCV E2.

Serial bleeds from five transfusion recipients which seroconverted to HCV antibody were also screened using the APP-HCV-E2 fusion protein expressed by pHCV-162. This analysis was conducted to ascertain the time interval after exposure to HCV at which E2 specific antibodies can be detected. Table 6 presents one such patient (AN) who seroconverted to NS3 at 154 days post transfusion (DPT). Antibodies to HCV E2 were not detected by RIPA until 271 DPT. Table 7 presents another such patient (WA), who seroconverted to CORE somewhere before 76 DPT and was positive for HCV E2 antibodies on the next available bleed date (103 DPT). Table 8 summarizes the serological results obtained from these five transfusion recipients indicating (a) some general antibody profile at seroconversion (AB Status); (b) the days post transfusion at which an ELISA test would most likely detect HCV antibody (2.0 GEN); (c) the samples in which HCV E2 antibody was detected by RIPA (E2 AB Status); and (d) the time interval covered by the bleed dates tested (Samples Tested). The results indicate that antibody to HCV E2, as detected in the RIPA procedure described here, appears after seroconversion to at least one other HCV marker (CORE, NS3, C100, etc.) and is persistent in nature once it appears. In addition, the absence of antibody to the structural gene CORE appears highly correlated with the absence of detectable antibody to E2, another putative structural antigen. Further work is ongoing to correlate the presence or absence of HCV gene specific antibodies with progression of disease and/or time interval since exposure to HCV viral antigens.

Example 4

Expression of HCV E1 and E2 Using Human Growth Hormone Secretion Signal

Figure 11:
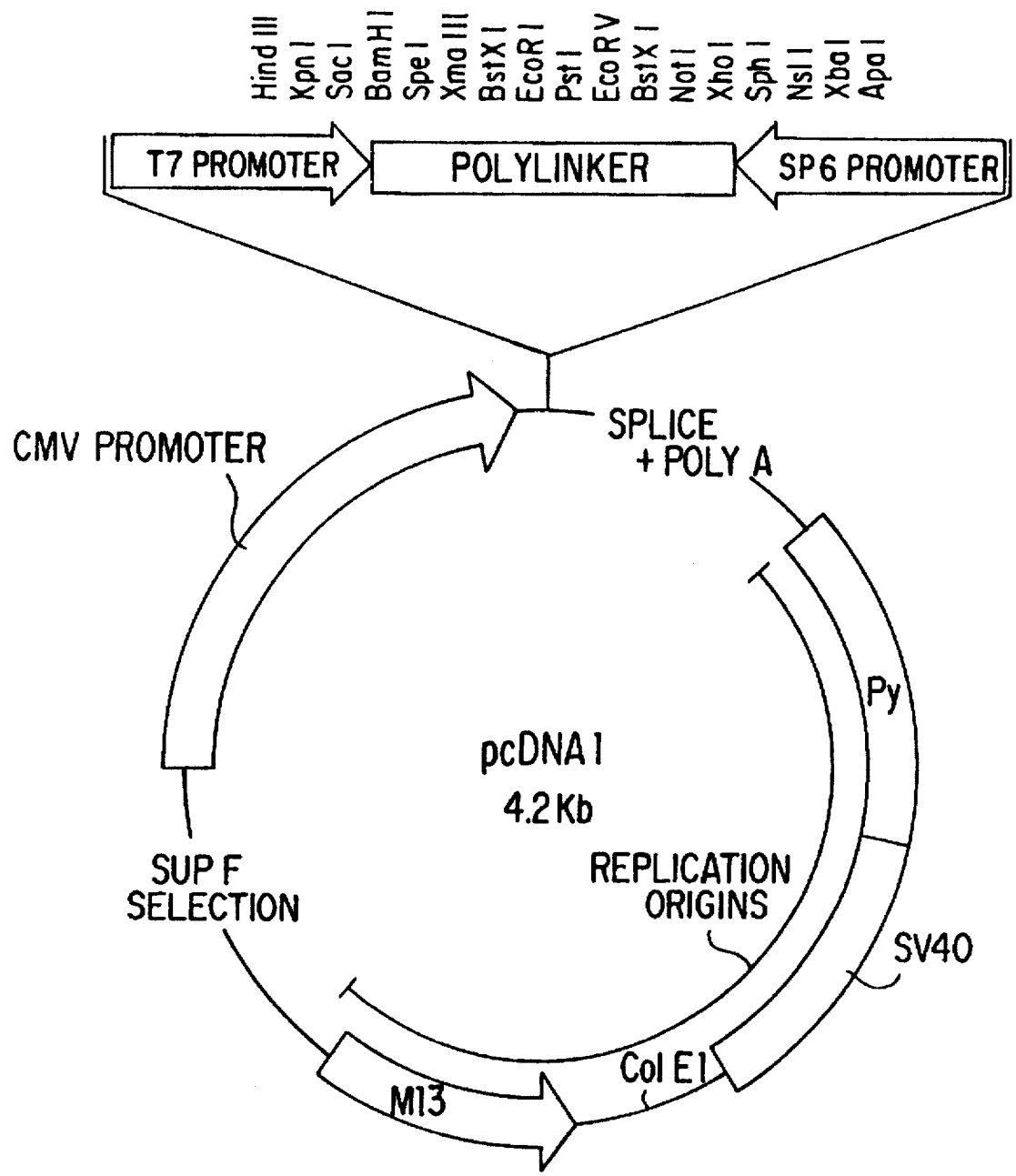
FIG. 11 presents a schematic representation of the mammalian expression vector pCDNA-I.
Figure 12:
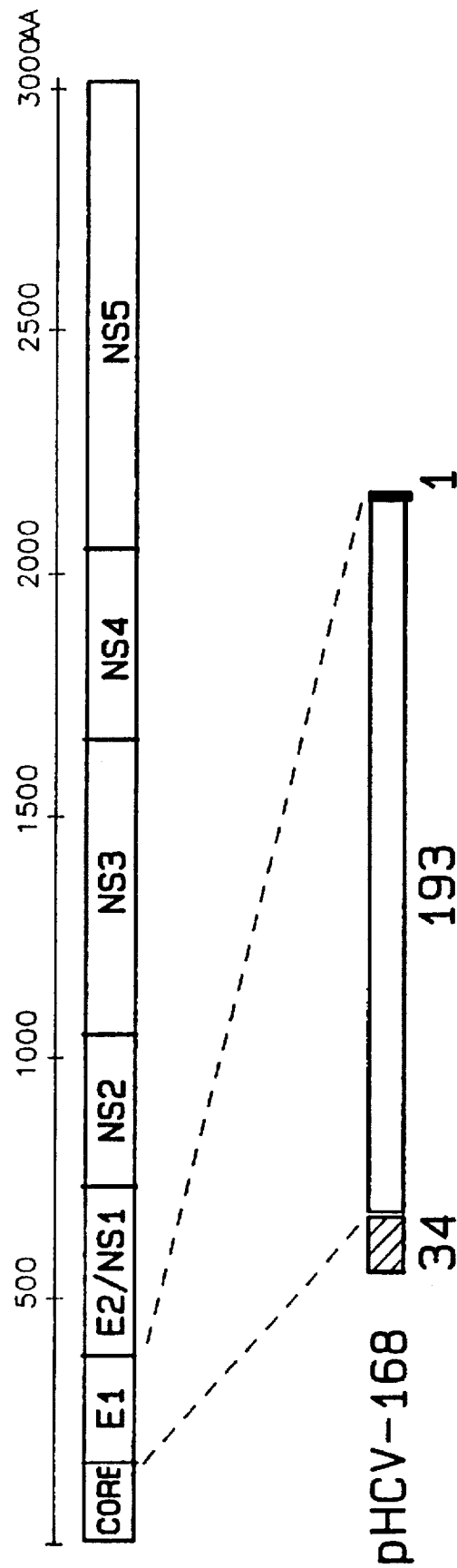
FIG. 12 presents a schematic representation of the location and amino acid composition of the HGH-HCV-E1 fusion protein expressed by the mammalian expression vector pHCV-168.
Figure 13:
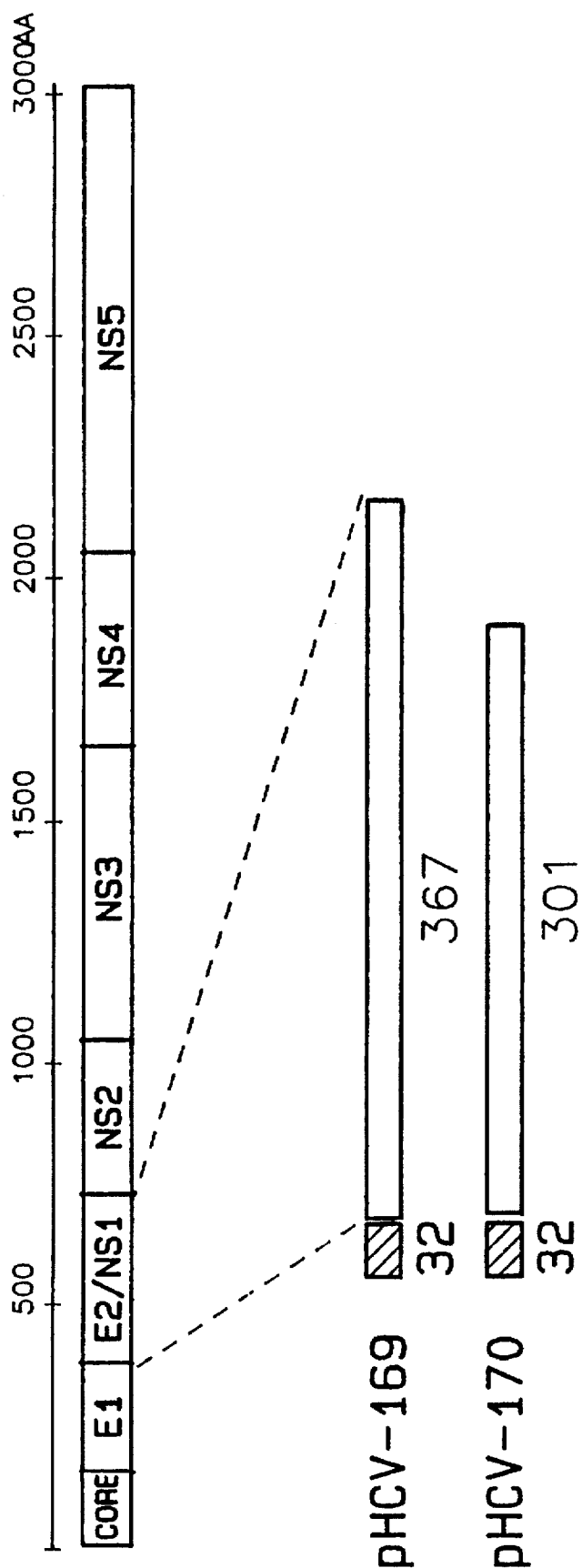
FIG. 13 presents a schematic representation of the location and amino acid composition of the HGH-HCV-E2 fusion proteins expressed by the mammalian expression vectors pHCV-169 and pHCV-170.
Figure 14:
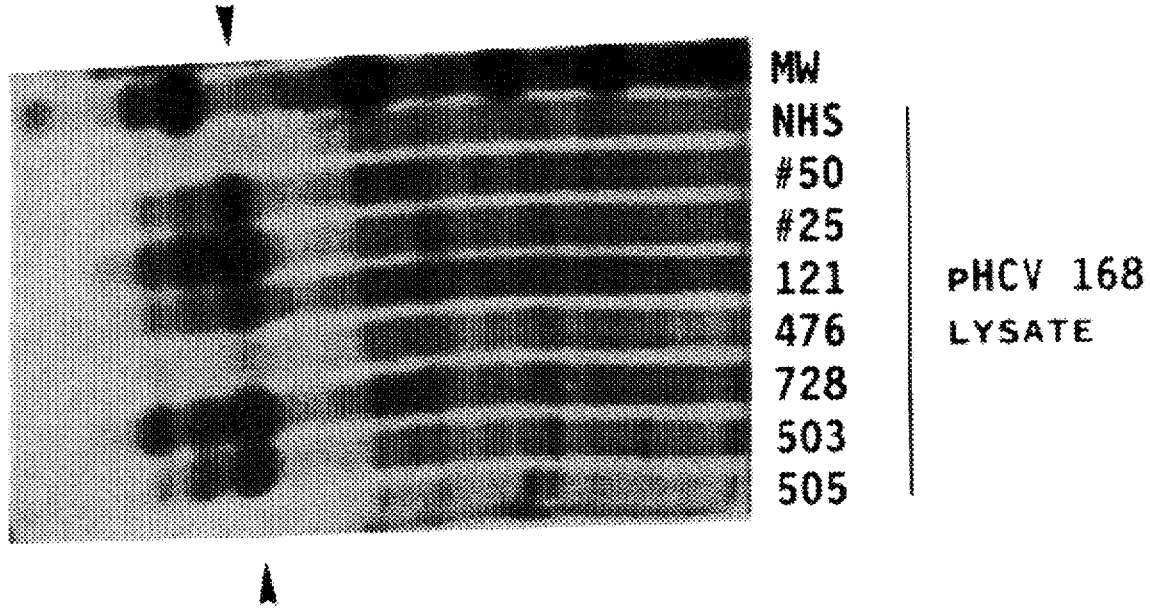
FIG. 14 presents the RIPA results obtained when HCV E2 antibody positive sera were screened against the HGH-HCV-E1 fusion protein expressed by pHCV-168 in HEK-293 cells.
Figure 15:
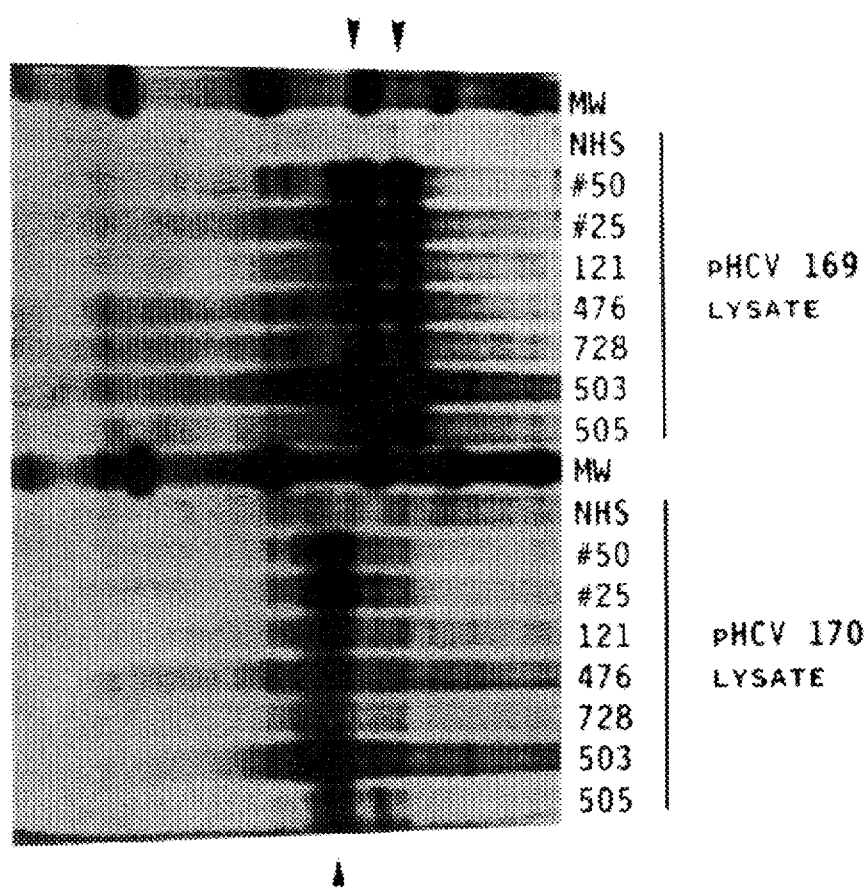
FIG. 15 presents the RIPA results obtained when HCV E2 antibody positive sera were screened against the HGH-HCV-E2 fusion proteins expressed by pHCV-169 and pHCV-170 in HEK-293 cells.

HCV DNA fragments representing HCV E1 (HCV amino acids 192 to 384) and HCV E2 (HCV amino acids 384–750 and 384–684) were generated from the CO isolate using PCR as described in Example 2. An Eco RI restriction site was used to attach a synthetic oligonucleotide encoding the Human Growth Hormone (HGH) secretion signal (Blak et al, Oncogene, 3 129–136, 1988) at the 5' end of these HCV sequence. The resulting fragment was then cloned into the commercially available mammalian expression vector pCDNA-I, (available from Invitrogen, San Diego, Calif.) illustrated in FIG. 11. Upon transformation into E. coli MC1061/P3, the resulting clones place the expression of the cloned sequence under control of the strong CMV promoter. Following the above outlined methods, a clone capable of expressing HCV-E1 (HCV amino acids 192–384) employing the HGH secretion signal at the extreme amino-terminal end was isolated. The clone was designated pHCV-168 and is schematically illustrated in FIG. 12. Similarly, clones capable of expressing HCV E2 (HCV amino acids 384–750 or 384–684) employing the HGH secretion signal were isolated, designated pHCV-169 and pHVC-170 respectively and illustrated in FIG. 13. The complete nucleotide sequence of the mammalian expression vectors pHCV-168, pHCV-169, and pHCV-170 are presented in Sequence ID. NO. 7, 9, and 11 respectively. Translation of nucleotides 2227 through 2913 results in the complete amino acid sequence of the HGH-HCV-E1 fusion protein expressed by pHCV-168 as presented in Sequence ID. NO. 8. Translation of nucleotides 2227 through 3426 results in the complete amino acid sequence of the HGH-HCV-E2 fusion protein expressed by pHCV-169 as presented in Sequence ID. NO. 10. Translation of nucleotides 2227 through 3228 results in the complete amino acid sequence of the HGH-HCV-E2 fusion protein expressed by pHCV-170 as presented in Sequence ID. NO. 12. Purified DNA from pHCV-168, pHCV-169, and pHCV-170 was transfected into HEK-293 cells which were then metabolically labelled, cell lysates prepared, and RIPA analysis performed as described previously herein. Seven sera samples previously shown to contain antibodies to the APP-HCV-E2 fusion protein expressed by pHCV-162 were screened against the labelled cell lysates of pHCV-168, pHCV-169, and pHCV-170. FIG. 14 presents the RIPA analysis for pHCV-168 and demonstrated that five sera containing HCV E2 antibodies also contain HCV E1 antibodies directed against as approximately 33K dalton HGH-HCV-E1 fusion protein (#25, #50, 121, 503, and 728), while two other sera do not contain those antibodies (476 and 505). FIG. 15 presents the RIPA results obtained when the same sera indicated above were screened against the labelled cell lysates of either pHCV-169 or pHCV-170. All seven HCV E1 antibody positive sera detected two protein species of approximately 70K and 75K daltons in cells transfected with pHCV-168. These two different HGH-HCV-E2 protein species could result from incomplete proteolytic cleavage of the HCV E2 sequence at the carboxyl-terminal end (at or near HCV amino acid 720) or from differences in carbohydrate processing between the two species. All seven HCV E2 antibody positive sera detected a single protein species of approximately 62K daltons for the HGH-HCV-E2 fusion protein expressed by pHCV-170. Table 9 summarizes the serological profile of six of the seven HCV E2 antibody positive sera screened against the HGH-HCV-E1 fusion protein expressed by pHCV-170. Further work is ongoing to correlate the presence or absence of HCV gene specific antibodies with progression of disease and/or time interval since exposure to HCV viral antigens.

Clones pHCV-167 and pHCV-162 have been deposited at the American Type Culture Collection, 12301 Parklawn Drive, Rockville, Md., 20852, as of Jan. 17, 1992 under the terms of the Budapest Treaty, and accorded the following ATCC Designation Numbers: Clone pHCV-167 was accorded ATCC deposit number 68893 and clone pHCV-162 was accorded ATCC deposit number 68894. Clones pHCV-168, pHCV-169 and pHCV-170 have been deposited at the American Type Culture Collection, 12301 Parklawn Drive, Rockville, Md., 20852, as of Jan. 26, 1993 under the terms of the Budapest Treaty, and accorded the following ATCC Designation Numbers: Clone pHCV-168 was accorded ATCC deposit number 69228, clone pHCV-169 was accorded ATCC deposit number 69229 and clone pHCV-170 was accorded ATCC deposit number 69230. The designated deposits will be maintained for a period of thirty (30) years from the date of deposit, or for five (5) years after the last request for the deposit; or for the enforceable life of the U.S. patent, whichever is longer. These deposits and other deposited materials mentioned herein are intended for convenience only, and are not required to practice the invention in view of the descriptions herein. The HCV cDNA sequences in all of the deposited materials are incorporated herein by reference.

Other variations of applications of the use of the proteins and mammalian expression systems provided herein will be apparent to those skilled in the art. Accordingly, the invention is intended to be limited only in accordance with the appended claims.

TABLE 1

| FRAG-MENT | PCR-1 PRIMERS | | PCR-2 PRIMERS | |
|---|---|---|---|---|
| | SENSE | ANTISENSE | SENSE | ANTISENSE |
| 1 | 1–17 | 1376–1400 | 14–31 | 1344–1364 |
| 2 | 1320–1344 | 2332–2357 | 1357–1377 | 2309–2327 |
| 3 | 2288–2312 | 3245–3269 | 2322–2337 | 3224–3242 |
| 4 | 3178–3195 | 5303–5321 | 3232–3252 | 5266–5289 |
| 5 | 5229–5249 | 6977–6996 | 5273–5292 | 6940–6962 |
| 6 | 6907–6925 | 8221–8240 | 6934–6954 | 8193–8216 |
| 7 | 8175–8194 | 9385–9401 | 8199–8225 | 9363–9387 |

TABLE 2

AMERICAN HCV POSITIVE SERA

| SAMPLE | C100 YEAST S/CO | C100 E. COLI S/CO | NS3 S/CO | CORE S/CO | E2 RIPA |
|---|---|---|---|---|---|
| 22 | 0.31 | 1.09 | 1.72 | 284.36 | + |
| 32 | 0.02 | 0.10 | 7.95 | 331.67 | − |
| 35 | 0.43 | 0.68 | 54.61 | 2.81 | − |
| 37 | 136.24 | 144.29 | 104.13 | 245.38 | + |
| 50 | 101.04 | 133.69 | 163.65 | 263.72 | + |
| 108 | 39.07 | 34.55 | 108.79 | 260.47 | − |
| 121 | 1.28 | 4.77 | 172.65 | 291.82 | + |
| 128 | 0.06 | 0.06 | 0.87 | 298.49 | − |
| 129 | 0.00 | 0.02 | 107.11 | 0.00 | − |
| 142 | 8.45 | 8.88 | 73.93 | 2.32 | − |
| 156 | 0.45 | 0.14 | 0.67 | 161.84 | − |
| 163 | 1.99 | 3.26 | 11.32 | 24.36 | − |
| MI | 89.9 | 118.1 | 242.6 | 120.4 | − |
| KE | 167.2 | 250.9 | 0.8 | 0.3 | − |
| WA | 164.4 | 203.3 | 223.9 | 160.9 | + |
| PA | 50.6 | 78.8 | 103.8 | 78.0 | + |
| AN | 224.8 | 287.8 | 509.9 | 198.8 | + |

TABLE 3

JAPANESE HCV POSITIVE POSITIVE BLOOD DONORS

| SAMPLE | C100 YEAST S/CO | C100 E. COLI S/CO | NS3 S/CO | CORE S/CO | E2 RIPA |
|---|---|---|---|---|---|
| 410 | 86.33 | 93.59 | 9.68 | 257.82 | + |
| 435 | 0.18 | 0.18 | 0.69 | 39.25 | + |
| 441 | 0.20 | 0.09 | 0.17 | 6.51 | − |
| 476 | 0.37 | 1.29 | 144.66 | 302.35 | + |
| 496 | 39.06 | 37.95 | 2.78 | 319.99 | − |
| 560 | 1.08 | 0.68 | 3.28 | 26.59 | − |
| 589 | 0.06 | 1.28 | 117.82 | 224.23 | + |
| 620 | 0.17 | 1.37 | 163.41 | 256.64 | + |
| 622 | 123.46 | 162.54 | 154.67 | 243.44 | + |
| 623 | 23.46 | 26.55 | 143.72 | 277.24 | + |
| 633 | 0.01 | 0.43 | 161.84 | 264.02 | + |
| 639 | 1.40 | 2.23 | 12.15 | 289.80 | + |
| 641 | 0.01 | 0.08 | 8.65 | 275.00 | + |
| 648 | −0.00 | 0.03 | 0.79 | 282.64 | + |
| 649 | 97.00 | 127.36 | 147.46 | 194.73 | + |
| 657 | 4.12 | 6.33 | 141.04 | 256.57 | + |
| 666 | 0.14 | 0.24 | 5.90 | 60.82 | − |
| 673 | 72.64 | 90.11 | 45.31 | 317.66 | + |
| 677 | 0.05 | 0.23 | 2.55 | 99.67 | − |
| 694 | 86.72 | 87.18 | 45.43 | 248.80 | + |
| 696 | 0.02 | −0.02 | 0.26 | 12.55 | − |
| 706 | 17.02 | 12.96 | 153.77 | 266.87 | + |
| 717 | 0.04 | 0.02 | 0.15 | 10.46 | − |
| 728 | −0.01 | 0.26 | 90.37 | 246.30 | + |
| 740 | 0.02 | 0.10 | 0.25 | 46.27 | − |
| 743 | 1.95 | 1.56 | 133.23 | 254.25 | + |

TABLE 4

SPANISH HEMODIALYSIS PATIENTS

| SAMPLE | C100 YEAST S/CO | C100 E. COLI S/CO | NS3 S/CO | CORE S/CO | E2 RIPA |
|---|---|---|---|---|---|
| 1 | 0.0 | 0.3 | 188.6 | −0.0 | − |
| 2 | 129.3 | 142.8 | 165.4 | 201.0 | + |
| 3 | 113.7 | 128.5 | 154.5 | 283.3 | + |
| 5 | 130.6 | 143.8 | 133.4 | 186.1 | + |

TABLE 4-continued

SPANISH HEMODIALYSIS PATIENTS

| SAMPLE | C100 YEAST S/CO | C100 E. COLI S/CO | NS3 S/CO | CORE S/CO | E2 RIPA |
|---|---|---|---|---|---|
| 6 | 56.2 | 63.4 | 93.6 | 32.0 | + |
| 7 | 0.0 | 0.2 | 72.1 | 211.5 | + |
| 8 | 156.7 | 171.9 | 155.1 | 227.0 | + |
| 9 | 65.3 | 78.9 | 76.1 | 102.6 | + |
| 10 | 136.7 | 149.3 | 129.4 | 190.2 | + |
| 11 | 0.0 | 0.7 | 155.7 | 272.4 | + |
| 12 | 1.0 | 1.9 | 143.6 | 210.6 | + |
| 13 | 0.0 | 0.3 | 111.2 | 91.1 | − |
| 14 | 1.1 | 3.1 | 94.7 | 214.8 | − |
| 15 | 45.9 | 66.1 | 106.3 | 168.2 | + |
| 16 | 36.3 | 68.8 | 149.3 | 0.1 | − |
| 17 | 121.0 | 129.9 | 113.4 | 227.8 | + |
| 18 | 64.8 | 99.7 | 138.9 | 0.2 | − |
| 19 | 25.6 | 34.1 | 157.4 | 254.9 | + |
| 20 | 104.9 | 125.1 | 126.8 | 218.3 | + |
| 21 | 48.1 | 68.5 | 0.8 | 49.4 | − |

TABLE 5

ANTIBODY RESPONSE TO HCV PROTEINS

| | C100 YEAST S/CO | C100 E. COLI S/CO | NS3 S/CO | CORE S/CO | E2 RIPA |
|---|---|---|---|---|---|
| AMERICAN BLOOD DONORS | 11/17 | 12/17 | 14/17 | 15/17 | 7/17 |
| SPANISH HEMODIALYSIS PATIENTS | 16/20 | 16/20 | 19/20 | 17/20 | 14/20 |
| JAPANESE BLOOD DONORS | 12/26 | 14/26 | 20/26 | 26/26 | 18/26 |

TABLE 6

HUMAN TRANSFUSION RECIPIENT (AN)

| DAYS POST TRANS. | C100 YEAST S/CO | C100 E. COLI S/CO | NS3 S/CO | CORE S/CO | E2 RIPA |
|---|---|---|---|---|---|
| 29 | 1.8 | 1.9 | 8.9 | 1.1 | − |
| 57 | 0.4 | 0.3 | 1.2 | 0.4 | − |
| 88 | 0.3 | 0.3 | 0.4 | 0.7 | − |
| 116 | 0.1 | 0.2 | 0.5 | 0.2 | − |
| 154 | 0.3 | 0.7 | 65.3 | 0.8 | − |
| 179 | 18.0 | 21.5 | 445.6 | 1.5 | − |
| 271 | 257.4 | 347.2 | 538.0 | 3.1 | + |
| 376 | 240.0 | 382.5 | 513.5 | 139.2 | + |
| 742 | 292.9 | 283.7 | 505.3 | 198.1 | + |
| 1105 | 282.1 | 353.9 | 456.1 | 202.2 | + |
| 1489 | 224.8 | 287.8 | 509.9 | 198.8 | + |

TABLE 7

HUMAN TRANSFUSION RECIPIENT (WA)

| DAYS POST TRANS. | C100 YEAST S/CO | C100 E. COLI S/CO | NS3 S/CO | CORE S/CO | E2 RIPA |
|---|---|---|---|---|---|
| 43 | 0.1 | 0.6 | 0.4 | 1.2 | − |
| 76 | 0.1 | 0.1 | 0.9 | 72.7 | − |
| 103 | 0.0 | 0.6 | 1.4 | 184.4 | + |
| 118 | 3.7 | 3.7 | 1.9 | 208.7 | + |
| 145 | 83.8 | 98.9 | 12.3 | 178.0 | + |
| 158 | 142.1 | 173.8 | 134.3 | 185.2 | + |
| 174 | 164.4 | 203.3 | 223.9 | 160.9 | + |

TABLE 8

HUMAN TRANSFUSION RECIPIENTS

| | AB STATUS | 2.0 GEN | E2 AB STATUS | SAMPLES TESTED |
|---|---|---|---|---|
| MI | STRONG RESPONSE | 78 DPT | NEG. | 1-178 DPT |
| KE | EARLY C100 | 103 DPT | NEG. | 1-166 DPT |
| WA | EARLY CORE | 76 DPT | Pos. 103-173 DPT | 1-173 DPT |
| PA | EARLY C100 | 127 DPT | Pos. 1491-3644 DPT | 1-3644 DPT |
| AN | EARLY 33C | 179 DPT | Pos. 271-1489 DPT | 1-1489 DPT |

TABLE 9

SELECTED HCV E2 ANTIBODY POSITIVE SAMPLES

| SAMPLE | C100 YEAST S/CO | C100 E. COLI S/CO | NS3 S/CO | CORE S/CO | E1 RIPA |
|---|---|---|---|---|---|
| 50 | 101.04 | 133.69 | 163.65 | 263.72 | + |
| 121 | 1.28 | 4.77 | 172.65 | 291.82 | + |
| 503 | 113.7 | 128.5 | 154.5 | 283.3 | + |
| 505 | 130.6 | 143.8 | 133.4 | 186.1 | − |
| 476 | 0.37 | 1.29 | 144.66 | 302.35 | − |
| 728 | −0.01 | 0.26 | 90.37 | 246.30 | + |

---

SEQ. ID. NO. 1

CO

```
          10         20         30         40         50         60         70
MSTNPKPQRK TKRNTNRRPQ DVRFPGGGQI VGGVYLLPRR GPRLGVRATR KTSERSQPRG RRQPIPKARR
```

|     |     |     |     |     |     |     |
| --- | --- | --- | --- | --- | --- | --- |
| 80<br>PEGRTWAQPG | 90<br>YPWPLYGNEG | 100<br>CGWAGWLLSP | 110<br>RGSRPSWGPT | 120<br>DPRRRSRNLG | 130<br>KVIDTLTCGF | 140<br>ADLMGYIPLV |
| 150<br>GAPLGGAARA | 160<br>LAHGVRVLED | 170<br>GVNYATGNLP | 180<br>GCSFSIFLLA | 190<br>LLSCLTVPAS | 200<br>AYQVRNSSGL | 210<br>YHVTNDCPNS |
| 220<br>SIVYEAADAI | 230<br>LHTPGCVPCV | 240<br>REGNASRCWV | 250<br>AVTPTVATRD | 260<br>GKLPTTQLRR | 270<br>HIDLLVGSAT | 280<br>LCSALYVGDL |
| 290<br>CGSVFLVGQL | 300<br>FTFSPRRHWT | 310<br>TQDCNCSIYP | 320<br>GHITGHRMAW | 330<br>DMMMNWSPTA | 340<br>ALVVAQLLRI | 350<br>PQAILDMIAG |
| 360<br>AHWGVLAGIA | 370<br>YFSMVGNWAK | 380<br>VLVVLLLFAG | 390<br>VDAETHVTGG | 400<br>SAGHTTAGLV | 410<br>RLLSPGAKQN | 420<br>IQLINTNGSW |
| 430<br>HINSTALNCN | 440<br>ESLNTGWLAG | 450<br>LFYHHKFNSS | 460<br>GCPERLASCR | 470<br>RLTDFAQGGG | 480<br>PISYANGSGL | 490<br>DERPYCWHYP |
| 500<br>PRPCGIVPAK | 510<br>SVCGPVYCFT | 520<br>PSPVVVGTTD | 530<br>RSGAPTYSWG | 540<br>ANDTDVFVLN | 550<br>NTRPPLGNWF | 560<br>GCTWMNSTGF |
| 570<br>TKVCGAPPCV | 580<br>IGGVGNNTLL | 590<br>CPTDCFRKHP | 600<br>EATYSRCGSG | 610<br>PWTTPRCMVD | 620<br>YPYRLWHYPC | 630<br>TINYTIFKYR |
| 640<br>MYVGGVEHRL | 650<br>EAACNWTRGE | 660<br>RCDLEDRDRS | 670<br>ELSPLLLSTT | 680<br>QWQVLPCSFT | 690<br>TLPALSTGLI | 700<br>HLHQNIVDVQ |
| 710<br>YLYGVGSSIA | 720<br>SWAIKWEYVV | 730<br>LLFLLLADAR | 740<br>VCSCLWMMLL | 750<br>ISQAEAALEN | 760<br>LVILNAASLA | 770<br>GTHGFVSFLV |
| 780<br>FFCFAWYLKG | 790<br>RWVPGAAYAL | 800<br>YGIWPLLLLL | 810<br>LALPQRAYAL | 820<br>DTEVAASCGG | 830<br>VVLVGLMALT | 840<br>LSPYYKRYIS |
| 850<br>WCMWWLQYFL | 860<br>TRVEAQLHVW | 870<br>VPPLNVRGGR | 880<br>DAVILLMCAV | 890<br>HPTLVFDITK | 900<br>LLLAIFGPLW | 910<br>ILQASLLKVP |
| 920<br>YFVRVQGLLR | 930<br>ICALARKIAG | 940<br>GHYVQMIFIK | 950<br>LGALTGTYVY | 960<br>NHLTPLRDWA | 970<br>HNGLRDLAVA | 980<br>VEPVVFSRME |
| 990<br>TKLITWGADT | 1000<br>AACGDIINGL | 1010<br>PVSARRGQEI | 1020<br>LLGPADGMVS | 1030<br>KGWRLLAPIT | 1040<br>AYAQQTRGLL | 1050<br>GCIITSLTGR |
| 1060<br>DKNQVEGEVQ | 1070<br>IVSTATQTFL | 1080<br>ATCINGVCWT | 1090<br>VYHGAGTRTI | 1100<br>ASPKGPVIQM | 1110<br>YTNVDQDLVG | 1120<br>WPAPQGSRSL |
| 1130<br>TPCTCGSSDL | 1140<br>YLVTRHADVI | 1150<br>PVRRQGDSRG | 1160<br>SLLSPRPISY | 1170<br>LKGSSGGPLL | 1180<br>CPAGHAVGLF | 1190<br>RAAVCTRGVA |
| 1200<br>KAVDFIPVEN | 1210<br>LETTMRSPVF | 1220<br>TDNSSPPAVP | 1230<br>QSFQVAHLHA | 1240<br>PTGSGKSTKV | 1250<br>PAAYAAQGYK | 1260<br>VLVLNPSVAA |
| 1270<br>TLGFGAYMSK | 1280<br>AHGVDPNIRT | 1290<br>GVRTITTGSP | 1300<br>ITYSTYGKFL | 1310<br>ADGGCSGGAY | 120<br>DIIICDECHS | 1330<br>TDATSILGIG |
| 1340<br>TVLDQAETAG | 1350<br>ARLVVLATAT | 1360<br>PPGSVTVPHP | 1370<br>NIEEVALSTT | 1380<br>GEIPFYGKAI | 1390<br>PLEVIKGGRH | 1400<br>LIFCHSKKKC |
| 1410<br>DELAAKLVAL | 1420<br>GINAVAYYRG | 1430<br>LDVSVIPASG | 1440<br>DVVVVSTDAL | 1450<br>MTGFTGDFDP | 1460<br>VIDCNTCVTQ | 1470<br>TVDFSLDPTF |
| 1480<br>TIETTTLPQD | 1490<br>AVSRTQRRGR | 1500<br>TGRGKPGIYR | 1510<br>FVAPGERPSG | 1520<br>MFDSSVLCEC | 1530<br>YDAGCAWYEL | 1540<br>TPAETTVRLR |
| 1550<br>AYMNTPGLPV | 1560<br>CQDHLEFWEG | 1570<br>VFTGLTHIDA | 1580<br>HFLSQTKQSG | 1590<br>ENFPYLVAYQ | 1600<br>ATVCARAQAP | 1610<br>PPSWDQMWKC |
| 1620<br>LIRLKPTLHG | 1630<br>PTPLIYRLGA | 1640<br>VQNEITLTHP | 1650<br>VTKYIMTCMS | 1660<br>ANPEVVTSTW | 1670<br>VLVGGVLAAL | 1680<br>AAYCLSTGCV |
| 1690<br>VIVGRIVLSG | 1700<br>KPAIIPDREV | 1710<br>LYQEFDEMEE | 1720<br>CSQHLPYIEQ | 1730<br>GMMLAEQFKQ | 1740<br>EALGLLQTAS | 1750<br>RQAEVITPAV |
| 1760<br>QTNWQKLEAF | 1770<br>WAKHMWNFIS | 1780<br>GTQYLAGLST | 1790<br>LPGNPAIASL | 1800<br>MAFTAAVTSP | 1810<br>LTTSQTLLFN | 1820<br>ILGGWVAAQL |
| 1830<br>AAPGAATAFV | 1840<br>GAGLAGAAIG | 1850<br>SVGLGKVLVD | 1860<br>ILAGYGAGVA | 1870<br>GALVAFKIMS | 1880<br>GEVPSTEDLV | 1890<br>NLLPAILSPG |
| 1900 | 1910 | 1920 | 1930 | 1940 | 1950 | 1960 |

|      |      |      |      |      |      |      |
|------|------|------|------|------|------|------|
| ALVVGVVCAA | ILRRHVGPGE | GAVQWMNRLI | AFASRGNHVS | PTHYVPESDA | AARVTAILSN | LTVTQLLRRL |
| 1970 HQWIGSECTT | 1980 PCSGSWLRDI | 1990 WDWICEVLSD | 2000 FKTWLKAKLM | 2010 PQLPGIPFVS | 2020 CQRGYRGVWR | 2030 GDGIMHTRCH |
| 2040 CGAEITGHVK | 2050 NGTMRIVGPR | 2060 TCRNMWSGTF | 2070 PINAYTTGPC | 2080 TPLPAPNYKF | 2090 ALWRVSAEEY | 2100 VEIRRVGDFH |
| 2110 YVSGMTTDNL | 2120 KCPCQIPSPE | 2130 FFTELDGVRL | 2140 HRFAPPCKPL | 2150 LREEVSFRVG | 2160 LHEYPVGSQL | 2170 PCEPEPDVAV |
| 2180 LTSMLTDPSH | 2190 ITAEAAGRRL | 2200 ARGSPPSMAS | 2210 SSASQLSAPS | 2220 LKATCTTNHD | 2230 SPDAELIEAN | 2240 LLWRQEMGGN |
| 2250 ITRVESENKV | 2260 VILDSFDPLV | 2270 AEEDEREVSV | 2280 PAEILRKSQR | 2290 FARALPVWAR | 2300 PDYNPPLIET | 2310 WKEPDYEPPV |
| 2320 VHGCPLPPPR | 2330 SPPVPPPRKK | 2340 RTVVLTESTL | 2350 STALAELATK | 2360 SFGSSSTSGI | 2370 TGDNTTTSSE | 2380 PAPSGCPPDS |
| 2390 DVESYSSMPP | 2400 LEGEPGDPDF | 2410 SDGSWSTVSS | 2420 GADTEDVVCC | 2430 SMSYSWTGAL | 2440 VTPCAAEEQK | 2450 LPINALSNSL |
| 2460 LRHHNLVYST | 2470 TSRSACQRQK | 2480 KVTFDRLQVL | 2490 DSHYQDVLKE | 2500 VKAAASRVKA | 2510 NLLSVEEACS | 2520 LTPPHSAKSK |
| 2530 FGYGAKDVRC | 2540 HARKAVAHIN | 2550 SVWKDLLEDS | 2560 VTPIDTTIMA | 2570 KNEVFCVQPE | 2580 KGGRKPARLI | 2590 VFPDLGVRVC |
| 2600 EKMALYDVVS | 2610 KLPLAVMGSS | 2620 YGFQYSPGQR | 2630 VEFLVQAWKS | 2640 KKTPMGFSYD | 2650 TRCFDSTVTE | 2660 SDIRTEEAIY |
| 2670 QCCDLDPQAR | 2680 VAIKSLTERL | 2690 YVGGPLTNSR | 2700 GENCGYRRCR | 2710 ASGVLTTSCG | 2720 NTLTCYIKAR | 2730 AACRAAGLQD |
| 2740 RTMLVCGDDL | 2750 VVICESAGVQ | 2760 EDAASLRAFT | 2770 EAMTRYSAPP | 2780 GDPPQPEYDL | 2790 ELITSCSSNV | 2800 SVAHDGAGKR |
| 2810 VYYLTRDPTT | 2820 PLARAAWETA | 2830 RHTPVNSWLG | 2840 NIIMFAPTLW | 2850 ARMILMTHFF | 2860 SVLIARDQFE | 2870 QALNCEIYGA |
| 2880 CYSIEPLDLP | 2890 PIIQRLHGLS | 2900 AFSLHSYSPG | 2910 EINRVAACLR | 2920 KLGVPPLRAW | 2930 KHRARSVRAR | 2940 LLSRGGRAAI |
| 2950 CGKYLFNWAV | 2960 RTKPKLTPIA | 2970 AAGRLDLSGW | 2980 FTAGYSGGDI | 2990 YHSVSHARPR | 3000 WSWFCLLLLA | 3010 AGVGIYLLPN |

R.

PEP:

SEQ. ID. NO. 2

LG

|      |      |      |      |      |      |      |
|------|------|------|------|------|------|------|
| 10 MSTNPKPQRK | 20 TKRNTNRRPQ | 30 DVKFPGGGQI | 40 VGGVYLLPRR | 50 GPRLGVRATR | 60 KTSERSQPRG | 70 RRQPIPKARR |
| 80 PEGRTWAQPG | 90 YPWPLYGNEG | 100 CGWAGWLLSP | 110 RGSRPSWGPT | 120 DPRRRSRNLG | 130 KVIDTLTCGF | 140 ADLMGYIPLV |
| 150 GAPLGGAARA | 160 LAHGVRVLED | 170 GVNYATGNLP | 180 GCSFSIFLLA | 190 LLSCLTVPAS | 200 AYQVRNSSGL | 210 YHVTNDCPNS |
| 220 SIVYETADTI | 230 LHSPGCVPCV | 240 REGNTSKCWV | 250 AVAPTVTTRD | 260 GKLPSTQLRR | 270 HIDLLVGSAT | 280 LCSALYVGDL |
| 290 CGSVFLVSQL | 300 FTFSPRRHWT | 310 TQDCNCSIYP | 320 GHITGHRMAW | 330 DMMMNWSPTT | 340 ALVVAQLLRI | 350 PQAILDMIAG |
| 360 AHWGVLAGIA | 370 YFSMVGNWAK | 380 VLVVLLLFSG | 390 VDAATYTTGG | 400 SVARTTHGLS | 410 SLFSQGAKQN | 420 IQLINTNGSW |
| 430 HINRTALNCN | 440 ASLDTGWVAG | 450 LFYYHKFNSS | 460 GCPERMASCR | 470 PLADFDQGWG | 480 PISYTNGSGP | 490 EHRPYCWHYP |
| 500 PKPCGIVPAQ | 510 SVCGPVYCFT | 520 PSPVVVGTTD | 530 KSGAPTYTWG | 540 SNDTDVFVLN | 550 NTRPPPGNWF | 560 GCTWMNSSGF |

| 570 | 580 | 590 | 600 | 610 | 620 | 630 |
|---|---|---|---|---|---|---|
| TKVCGAPPCV | IGGAGNNILH | CPTDCFRKHP | EATYSRCGSG | PWITPRCLVH | YPYRLWHYPC | TINYTLFKVR |
| 640 | 650 | 660 | 670 | 680 | 690 | 700 |
| MYVGGVEHRL | EVACNWTRGE | RCDLDDRDRS | ELSPLLLSTT | QWQVLPCSFT | TLPALTTGLI | HLHQNIVDVQ |
| 710 | 720 | 730 | 740 | 750 | 760 | 770 |
| YLYGVGSSIV | SWAIKWEYVI | LLFLLLADAR | ICSCLWMMLL | ISQAEAALEN | LVLLNAASLA | GTHGLVSFLV |
| 780 | 790 | 800 | 810 | 820 | 830 | 840 |
| FFCFAWYLKG | KWVPGVAYAF | YGMWPFLLLL | LALPQRAYAL | DTEMAASCGG | VVLVGLMALT | LSPHYKRYIC |
| 850 | 860 | 870 | 880 | 890 | 900 | 910 |
| WCVWWLQYFL | TRAEALLHGW | VPPLNVRGGR | DAVILLMCVV | HPALVFDITK | LLLAVLGPLW | ILQTSLLKVP |
| 920 | 930 | 940 | 950 | 960 | 970 | 980 |
| YFVRVQGLLR | ICALARKMAG | GHYVQMVTIK | MGALAGTYVY | NHLTPLRDWA | HNGLRDLAVA | VEPVVFSQME |
| 990 | 1000 | 1010 | 1020 | 1030 | 1040 | 1050 |
| TKLITWGADT | AACGDIINGL | PVSARRGREI | LLGPADGMVS | KGWRLLAPIT | AYAQQTRGLL | GCIITSLTGR |
| 1060 | 1070 | 1080 | 1090 | 1100 | 1110 | 1120 |
| DKNQVEGEVQ | IVSTAAQTFL | ATCINGVCWT | VYHGAGTRTI | ASPKGPVIQM | YTNVDRDLVG | WPAPQGARSL |
| 1130 | 1140 | 1150 | 1160 | 1170 | 1180 | 1190 |
| TPCTCGSSDL | YLVTRHADVI | PVRRRGDSRG | SLLSPRPISY | LKGSSGGPLL | CPAGHAVGIF | RAAVCTRGVA |
| 1200 | 1210 | 1220 | 1230 | 1240 | 1250 | 1260 |
| KAVDFIPVES | LETTMRSPVF | TDNSSPPAVP | QSFQVAHLHA | PTGSGKSTKV | PAAYAAQGYK | VLVLNPSVAA |
| 1270 | 1280 | 1290 | 1300 | 1310 | 1320 | 1330 |
| TLGFGAYMSK | AHGIDPNIRT | GVRTITTGSP | ITYSTYGKFL | ADGGCSGGAY | DIIICDECHS | TDATSILGIG |
| 1340 | 1350 | 1360 | 1370 | 1380 | 1390 | 1400 |
| TVLDQAETAG | ARLVVLATAT | PPGSVTVPHP | NIEEVALSTT | GEIPFYGKAI | PLEAIKGGRH | LIFCHSKKKC |
| 1410 | 1420 | 1430 | 1440 | 1450 | 1460 | 1470 |
| DELAAKLVTL | GINAVAYYRG | LDVSVIPTSG | DVVVVATDAL | MTGFTGDFDS | VIDCNTCVTQ | AVDFSLDPTF |
| 1480 | 1490 | 1500 | 1510 | 1520 | 1530 | 1540 |
| TIETTTLPQD | AVSRTQRRGR | TGRGKPGIYR | FVAPGERPSG | MFDSSVLCEC | YDAGCAWYEL | TPAETTVRLR |
| 1550 | 1560 | 1570 | 1580 | 1590 | 1600 | 1610 |
| AYMNTPGLPV | CQDHLEFWEG | VFTGLTHIDA | HFLSQTKQSG | ENLPYLVAYQ | ATVCARAQAP | PPSWDQMMKC |
| 1620 | 1630 | 1640 | 1650 | 1660 | 1670 | 1680 |
| LIRLKPTLHG | PTPLLYRLGA | VQNEVTLTHP | ITKYIMTCMS | ADLEVVTSTW | VLVGGVLAAL | AAYCLSTGCV |
| 1690 | 1700 | 1710 | 1720 | 1730 | 1740 | 1750 |
| VIVGRIVLSG | KPAIIPDREV | LYREFDEMEE | CSQHLPYIEQ | GMMLAEQFKQ | KALGLLQTAS | HQAEVIAPAV |
| 1760 | 1770 | 1780 | 1790 | 1800 | 1810 | 1820 |
| QTNWQRLETF | WAKHMWNFIS | GIQYLAGLST | LPGNPAIASL | MAFTAAVTSP | LTTSQTLLFN | ILGGWVAAQL |
| 1830 | 1840 | 1850 | 1860 | 1870 | 1880 | 1890 |
| AAPSAATAFV | GAGLAGAAIG | SVGLGKVLVD | ILAGYGAGVA | GALVAFKIMS | GEVPSTEDLV | NLLPAILSPG |
| 1900 | 1910 | 1920 | 1930 | 1940 | 1950 | 1960 |
| ALVVGVVCAA | ILRRHVGPGE | GAVQWMNRLI | AFASRGNHVS | PTHYVPGSDA | AARVTAILSS | LTVTQLLRRL |
| 1970 | 1980 | 1990 | 2000 | 2010 | 2020 | 2030 |
| HQWVSSECTT | PCSGSWLRDI | WDWICEVLSD | FKTWLKAKLM | PQLPGIPFVS | CQRGYKGVWR | GDGIMHTRCH |
| 2040 | 2050 | 2060 | 2070 | 2080 | 2090 | 2100 |
| CGAEIAGHVK | NGTMRIVGPK | TCRNMWSGTF | PINAYTTGPC | TPLPAPNYKF | ALWRVSAEEY | VEIRQVGDFH |
| 2110 | 2120 | 2130 | 2140 | 2150 | 2160 | 2170 |
| YVTGMTADNL | KCPCQVPSPE | FFTELDGVRL | HRFAPPCKPL | LRDEVSFRVG | LHDYPVGSQL | PCEPEPDVAV |
| 2180 | 2190 | 2200 | 2210 | 2220 | 2230 | 2240 |
| LTSMLTDPSH | ITAETAGRRL | ARGSPPSMAS | SSASQLSAPS | LKATCTTNHD | SPDAELLEAN | LLWRQENGGN |
| 2250 | 2260 | 2270 | 2280 | 2290 | 2300 | 2310 |
| ITRVESENKV | VVLDSFDPLV | AEEDEREVSV | PAEILRKSRR | FAQALPSWAR | PDYNPPLLET | WKKPDYEPPV |
| 2320 | 2330 | 2340 | 2350 | 2360 | 2370 | 2380 |
| VHGCPLPPPQ | SPPVPPPRKK | RTVVLTESTV | SSALAELATK | SFGSSSTSGI | TGDNTTTSSE | PAPSVCPPDS |
| 2390 | 2400 | 2410 | 2420 | 2430 | 2440 | 2450 |
| DAESYSSMPP | LEGEPGDPDL | SDGSWSTVSS | GADTEDVVCC | SMSYSWTGAL | ITPCAAEEQK | LPINALSNSL |

|  2460      | 2470       | 2480       | 2490       | 2500       | 2510       | 2520       |
|------------|------------|------------|------------|------------|------------|------------|
| LRHHNLVYST | TSRNACLRQK | KVTFDRLQVL | DNHYQDVLKE | VKAAASKVKA | NLLSVEEACS | LTPPHSARSK |
| 2530       | 2540       | 2550       | 2560       | 2570       | 2580       | 2590       |
| FGYGAKDVRC | HARKAVSHIN | SVWKDLLEDS | VTPIDTTIMA | KNEVFCVQPE | KGGRKPARLI | VFPDLGVRVC |
| 2600       | 2610       | 2620       | 2630       | 2640       | 2650       | 2660       |
| EKMALYDVVS | KLPLAVMGSS | YGFQYSPGQR | VEFLVQAWKS | KKTPMGFSYD | TRCFDSTVTE | SDIRTEEAIY |
| 2670       | 2680       | 2690       | 2700       | 2710       | 2720       | 2730       |
| QCCDLDPQAR | VAIKSLTERL | YVGGPLTNSR | GENCGYRRCR | ASGVLTTSCG | NTLTCYIKAR | AACRAAGLQD |
| 2740       | 2750       | 2760       | 2770       | 2780       | 2790       | 2800       |
| CTMLVCGDDL | VVICESQGVQ | EDAASLRAFT | EAMTRYSAPP | GDPPQPEYDL | ELITPCSSNV | SVAHDGAGKR |
| 2810       | 2820       | 2830       | 2840       | 2850       | 2860       | 2870       |
| VYYLTRDPTT | PLARAAWETA | RHTPVNSWLG | NIIMFAPTLW | ARMILMTHFF | SVLIARDQLE | QALDCEIYGA |
| 2880       | 2890       | 2900       | 2910       | 2920       | 2930       | 2940       |
| CYSIEPLDLP | PIIQRLHGLS | AFSLHSYSPG | EINRVAACLR | KLGVPPLRAW | RHRARSVRAR | LLSRGGRAAI |
| 2950       | 2960       | 2970       | 2980       | 2990       | 3000       | 3010       |
| CGKYLFNWAV | RTKLKLTPIA | AAGQLDLSGW | FTAGYGGGDI | YHSVSRARPR | WFWFCLLLLA | AGVGIYLLPN |

R.

PEP:

SEQ. ID. NO. 3

PHCV_162
Circular sequence with junction at 7298

|  10        | 20         | 30         | 40         | 50         | 60         | 70         |
|------------|------------|------------|------------|------------|------------|------------|
| GACGGATCGG | GAGATCTCCC | GATCCCCTAT | GGTCGACTCT | CAGTACAATC | TGCTCTGATG | CCGCATAGTT |
| 80         | 90         | 100        | 110        | 120        | 130        | 140        |
| AAGCCAGTAT | CTGCTCCCTG | CTTGTGTGTT | GGAGGTCGCT | GAGTAGTGCG | CGAGCAAAAT | TTAAGCTACA |
| 150        | 160        | 170        | 180        | 190        | 200        | 210        |
| ACAAGGCAAG | GCTTGACCGA | CAATTGCATG | AAGAATCTGC | TTAGGGTTAG | GCGTTTTGCG | CTGCTTCGCG |
| 220        | 230        | 240        | 250        | 260        | 270        | 280        |
| ATGTACGGGC | CAGATATACG | CGTTGACATT | GATTATTGAC | TAGTTATTAA | TAGTAATCAA | TTACGGGTC  |
| 290        | 300        | 310        | 320        | 330        | 340        | 350        |
| ATTAGTTCAT | AGCCCATATA | TGGAGTTCCG | CGTTACATAA | CTTACGGTAA | ATGGCCCGCC | TGGCTGACCG |
| 360        | 370        | 380        | 390        | 400        | 410        | 420        |
| CCCAACGACC | CCCGCCCATT | GACGTCAATA | ATGACGTATG | TTCCCATAGT | AACGCCAATA | GGGACTTTCC |
| 430        | 440        | 450        | 460        | 470        | 480        | 490        |
| ATTGACGTCA | ATGGGTGGAC | TATTTACGGT | AAACTGCCCA | CTTGGCAGTA | CATCAAGTGT | ATCATATGCC |
| 500        | 510        | 520        | 530        | 540        | 550        | 560        |
| AAGTACGCCC | CCTATTGAGG | TCAATGACGG | TAAATGGCCC | GCCTGGCATT | ATGCCCAGTA | CATGACCTTA |
| 570        | 580        | 590        | 600        | 610        | 620        | 630        |
| TGGGACTTTC | CTACTTGGCA | GTACATCTAC | GTATTAGTCA | TCGCTATTAC | CATGGTGATG | CGGTTTTGGC |
| 640        | 650        | 660        | 670        | 680        | 690        | 700        |
| AGTACATCAA | TGGGCGTGGA | TAGCGGTTTG | ACTCACGGGG | ATTTCCAAGT | CTCCACCCCA | TTGACGTCAA |
| 710        | 720        | 730        | 740        | 750        | 760        | 770        |
| TGGGAGTTTG | TTTTGGCACC | AAAATCAACG | GGACTTTCCA | AAATGTCGTA | ACAACTCCGC | CCCATTGACG |
| 780        | 790        | 800        | 810        | 820        | 830        | 840        |
| CAAATGGGCG | GTAGGCGTGT | ACGGTGGGAG | GTCTATATAA | GCAGAGCTCT | CTGGCTAACT | AGAGAACCCA |
| 850        | 860        | 870        | 880        | 890        | 900        | 910        |
| CTGCTTAACT | GGCTTATCGA | AATTAATACG | ACTCACTATA | GGGAGACCGG | AAGCTTTGCT | CTAGACTGGA |
| 920        | 930        | 940        | 950        | 960        | 970        | 980        |
| ATTCGGGCGC | GATGCTGCCC | GGTTTGGCAC | TGCTCCTGCT | GGCCGCCTGG | ACGGCTCGGG | CGCTGGAGGT |
| 990        | 1000       | 1010       | 1020       | 1030       | 1040       | 1050       |
| ACCCACTGAT | GGTAATGCTG | GCCTGCTGGC | TGAACCCAG  | ATTGCCATGT | TCTGTGGCAG | ACTGAACATG |

| 1060 | 1070 | 1080 | 1090 | 1100 | 1110 | 1120 |
|---|---|---|---|---|---|---|
| CACATGAATG | TCCAGAATGG | GAAGTGGGAT | TCAGATCCAT | CAGGGACCAA | AACCTGCATT | GATACCAAGG |
| 1130 | 1140 | 1150 | 1160 | 1170 | 1180 | 1190 |
| AAAACCCACGT | CACCGGGGGA | AGTGCCGGCC | ACACCACGGC | TGGGCTTGTT | CGTCTCCTTT | CACCAGGCGC |
| 1200 | 1210 | 1220 | 1230 | 1240 | 1250 | 1260 |
| CAAGCAGAAC | ATCCAACTGA | TCAACACCAA | CGGCAGTTGG | CACATCAATA | GCACGGCCTT | GAACTGCAAT |
| 1270 | 1280 | 1290 | 1300 | 1310 | 1320 | 1330 |
| GAAAAGCCTTA | ACACCGGCTG | GTTAGCAGGG | CTCTTCTATC | ACCACAAAATT | CAACTCTTCA | GGTTGTCCTG |
| 1340 | 1350 | 1360 | 1370 | 1380 | 1390 | 1400 |
| AGAGGTTGGC | CAGCTGCCGA | CGCCTTACCG | ATTTTGCCCA | GGGCGGGGGT | CCTATCAGTT | ACGCCAACGG |
| 1410 | 1420 | 1430 | 1440 | 1450 | 1460 | 1470 |
| AAGCGGCCTC | GATGAACGCC | CCTACTGCTG | GCACTACCCT | CCAAGACCTT | GTGGCATTGT | GCCCGCAAAG |
| 1480 | 1490 | 1500 | 1510 | 1520 | 1530 | 1540 |
| AGCGTGTGTG | GCCCGGTTA | TTGCTTCACT | CCCAGCCCCG | TGGTGGTGGG | AACGACCGAC | AGGTCGGGCG |
| 1550 | 1560 | 1570 | 1580 | 1590 | 1600 | 1610 |
| CGCCTACCTA | CAGCTGGGGT | GCAAATGATA | CGGATGTCTT | TGTCCTTAAC | AACACCAGGC | CACCGCTGGG |
| 1620 | 1630 | 1640 | 1650 | 1660 | 1670 | 1680 |
| CAATTGGTTC | GGTTGCACCT | GGATGAACTC | AACTGGATTC | ACCAAAGTGT | GCGGAGCGCC | CCCTTGTGTC |
| 1690 | 1700 | 1710 | 1720 | 1730 | 1740 | 1750 |
| ATCGGAGGGG | TGGGCAACAA | CACCTTGCTC | TGCCCCACTG | ATTGCTTCCG | CAAGCATCCG | GAAGCCACAT |
| 1760 | 1770 | 1780 | 1790 | 1800 | 1810 | 1820 |
| ACTCTCGGTG | CGGCTCCGGT | CCCTGGATTA | CACCCAGGTG | CATGGTCGAC | TACCCGTATA | GGCTTTGGCA |
| 1830 | 1840 | 1850 | 1860 | 1870 | 1880 | 1890 |
| CTATCCTTGT | ACCATCAATT | ACACCATATT | CAAAGTCAGG | ATGTACGTGG | GAGGGGTCGA | GCACAGGCTG |
| 1900 | 1910 | 1920 | 1930 | 1940 | 1950 | 1960 |
| GAAGCGGCCT | GCAACTGGAC | GCGGGGCGAA | CGCTGTGATC | TGGAAGACAG | GGACAGGTCC | GAGCTCAGCC |
| 1970 | 1980 | 1990 | 2000 | 2010 | 2020 | 2030 |
| CGTTACTGCT | GTCCACCACG | CAGTGGCAGG | TCCTTCCGTG | TTCTTTCACG | ACCCTGCCAG | CCTTGTCCAC |
| 2040 | 2050 | 2060 | 2070 | 2080 | 2090 | 2100 |
| CGGCCTCATC | CACCTCCACC | AGAACATTGT | GGACGTGCAG | TACTTGTACG | GGGTAGGGTC | AAGCATCGCG |
| 2110 | 2120 | 2130 | 2140 | 2150 | 2160 | 2170 |
| TCCTGGGCTA | TTAAGTGGGA | GTACGACGTT | CTCCTGTTCC | TTCTGCTTGC | AGACGCGCGC | GTTTGCTCCT |
| 2180 | 2190 | 2200 | 2210 | 2220 | 2230 | 2240 |
| GCTTGTGGAT | GATGTTACTC | ATATCCCAAG | CGGAGGCGGC | TTTGGAGATC | TCTGAAGTGA | AGATGGATGC |
| 2250 | 2260 | 2270 | 2280 | 2290 | 2300 | 2310 |
| AGAATTCCGA | CATGACTCAG | GATATGAAGT | TCATCATCAA | AAAATTGGTGT | TCTTTGCAGA | AGATGTGGGT |
| 2320 | 2330 | 2340 | 2350 | 2360 | 2370 | 2380 |
| TCAAACAAAG | GTGCAATCAT | TGGACTCATG | GTGGGCGGTG | TTGTCATAGC | GACAGTGATC | GTCATCACCT |
| 2390 | 2400 | 2410 | 2420 | 2430 | 2440 | 2450 |
| TGGTGATGCT | GAAGAAGAAA | CAGTACACAT | CCATTCATCA | TGGTGTGGTG | GAGGTTGACG | CCGCTGTCAC |
| 2460 | 2470 | 2480 | 2490 | 2500 | 2510 | 2520 |
| CCCAGAGGAG | CGCCACCTGT | CCAAGATGCA | GCAGAACGGC | TACGAAAATC | CAACCTACAA | GTTCTTTGAG |
| 2530 | 2540 | 2550 | 2560 | 2570 | 2580 | 2590 |
| CAGATGCAGA | ACTAGACCCC | CGCCACAGCA | GCCTCTGAAG | TTGGACAGCA | AAACCATTGC | TTCACTACCC |
| 2600 | 2610 | 2620 | 2630 | 2640 | 2650 | 2660 |
| ATCGGTGTCC | ATTTATAGAA | TAATGTGGGA | AGAAACAAAC | CCGTTTTATG | ATTTACTCAT | TATCGCCTTT |
| 2670 | 2680 | 2690 | 2700 | 2710 | 2720 | 2730 |
| TGACAGCTGT | GCTGTAACAC | AAGTAGATGC | CTGAACTTGA | ATTAATCCAC | ACATCAGTAT | TGTAATCTAT |
| 2740 | 2750 | 2760 | 2770 | 2780 | 2790 | 2800 |
| CTCTCTTTAC | ATTTTGGTCT | CTATACTACA | TTATTAATGG | GTTTTGTGTA | CTGTAAAGAA | TTTAGCTGTA |
| 2810 | 2820 | 2830 | 2840 | 2850 | 2860 | 2870 |
| TCAAACTAGT | GCATGAATAG | GCCGCTCGAG | CATGCATCTA | GAGGGCCCTA | TTCTATAGTG | TCACCTAAAT |
| 2880 | 2890 | 2900 | 2910 | 2920 | 2930 | 2940 |
| GCTCGCTGAT | CAGCCTCGAC | TGTGCCTTCT | AGTTGCCAGC | CATCTGTTGT | TTGCCCCTCC | CCCGTGCCTT |

|      |      |      |      |      |      |      |
|------|------|------|------|------|------|------|
| 2950 | 2960 | 2970 | 2980 | 2990 | 3000 | 3010 |
| CCTTGACCCT | GGAAGGTGCC | ACTCCCACTG | TCCTTTCCTA | ATAAAATGAG | GAAATTGCAT | CGCATTGTCT |
| 3020 | 3030 | 3040 | 3050 | 3060 | 3070 | 3080 |
| GAGTAGGTGT | CATTCTATTC | TGGGGGGTGG | GGTGGGCAG | GACAGCAAGG | GGGAGGATTG | GGAAGACAAT |
| 3090 | 3100 | 3110 | 3120 | 3130 | 3140 | 3150 |
| AGCAGGCATG | CTGGGGATGC | GGTGGGCTCT | ATGGAACCAG | CTGGGGCTCG | AGGGGGGATC | CCCACGCGCC |
| 3160 | 3170 | 3180 | 3190 | 3200 | 3210 | 3220 |
| CTGTAGCGGC | GCATTAAGCG | CGGCGGGTGT | GGTGGTTACG | CGCAGCGTGA | CCGCTACACT | TGCCAGCGCC |
| 3230 | 3240 | 3250 | 3260 | 3270 | 3280 | 3290 |
| CTAGCGCCCG | CTCCTTTCGC | TTTCTTCCCT | TCCTTTCTCG | CCACGTTCGC | CGGCTTTCCC | CGTCAAGCTC |
| 3300 | 3310 | 3320 | 3330 | 3340 | 3350 | 3360 |
| TAAATCGGGG | CATCCCTTTA | GGGTTCCGAT | TTAGTGCTTT | ACGGCACCTC | GACCCCAAAA | AACTTGATTA |
| 3370 | 3380 | 3390 | 3400 | 3410 | 3420 | 3430 |
| GGGTGATGGT | TCACGTA6TG | GGCCATCGCC | CTGATAGACG | GTTTTTCGCC | TTTACTGAGC | ACTCTTTAAT |
| 3440 | 3450 | 3460 | 3470 | 3480 | 3490 | 3500 |
| AGTGGACTCT | TGTTCCAAAAC | TGGAACAACA | CTCAACCCTA | TCTCGGTCTA | TTCTTTTGAT | TTATAAGATT |
| 3510 | 3520 | 3530 | 3540 | 3550 | 3560 | 3570 |
| TCCATCGCCA | TGTAAAAGTG | TTACAATTAG | CATTAAATTA | CTTCTTTATA | TGCTACTATT | CTTTTGGCTT |
| 3580 | 3590 | 3600 | 3610 | 3620 | 3630 | 3640 |
| CGTTCACGGG | GTGGGTACCG | AGCTCGAATT | CTGTGGAATG | TGTGTCAGTT | AGGGTGTGGA | AAGTCCCCAG |
| 3650 | 3660 | 3670 | 3680 | 3690 | 3700 | 3710 |
| GCTCCCCAGG | CAGGCAGAAG | TATGCAAAGC | ATGCATCTCA | ATTAGTCAGC | AACCAGGTGT | GGAAAGTCCC |
| 3720 | 3730 | 3740 | 3750 | 3760 | 3770 | 3780 |
| CAGGCTCCCC | AGCAGGCAGA | AGTATGCAAA | GCATGCATCT | CAATTAGTCA | GCAACCATAG | TCCCGCCCCT |
| 3790 | 3800 | 3810 | 3820 | 3830 | 3840 | 3850 |
| AACTCCGCCC | ATCCCGCCCC | TAACTCCGCC | CAGTTCCGCC | CATTCTCCGC | CCCATGGCTG | ACTAATTTTT |
| 3860 | 3870 | 3880 | 3890 | 3900 | 3910 | 3920 |
| TTTATTTATG | CAGAGGCCGA | GGCCGCCTCG | GCCTCTGAGC | TATTCCAGAA | GTAGTGAGGA | GGCTTTTTTG |
| 3930 | 3940 | 3950 | 3960 | 3970 | 3980 | 3990 |
| GAGGCCTAGG | CTTTTGCAAA | AAGCTCCCGG | GAGCTTGGAT | ATCCATTTTC | GGATCTGATC | AAGAGACAGG |
| 4000 | 4010 | 4020 | 4030 | 4040 | 4050 | 4060 |
| ATGAGGATCG | TTTCGCATGA | TTGAACAAGA | TGGATTGCAC | GCAGGTTCTC | CGGCCGCTTG | GGTGGAGAGG |
| 4070 | 4080 | 4090 | 4100 | 4110 | 4120 | 4130 |
| CTATTCGGCT | ATGACTGGGC | ACAACAGACA | ATCGGCTGCT | CTGATGCCGC | CGTGTTCCGG | CTGTCAGCGC |
| 4140 | 4150 | 4160 | 4170 | 4180 | 4190 | 4200 |
| AGGGGCGCCC | GGTTCTTTTT | GTCAAGACCG | ACCTGTCCGG | TGCCCTGAAT | GAACTGCAGG | ACGAGGCAGC |
| 4210 | 4220 | 4230 | 4240 | 4250 | 4260 | 4270 |
| GCGGCTATCG | TGGCTGGCCA | CGACGGGCGT | TCCTTGCGCA | GCTGTGCTCG | ACGTTGTCAC | TGAAGCGGGA |
| 4280 | 4290 | 4300 | 4310 | 4320 | 4330 | 4340 |
| AGGGACTGGC | TGCTATTGGG | CGAAGTGCCG | GGGCAGGATC | TCCTGTCATC | TCACCTTGCT | CCTGCCGAGA |
| 4350 | 4360 | 4370 | 4380 | 4390 | 4400 | 4410 |
| AAGTATCCAT | CATGGCTGAT | GCAATGCGGC | GGCTGCATAC | GCTTGATCCG | GCTACCTGCC | CATTCGACCA |
| 4420 | 4430 | 4440 | 4450 | 4460 | 4470 | 4480 |
| CCAAGCGAAA | CATCGCATCG | AGCGAGCACG | TACTCGGATG | GAAGCCGGTC | TTGTCGATCA | GGATGATCTG |
| 4490 | 4500 | 4510 | 4520 | 4530 | 4540 | 4550 |
| GACGAAGAGC | ATCAGGGGCT | CGCGCCAGCC | GAACTGTTCG | CCAGGCTCAA | GGCGCGCATG | CCCGACGGCG |
| 4560 | 4570 | 4580 | 4590 | 4600 | 4610 | 4620 |
| AGGATCTCGT | CGTGACCCAT | GGCGATGCCT | GCTTGCCGAA | TATCATGGTG | GAAAATGGCC | GCTTTTCTGG |
| 4630 | 4640 | 4650 | 4660 | 4670 | 4680 | 4690 |
| ATTCATCGAC | TGTGGCCGGC | TGGGTGTGGC | GGACCGCTAT | CAGGACATAG | CGTTGGCTAC | CCGTGATATT |
| 4700 | 4710 | 4720 | 4730 | 4740 | 4750 | 4760 |
| GCTGAAGAGC | TTGGCGGC6A | ATGGGCTGAC | CGCTTCCTCG | TGCAAACGG | TATCGCCGCT | CCCGATTCGC |
| 4770 | 4780 | 4790 | 4800 | 4810 | 4820 | 4830 |

-continued

| | | | | | | |
|---|---|---|---|---|---|---|
| AGCGCATCGC | CTTCTATCGC | CTTCTTGACG | AGTTCTTCTG | AGCGGGACTC | TGGGGTTCGA | AATGACCGAC |
| 4840 | 4850 | 4860 | 4870 | 4880 | 4890 | 4900 |
| CAAGCGACGC | CCAACCTGCC | ATCACGAGAT | TTCGATTCCA | CCGCCGCCTT | CTATGAAAGG | TTGGGCTTCG |
| 4910 | 4920 | 4930 | 4940 | 4950 | 4960 | 4970 |
| GAATCGTTTT | CCGGGACGCC | GGCTGGATGA | TCCTCCAGCG | CGGGGATCTC | ATGCTGGAGT | TCTTCGCCCA |
| 4980 | 4990 | 5000 | 5010 | 5020 | 5030 | 5040 |
| CCCCAACTTG | TTTATTGCAG | CTTATAATGG | TTACAAATAA | AGCAATAGCA | TCACAAATTT | CACAAATAAA |
| 5050 | 5060 | 5070 | 5080 | 5090 | 5100 | 5110 |
| GCATTTTTTT | CACTGCATTC | TAGTTGTGGT | TTGTCCAAAC | TCATCAATGT | ATCTTATCAT | GTCTGGATCC |
| 5120 | 5130 | 5140 | 5150 | 5160 | 5170 | 5180 |
| CGTCGACCTC | GAGAGCTTGG | CGTAATCATG | GTCATAGCTG | AACCTGTGTG | AAAATTGTTA | TCCGCTCACA |
| 5190 | 5200 | 5210 | 5220 | 5230 | 5240 | 5250 |
| ATTCCACACA | ACATACGAGC | CGGAAGCATA | AAGTGTAAAG | CCTGGGGTGC | CTAATGAGTG | AGCTAACTCA |
| 5260 | 5270 | 5280 | 5290 | 5300 | 5310 | 5320 |
| CATTAATTGC | GTTGCGCTCA | CTGCCCGCTT | TCCAGTCGGG | AAACCTGTCG | TGCCAGCTGC | ATTAATGAAT |
| 5330 | 5340 | 5350 | 5360 | 5370 | 5380 | 5390 |
| CGGCCAACGC | GCGGTTTGCG | GCGGAAGCG | TATTGGGCGC | TCTTCCGCTT | CCTCGCTCAC | TGACTCGCTG |
| 5400 | 5410 | 5420 | 5430 | 5440 | 5450 | 5460 |
| CGCTCGGTCG | TTCGGCTGCG | GCGAGCGGTA | TCAGCTCACT | CAAAGGCGGT | AATACGGTTA | TCCACAGAAT |
| 5470 | 5480 | 5490 | 5500 | 5510 | 5520 | 5530 |
| CAGGGGATAA | CGCAGGAAAG | AACATGTGAG | CAAAAGGCCA | GCAAAAGGCC | AGGAACCGTA | AAAAGGCCGC |
| 5540 | 5550 | 5560 | 5570 | 5580 | 5590 | 5600 |
| GTTGCTGGCG | TTTTTCCATA | GGCTCCGCCC | CCCTGACGAG | CATCACAAAA | ATCGACGCTC | AAGTCAGAGG |
| 5610 | 5620 | 5630 | 5640 | 5650 | 5660 | 5670 |
| TGGCGAAACC | CGACAGGACT | ATAAAGATAC | CAGGCGTTTC | CCCCTGGAAG | CTCCCTCGTG | CGCTCTCCTG |
| 5680 | 5690 | 5700 | 5710 | 5720 | 5730 | 5740 |
| TTCCGACCCT | GCCGCTTACC | GGATACCTGT | CCGCCTTTCT | CCCTTCGGGA | AGCGTGGCGC | TTTCTCAATG |
| 5750 | 5760 | 5770 | 5780 | 5790 | 5800 | 5810 |
| CTCACGCTGT | AGGTATCTCA | GTTCGGTGTA | GGTCGTTCGC | TCCAAGCTGG | GCTGTGTGCA | CGAACCCCCC |
| 5820 | 5830 | 5840 | 5850 | 5860 | 5870 | 5880 |
| GTTCAGCCCG | ACCGCTGCGC | CTTATCCGGT | AACTATCGTC | TTGAGTCCAA | CCCGGTAAGA | CACGACTTAT |
| 5890 | 5900 | 5910 | 5920 | 5930 | 5940 | 5950 |
| CGCCAtTGGC | AGCAGCCACT | GGTAACAGGA | TTAGCAGAGC | GAGGTATGTA | GGCGGTGCTA | CAGAGTTCTT |
| 5960 | 5970 | 5980 | 5990 | 6000 | 6010 | 6020 |
| GAAGTGGTGG | CCTAACTACG | GCTACACTAG | AAGGACAGTA | TTTGGTATCT | GCGCTCTGCT | GAAGCCAGTT |
| 6030 | 6040 | 6050 | 6060 | 6070 | 6080 | 6090 |
| ACCTTCGGAA | AAAGAGTTGG | TAGCTCTTGA | TCCGGCAAAC | AAACCACCGC | TGGTAGCGGT | GGTTTTTTTG |
| 6100 | 6110 | 6120 | 6130 | 6140 | 6150 | 6160 |
| TTTGCAAGCA | GCAGATTACG | CGCAGAAAAA | AAGGATCTCA | AGAA6ATCCT | TTGATCTTTT | CTACGGGGTC |
| 6170 | 6180 | 6190 | 6200 | 6210 | 6220 | 6230 |
| TGACGCTCAG | TGGAACGAAA | ACTCACGTTA | AGGGATTTTG | GTCATGAGAT | TATCAAAAAG | GATCTTCACC |
| 6240 | 6250 | 6260 | 6270 | 6280 | 6290 | 6300 |
| TAGATCCTTT | TAAAATTAAA | ATGAAGTTTT | AAATCAATCT | AAAGTATATA | TGAGTAAACT | TGGTCTGACA |
| 6310 | 6320 | 6330 | 6340 | 6350 | 6360 | 6370 |
| GTTACCAATG | CTTAATCAGT | GAGGCACCTA | TCTCAGCGAT | CTGTCTATTT | CGTTCATCCA | TAGTTGCCTG |
| 6380 | 6390 | 6400 | 6410 | 6420 | 6430 | 6440 |
| ACTCCCCGTC | GTGTAGATAA | CTACGATACG | GGAGGGCTTA | CCATCTGGCC | CCAGTGCTGC | AATGATACCG |
| 6450 | 6460 | 6470 | 6480 | 6490 | 6500 | 6510 |
| CGAGACCCAC | GCTCACCGGC | TCCAGATTTA | TCAGCAATAA | ACCAGCCAGC | CGGAAGGGCC | GAGCGCAGAA |
| 6520 | 6530 | 6540 | 6550 | 6560 | 6570 | 6580 |
| GTGGTCCTGC | AACTTTATCC | GCCTCCATCC | AGTCTATTAA | TTGTTGCCGG | GAAGCTAGAG | TAAGTAGTTC |
| 6590 | 6600 | 6610 | 6620 | 6630 | 6640 | 6650 |
| GCCAGTTAAT | AGTTTGCGCA | ACGTTGTTGC | CATTGCTACA | GGCATCGTGG | TGTCACGCTC | GTCGTTTGGT |

-continued

| | | | | | | |
|---|---|---|---|---|---|---|
| 6660 | 6670 | 6680 | 6690 | 6700 | 6710 | 6720 |
| ATGGCTTCAT | TCAGCTCCGG | TTCCCAACGA | TCAAGGCGAG | TTACATGATC | CCCCATGTTG | TGCAAAAAAG |
| 6730 | 6740 | 6750 | 6760 | 6770 | 6780 | 6790 |
| CGGTTAGCTC | CTTCGGTCCT | CCGATCGTTG | TCAGAAGTAA | GTTGGCCGCA | GTGTTATCAC | TCATGGTTAT |
| 6800 | 6810 | 6820 | 6830 | 6840 | 6850 | 6860 |
| GGCAGCACTG | CATAATTCTC | TTACTGTCAT | GCCATCCGTA | AGATGCTTTT | CTGTGACTGG | TGAGTACTCA |
| 6870 | 6880 | 6890 | 6900 | 6910 | 6920 | 6930 |
| ACCAAGTCAT | TCTGAGAATA | GTGTATGCGG | CGACCGAGTT | GCTCTTGCCC | GGCGTCAATA | CGGGATAATA |
| 6940 | 6950 | 6960 | 6970 | 6980 | 6990 | 7000 |
| CCGCGCCACA | TAGCAGAACT | TTAAAAGTGC | TCATCATTGG | AAAACGTTCT | TCGGGGCGAA | AACTCTCAAG |
| 7010 | 7020 | 7030 | 7040 | 7050 | 7060 | 7070 |
| GATCTTACCG | CTGTTGAGAT | CCAGTTCGAT | GTAACCCACT | CGTGCACCCA | ACTGATCTTC | AGCATCTTTT |
| 7080 | 7090 | 7100 | 7110 | 7120 | 7130 | 7140 |
| ACTTTCACCA | GCGTTTCTGG | GTGAGCAAAA | ACAGGAAGGC | AAAATGCCGC | AAAAAAGGGA | ATAAGGGCGA |
| 7150 | 7160 | 7170 | 7180 | 7190 | 7200 | 7210 |
| CACGGAAATG | TTGAATACTC | ATACTCTTCC | TTTTTCAATA | TTATTGAAGC | ATTTATCAGG | GTTATTGTCT |
| 7220 | 7230 | 7240 | 7250 | 7260 | 7270 | 7280 |
| CATGAGCGGA | TACATATTTG | AATGTATTTA | GAAAAATAAA | CAAATAGGGG | TTCCGCGCAC | ATTTCCCCGA |
| 7290 | | | | | | |
| AAAGTGCCAC | CTGACGTC | | | | | |

SEQ:

SEQ. ID. NO. 4

PHCV-162

| | | | | | | |
|---|---|---|---|---|---|---|
| 10 | 20 | 30 | 40 | 50 | 60 | 70 |
| MLPGLALLLL | AAWTARALEV | PTDGNAGLLA | EPQIAMFCGR | LNMHMNVQNG | KWDSDPSGTK | TCIDTKETHV |
| 80 | 90 | 100 | 110 | 120 | 130 | 140 |
| TGGSAGHTTA | GLVRLLSPGA | KQNIQLINTN | GSWHINSTAL | NCNESLNTGW | LAGLFYHHKF | NSSGCPERLA |
| 150 | 160 | 170 | 180 | 190 | 200 | 210 |
| SCRRLTDFAQ | GGGPISYANG | SGLDERPYCW | HYPPRPCGIV | PAKSVCGPVY | CFTPSPVVVG | TTDRSGAPTY |
| 220 | 230 | 240 | 250 | 260 | 270 | 280 |
| SWGANDTDVF | VLNNTRPPLG | NWFGCTWMNS | TGFTKVCGAP | PCVIGGVGNN | TLLCPTDCFR | KHPEATYSRC |
| 290 | 300 | 310 | 320 | 330 | 340 | 350 |
| GSGPWITPRC | MVDYPYRLWH | YPCTINYTIF | KVRMYVGGVE | HRLEAACNWT | RGERCDLEDR | DRSELSPLLL |
| 360 | 370 | 380 | 390 | 400 | 410 | 420 |
| STTQWQVLPC | SFTTLPALST | GLIHLHQNIV | DVQYLYGVGS | SIASWAIKWE | YDVLLFLLLA | DARVCSCLWM |
| 430 | 440 | 450 | 460 | 470 | 480 | 490 |
| MLLISQAEAA | LEISEVKMDA | EFRHDSGYEV | HHQKLVFFAE | DVGSNKGAII | GLMVGGVVIA | TVIVITLVML |
| 500 | 510 | 520 | 530 | | | |
| KKKQYTSIHH | GVVEVDAAVT | PEERHLSKMQ | QNGYENPTYK | FFEQMQN. | | |

PEP:

SEQ. ID. NO. 5

PHCV_167
Circular sequence with junction at 7106

| | | | | | | |
|---|---|---|---|---|---|---|
| 10 | 20 | 30 | 40 | 50 | 60 | 70 |
| GACGGATCGG | GAGATCTCCC | GATCCCCTAT | GGTCGACTCT | CAGTACAATC | TGCTCTGATG | CCGCATAGTT |
| 80 | 90 | 100 | 110 | 120 | 130 | 140 |
| AAGCCAGTAT | CTGCTCCCTG | CTTGTGTGTT | GGAGGTCGCT | GAGTAGTGCG | CGAGCAAAAT | TTAAGCTACA |
| 150 | 160 | 170 | 180 | 190 | 200 | 210 |
| ACAAGGCAAG | GCTTGACCGA | CAATTGCATG | AAGAATCTGC | TTAGGGTTAG | GCGTTTTGCG | CTGCTTCGCG |
| 220 | 230 | 240 | 250 | 260 | 270 | 280 |
| ATGTACGGGC | CAGATATACG | CGTTGACATT | GATTATTGAC | TAGTTATTAA | TAGTAATCAA | TTACGGGQTQ |

| 290 | 300 | 310 | 320 | 330 | 340 | 350 |
|---|---|---|---|---|---|---|
| ATTAGTTCAT | AGCCCATATA | TGGAGTTCCG | CGTTACATAA | CTTACGGTAA | ATGGCCCGCC | TGGCTGACCG |
| 360 | 370 | 380 | 390 | 400 | 410 | 420 |
| CCCAACGACC | CCCGCCCATT | GACGTCAATA | ATGACGTATG | TTCCCATAGT | AACGCCAATA | GGGACTTTCC |
| 430 | 440 | 450 | 460 | 470 | 480 | 490 |
| ATTGACGTCA | ATGGGTGGAC | TATTTTCGGT | AAACTGCCCA | CTTGGCAGTA | CATCAAGTGT | ATCATATGCC |
| 500 | 510 | 520 | 530 | 540 | 550 | 560 |
| AAGTACGCCC | CCTATTGACG | TCAATGACGG | TAAATGGCCC | GCCTGGCATT | ATGCCCAGTA | CATGACCTTA |
| 570 | 580 | 590 | 600 | 610 | 620 | 630 |
| TGGGACTTTC | CTACTTGGCA | GTACATCTAC | GTATTAGTCA | TCGCTATTAC | CATGGTGATG | CGGTTTTGGC |
| 640 | 650 | 660 | 670 | 680 | 690 | 700 |
| AGTACATCAA | TGGGCGTGGA | TAGCGGTTTG | ACTCACGGGG | ATTTCCAAGT | CTCCACCCCA | TTGACGTCAA |
| 710 | 720 | 730 | 740 | 750 | 760 | 770 |
| TGGGAGTTTG | TTTTGGCACC | AAAATCAACG | GGACTTTCCA | AAATGTCGTA | ACAACTCCGC | CCCATTGACG |
| 780 | 790 | 800 | 810 | 820 | 830 | 840 |
| CAAATGGGCG | GTAGGCGTGT | ACGGTGGGAG | GTCTATATAA | GCAGAGCTCT | CTGGCTAACT | AGAGAACCCA |
| 850 | 860 | 870 | 880 | 890 | 900 | 910 |
| CTGCTTAACT | GGCTTATCGA | AATTAATACG | ACTCACTATA | GGGAGACCGG | AAGCTTTGCT | CTAGACTGGA |
| 920 | 930 | 940 | 950 | 960 | 970 | 980 |
| ATTCGGGCGC | GATGCTGCCC | GGTTTGGCAC | TGCTCCTGCT | GGCCGCCTGG | ACGGCTCGGG | CGCTGGAGGT |
| 990 | 1000 | 1010 | 1020 | 1030 | 1040 | 1050 |
| ACCCACTGAT | GGTAATGCTG | GCCTGCTGGC | TGAACCCCAG | ATTGCCATGT | TCTGTGGCAG | ACTGAACATG |
| 1060 | 1070 | 1080 | 1090 | 1100 | 1110 | 1120 |
| CACATGAATG | TCCAGAATGG | GAAGTGGGAT | TCAGATCCAT | CAGGGACCAA | AACCTGCATT | GATACCAAGG |
| 1130 | 1140 | 1150 | 1160 | 1170 | 1180 | 1190 |
| AAACCCACGT | CACCGGGGGA | AGTGCCGGCC | ACACCACGGC | TGGGCTTGTT | CGTCTCCTTT | CACCAGGCGC |
| 1200 | 1210 | 1220 | 1230 | 1240 | 1250 | 1260 |
| CAAGCAGAAC | ATCCAACTGA | TCAACACCAA | CGGCAGTTGG | CACATCAATA | GCACGGCCTT | GAACTGCAAT |
| 1270 | 1280 | 1290 | 1300 | 1310 | 1320 | 1330 |
| GAAAGCCTTA | ACACCGGCTG | GTTAGCAGGG | CTCTTCTATC | ACCACAAATT | CAACTCTTCA | GGTTGTCCTG |
| 1340 | 1350 | 1360 | 1370 | 1380 | 1390 | 1400 |
| AGAGGTTGGC | CAGCTGCCGA | CGCCTTACCG | ATTTTGCCCA | GGGCGGGGGT | CCTATCAGTT | ACGCCAACGG |
| 1410 | 1420 | 1430 | 1440 | 1450 | 1460 | 1470 |
| AAGCGGCCTC | GATGAACGCC | CCTACTGCTG | GCACTACCCT | CCAAGACCTT | GTGGCATTGT | GCCCGCAAAG |
| 1480 | 1490 | 1500 | 1510 | 1520 | 1530 | 1540 |
| AGCGTGTGTG | GCCCGGTATA | TTGCTTCACT | CCCAGCCCCG | TGGTGGTGGG | AACGACCGAC | AGGTCGGGCG |
| 1550 | 1560 | 1570 | 1580 | 1590 | 1600 | 1610 |
| CGCCTACCTA | CAGCTGGGGT | GCAAATGATA | CGGATGTCTT | TGTCCTTAAC | AACACCAGGC | CACCGCTGGG |
| 1620 | 1630 | 1640 | 1650 | 1660 | 1670 | 1680 |
| CAATTGGTTC | GGTTGCACCT | GGATGAACTC | AACTGGATTC | ACCAAAGTGT | GCGGAGCGCC | CCCTTGTGTC |
| 1690 | 1700 | 1710 | 1720 | 1730 | 1740 | 1750 |
| ATCGGAGGGG | TGGGCAACAA | CACCTTGCTC | TGCCCCACTG | ATTGCTTCCG | CAAGCATCCG | GAAGCCACAT |
| 1760 | 1770 | 1780 | 1790 | 1800 | 1810 | 1820 |
| ACTCTCGGTG | CGGCTCCGGT | CCCTGGATTA | CACCCAGGTG | CATGGTCGAC | TACCCGTATA | GGCTTTGGCA |
| 1830 | 1840 | 1850 | 1860 | 1870 | 1880 | 1890 |
| CTATCCTTGT | ACCATCAATT | ACACCATATT | CAAAGTCAGG | ATGTACGTGG | GAGGGGTCGA | GCACAGGCTG |
| 1900 | 1910 | 1920 | 1930 | 1940 | 1950 | 1960 |
| GAAGCGGCCT | GCAACTGGAC | GCGGGGCGAA | CGCTGTGATC | TGGAAGACAG | GGACAGGTCC | GAGCTCAGCC |
| 1970 | 1980 | 1990 | 2000 | 2010 | 2020 | 2030 |
| CGTTACTGCT | GTCCACCACG | CAGTGGCAGG | TCCTTCCGTG | TTCTTTCACG | ACCCTGCCAG | CCTAGATCTC |
| 2040 | 2050 | 2060 | 2070 | 2080 | 2090 | 2100 |
| TGAAGTGAAG | ATGGATGCAG | AATTCCGACA | TGACTCAGGA | TATGAAGTTC | ATCATCAAAA | ATTGGTGTTC |
| 2110 | 2120 | 2130 | 2140 | 2150 | 2160 | 2170 |

|            |            |            |            |            |            |            |
|------------|------------|------------|------------|------------|------------|------------|
| TTTGCAGAAG | ATGTGGGTTC | AAACAAAGGT | GCAATCATTG | GACTCATGGT | GGGCGGTGTT | GTCATAGCGA |
| 2180       | 2190       | 2200       | 2210       | 2220       | 2230       | 2240       |
| CAGTGATCGT | CATCACCTTG | GTGATGCTGA | AGAAGAAACA | GTACACATCC | ATTCATCATG | GTGTGGTGGA |
| 2250       | 2260       | 2270       | 2280       | 2290       | 2300       | 2310       |
| GGTTGACGCC | GCTGTCACCC | CAGAGGAGCG | CCACCTGTCC | AAGATGCAGC | AGAACGGCTA | CGAAAATCCA |
| 2320       | 2330       | 2340       | 2350       | 2360       | 2370       | 2380       |
| ACCTACAAGT | TCTTTGAGCA | GATGCAGAAC | TAGACCCCCG | CCACAGCAGC | CTCTGAAGTT | GGACAGCAAA |
| 2390       | 2400       | 2410       | 2420       | 2430       | 2440       | 2450       |
| ACCATTGCTT | CACTACCCAT | CGGTGTCCAT | TTATAGAATA | ATGTGGAAG  | AAACAAACCC | GTTTTATGAT |
| 2460       | 2470       | 2480       | 2490       | 2500       | 2510       | 2520       |
| TTACTCATTA | TCGCCTTTTG | ACAGCTGTGC | TGTAACACAA | GTAGATGCCT | GAACTTGAAT | TAATCCACAC |
| 2530       | 2540       | 2550       | 2560       | 2570       | 2580       | 2590       |
| ATCAGTAATG | TATTCTATCT | CTCTTTACAT | TTTGGTCTCT | ATACTACATT | ATTAATGGGT | TTTGTGTACT |
| 2600       | 2610       | 2620       | 2630       | 2640       | 2650       | 2660       |
| GTAAAGAATT | TAGCTGTATC | AAACTAGTGC | ATGAATAGGC | CGCTCGAGCA | TGCATCTAGA | GGGCCCTATT |
| 2670       | 2680       | 2690       | 2700       | 2710       | 2720       | 2730       |
| CTATAGTGTC | ACCTAAATGC | TCGCTGATCA | GCCTCGACTG | TGCCTTCTAG | TTGCCAGCCA | TCTGTTGTTT |
| 2740       | 2750       | 2760       | 2770       | 2780       | 2790       | 2800       |
| GCCCCTCCCC | CGTGCCTTCC | TTGACCCTGG | AAGGTGCCAC | TCCCACTGTC | CTTTCCTAAT | AAAATGAGGA |
| 2810       | 2820       | 2830       | 2840       | 2850       | 2860       | 2870       |
| AATTGCATCG | CATTGTCTGA | GTAGGTGTCA | TTCTATTCTG | GGGGGTGGGG | TGGGGCAGGA | CAGCAAGGGG |
| 2880       | 2890       | 2900       | 2910       | 2920       | 2930       | 2940       |
| GAGGATTGGG | AAGACAATAG | CAGGCATGCT | GGGGATGCGG | TGGGCTCTAT | GGAACCAGCT | GGGGCTCGAG |
| 2950       | 2960       | 2970       | 2980       | 2990       | 3000       | 3010       |
| GGGGGATCCC | CACGCGCCCT | GTAGCGGCGC | ATTAAGCGCG | GCGGGTGTGG | TGGTTACGCG | CAGCGTGACC |
| 3020       | 3030       | 3040       | 3050       | 3060       | 3070       | 3080       |
| GCTACACTTG | CCAGCGCCCT | AGCGCCCGCT | CCTTTCGCTT | TCTTCCCTTC | CTTTCTCGCC | ACGTTCGCCG |
| 3090       | 3100       | 3110       | 3120       | 3130       | 3140       | 3150       |
| GCTTTCCCCG | TCAAGCTCTA | AATCGGGGCA | TCCCTTTAGG | GTTCCGATTT | AGTGCTTTAC | GGCACCTCGA |
| 3160       | 3170       | 3180       | 3190       | 3200       | 3210       | 3220       |
| CCCCAAAAAA | CTTGATTAGG | GTGATGGTTC | ACGTAGTGGG | CCATCGCCCT | GATAGACGGT | TTTTCGCCTT |
| 3230       | 3240       | 3250       | 3260       | 3270       | 3280       | 3290       |
| TACTGAGCAC | TCTTTAATAG | TGGACTCTTG | TTCCAAACTG | GAACAACACT | CAACCCTATC | TCGGTCTATT |
| 3300       | 3310       | 3320       | 3330       | 3340       | 3350       | 3360       |
| CTTTTGATTT | ATAAGATTTC | CATCGCCATG | TAAAAGTGTT | ACAATTAGCA | TTAAATTACT | TCTTTATATG |
| 3370       | 3380       | 3390       | 3400       | 3410       | 3420       | 3430       |
| CTACTATTCT | TTTGGCTTCG | TTCACGGGGT | GGGTACCGAG | CTCGAATTCT | GTGGAATGTG | TGTCAGTTAG |
| 3440       | 3450       | 3460       | 3470       | 3480       | 3490       | 3500       |
| GGTGTGGAAA | GTCCCCAGGC | TCCCCAGGCA | GGCAGAAGTA | TGCAAAGCAT | GCATCTCAAT | TAGTCAGCAA |
| 3510       | 3520       | 3530       | 3540       | 3550       | 3560       | 3570       |
| CCAGGTGTGG | AAAGTCCCCA | GGCTCCCCAG | CAGGCAGAAG | TATGCAAAGC | ATGCATCTCA | ATTAGTCAGC |
| 3580       | 3590       | 3600       | 3610       | 3620       | 3630       | 3640       |
| AACCATAGTC | CCGCCCCTAA | CTCCGCCCAT | CCCGCCCCTA | ACTCCGCCCA | GTTCCGCCCA | TTCTCCGCCC |
| 3650       | 3660       | 3670       | 3680       | 3690       | 3700       | 3710       |
| CATGGCTGAC | TAATTTTTTT | TATTTATGCA | GAGGCCGAGG | CCGCCTCGGC | CTCTGAGCTA | TTCCAGAAGT |
| 3720       | 3730       | 3740       | 3750       | 3760       | 3770       | 3780       |
| AGTGAGGAGG | CTTTTTTGGA | GGCCTAGGCT | TTTGCAAAAA | GCTCCCGGGA | GCTTGGATAT | CCATTTTCGG |
| 3790       | 3800       | 3810       | 3820       | 3830       | 3840       | 3850       |
| ATCTGATCAA | GAGACAGGAT | GAGGATCGTT | TCGCATGATT | GAACAAGATG | GATTGCACGC | AGGTTCTCCG |
| 3860       | 3870       | 3880       | 3890       | 3900       | 3910       | 3920       |
| GCCGCTTGGG | TGGAGAGGCT | ATTCGGCTAT | GACTGGGCAC | AACAGACAAT | CGGCTGCTCT | GATGCCGCCG |
| 3930       | 3940       | 3950       | 3960       | 3970       | 3980       | 3990       |
| TGTTCCGGCT | GTCAGCGCAG | GGGCGCCCGG | TTCTTTTTGT | CAAGACCGAC | CTGTCCGGTG | CCCTGAATGA |

| 4000 | 4010 | 4020 | 4030 | 4040 | 4050 | 4060 |
|---|---|---|---|---|---|---|
| ACTGCAGGAC | GAGGCAGCGC | GGCTATCGTG | GCTGGCCACG | ACGGGCGTTC | CTTGCGCAGC | TGTGCTCGAC |
| 4070 | 4080 | 4090 | 4100 | 4110 | 4120 | 4130 |
| GTTGTCACTG | AAGCGGGAAG | GGACTGGCTG | CTATTGGGCG | AAGTGCCGGG | GCAGGATCTC | CTGTCATCTC |
| 4140 | 4150 | 4160 | 4170 | 4180 | 4190 | 4200 |
| ACCTTGCTCC | TGCCGAGAAA | GTATCCATCA | TGGCTGATGC | AATGCGGCGG | CTGCATACGC | TTGATCCGGC |
| 4210 | 4220 | 4230 | 4240 | 4250 | 4260 | 4270 |
| TACCTGCCCA | TTCGACCACC | AAGCGAAACA | TCGCATCGAG | CGAGCACGTA | CTCGGATGGA | AGCCGGTCTT |
| 4280 | 4290 | 4300 | 4310 | 4320 | 4330 | 4340 |
| GTCGATCAGG | ATGATCTGGA | CGAAGAGCAT | CAGGGGCTCG | CGCCAGCCGA | ACTGTTCGCC | AGGCTCAAGG |
| 4350 | 4360 | 4370 | 4380 | 4390 | 4400 | 4410 |
| CGCGCATGCC | CGACGGCGAG | GATCTCGTCG | TGACCCATGG | CGATGCCTGC | TTGCCGAATA | TCATGGTGGA |
| 4420 | 4430 | 4440 | 4450 | 4460 | 4470 | 4480 |
| AAATGGCCGC | TTTTCTGGAT | TCATCGACTG | TGGCCGGCTG | GGTGTGGCGG | ACCGCTATCA | GGACATAGCG |
| 4490 | 4500 | 4510 | 4520 | 4530 | 4540 | 4550 |
| TTGGCTACCC | GTGATATTGC | TGAAGAGCTT | GGCGGCGAAT | GGGCTGACCG | CTTCCTCGTG | CTTTACGGTA |
| 4560 | 4570 | 4580 | 4590 | 4600 | 4610 | 4620 |
| TCGCCGCTCC | CGATTCGCAG | CGCATCGCCT | TCTATCGCCT | TCTTGACGAG | TTCTTCTGAG | CGGGACTCTG |
| 4630 | 4640 | 4650 | 4660 | 4670 | 4680 | 4690 |
| GGGTTCGAAA | TGACCGACCA | AGCGACGCCC | AACCTGCCAT | CACGAGATTT | CGATTCCACC | GCCGCCTTCT |
| 4700 | 4710 | 4720 | 4730 | 4740 | 4750 | 4760 |
| ATGAAAGGTT | GGGCTTCGGA | ATCGTTTTCC | GGGACGCCGG | CTGGATGATC | CTCCAGCGCG | GGGATCTCAT |
| 4770 | 4780 | 4790 | 4800 | 4810 | 4820 | 4830 |
| GCTGGAGTTC | TTCGCCCACC | CCAACTTGTT | TATTGCAGCT | TATAATGGTT | ACAAATAAAG | CAATAGCATC |
| 4840 | 4850 | 4860 | 4870 | 4880 | 4890 | 4900 |
| ACAAATTTCA | CAAATAAAGC | ATTTTTTTCA | CTGCATTCTA | GTTGTGGTTT | GTCCAAACTC | ATCAATGTAT |
| 4910 | 4920 | 4930 | 4940 | 4950 | 4960 | 4970 |
| CTTATCATGT | CTGGATCCCG | TCGACCTCGA | GAGCTTGGCG | TAATCATGGT | CATAGCTGTT | TCCTGTGTGA |
| 4980 | 4990 | 5000 | 5010 | 5020 | 5030 | 5040 |
| AATTGTTATC | CGCTCACAAT | TCCACACAAC | ATACGAGCCG | GAAGCATAAA | GTGTAAAGCC | TGGGGTGCCT |
| 5050 | 5060 | 5070 | 5080 | 5090 | 5100 | 5110 |
| ATTGAGTGAG | CTAACTCACA | TTAATTGCGT | TGCGCTCACT | GCCCGCTTTC | CAGTCGGGAA | ACCTGTCGTG |
| 5120 | 5130 | 5140 | 5150 | 5160 | 5170 | 5180 |
| CCAGCTGCAT | TAATGAATCG | GCCAACGCGC | GGGGAGAGGC | GGTTTGCGTA | TTGGGCGCTC | TTCCGCTTCC |
| 5190 | 5200 | 5210 | 5220 | 5230 | 5240 | 5250 |
| TCGCTCACTG | ACTCGCTGCG | CTCGGTCGTT | CGGCTGCGGC | GAGCGGTATC | AGCTCACTCA | AAGGCGGTAA |
| 5260 | 5270 | 5280 | 5290 | 5300 | 5310 | 5320 |
| TACGGTTATC | CACAGAATCA | GGGGATAACG | CAGGAAAGAA | CATGTGAGCA | AAAGGCCAGC | AAAAGGCCAG |
| 5330 | 5340 | 5350 | 5360 | 5370 | 5380 | 5390 |
| GAACCGTAAA | AAGGCCGCGT | TGCTGGCGTT | TTTCCATAGG | CTCCGCCCCC | CTGACGAGCA | TCACAAAAAT |
| 5400 | 5410 | 5420 | 5430 | 5440 | 5450 | 5460 |
| CGACGCTCAA | GTCAGAGGTG | GCGAAACCCG | ACAGGACTAT | AAAGATACCA | GGCGTTTCCC | CCTGGAAGCT |
| 5470 | 5480 | 5490 | 5500 | 5510 | 5520 | 5530 |
| CCCTCGTGCG | CTCTCCTGTT | CCGACCCTGC | CGCTTACCGG | ATACCTGTCC | GCCTTTCTCC | CTTCGGGAAG |
| 5540 | 5550 | 5560 | 5570 | 5580 | 5590 | 5600 |
| CGTGGCGCTT | TCTCAATGCT | CACGCTGTAG | GTATCTCAGT | TCGGTGTAGG | TCGTTCGCTC | CAAGCTGGGC |
| 5610 | 5620 | 5630 | 5640 | 5650 | 5660 | 5670 |
| TGTGTGCACG | AACCCCCCGT | TCAGCCCGAC | CGCTGCGCCT | TATCCGGTAA | CTATCGTCTT | GAGTCCAACC |
| 5680 | 5690 | 5700 | 5710 | 5720 | 5730 | 5740 |
| CGGTAAGACA | CGACTTATCG | CCACTGGCAG | CAGCCACTGG | TAACAGGATT | AGCAGAGCGA | GGTATGTAGG |
| 5750 | 5760 | 5770 | 5780 | 5790 | 5800 | 5810 |
| CGGTGCTACA | GAGTTCTTGA | AGTGGTGGCC | TAACTACGGC | TACACTAGAA | GGACAGTATT | TGGTATCTGC |
| 5820 | 5830 | 5840 | 5850 | 5860 | 5870 | 5880 |
| GCTCTGCTGA | AGCCAGTTAC | CTTCGGAAAA | AGAGTTGGTA | GCTCTTGATC | CGGCAAACAA | ACCACCGPTG |

|  |  |  |  |  |  |  |
|---|---|---|---|---|---|---|
| 5890 GTAGCGGTGG | 5900 TTTTTTTGTT | 5910 TGCAAGCAGC | 5920 AGATTACGCG | 5930 CAGAAAAAAA | 5940 GGATCTCAAG | 5950 AAGATCCTTT |
| 5960 GATCTTTTCT | 5970 ACGGGGTCTG | 5980 ACGCTCAGTG | 5990 GAACGAAAAC | 6000 TCACGTTAAG | 6010 GGATTTTGGT | 6020 CATGAGATTA |
| 6030 TCAAAAGGA | 6040 TCTTCACCTA | 6050 GATCCTTTTA | 6060 AATTAAAAAT | 6070 GAAGTTTTAA | 6080 ATCAATCTAA | 6090 AGTATATATG |
| 6100 AGTAAACTTG | 6110 GTCTGACAAT | 6120 TACCAATGCT | 6130 TAATCAGTGA | 6140 GGCACCTATC | 6150 TCAGCGATCT | 6160 GTCTATTTCG |
| 6170 TTCATCCATA | 6180 GTTGCCTGAC | 6190 TCCCCGTCGT | 6200 GTAGATAACT | 6210 ACGATACGGG | 6220 AGGGCTTACC | 6230 ATCTGGCCCC |
| 6240 AGTGCTGCAA | 6250 TGATACCGCG | 6260 AGACCCACGC | 6270 TCACCGGCTC | 6280 CAGATTTATC | 6290 AGCAATAAAC | 6300 CAGCCAGCCG |
| 6310 GAAGGGCCGA | 6320 GCGCAGAAGT | 6330 GGTCCTGCAA | 6340 CTTTATCCGC | 6350 CTCCATCCAG | 6360 TCTATTAATT | 6370 GTTGCCGGGA |
| 6380 AGCTAGAGTA | 6390 AGTAGTTCGC | 6400 CAGTTAATAG | 6410 TTTGCGCAAC | 6420 GTTGTTGCCA | 6430 TTGCTACAGG | 6440 CATCGTGGTG |
| 6450 TCACGCTCGT | 6460 CGTTTGGTAT | 6470 GGCTTCATTC | 6480 AGCTCCGGTT | 6490 CCCAACGATC | 6500 AAGGCGAGTT | 6510 ACATGATCCC |
| 6520 CCATGTTGTG | 6530 CAAAAAAGCG | 6540 GTTAGCTCCT | 6550 TCGGTCCTCC | 6560 GATCGTTGTC | 6570 AGAAGTAAGT | 6580 TGGCCGCAGT |
| 6590 GTTATCACTC | 6600 ATGGTTATGG | 6610 CAGCACTGCA | 6620 TAATTCTCTT | 6630 ACTGTCATGC | 6640 CATCCGTAAG | 6650 ATGCTTTTCT |
| 6660 GTGACTGGTG | 6670 AGTACTCAAC | 6680 CAAGTCATTC | 6690 TGAGAATAGT | 6700 GTATGCGGCG | 6710 ACCGAGTTGC | 6720 TCTTGCCCGG |
| 6730 CGTCAATACG | 6740 GGATAATACC | 6750 GCGCCACATA | 6760 GCAGAACTTT | 6770 AAAAGTGCTC | 6780 ATCATTGGAA | 6790 AACGTTCTTC |
| 6800 GGGGCGAAAA | 6810 CTCTCAAGGA | 6820 TCTTACCGCT | 6830 GTTGAGATCC | 6840 AGTTCGATGT | 6850 AACCCACTCG | 6860 TGCACCCAAC |
| 6870 TGATCTTCAG | 6880 CATCTTTTAC | 6890 TTTCACCAGC | 6900 GTTTCTGGGT | 6910 GAGCAAAAAC | 6920 AGGAAGGCAA | 6930 AATGCCGCAA |
| 6940 AAAAGGGAAT | 6950 AAGGGCGACA | 6960 CGGAAATGTT | 6970 GAATACTCAT | 6980 ACTCTTCCTT | 6990 TTTCAATATT | 7000 ATTGAAGCAT |
| 7010 TTATCAGGGT | 7020 TATTGTCTCA | 7030 TGAGCGGATA | 7040 CATATTTGAA | 7050 TGTATTTAGA | 7060 AAAATAAACA | 7070 AATAGGGGTT |
| 7080 CCGCGCACAT | 7090 TTCCCCGAAA | 7100 AGTGCCACCT | GACGTC |  |  |  |

SEQ:

SEQ. ID. NO. 6

PHCV-167

|  |  |  |  |  |  |  |
|---|---|---|---|---|---|---|
| 10 MLPGLALLLL | 20 AAWTARALEV | 30 PTDGNAGLLA | 40 EPQIAMFCGR | 50 LNMHMNVQNG | 60 KWDSDPSGTK | 70 TCIDTKETHV |
| 80 TGGSAGHTTA | 90 GLVRLLSPGA | 100 KQNIQLINTN | 110 GSWHINSTAL | 120 NCNESLNTGW | 130 LAGLFYHHKF | 140 NSSGCPERLA |
| 150 SCRRLTDFAQ | 160 GGGPISYANG | 170 SGLDERPYCW | 180 HYPPRPCGIV | 190 PAKSVCGPVY | 200 CFTPSPVVVG | 210 TTDRSGAPTY |
| 220 SWGANDTDVF | 230 VLNNTRPPLG | 240 NWFGCTWMNS | 250 TGFTKVCGAP | 260 PCVIGGVGNN | 270 TLLCPTDCFR | 280 KHPEATYSRC |
| 290 GSGPWITPRC | 300 MVDYPYRLWH | 310 YPCTINYTIF | 320 KVRMYVGGVE | 330 HRLEAACNWT | 340 RGERCDLEDR | 350 DRSELSPLLL |
| 360 STTQWQVLPC | SFTTLPA. |  |  |  |  |  |

PEP:

SEQ. ID. NO. 7

PHCV_168

Circular sequence with junction at 4810

```
         10          20          30          40          50          60          70
    GCGTAATCTG  CTGCTTGCAA  ACAAAAAAAC  CACCGCTACC  AGCGGTGGTT  TGTTTGCCGG  ATCAAGAGCT 80          90         100         110         120         130         140
    ACCAACTCTT  TTTCCGAAGG  TAACTGGCTT  CAGCAGAGCG  CAGATACCAA  ATACTGTCCT  TCTAGTGTAG 150         160         170         180         190         200         210
    CCGTAGTTAG  GCCACCACTT  CAAGAACTCT  GTAGCACCGC  CTACATACCT  CGCTCTGCTA  ATCCTGTTAC 220         230         240         250         260         270         280
    CAGTGGCTGC  TGCCAGTGGC  GATAAGTCGT  GTCTTACCGG  GTTGGACTCA  AGACGATAGT  TACCGGATAA 290         300         310         320         330         340         350
    GGCGCAGCGG  TCGGGCTGAA  CGGGGGGTTC  GTGCACACAG  CCCAGCTTGG  AGCGAACGAC  CTACACCGAA 360         370         380         390         400         410         420
    CTGAGATACC  TACAGCGTGA  GCATTGAGAA  AGCGCCACGC  TTCCCGAAGG  GAGAAAGGCG  GACAGGTATC 430         440         450         460         470         480         490
    CGGTAAGCGG  CAGGGTCGGA  ACAGGAGAGC  GCACGAGGGA  GCTTCCAGGG  GGAAACGCCT  GGTATCTTTA 500         510         520         530         540         550         560
    TAGTCCTGTC  GGGTTTCGCC  ACCTCTGACT  TGAGCGTCGA  TTTTTGTGAT  GCTCGTCAGG  GGGGCGGAGC 570         580         590         600         610         620         630
    CTATGGAAAA  ACGCCAGCAA  CGCAAGCTAG  CTTCTAGCTA  GAAATTGTAA  ACGTTAATAT  TTTGTTAAAA 640         650         660         670         680         690         700
    TTCGCGTTAA  ATTTTTGTTA  AATCAGCTCA  TTTTTTAACC  AATAGGCCGA  AATCGGCAAA  ATCCCTTATA 710         720         730         740         750         760         770
    AATCAAAAGA  ATAGCCCGAG  ATAGGGTTGA  GTGTTGTTCC  AGTTTGGAAC  AAGAGTCCAC  TATTAAAGAA 780         790         800         810         820         830         840
    CGTGGACTCC  AACGTCAAAG  GGCGAAAAAC  CGTCTATCAG  GGCGATGGCC  GCCCACTACG  TGAACCATCA 850         860         870         880         890         900         910
    CCCAAATCAA  GTTTTTTGGG  GTCGAGGTGC  CGTAAAGCAC  TAAATCGGAA  CCCTAAAGGG  AGCCCCCGAT 920         930         940         950         960         970         980
    TTAGAGCTTG  ACGGGGAAAG  CCGGCGAACG  TGGCGAGAAA  GGAAGGGAAG  AAAGCGAAAG  GAGCGGGCGC 990        1000        1010        1020        1030        1040        1050
    TAGGGCGCTG  GCAAGTGTAG  CGGTCACGCT  GCGCGTAACC  ACCACACCCG  CCGCGCTTAA  TGCGCCGCTA 1060        1070        1080        1090        1100        1110        1120
    CAGGGCGCGT  ACTATGGTTG  CTTTGACGAG  ACCGTATAAC  GTGCTTTCCT  CGTTGGAATC  AGAGCGGGAG 1130        1140        1150        1160        1170        1180        1190
    CTAAACAGGA  GGCCGATTAA  AGGGATTTTA  GACAGGAACG  GTACGCCAGC  TGGATCACCG  CGGTCTTTCT 1200        1210        1220        1230        1240        1250        1260
    CAACGTAACA  CTTTACAGCG  GCGCGTCATT  TGATATGATG  CGCCCCGCTT  CCCGATAAGG  GAGCAGGCCA 1270        1280        1290        1300        1310        1320        1330
    GTAAAAGCAT  TACCCGTGGT  GGGGTTCCCG  AGCGGCCAAA  GGGAGCAGAC  TCTAAATCTG  CCGTCATCGA 1340        1350        1360        1370        1380        1390        1400
    CTTCGAAGGT  TCGAATCCTT  CCCCCACCAC  CATCACTTTC  AAAAGTCCGA  AAGAATCTGC  TCCCTGCTTG 1410        1420        1430        1440        1450        1460        1470
    TGTGTTGGAG  GTCGCTGAGT  AGTGCGCGAG  TAAAATTTAA  GCTACAACAA  GGCAAGGCTT  GACCGACAAT 1480        1490        1500        1510        1520        1530        1540
    TGCATGAAGA  ATCTGCTTAG  GGTTAGGCGT  TTTGCGCTGC  TTCGCGATGT  ACGGGCCAGA  TATACGCGTT 1550        1560        1570        1580        1590        1600        1610
    GACATTGATT  ATTGACTAGT  TATTAATAGT  AATCAATTAC  GGGGTCATTA  GTTCATAGCC  CATATATGGA 1620        1630        1640        1650        1660        1670        1680
    GTTCCGCGTT  ACATAACTTA  CGGTAAATGG  CCCGCCTGGC  TGACCGCCCA  ACGACCCCCG  CCCATTGACG
```

-continued

| | | | | | | |
|---|---|---|---|---|---|---|
| 1690 TCAATAATGA | 1700 CGTATGTTCC | 1710 CATAGTAACG | 1720 CCAATAGGGA | 1730 CTTTCCATTG | 1740 ACGTCAATGG | 1750 GTGGACTATT |
| 1760 TACGGTAAAC | 1770 TGCCCACTTG | 1780 GCAGTACATC | 1790 AAGTGTATCA | 1800 TATGCCAAGT | 1810 ACGCCCCTA | 1820 TTGACGTCAA |
| 1830 TGACGGTAAA | 1840 TGGCCCGCCT | 1850 GGCATTATGC | 1860 CCAGTACATG | 1870 ACCTTATGGG | 1880 ACTTTCCTAC | 1890 TTGGCAGTAC |
| 1900 ATCTACGTAT | 1910 TAGTCATCGT | 1920 TATTACCATG | 1930 GTGATGCGGT | 1940 TTTGGCAGTA | 1950 CATCAATGGG | 1960 CGTGGATAGC |
| 1970 GGTTTGACTC | 1980 ACGGGGATTT | 1990 CCAAGTCTCC | 2000 ACCCCATTGA | 2010 CGTCAATGGG | 2020 AGTTTGTTTT | 2030 GGCACCAAAA |
| 2040 TCAACGGGAC | 2050 TTTCCAAAAT | 2060 GTCGTAACAA | 2070 CTCCGCCCCA | 2080 TTGACGCAAA | 2090 TGGGCGGTAG | 2100 GCGTGTACGG |
| 2110 TGGGAGGTCT | 2120 ATATAAGCAG | 2130 AGCTCTCTGG | 2140 CTAACTAGAG | 2150 AACCCACTGC | 2160 TTAACTGGCT | 2170 TATCGAAATT |
| 2180 AATACGACTC | 2190 ACTATAGGGA | 2200 GACCGGAAGC | 2210 TTGGTACCGA | 2220 GCTCGGATCT | 2230 GCCACCATGG | 2240 CAACAGGATC |
| 2250 AAGAACATCA | 2260 CTGCTGCTGG | 2270 CATTTGGACT | 2280 GCTGTGTCTG | 2290 CCATGGCTGC | 2300 AAGAAGGATC | 2310 AGCAGCAGCA |
| 2320 GCAGCGAATT | 2330 CGGATCCCTA | 2340 CCAAGTGCGC | 2350 AATTCCTCGG | 2360 GGCTTTACCA | 2370 TGTCACCAAT | 2380 GATTGCCCTA |
| 2390 ATTCGAGTAT | 2400 TGTGTACGAG | 2410 GCGGCCGATG | 2420 CCATCCTACA | 2430 CACTCCGGGG | 2440 TGTGTCCCTT | 2450 GCGTTCGCGA |
| 2460 GGGTAACGCC | 2470 TCGAGGTGTT | 2480 GGGTGGCGGT | 2490 GACCCCCACG | 2500 GTGGCCACCA | 2510 GGGACGGTAA | 2520 ACTCCCCACA |
| 2530 ACGCAGCTTC | 2540 GACGTCATAT | 2550 CGATCTGCTC | 2560 GTCGGGAGCG | 2570 CCACCCTCTG | 2580 CTCGGCCCTC | 2590 TACGTGGGGG |
| 2600 ACCTGTGCGG | 2610 GTCTGTCTTT | 2620 CTTGTTGGTC | 2630 AACTGTTTAC | 2640 CTTCTCTCCC | 2650 AGGCGCCACT | 2660 GGACGACGCA |
| 2670 AGACTGCAAT | 2680 TGTTCTATCT | 2690 ATCCCGGCCA | 2700 TATAACGGGT | 2710 CATCGTATGG | 2720 CATGGGATAT | 2730 GATGATGAAC |
| 2740 TGGTCCCCTA | 2750 CGGCAGCGTT | 2760 GGTGGTAGCT | 2770 CAGCTGCTCC | 2780 GGATCCCACA | 2790 AGCCATCTTG | 2800 GACATGATCG |
| 2810 CTGGTGCCCA | 2820 CTGGGAGTC | 2830 CTGGCGGGCA | 2840 TAGCGTATTT | 2850 CTCCATGGTG | 2860 GGGAACTGGG | 2870 CGAAGGTCCT |
| 2880 GGTAGTGCTG | 2890 CTGCTATTTG | 2900 CCGGCGTTGA | 2910 CGCGGAGATC | 2920 TAATCTAGAG | 2930 GGCCCTATTC | 2940 TATAGTGTCA |
| 2950 CCTAAATGCT | 2960 AGAGGATCTT | 2970 TGTGAAGGAA | 2980 CCTTACTTCT | 2990 GTGGTGTGAC | 3000 ATAATTGGAC | 3010 AAACTACCTA |
| 3020 CAGAGATTTA | 3030 AAGCTCTAAG | 3040 GTAAATATAA | 3050 AATTTTTAAG | 3060 TGTATAATGT | 3070 GTTAAACTAC | 3080 TGATTCTAAT |
| 3090 TGTTTGTGTA | 3100 TTTTAGATTC | 3110 CAACCTATGG | 3120 AACTGATGAA | 3130 TGGGAGCAGT | 3140 GGTGGAATGC | 3150 CTTTAATGAG |
| 3160 GAAAACCTGT | 3170 TTTGCTCAGA | 3180 AGAAATGCCA | 3190 TCTAGTGATG | 3200 ATGAGGCTAC | 3210 TGCTGACTCT | 3220 CAACATTCTA |
| 3230 CTCCTCCAAA | 3240 AAAGAAGAGA | 3250 AAGGTAGAAG | 3260 ACCCCAAGGA | 3270 CTTTCCTTCA | 3280 GAATTGCTAA | 3290 GTTTTTTGAG |
| 3300 TCATGCTGTG | 3310 TTTAGTAATA | 3320 GAACTCTTGC | 3330 TTGCTTTGCT | 3340 ATTTACACCA | 3350 CAAAGGAAAA | 3360 AGCTGCACTG |
| 3370 CTATACAAGA | 3380 AAATTATGGA | 3390 AAAATATTCT | 3400 GTAACCTTTA | 3410 TAAGTAGGCA | 3420 TAACAGTTAT | 3430 AATCATAACA |
| 3440 TACTGTTTTT | 3450 TCTTACTCCA | 3460 CACAGGCATA | 3470 GAGTGTCTGC | 3480 TATTAATAAC | 3490 TATGCTCAAA | 3500 AATTGTGTAC |
| 3510 | 3520 | 3530 | 3540 | 3550 | 3560 | 3570 |

|       |       |       |       |       |       |       |
|-------|-------|-------|-------|-------|-------|-------|
| CTTTAGCTTT | TTAATTTGTA | AAGGGGTTAA | TAAGGAATAT | TTGATGTATA | GTGCCTTGAC | TAGAGATCAT |
| 3580 AATCAGCCAT | 3590 ACCACATTTG | 3600 TAGAGGTTTT | 3610 ACTTGCTTTA | 3620 AAAAACCTCC | 3630 CACACCTCCC | 3640 CCTGAACCTG |
| 3650 AAACATAAAA | 3660 TGAATGCAAT | 3670 TGTTGTTGTT | 3680 AACTTGTTTA | 3690 TTGCAGCTTA | 3700 TAATGGTTAC | 3710 AAATAAAGCA |
| 3720 ATAGCATCAC | 3730 AAATTTCACA | 3740 AATAAAGCAT | 3750 TTTTTTCACT | 3760 GCATTCTAGT | 3770 TGTGGTTTGT | 3780 CCAAACTCAT |
| 3790 CAATGTATCT | 3800 TATCATGTCT | 3810 GGATCGATCC | 3820 CGCCATGGTA | 3830 TCAACGCCAT | 3840 ATTTCTATTT | 3850 ACAGTAGGGA |
| 3860 CCTCTTCGTT | 3870 GTGTAGGTAC | 3880 CGCTGTATTC | 3890 CTAGGGAAAT | 3900 AGTAGAGGCA | 3910 CCTTGAACTG | 3920 TCTGCATCAG |
| 3930 CCATATAGCC | 3940 CCCGCTGTTC | 3950 GACTTACAAA | 3960 CACAGGCACA | 3970 GTACTGACAA | 3980 ACCCATACAC | 3990 CTCCTCTGAA |
| 4000 ATACCCATAG | 4010 TTGCTAGGGC | 4020 TGTCTCCGAA | 4030 CTCATTACAC | 4040 CCTCCAAAGT | 4050 CAGAGCTGTA | 4060 ATTTCGCCAT |
| 4070 CAAGGGCAGC | 4080 GAGGGCTTCT | 4090 CCAGATAAAA | 4100 TAGCTTCTGC | 4110 CGAGAGTCCC | 4120 GTAAGGGTAG | 4130 ACACTTCAGC |
| 4140 TAATCCCTCG | 4150 ATGAGGTCTA | 4160 CTAGAATAGT | 4170 CAGTGCGGCT | 4180 CCCATTTTGA | 4190 AAATTCACTT | 4200 ACTTGATCAG |
| 4210 CTTCAGAAGA | 4220 TGGCGGAGGG | 4230 CCTCCAACAC | 4240 AGTAATTTTC | 4250 CTCCCGACTC | 4260 TTAAAATAGA | 4270 AAATGTCAAG |
| 4280 TCAGTTAAGC | 4290 AGGAAGTGGA | 4300 CTAACTGACG | 4310 CAGCTGGCCG | 4320 TGCGACATCC | 4330 TCTTTTAATT | 4340 AGTTGCTAGG |
| 4350 CAACGCCCTC | 4360 CAGAGGGCGT | 4370 GTGGTTTTGC | 4380 AAGAGGAAGC | 4390 AAAAGCCTCT | 4400 CCACCCAGGC | 4410 CTAGAATGTT |
| 4420 TCCACCCAAT | 4430 CATTACTATG | 4440 ACAACAGCTG | 4450 TTTTTTTTAG | 4460 TATTAAGCAG | 4470 AGGCCGGGGA | 4480 CCCCTGGCCC |
| 4490 GCTTACTCTG | 4500 GAGAAAAAGA | 4510 AGAGAGGCAT | 4520 TGTAGAGGCT | 4530 TCCAGAGGCA | 4540 ACTTGTCAAA | 4550 ACAGGACTGC |
| 4560 TTCTATTTCT | 4570 GTCACACTGT | 4580 CTGGCCCTGT | 4590 CACAAGGTCC | 4600 AGCACCTCCA | 4610 TACCCCCTTT | 4620 AATAAGCAGT |
| 4630 TTGGGAACGG | 4640 GTGCGGGTCT | 4650 TACTCCGCCC | 4660 ATCCCGCCCC | 4670 TAACTCCGCC | 4680 CAGTTCCGCC | 4690 CATTCTCCGC |
| 4700 CCCATGGCTG | 4710 ACTAATTTTT | 4720 TTTATTTATG | 4730 CAGAGGCCGA | 4740 GGCCGCCTCG | 4750 GCCTCTGAGC | 4760 TATTCCAGAA |
| 4770 GTAGTGAGGA | 4780 GGCTTTTTTG | 4790 GAGGCCTAGG | 4800 CTTTTGCAAA | 4810 AAGCTAATTC |  |  |

SEQ:

---

SEQ. ID. NO. 8

PHCV-168

|       |       |       |       |       |       |       |
|-------|-------|-------|-------|-------|-------|-------|
| 10 MATGSRTSLL | 20 LAFGLLCLPW | 30 LQEGSAAAAA | 40 NSDPYQVRNS | 50 SGLYHVTNDC | 60 PNSSIVYEAA | 70 DAILHTPGCV |
| 80 PCVREGNASR | 90 CWVAVTPTVA | 100 TRDGKLPTTQ | 110 LRRHIDLLVG | 120 SATLCSALYV | 130 GDLCGSVFLV | 140 GQLFTFSPRR |
| 150 HWTTQDCNCS | 160 IYPGHITGHR | 170 MAWDMMMNWS | 180 PTAALVVAQL | 190 LRIPQAILDM | 200 IAGAHWGVLA | 210 GIAYFSMVGN |
| 220 WAKVLVVLLL | FAGVDAEL |  |  |  |  |  |

PEP:

SEQ. ID. NO. 9

PHCV_169

Circular sequence with junction at 5323

|  |  |  |  |  |  |  |
|---|---|---|---|---|---|---|
| 10 | 20 | 30 | 40 | 50 | 60 | 70 |
| GCGTAATCTG | CTGCTTGCAA | ACAAAAAAAC | CACCGCTACC | AGCGGTGGTT | TGTTTGCCGG | ATCAAGAGCT |
| 80 | 90 | 100 | 110 | 120 | 130 | 140 |
| ACCAACTCTT | TTTCCGAAGG | TAACTGGCTT | CAGCAGAGCG | CAGATACCAA | ATACTGTCCT | TCTAGTGTAG |
| 150 | 160 | 170 | 180 | 190 | 200 | 210 |
| CCGTAGTTAG | GCCACCACTT | CAAGAACTCT | GTAGCACCGC | CTACATACCT | CGCTCTGCTA | ATCCTGTTAC |
| 220 | 230 | 240 | 250 | 260 | 270 | 280 |
| CAGTGGCTGC | TGCCAGTGGC | GATAAGTCGT | GTCTTACCGG | GTTGGACTCA | AGACGATAGT | TACCGGATAA |
| 290 | 300 | 310 | 320 | 330 | 340 | 350 |
| GGCGCAGCGG | TCGGGCTGAA | CGGGGGGTTC | GTGCACACAG | CCCAGCTTGG | AGCGAACGAC | CTACACCGAA |
| 360 | 370 | 380 | 390 | 400 | 410 | 420 |
| CTGAGATACC | TACAGCGTGA | GCATTGAGAA | AGCGCCACGC | TTCCCGAAGG | GAGAAAGGCG | GACAGGTATC |
| 430 | 440 | 450 | 460 | 470 | 480 | 490 |
| CGGTAAGCGG | CAGGGTCGGA | ACAGGAGAGC | GCACGAGGGA | GCTTCCAGGG | GGAAACGCCT | GGTATCTTTA |
| 500 | 510 | 520 | 530 | 540 | 550 | 560 |
| TAGTCCTGTC | GGGTTTCGCC | ACCTCTGACT | TGAGCGTCGA | TTTTTGTGAT | GCTCGTCAGG | GGGGCGGAGC |
| 570 | 580 | 590 | 600 | 610 | 620 | 630 |
| CTATGGAAAA | ACGCCAGCPA | CGCAAGCTAG | CTTCTAGCTA | GAAATTGTAA | ACGTAATAT | TTTGTTAAAA |
| 640 | 650 | 660 | 670 | 680 | 690 | 700 |
| TTCGCGTTAA | ATTTTTGTTA | AATCAGCTCA | TTTTTTAACC | AATAGGCCGA | AATCGGCAAA | ATCCCTTATA |
| 710 | 720 | 730 | 740 | 750 | 760 | 770 |
| AATCAAAAGA | ATAGCCCGAG | ATAGGGTTGA | GTGTTGTTCC | AGTTTGGAAC | AAGAGTCCAC | TATTAAAGAA |
| 780 | 790 | 800 | 810 | 820 | 830 | 840 |
| CGTGGACTCC | AACGTCAAAG | GGCGAAAAAC | CGTCTATCAG | GGCGATGGCC | GCCCACTACG | TGAACCATCA |
| 850 | 860 | 870 | 880 | 890 | 900 | 910 |
| CCCAAATCAA | GTTTTTTGGG | GTCGAGGTGC | CGTAAAGCAC | TAAATCGGAA | CCCTAAAGGG | AGCCCCCGAT |
| 920 | 930 | 940 | 950 | 960 | 970 | 980 |
| TTAGAGCTTG | ACGGGGAAAG | CCGGCGAACG | TGGCGAGAAA | GGAAGGGAAG | AAAGCGAAAG | GAGCGGGCGC |
| 990 | 1000 | 1010 | 1020 | 1030 | 1040 | 1050 |
| TAGGGCGCTG | GCAAGTGTAG | CGGTCACGCT | GCGCGTAACC | ACCACACCCG | CCGCGCTTAA | TGCGCCGCTA |
| 1060 | 1070 | 1080 | 1090 | 1100 | 1110 | 1120 |
| CAGGGCGCGT | ACTATGGTTG | CTTTGACGAG | ACCGTATAAC | GTGCTTTCCT | CGTTGGAATC | AGAGCGGGAG |
| 1130 | 1140 | 1150 | 1160 | 1170 | 1180 | 1190 |
| CTAAACAGGA | GGCCGATTAA | AGGGATTTTA | GACAGGAACG | GTACGCCAGC | TGGATCACCG | CGGTCTTTCT |
| 1200 | 1210 | 1220 | 1230 | 1240 | 1250 | 1260 |
| CAACGTAACA | CTTTACAGCG | GCGCGTCATT | TGATATGATG | CGCCCCGCTT | CCCGATAAGG | GAGCAGGCCA |
| 1270 | 1280 | 1290 | 1300 | 1310 | 1320 | 1330 |
| GTAAAAGCAT | TACCCGTGGT | GGGGTTCCCG | AGCGGCCAAA | GGGAGCAGAC | TCTAAATCTG | CCGTCATCGA |
| 1340 | 1350 | 1360 | 1370 | 1380 | 1390 | 1400 |
| CTTCGAAGGT | TCGAATCCTT | CCCCCACCAC | CATCACTTTC | AAAAGTCCGA | AAGAATCTGC | TCCCTGCTTG |
| 1410 | 1420 | 1430 | 1440 | 1450 | 1460 | 1470 |
| TGTGTTGGAG | GTCGCTGAGT | AGTGCGCGAG | TAAAATTTAA | GCTACAACAA | GGCAAGGCTT | GACCGACAAT |
| 1480 | 1490 | 1500 | 1510 | 1520 | 1530 | 1540 |
| TGCATGAAGA | ATCTGCTTAG | GGTTAGGCGT | TTTGCGCTGC | TTCGCGATGT | ACGGGCCAGA | TATACGCGTT |
| 1550 | 1560 | 1570 | 1580 | 1590 | 1600 | 1610 |
| GACATTGATT | ATTGACTAGT | TATTAATAGT | AATCAATTAC | GGGGTCATTA | GTTCATAGCC | CATATATGGA |
| 1620 | 1630 | 1640 | 1650 | 1660 | 1670 | 1680 |
| GTTCCGCGTT | ACATAACTTA | CGGTAAATGG | CCCGCCTGGC | TGACCGCCCA | ACGACCCCCG | CCCATTGACG |
| 1690 | 1700 | 1710 | 1720 | 1730 | 1740 | 1750 |

|            |            |            |            |            |            |            |
|------------|------------|------------|------------|------------|------------|------------|
| TCAATAATGA | CGTATGTTCC | CATAGTAACG | CCAATAGGGA | CTTTCCATTG | ACGTCAATGG | GTGGACTATT |
| 1760       | 1770       | 1780       | 1790       | 1800       | 1810       | 1820       |
| TACGGTAAAC | TGCCCACTTG | GCAGTACATC | AAGTGTATCA | TATGCCAAGT | ACGCCCCTA  | TTGACGTCAA |
| 1830       | 1840       | 1850       | 1860       | 1870       | 1880       | 1890       |
| TGACGGTAAA | TGGCCCGCCT | GGCATTATGC | CCAGTACATG | ACCTTATGGG | ACTTTCCTAC | TTGGCAGTAC |
| 1900       | 1910       | 1920       | 1930       | 1940       | 1950       | 1960       |
| ATCTACGTAT | TAGTCATCGC | TATTACCATG | GTGATGCGGT | TTTGGCAGTA | CATCAATGGG | CGTGGATAGC |
| 1970       | 1980       | 1990       | 2000       | 2010       | 2020       | 2030       |
| GGTTTGACTC | ACGGGGATTT | CCAAGTCTCC | ACCCCATTGA | CGTCAATGGG | AGTTTGTTTT | GGCACCAAAA |
| 2040       | 2050       | 2060       | 2070       | 2080       | 2090       | 2100       |
| TCAACGGGAC | TTTCCAAAAT | GTCGTAACAA | CTCCGCCCCA | TTGACGCAAA | TGGGCGGTAG | GCGTGTACGG |
| 2110       | 2120       | 2130       | 2140       | 2150       | 2160       | 2170       |
| TGGGAGGTCT | ATATAAGCAG | AGCTCTCTGG | CTAACTAGAG | AACCCACTGC | TTAACTGGCT | TATCGAAATT |
| 2180       | 2190       | 2200       | 2210       | 2220       | 2230       | 2240       |
| AATACGACTC | ACTATAGGGA | GACCGGAAGC | TTGGTACCGA | GCTCGGATCT | GCCACCATGG | CAACAGGATC |
| 2250       | 2260       | 2270       | 2280       | 2290       | 2300       | 2310       |
| AAGAACATCA | CTGCTGCTGG | CATTTGGACT | GCTGTGTCTG | CCATGGCTGC | AAGAAGGATC | AGCAGCAGCA |
| 2320       | 2330       | 2340       | 2350       | 2360       | 2370       | 2380       |
| GCAGCGAATT | CAGAAACCCA | CGTCACCGGG | GGAAGTGCCG | GCCACACCAC | GGCTGGGCTT | GTTCGTCTCC |
| 2390       | 2400       | 2410       | 2420       | 2430       | 2440       | 2450       |
| TTTCACCAGG | CGCCAAGCAG | AACATCCAAC | TGATCAACAC | CAACGGCAGT | TGGCACATCA | ATAGCACGGC |
| 2460       | 2470       | 2480       | 2490       | 2500       | 2510       | 2520       |
| CTTGAACTGC | AATGAAAGCC | TTAACACCGG | CTGGTTAGCA | GGGCTCTTCT | ATCACCACAA | ATTCAACTCT |
| 2530       | 2540       | 2550       | 2560       | 2570       | 2580       | 2590       |
| TCAGGTTGTC | CTGAGAGGTT | GGCCAGCTGC | CGACGCCTTA | CCGAT TTT GC | CCAGGGCGGG | GGTCCTATCA |
| 2600       | 2610       | 2620       | 2630       | 2640       | 2650       | 2660       |
| GTTACGCCAA | CGGAAGCGGC | CTCGATGAAC | GCCCTACTG  | CTGGCACTAC | CCTCCAAGAC | CTTGTGGCAT |
| 2670       | 2680       | 2690       | 2700       | 2710       | 2720       | 2730       |
| TGTGCCCGCA | AAGAGCGTGT | GTGGCCCGGT | ATATTGCTTC | ACTCCCAGCC | CCGTGGTGGT | GGGAACGACC |
| 2740       | 2750       | 2760       | 2770       | 2780       | 2790       | 2800       |
| GACAGGTCGG | GCGCGCCTAC | CTACAGCTGG | GGTGCAAATG | ATACGGATGT | CTTTGTCCTT | AACAACACCA |
| 2810       | 2820       | 2830       | 2840       | 2850       | 2860       | 2870       |
| GGCCACCGCT | GGGCAATTGG | TTCGGTTGCA | CCTGGATGAA | CTCAACTGGA | TTCACCAAAG | TGTGCGGAGC |
| 2880       | 2890       | 2900       | 2910       | 2920       | 2930       | 2940       |
| GCCCCCTTGT | GTCATCGGAG | GGGTGGGCAA | CAACACCTTG | CTCTGCCCCA | CTGATTGTTT | CCGCAAGCAT |
| 2950       | 2960       | 2970       | 2980       | 2990       | 3000       | 3010       |
| CCGGAAGCCA | CATACTCTCG | GTGCGGCTCC | GGTCCCTGGA | TTACACCCAG | GTGCATGGTC | GACTACCCGT |
| 3020       | 3030       | 3040       | 3050       | 3060       | 3070       | 3080       |
| ATAGGCTTTG | GCACTATCCT | TGTACCATCA | ATTACACCAT | ATTCAAAGTC | AGGATGTACG | TGGGAGGGGT |
| 3090       | 3100       | 3110       | 3120       | 3130       | 3140       | 3150       |
| CGAGCACAGG | CTGGAAGCGG | CCTGCAACTG | GACGCGGGC  | GAACGCTGTG | ATCTGGAAGA | CAGGGACAGG |
| 3160       | 3170       | 3180       | 3190       | 3200       | 3210       | 3220       |
| TCCGAGCTCA | GCCCGTTACT | GCTGTCCACC | ACGCAGTGGC | AGGTCCTTCC | GTGTTCTTTC | ACGACCCTGC |
| 3230       | 3240       | 3250       | 3260       | 3270       | 3280       | 3290       |
| CAGCCTTGTC | CACCGGCCTC | ATCCACCTCC | ACCAGAACAT | TGTGGACGTG | CAGTACTTGT | ACGGGGTAGG |
| 3300       | 3310       | 3320       | 3330       | 3340       | 3350       | 3360       |
| GTCAAGCATC | GCGTCCTGGG | CTATTAAGTG | GGAGTACGAC | GTTCTCCTGT | TCCTTCTGCT | TGCAGACGCG |
| 3370       | 3380       | 3390       | 3400       | 3410       | 3420       | 3430       |
| CGCGTTTGCT | CCTGCTTGTG | GATGATGTTA | CTCATATCCC | AAGCGGAGGC | GGCTTTGGAG | AACTAATCTA |
| 3440       | 3450       | 3460       | 3470       | 3480       | 3490       | 3500       |
| GAGGGCCCTA | TTCTATAGTG | TCACCTAAAT | GCTAGAGGAT | CTTTGTGAAG | GAACCTTACT | TCTGTGGTGT |
| 3510       | 3520       | 3530       | 3540       | 3550       | 3560       | 3570       |
| GACATAATTG | GACAAACTAC | CTACAGAGAT | TTAAAGCTCT | AAGGTAAATA | TAAAATTTTT | AAGTGTATAA |

| 3580 | 3590 | 3600 | 3610 | 3620 | 3630 | 3640 |
|---|---|---|---|---|---|---|
| TGTGTTAAAC | TACTGATTCT | AATTGTTTGT | GTATTTAGA | TTCCAACCTA | TGGAACTGAT | GAATGGGAGC |
| 3650 | 3660 | 3670 | 3680 | 3690 | 3700 | 3710 |
| AGTGGTGGAA | TGCCTTTAAT | GAGGAAAACC | TGTTTTGCTC | AGAAGAAATG | CCATCTAGTG | ATGATGAGGC |
| 3720 | 3730 | 3740 | 3750 | 3760 | 3770 | 3780 |
| TACTGCTGAC | TCTCAACATT | CTACTCCTCC | AAAAAAGAAG | AGAAAGGTAG | AAGACCCCAA | GGACTTTCCT |
| 3790 | 3800 | 3810 | 3820 | 3830 | 3840 | 3850 |
| TCAGAATTGC | TAAGTTTTTT | GAGTCATGCT | GTGTTTAGTA | ATAGAACTCT | TGCTTGCTTT | GCTATTTACA |
| 3860 | 3870 | 3880 | 3890 | 3900 | 3910 | 3920 |
| CCACAAAGGA | AAAAGCTGCA | CTGCTATACA | AGAAAATTAT | GGAAAAATAT | TCTGTAACCT | TTATAAGTAG |
| 3930 | 3940 | 3950 | 3960 | 3970 | 3980 | 3990 |
| GCATAACAGT | TATAATCATA | ACATACTGTT | TTTTCTTACT | CCACACAGGC | ATAGAGTGTC | TGCTATTAAT |
| 4000 | 4010 | 4020 | 4030 | 4040 | 4050 | 4060 |
| AACTATGCTC | AAAAATTGTG | TACCTTT AGC | TTTTTAATTT | GTAAAGGGGT | TAATAAGGAA | TATTTGATGT |
| 4070 | 4080 | 4090 | 4100 | 4110 | 4120 | 4130 |
| ATAGTGCCTT | GACTAGAGAT | CATAATCAGC | CATACCACAT | TTGTAGAGGT | TTTACTTGCT | TTAAAAAACC |
| 4140 | 4150 | 4160 | 4170 | 4180 | 4190 | 4200 |
| TCCCACACCT | CCCCCTGAAC | CTGAAACATA | AAATGAATGC | AATTGTTGTT | GTTAACTTGT | TTATTGCAGC |
| 4210 | 4220 | 4230 | 4240 | 4250 | 4260 | 4270 |
| TTATAATGGT | TACAAATAAA | GCAATAGCAT | CACAAATTTC | ACAAATAAAG | CATTTTTTTC | ACTGCATTCT |
| 4280 | 4290 | 4300 | 4310 | 4320 | 4330 | 4340 |
| AGTTGTGGTT | TGTCCAAACT | CATCAATGTA | TCTTATCATG | TCTGGATCGA | TCCCGCCATG | GTATCAACGC |
| 4350 | 4360 | 4370 | 4380 | 4390 | 4400 | 4410 |
| CATATTTCTA | TTTACAGTAG | GGACCTCTTC | GTTGTGTAGG | TACCGCTGTA | TTCCTAGGGA | AATAGTAGAG |
| 4420 | 4430 | 4440 | 4450 | 4460 | 4470 | 4480 |
| GCACCTTGAA | CTGTCTGCAT | CAGCATATA | GCCCCGCTG | TTCGACTTAC | AAACACAGGC | ACAGTACTGA |
| 4490 | 4500 | 4510 | 4520 | 4530 | 4540 | 4550 |
| CAAACCCATA | CACCTCCTCT | GAAATACCCA | TAGTTGCTAG | GGCTGTCTCC | GAACTCATTA | CACCCTCCAA |
| 4560 | 4570 | 4580 | 4590 | 4600 | 4610 | 4620 |
| AGTCAGAGCT | GTAATTTCGC | CATCAAGGGC | AGCGAGGGCT | TCTCCAGATA | AAATAGCTTC | TGCCGAGAGT |
| 4630 | 4640 | 4650 | 4660 | 4670 | 4680 | 4690 |
| CCCGTAAGGG | TAGACACTTC | AGCTAATCCC | TCGATGAGGT | CTACTAGAAT | AGTCAGTGCG | GCTCCCATTT |
| 4700 | 4710 | 4720 | 4730 | 4740 | 4750 | 4760 |
| TGAAAATTCA | CTTACTTGAT | CAGCTTCAGA | AGATGGCGGA | GGGCCTCCAA | CACAGTAATT | TTCCTCCCGA |
| 4770 | 4780 | 4790 | 4800 | 4810 | 4820 | 4830 |
| CTCTTAAAAT | AGAAAATGTC | AAGTCAGTTA | AGCAGGAAGT | GGACTAACTG | ACGCAGCTGG | CCGTGCGACA |
| 4840 | 4850 | 4860 | 4870 | 4880 | 4890 | 4900 |
| TCCTCTTTTA | ATTAGTTGCT | AGGCAACGCC | CTCCAGAGGG | CGTGTGGTTT | TGCAAGAGGA | AGCAAAAGCC |
| 4910 | 4920 | 4930 | 4940 | 4950 | 4960 | 4970 |
| TCTCCACCCA | GGCCTAGAAT | GTTTCCACCC | AATCATTACT | ATGACAACAG | CTGTTTTTTT | TAGTATTAAG |
| 4980 | 4990 | 5000 | 5010 | 5020 | 5030 | 5040 |
| CAGAGGCCGG | GGACCCCTGG | CCCGCTTACT | CTGGAGAAAA | AGAAGAGAGG | CATTGTAGAG | GCTTCCAGAG |
| 5050 | 5060 | 5070 | 5080 | 5090 | 5100 | 5110 |
| GCAACTTGTC | AAAACAGGAC | TGCTTCTATT | TCTGTCACAC | TGTCTGGCCC | TGTCACAAGG | TCCAGCACCT |
| 5120 | 5130 | 5140 | 5150 | 5160 | 5170 | 5180 |
| CCATACCCCC | TTTAATAAGC | AGTTTGGGAA | CGGGTGCGGG | TCTTACTCCG | CCCATCCCGC | CCCTAACTCC |
| 5190 | 5200 | 5210 | 5220 | 5230 | 5240 | 5250 |
| GCCCAGTTCC | GCCCATTCTC | CGCCCCATGG | CTGACTAATT | TTTTTATTT | ATGCAGAGGC | CGAGGCCGCC |
| 5260 | 5270 | 5280 | 5290 | 5300 | 5310 | 5320 |
| TCGGCCTCTG | AGCTATTCCA | GAAGTAGTGA | GGAGGCTTTT | TTGGAGGCCT | AGGCTTTTGC | AAAAAGCTAA |
| TCC | | | | | | |

SEQ:

SEQ. ID. NO. 10

PHCV-169

| | | | | | | |
|---|---|---|---|---|---|---|
| 10 | 20 | 30 | 40 | 50 | 60 | 70 |
| MATGSRTSLL | LAFGLLCLPW | LQEGSAAAAA | NSETHVTGGS | AGHTTAGLVR | LLSPGAKQNI | QLINTNGSWH |
| 80 | 90 | 100 | 110 | 120 | 130 | 140 |
| INSTALNCNE | SLNTGWLAGL | FYHHKFNSSG | CPERLASCRR | LTDFAQGGGP | ISYANGSGLD | ERPYCWHYPP |
| 150 | 160 | 170 | 180 | 190 | 200 | 210 |
| RPCGIVPAKS | VCGPVYCFTP | SPVVVGTTDR | SGAPTYSWGA | NDTDVFVLNN | TRPPIGNWFG | CTWMNSTGFT |
| 220 | 230 | 240 | 250 | 260 | 270 | 280 |
| KVCGAPPCVI | GGVGNUTLLC | PTDCFRKHPE | ATYSRCGSGP | WITPRCMVDY | PYRLWHYPCT | NTYTIFKVRM |
| 290 | 300 | 310 | 320 | 330 | 340 | 350 |
| YVGGVEHRLE | AACNWTRGER | CDLEDRDRSE | LSPLLLSTTQ | WQVLPCSFTT | LPALSTGLIH | LHQNIVDVQY |
| 360 | 370 | 380 | 390 | 400 | | |
| LYGVGSSIAS | WAIKWEYDVL | LFLLLADARV | CSCLWMMLLI | SQAEAALEN. | | |

PEP:

SEQ. ID. NO. 11

PHCV_170

Circular sequence with junction at 5125

| | | | | | | |
|---|---|---|---|---|---|---|
| 10 | 20 | 30 | 40 | 50 | 60 | 70 |
| GCGTAATCTG | CTGCTTGCAA | ACAAAAAAAC | CACCGCTACC | AGCGGTGGTT | TGTTTGCCGG | ATCAAGAGCT |
| 80 | 90 | 100 | 110 | 120 | 130 | 140 |
| ACCAACTCTT | TTTCCGAAGG | TAACTGGCTT | CAGCAGAGCG | CAGATACCAA | ATACTGTCCT | TCTAGTGTAG |
| 150 | 160 | 170 | 180 | 190 | 200 | 210 |
| CCGTAGTTAG | GCCACCACTT | CAAGAACTCT | GTAGCACCGC | CTACATACCT | CGCTCTGCTA | ATCCTGTTAC |
| 220 | 230 | 240 | 250 | 260 | 270 | 280 |
| CAGTGGCTGC | TGCCAGTGGC | GATAAGTCGT | GTCTTACCGG | GTTGGACTCA | AGACGATAGT | TACCGGATAA |
| 290 | 300 | 310 | 320 | 330 | 340 | 350 |
| GGCGCAGCGG | TCGGGCTGAA | CGGGGGGTTC | GTGCACACAG | CCCAGCTTGG | AGCGAACGAC | CTACACCGAA |
| 360 | 370 | 380 | 390 | 400 | 410 | 420 |
| CTGAGATACC | TACAGCGTGA | GCATTGAGAA | AGCGCCACGC | TTCCCGAAGG | GAGAAAGGCG | GACAGGTATC |
| 430 | 440 | 450 | 460 | 470 | 480 | 490 |
| CGGTAAGCGG | CAGGGTCGGA | ACAGGAGAGC | GCACGAGGGA | GCTTCCAGGG | GGAAACGCCT | GGTATCTTTA |
| 500 | 510 | 520 | 530 | 540 | 550 | 560 |
| TAGTCCTGTC | GGGTTTCGCC | ACCTCTGACT | TGAGCGTCGA | TTTTTGTGAT | GCTCGTCAGG | GGGGCGGAGC |
| 570 | 580 | 590 | 600 | 610 | 620 | 630 |
| CTATGGAAAA | ACGCCAGCAA | CGCAAGCTAG | CTTCTAGCTA | GAAATTGTAA | ACGTTAATAT | TTTGTTAAAA |
| 640 | 650 | 660 | 670 | 680 | 690 | 700 |
| TTCGCGTTAA | ATTTTTGTTA | AATCAGCTCA | TTTTTTAACC | AATAGGCCGA | AATCGGCAAA | ATCCCTTATA |
| 710 | 720 | 730 | 740 | 750 | 760 | 770 |
| AATCAAAAGA | ATAGCCCGAG | ATAGGGTTGA | GTGTTGTTCC | AGTTTGGAAC | AAGAGTCCAC | TATTAAAGAA |
| 780 | 790 | 800 | 810 | 820 | 830 | 840 |
| CGTGGACTCC | AACGTCAAAG | GGCGAAAAAC | CGTCTATCAG | GGCGATGGCC | GCCCACTACG | TGAACCATCA |
| 850 | 860 | 870 | 880 | 890 | 900 | 910 |
| CCCAAATCAA | GTTTTTTGGG | GTCGAGGTGC | CGTAAAGCAC | TAAATCGGAA | CCCTAAAGGG | AGCCCCCGAT |
| 920 | 930 | 940 | 950 | 960 | 970 | 980 |
| TTAGAGCTTG | ACGGGGAAAG | CCGGCGAACG | TGGCGAGAAA | GGAAGGGAAG | AAAGCGAAAG | GAGCGGGCGC |
| 990 | 1000 | 1010 | 1020 | 1030 | 1040 | 1050 |
| TAGGGCGCTG | GCAAGTGTAG | CGGTCACGCT | GCGCGTAACC | ACCACACCCG | CCGCGCTTAA | TGCGCCGCTA |
| 1060 | 1070 | 1080 | 1090 | 1100 | 1110 | 1120 |
| CAGGGCGCGT | ACTATGGTTG | CTTTGACGAG | ACCGTATAAC | GTGCTTTCCT | CGTTGGAATC | AGAGCGGGAG |
| 1130 | 1140 | 1150 | 1160 | 1170 | 1180 | 1190 |
| CTAAACAGGA | GGCCGATTAA | AGGGATTTTA | GACAGGAACG | GTACGCCAGC | TGGATCACCG | CGGTCTTTCT |

| 1200 | 1210 | 1220 | 1230 | 1240 | 1250 | 1260 |
|---|---|---|---|---|---|---|
| CAACGTAACA | CTTTACAGCG | GCGCGTCATT | TGATATGATG | CGCCCCGCTT | CCCGATAAGG | GAGCAGGCCA |
| 1270 | 1280 | 1290 | 1300 | 1310 | 1320 | 1330 |
| GTAAAAGCAT | TACCCGTGGT | GGGGTTCCCG | AGCGGCCAAA | GGGAGCAGAC | TCTAAATCTG | CCGTCATCGA |
| 1340 | 1350 | 1360 | 1370 | 1380 | 1390 | 1400 |
| CTTCGAAGGT | TCGAATCCTT | CCCCCACCAC | CATCACTTTC | AAAAGTCCGA | AAGAATCTGC | TCCCTGCTTG |
| 1410 | 1420 | 1430 | 1440 | 1450 | 1460 | 1470 |
| TGTGTTGGAG | GTCGCTGAGT | AGTGCGCGAG | TAAAATTTAA | GCTACAACAA | GGCAAGGCTT | GACCGACAAT |
| 1480 | 1490 | 1500 | 1510 | 1520 | 1530 | 1540 |
| TGCATGAAGA | ATCTGCTTAG | GGTTAGGCGT | TTTGCGCTGC | TTCGCGATGT | ACGGGCCAGA | TATACGCGTT |
| 1550 | 1560 | 1570 | 1580 | 1590 | 1600 | 1610 |
| GACATTGATT | ATTGACTAGT | TATTAATAGT | AATCAATTAC | GGGGTCATTA | GTTCATAGCC | CATATATGGA |
| 1620 | 1630 | 1640 | 1650 | 1660 | 1670 | 1680 |
| GTTCCGCGTT | ACATAACTTA | CGGTAAATGG | CCCGCCTGGC | TGACCGCCCA | ACGACCCCG | CCCATTGACG |
| 1690 | 1700 | 1710 | 1720 | 1730 | 1740 | 1750 |
| TCAATAATGA | CGTATGTTCC | CATAGTAACG | CCAATAGGGA | CTTTCCATTG | ACGTCAATGG | GTGGACTATT |
| 1760 | 1770 | 1780 | 1790 | 1800 | 1810 | 1820 |
| TACGGTAAAC | TGCCCACTTG | GCAGTACATC | AAGTGTATCA | TATGCCAAGT | ACGCCCCTA | TTGACGTCAA |
| 1830 | 1840 | 1850 | 1860 | 1870 | 1880 | 1890 |
| TGACGGTAAA | TGGCCCGCCT | GGCATTATGC | CCAGTACATG | ACCTTATGGG | ACTTTCCTAC | TTGGCAGTAC |
| 1900 | 1910 | 1920 | 1930 | 1940 | 1950 | 1960 |
| ATCTACGTAT | TAGTCATCGC | TATTACCATG | GTGATGCGGT | TTTGGCAGTA | CATCAATGGG | CGTGGATAGC |
| 1970 | 1980 | 1990 | 2000 | 2010 | 2020 | 2030 |
| GGTTTGACTC | ACGGGGATTT | CCAAGTCTCC | ACCCCATTGA | CGTCAATGGG | AGTTTGTTTT | GGCACCAAAA |
| 2040 | 2050 | 2060 | 2070 | 2080 | 2090 | 2100 |
| TCAACGGGAC | TTTCCAAAAT | GTCGTAACAA | CTCCGCCCCA | TTGACGCAAA | TGGGCGGTAG | GCGTGTACGG |
| 2110 | 2120 | 2130 | 2140 | 2150 | 2160 | 2170 |
| TGGGAGGTCT | ATATAAGCAG | AGCTCTCTGG | CTAACTAGAG | AACCCACTGC | TTAACTGGCT | TATCGAAATT |
| 2180 | 2190 | 2200 | 2210 | 2220 | 2230 | 2240 |
| AATACGACTC | ACTATAGGGA | GACCGGAAGC | TTGGTACCGA | GCTCGGATCT | GCCACCATGG | CAACAGGATC |
| 2250 | 2260 | 2270 | 2280 | 2290 | 2300 | 2310 |
| AAGAACATCA | CTGCTGCTGG | CATTTGGACT | GCTGTGTCTG | CCATGGCTGC | AAGAAGGATC | AGCAGCAGCA |
| 2320 | 2330 | 2340 | 2350 | 2360 | 2370 | 2380 |
| GCAGCGAATT | CAGAAACCCA | CGTCACCGGG | GGAAGTGCCG | GCCACACCAC | GGCTGGGCTT | GTTCGTCTCC |
| 2390 | 2400 | 2410 | 2420 | 2430 | 2440 | 2450 |
| TTTCACCAGG | CGCCAAGCAG | AACATCCAAC | TGATCAACAC | CAACGGCAGT | TGGCACATCA | ATAGCACGGC |
| 2460 | 2470 | 2480 | 2490 | 2500 | 2510 | 2520 |
| CTTGAACTGC | AATGAAAGCC | TTAACACCGG | CTGGTTAGCA | GGGCTCTTCT | ATCACCACAA | ATTCAACTCT |
| 2530 | 2540 | 2550 | 2560 | 2570 | 2580 | 2590 |
| TCAGGTTGTC | CTGAGAGGTT | GGCCAGCTGC | CGACGCCTTA | CCGATTTTGC | CCAGGGCGGG | GGTCCTATCA |
| 2600 | 2610 | 2620 | 2630 | 2640 | 2650 | 2660 |
| GTTACGCCAA | CGGAAGCGGC | CTCGATGAAC | GCCCCTACTG | CTGGCACTAC | CCTCCAAGAC | CTTGTGGCAT |
| 2670 | 2680 | 2690 | 2700 | 2710 | 2720 | 2730 |
| TGTGCCCGCA | AAGAGCGTGT | GTGGCCCGGT | ATATTGCTTC | ACTCCCAGCC | CCGTGGTGGT | GGGAACGACC |
| 2740 | 2750 | 2760 | 2770 | 2780 | 2790 | 2800 |
| GACAGGTCGG | GCGCGCCTAC | CTACAGCTGG | GCTGCAAATG | ATACGGATGT | CTTTGTCCTT | AACAACACCA |
| 2810 | 2820 | 2830 | 2840 | 2850 | 2860 | 2870 |
| GGCCACCGCT | GGGCAATTGG | TTCGGTTGCA | CCTGGATGAA | CTCAACTGGA | TTCACCAAAG | TGTGCGGAGC |
| 2880 | 2890 | 2900 | 2910 | 2920 | 2930 | 2940 |
| GCCCCCTTGT | GTCATCGGAG | GGGTGGGCAA | CAACACCTTG | CTCTGCCCCA | CTGATTGCTT | CCGCAAGCAT |
| 2950 | 2960 | 2970 | 2980 | 2990 | 3000 | 3010 |
| CCGGAAGCCA | CATACTCTCG | GTGCGGCTCC | GGTCCCTGGA | TTACACCCAG | GTGCATGGTC | GACTACCCGT |
| 3020 | 3030 | 3040 | 3050 | 3060 | 3070 | 3080 |

|            |            |            |            |            |            |            |
|------------|------------|------------|------------|------------|------------|------------|
| ATAGGCTTTG | GCACTATCCT | TGTACCATCA | ATTACACCAT | ATTCAAAGTC | AGGATGTACG | TGGGAGGGGT |
| 3090       | 3100       | 3110       | 3120       | 3130       | 3140       | 3150       |
| CGAGCACAGG | CTGGAAGCGG | CCTGCAACTG | GACGCGGGC  | GAACGCTGTG | ATCTGGAAGA | CAGGGACAGG |
| 3160       | 3170       | 3180       | 3190       | 3200       | 3210       | 3220       |
| TCCGAGCTCA | GCCCGTTACT | GCTGTCCACC | ACGCAGTGGC | AGGTCCTTCC | GTGTTCTTTC | ACGACCCTGC |
| 3230       | 3240       | 3250       | 3260       | 3270       | 3280       | 3290       |
| CAGCCTAATC | TAGAGGGCCC | TATTCTATAG | TGTCACCTAA | ATGCTAGAGG | ATCTTTGTGA | AGGAACCTTA |
| 3300       | 3310       | 3320       | 3330       | 3340       | 3350       | 3360       |
| CTTCTGTGGT | GTGACATAAT | TGGACAAACT | ACCTACAGAG | ATTTAAAGCT | CTAAGGTAAA | TATAAAATTT |
| 3370       | 3380       | 3390       | 3400       | 3410       | 3420       | 3430       |
| TTAAGTGTAT | AATGTGTTAA | ACTACTGATT | CTAATTGTTT | GTGTATTTTA | GATTCCAACC | TATGGAACTG |
| 3440       | 3450       | 3460       | 3470       | 3480       | 3490       | 3500       |
| ATGAATGGGA | GCAGTGGTGG | AATGCCTTTA | ATGAGGAAAA | CCTGTTTTGC | TCAGAAGAAA | TGCCATCTAG |
| 3510       | 3520       | 3530       | 3540       | 3550       | 3560       | 3570       |
| TGATGATGAG | GCTACTGCTG | ACTCTCAACA | TTCTACTCCT | CCAAAAAAGA | AGAGAAAGGT | AGAAGACCCC |
| 3580       | 3590       | 3600       | 3610       | 3620       | 3630       | 3640       |
| AAGGACTTTC | CTTCAGAATT | GCTAAGTTTT | TTGAGTCATG | CTGTGTTTAG | TAATAGAACT | CTTGCTTGCT |
| 3650       | 3660       | 3670       | 3680       | 3690       | 3700       | 3710       |
| TTGCTATTTA | CACCACAAAG | GAAAAGCTG  | CACTGCTATA | CAAGAAAATT | ATGGAAAAT  | ATTCTGTAAC |
| 3720       | 3730       | 3740       | 3750       | 3760       | 3770       | 3780       |
| CTTTATAAGT | AGGCATAACA | GTTATAATCA | TAACATACTG | TTTTTTCTTA | CTCCACACAG | GCATAGAGTG |
| 3790       | 3800       | 3810       | 3820       | 3830       | 3840       | 3850       |
| TCTGCTATTA | ATAACTATGC | TCAAAAATTG | TGTACCTTTA | GCTTTTTAAT | TTGTAAAGGG | GTTAATAAGG |
| 3860       | 3870       | 3880       | 3890       | 3900       | 3910       | 3920       |
| AATATTTGAT | GTATAGTGCC | TTGACTAGAG | ATCATAATCA | GCCATACCAC | ATTTGTAGAG | GTTTTACTTG |
| 3930       | 3940       | 3950       | 3960       | 2970       | 3980       | 3990       |
| CTTTAAAAAA | CCTCCCACAC | CTCCCCCTGA | ACCTGAAACA | TAAAATGAAT | GCAATTGTTG | TTGTTAACTT |
| 4000       | 4010       | 4020       | 4030       | 4040       | 4050       | 4060       |
| GTTTATTGCA | GCTTATAATG | GTTACAAATA | AAGCAATAGC | ATCACAAATT | TCACAAATAA | AGCATTTTTT |
| 4070       | 4080       | 4090       | 4100       | 4110       | 4120       | 4130       |
| TCACTGCATT | CTAGTTGTGG | TTTGTCCAAA | CTCATCAATG | TATCTTATCA | TGTCTGGATC | GATCCCGCCA |
| 4140       | 4150       | 4160       | 4170       | 4180       | 4190       | 4200       |
| TGGTATCAAC | GCCATATTTC | TATTTACAGT | AGGGACCTCT | TCGTTGTGTA | GGTACCGCTG | TATTCCTAGG |
| 4210       | 4220       | 4230       | 4240       | 4250       | 4260       | 4270       |
| GAAATAGTAG | AGGCACCTTG | AACTGTCTGC | ATCAGCCATA | TAGCCCCCGC | TGTTCGACTT | ACAAACACAG |
| 4280       | 4290       | 4300       | 4310       | 4320       | 4330       | 4340       |
| GCACAGTACT | GACAAACCCA | TACACCTCCT | CTGAAATACC | CATAGTTGCT | AGGGCTGTCT | CCGAACTCAT |
| 4350       | 4360       | 4370       | 4380       | 4390       | 4400       | 4410       |
| TACACCCTCC | AAAGTCAGAG | CTGTAATTTC | GCCATCAAGG | GCAGCGAGGG | CTTCTCCAGA | TAAAATAGCT |
| 4420       | 4430       | 4440       | 4450       | 4460       | 4470       | 4480       |
| TCTGCCGAGA | GTCCCGTAAG | GGTAGACACT | TCAGCTAATC | CCTCGATGAG | GTCTACTAGA | ATAGTCAGTG |
| 4490       | 4500       | 4510       | 4520       | 4530       | 4540       | 4550       |
| CGGCTCCCAT | TTTGAAAATT | CACTTACTTG | ATCAGCTTCA | GAAGATGGCG | GAGGGCCTCC | AACACAGTAA |
| 4560       | 4570       | 4580       | 4590       | 4600       | 4610       | 4620       |
| TTTTCCTCCC | GACTCTTAAA | ATAGAAAATG | TCAAGTCAGT | TAAGCAGGAA | GTGGACTAAC | TGACGCAGCT |
| 4630       | 4640       | 4650       | 4660       | 4670       | 4680       | 4690       |
| GGCCGTGCGA | CATCCTCTTT | TAATTAGTTG | CTAGGCAACG | CCCTCCAGAG | GGCGTGTGGT | TTTGCAAGAG |
| 4700       | 4710       | 4720       | 4730       | 4740       | 4750       | 4760       |
| GAAGCAAAAG | CCTCTCCACC | CAGGCCTAGA | ATGTTTCCAC | CCAATCATTA | CTATGACAAC | AGCTGTTTTT |
| 4770       | 4780       | 4790       | 4800       | 4810       | 4820       | 4830       |
| TTTAGTATTA | AGCAGAGGCC | GGGGACCCCT | GGCCCGCTTA | CTCTGGAGAA | AAAGAAGAGA | GGCATTGTAG |
| 4840       | 4850       | 4860       | 4870       | 4880       | 4890       | 4900       |
| AGGCTTCCAG | AGGCAACTTG | TCAAAACAGG | ACTGCTTCTA | TTTCTGTCAC | ACTGTCTGGC | CCTGTCACAA |

|  | 4910 | 4920 | 4930 | 4940 | 4950 | 4960 | 4970 |
|---|---|---|---|---|---|---|---|
|  | GGTCCAGCAC | CTCCATACCC | CCTTTAATAA | GCAGTTGGG | AACGGGTGCG | GGTCTTACTC | CGCCCATCCC |
|  | 4980 | 4990 | 5000 | 5010 | 5020 | 5030 | 5040 |
|  | GCCCCTAACT | CCGCCCAGTT | CCGCCCATTC | TCCGCCCCAT | GGCTGACTAA | TTTTTTTTAT | TTATGCAGAG |
|  | 5050 | 5060 | 5070 | 5080 | 5090 | 5100 | 5110 |
|  | GCCGAGGCCG | CCTCGGCCTC | TGAGCTATTC | CAGAAGTAGT | GAGGAGGCTT | TTTTGGAGGC | CTAGGCTTTT |
|  | 5120 |  |  |  |  |  |  |
|  | GCAAAAAGCT | AATTC |  |  |  |  |  |

SEQ:

SEQ. ID. NO. 12

PHCV-170

|  | 10 | 20 | 30 | 40 | 50 | 60 | 70 |
|---|---|---|---|---|---|---|---|
|  | MATGSRTSLL | LAFGLLCLPW | LQEGSAAAAA | NSETHVTGGS | AGHTTAGLVR | LLSPGAKQNI | QLINTNGSWH |
|  | 80 | 90 | 100 | 110 | 120 | 130 | 140 |
|  | INSTALNCNE | SLNTGWLAGL | FYHHKFNSSG | CPERLASCRR | LTDFAQGGGP | ISYANGSGLD | ERPYCWHYPP |
|  | 150 | 160 | 170 | 150 | 190 | 200 | 210 |
|  | RPCGIVPAKS | VCGPVYCFTP | SPVVVGTTDR | SGAPTYSWGA | NDTDVFVLNN | TRPPLGNWFG | CTWMNSTGFT |
|  | 220 | 230 | 240 | 250 | 260 | 270 | 280 |
|  | KVCGAPPCVI | GGVGNNTLLC | PTDCFRKHPE | ATYSRCGSGP | WTTPRCMVDY | PYRLWHYPCT | INYTIFKVRM |
|  | 290 | 300 | 310 | 320 | 330 |  |  |
|  | YVGGVEHRLE | AACNWTRGER | CDLEDRDRSE | LSPLLLSTTQ | WQVLPCSFTT |  | LPA. |

PEP:

---

What is claimed is:

1. Plasmid pHCV-162.

2. Plasmid pHCV-167.

\* \* \* \* \*